US012281127B2

United States Patent
Burke et al.

(10) Patent No.: US 12,281,127 B2
(45) Date of Patent: Apr. 22, 2025

(54) PYRIDO[4,3-D]PYRIMIDINE COMPOUNDS

(71) Applicant: PFIZER INC., New York, NY (US)

(72) Inventors: Benjamin Joseph Burke, San Diego, CA (US); Jacob Cole Deforest, San Diego, CA (US); Asako Nagata, San Diego, CA (US); Simon Paul Planken, San Marcos, CA (US); Jillian Elyse Spangler, San Diego, CA (US); Scott Channing Sutton, San Diego, CA (US); Hanna Maria Wisniewska, San Diego, CA (US); Shouliang Yang, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 18/903,345

(22) Filed: Oct. 1, 2024

(65) Prior Publication Data

US 2025/0034173 A1    Jan. 30, 2025

Related U.S. Application Data

(63) Continuation of application No. 18/625,795, filed on Apr. 3, 2024.

(60) Provisional application No. 63/568,399, filed on Mar. 21, 2024, provisional application No. 63/550,564, filed on Feb. 6, 2024, provisional application No. 63/598,907, filed on Nov. 14, 2023, provisional application No. 63/540,044, filed on Sep. 22, 2023, provisional application No. 63/507,621, filed on Jun. 12, 2023, provisional application No. 63/494,346, filed on Apr. 5, 2023.

(51) Int. Cl.
*C07D 519/00*     (2006.01)
*A61K 31/553*     (2006.01)
*A61P 35/00*      (2006.01)

(52) U.S. Cl.
CPC .......... *C07D 519/00* (2013.01); *A61K 31/553* (2013.01); *A61P 35/00* (2018.01)

(58) Field of Classification Search
CPC ...... C07D 519/00; A61K 31/553; A61P 35/00
See application file for complete search history.

(56) References Cited

U.S. PATENT DOCUMENTS

2024/0279241 A1*   8/2024   Jones .................. C07D 519/00

FOREIGN PATENT DOCUMENTS

| WO | 2023/046135 A1 | 3/2023 |
|----|----------------|--------|
| WO | 2024/009191 A1 | 1/2024 |
| WO | 2024/015262 A1 | 1/2024 |
| WO | 2024/031088 A1 | 2/2024 |
| WO | 2024/032704 A1 | 2/2024 |
| WO | 2024/041573 A1 | 2/2024 |

OTHER PUBLICATIONS

International Search Report, mailed on Oct. 5, 2024 for WO Application No. PCT/IB2024/053182, 3 pages.
Written Opinion, mailed on Oct. 5, 2024 for WO Application No. PCT/IB2024/053182, 5 pages.

* cited by examiner

*Primary Examiner* — John M Mauro
(74) *Attorney, Agent, or Firm* — Beau Burton

(57) ABSTRACT

The invention relates to compounds of Formula (I)-(III) and pharmaceutically acceptable salts thereof to their use in medicine; to compositions containing them; to processes for their preparation; and to intermediates used in such processes. The compounds the present invention may be useful in the treatment, prevention, suppression and amelioration diseases, disorders and conditions such as cancers.

9 Claims, No Drawings

PYRIDO[4,3-D]PYRIMIDINE COMPOUNDS

This application is a continuation of U.S. application Ser. No. 18/625,795, filed Apr. 3, 2024, and claims the benefit of U.S. Provisional Application No. 63/494,346 filed Apr. 5, 2023, U.S. Provisional Application No. 63/507,621 filed Jun. 12, 2023, U.S. Provisional Application No. 63/540,044 filed Sep. 22, 2023, U.S. Provisional Application No. 63/598,907 filed Nov. 14, 2023, U.S. Provisional Application No. 63/550,564 filed Feb. 6, 2024, and U.S. Provisional Application No. 63/568,399 filed Mar. 21, 2024, the contents of which are hereby incorporated by reference in their entireties.

BACKGROUND OF THE INVENTION

The present invention relates to novel pyrido[4,3-d]pyrimidine compounds as Kirsten rat sarcoma viral oncogene homolog (KRAS) inhibitors. The invention also relates to the preparation of the compounds, intermediates used in preparation thereof, compositions containing the compounds, and uses of the compounds for the treatment of KRAS related diseases such as cancers.

KRAS, HRAS (Harvey Rat sarcoma virus) and NRAS (Neuroblastoma RAS Viral Oncogene Homolog) belong to a group of GTPases that are critical in the survival and proliferation of cells through complex signaling cascades. Mutated RAS genes are found in approximately 30% of all cancers (Hyun et al 2021 Int. J. Mol. Sci. 22 (22), 12142). KRAS is the most frequently mutated RAS isoform in cancer cells (up to 85%), leading to development of cancers including non-small cell lung cancer (NSCLC), colorectal and pancreatic cancer that collectively and individually have significant unmet medical needs for affected patients. KRAS mutations are seen extensively in pancreatic ductal adenocarcinoma (PDAC). Mutations in KRAS have been observed in 30% of NSCLC cases, which is the major (80%) form of lung cancer. KRAS mutations seen in NSCLC include 39% of G12C, 18-21% of G12V, and 17-18% of G12D. KRAS mutations occur in 35-45% of colon cancers, leading to drug resistance.

Inhibitors of KRAS have been sought for decades, with recent advances seeing approval of sotorasib and subsequent KRAS G12C targeting compounds in trials (Palmer et al 2021 NPJ Precision Oncology, 5, 98). Sotorasib specifically targets mutations in KRAS through covalent modification of mutant cysteine at position 12. For this reason, sotorasib and other currently known KRAS inhibitors that rely on the same mechanism of action may be narrow in treatment scope and be of limited use when considering other major KRAS mutations such as G12V and G12D.

A vast majority of active KRAS mutant inhibitors that are capable of targeting mutants beyond G12C rely on a phenolic component to afford adequate binding potency. Phenols have the propensity to undergo conjugative metabolism in the gut and liver, which can result in reduced bioavailability. Chemotypes devoid of phenols may thus have advantages regarding bioavailability and dosing (Fell et al 2020 J. Med. Chem 63, 6679-6693).

Accordingly, there remains a need for new KRAS inhibitors that may be used for the treatment of a broader scope of cancers.

SUMMARY OF THE INVENTION

The present invention provides, in part, compounds of Formula (I), Formula (II), and Formula (II), and pharmaceutically acceptable salts thereof. The compounds of the present invention may inhibit the activities of all KRAS G12C, KRAS G12D, and KRAS G12V receptors, and may be useful in the treatment, prevention, suppression, and amelioration of diseases such as cancers, disorders and conditions mediated by any of KRAS G12C, KRAS G12D, and KRAS G12V receptors, or a combination thereof. In particular, the present invention provides compounds containing an indazole component with unexpectedly high cellular potency against one or more KRAS G12C, KRAS G12D, and KRAS G12V receptors. Also provided are pharmaceutical compositions, comprising the compounds or salts of the invention, alone or in combination with additional anticancer therapeutic agents. The present invention also provides, in part, methods for preparing such compounds, pharmaceutically acceptable salts and compositions of the invention, and methods of using the foregoing. This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

According to an embodiment of the invention there is provided a compound of Formula (I):

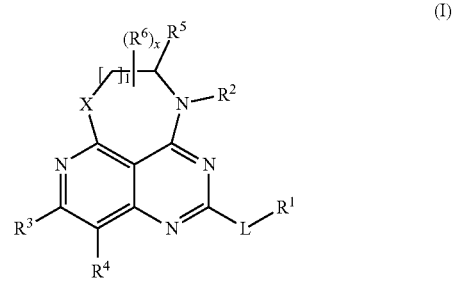

(I)

or a pharmaceutically acceptable salt thereof, wherein:

$R^1$ is $C_3$-$C_{10}$ cycloalkyl or 4-12 membered heterocycloalkyl comprising one, two or three heteroatoms selected from the group consisting of N, O, and S, each $C_3$-$C_{10}$ cycloalkyl or 4-12 membered heterocycloalkyl may optionally be substituted with one, two or three substituents independently selected from the group consisting of —OH, —CN, halogen, $C_1$-$C_3$ alkylidenyl, $C_1$-$C_3$ haloalkylidenyl, $C_1$-$C_3$ alkyl wherein when present two of the $C_1$-$C_3$ alkyl together with the carbon from which they attach may form a spirocyclic ring, $C_1$-$C_3$ alkoxy, —OC(O)NH$_2$, —OC(O)NHCH$_3$, —OC(O)N(CH$_3$)$_2$, wherein the $C_1$-$C_3$ alkyl, $C_1$-$C_3$ alkoxy, $C_1$-$C_3$ haloalkylidenyl or $C_1$-$C_3$ alkylidenyl, is each optionally further substituted with one, two or three $R^{11}$ substituents;

$R^2$ is H or is selected from the group consisting of —($C_1$-$C_6$ alkylene)-OH, —($C_1$-$C_6$ alkylene)-CN, —($C_1$-$C_6$ alkylene)-SH, —($C_1$-$C_3$ alkylene)-S—($C_1$-$C_3$ alkyl), —($C_1$-$C_3$ alkylene)-(S═O)—($C_1$-$C_3$ alkyl), —($C_1$-$C_3$ alkylene)-(SO$_2$)—($C_1$-$C_3$ alkyl), $C_1$-$C_6$ alkyl, $C_3$-$C_6$ cycloalkyl, $C_1$-$C_6$ fluoroalkyl, $C_3$-$C_6$ fluorocycloalkyl, and $C_1$-$C_6$ alkoxy, each optionally substituted with one, two or three substituents independently selected from the group consisting of —OH, —CN, —NH$_2$, —NH($C_1$-$C_3$ alkyl), —N($C_1$-$C_3$ alkyl)$_2$, —SH, —(C$_1$-C$_4$ alkylene)-CN, —(C$_1$-C$_4$ alkylene)-OH, halogen, C$_1$-C$_3$ alkyl, C$_3$-C$_6$ cycloalkyl, C$_1$-C$_3$ fluoroalkyl, and C$_1$-C$_3$ alkoxy;

R$^3$ is:

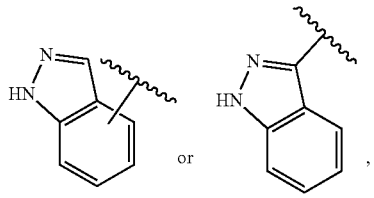

wherein R$^3$ is optionally substituted with one, two or three R$^{10}$;

R$^4$ is H, halogen, —CN, C$_1$-C$_3$ alkyl, C$_1$-C$_3$ alkoxy, or C$_1$-C$_3$ fluoroalkyl;

R$^5$ is H, —OH, halogen, —NH$_2$, CN, or selected from the group consisting of —(C$_1$-C$_6$ alkylene)-OH, —(C$_1$-C$_6$ alkylene)-CN, —(C$_1$-C$_6$ alkylene)-SH, —(C$_1$-C$_3$ alkylene)-S—(C$_1$-C$_3$ alkyl), —(C$_1$-C$_3$ alkylene)-(S=O)—(C$_1$-C$_3$ alkyl), —(C$_1$-C$_3$ alkylene)-(SO$_2$)—(C$_1$-C$_3$ alkyl), C$_1$-C$_6$ alkyl, C$_3$-C$_6$ cycloalkyl, C$_1$-C$_6$ fluoroalkyl, C$_3$-C$_6$ fluorocycloalkyl, and C$_1$-C$_3$ alkoxy each is optionally substituted with one, two or three substituents independently selected from the group consisting of —OH, —CN, —NH$_2$, —SH, —(C$_1$-C$_4$ alkylene)-CN, halogen, C$_1$-C$_3$ alkyl, C$_3$-C$_6$ cycloalkyl, C$_1$-C$_3$ fluoroalkyl, and C$_1$-C$_3$ alkoxy; or alternatively, R$^5$ and the carbon that R$^5$ is attached to, and R$^2$ and the nitrogen that R$^2$ is attached to together to form a 4-8 membered heterocycloalkyl comprising one, two or three heteroatoms selected from the group consisting of N, O, and S, or heteroatom-containing groups selected from the group consisting of N(C$_1$-C$_6$ alkyl), —(S=O)—, and —(SO$_2$)—, wherein said 4-8 membered heterocycloalkyl is optionally substituted with one, two or three substituent groups selected from the group consisting of —OH, —OCH$_3$, —CN, halogen, C$_1$-C$_3$ alkyl, —(C$_1$-C$_6$ alkylene)-CN, and —(C$_1$-C$_6$ alkylene)-OH;

R$^6$ at each occurrence is independently H, —OH, halogen, CN, or selected from the group consisting of —(C$_1$-C$_6$ alkylene)-OH, —(C$_1$-C$_6$ alkylene)-CN, C$_1$-C$_6$ alkyl, C$_3$-C$_6$ cycloalkyl, C$_1$-C$_6$ fluoroalkyl, C$_3$-C$_6$ fluorocycloalkyl, and C$_1$-C$_6$ alkoxy, each optionally substituted with one, two or three substituents independently selected from the group consisting of —OH, —CN, —(C$_1$-C$_4$ alkylene)-CN, halogen, C$_1$-C$_3$ alkyl, C$_3$-C$_6$ cycloalkyl, C$_1$-C$_3$ fluoroalkyl, and C$_1$-C$_3$ alkoxy;

L is L1-L2-L3 wherein each of L1, L2 and L3 independently selected from the group consisting of a bond, —O(CH$_2$)$_n$— wherein n or 0 or 1, —S—, —NR$^7$—, and —CR$^8$R$^9$—, provided that at least one of L1, L2 and L3 is not a bond;

R$^7$, R$^8$, and R$^9$ are each independently H or C$_1$-C$_3$ alkyl;

R$^{10}$ are each independently selected from the group consisting of —NH$_2$, halogen, —CN, C$_1$-C$_3$ alkyl, C$_1$-C$_3$ fluoroalkyl, C$_1$-C$_3$ alkoxy, C$_2$-C$_3$ alkynyl, C$_3$-C$_5$ cycloalkyl, and 4-6 membered heterocycloalkyl comprising one or two heteroatoms selected from the group consisting of N, O, and S, wherein the C$_1$-C$_3$ alkyl, C$_3$-C$_5$ cycloalkyl or 4-6 membered heterocycloalkyl is further optionally substituted with one or two substituents independently selected from the group consisting of —OH, C$_1$-C$_3$ alkoxy, —C$_1$-C$_3$ alkyl and halogen, or alternatively two R$^{10}$ may together with the C atoms to which they are attached, form a C$_3$-C$_6$ cycloalkyl ring further optionally substituted with one, two or three R$^{12}$;

R$^{11}$ are each independently selected from the group consisting of H, —CN, —OH, methyl, —OCH$_3$, C$_1$-C$_3$alkoxy, -cyclopropyl, -oxetane, —C(O)NR$^7$R$^8$, —SO$_2$R$^9$ and halogen, or alternately two of the R$^{11}$ together with the carbon they are attached form a C$_3$-C$_6$ cycloalkyl ring or a 3-6 membered heterocycloalkyl ring;

R$^{12}$ are each independently selected from the group consisting of —OH, C$_1$-C$_3$ alkoxy, —C$_1$-C$_3$ alkyl and halogen;

X is O, N, or S;

l is 1 or 2; and x is 1 or 2.

Described below are embodiments of the invention, where for convenience Embodiment 1 (E1) is identical to the embodiment of Formula (I) provided above.

It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of the embodiments of the invention and the Examples included herein. It is to be understood that this invention is not limited to specific synthetic methods of making that may of course vary. It is to be also understood that the terminology used herein is for the purpose of describing specific embodiments only and is not intended to be limiting.

E1 A compound of Formula (I) or a pharmaceutically acceptable salt thereof, as defined above.

E2 A compound of embodiment E1, or a pharmaceutically acceptable salt thereof, wherein the linker L is —(O—CH$_2$)—.

E3 A compound of embodiment E1 or embodiment E2, or a pharmaceutically acceptable salt thereof, wherein R$^1$ is a 5-10 membered heterocycloalkyl comprising one or two heteroatoms selected from the group consisting of N and O, and said 5-10 membered heterocycloalkyl is optionally substituted with one, two or three substituents independently selected from the group consisting of —OH, —CN, halogen, C$_1$-C$_3$ alkylidenyl, C$_1$-C$_3$ haloalkylidenyl, C$_1$-C$_3$ alkyl wherein when present two of the C$_1$-C$_3$alkyl together with the carbon from which they attach may form a spirocyclic ring, C$_1$-C$_3$ alkoxy, —OC(O)NH$_2$, —OC(O)NHCH$_3$, —OC(O)N(CH$_3$)$_2$, wherein the C$_1$-C$_3$ alkyl, C$_1$-C$_3$ alkoxy, C$_1$-C$_3$ haloalkylidenyl or C$_1$-C$_3$ alkylidenyl, is each optionally further substituted with one, two or three R$^{11}$ substituents.

E3a A compound of embodiment E1 or embodiment E2, or a pharmaceutically acceptable salt thereof, wherein L-R$^1$ is:

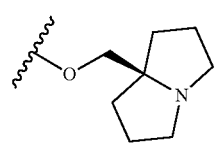

optionally substituted with one, two or three substituents independently selected from the group consisting of —OH, —CN, halogen, $C_1$-$C_3$ alkylidenyl, $C_1$-$C_3$ haloalkylidenyl, $C_1$-$C_3$ alkyl wherein when present two of the $C_1$-$C_3$ alkyl together with the carbon from which they attach may form a spirocyclic ring, $C_1$-$C_3$ alkoxy, —OC(O)NH$_2$, —OC(O)NHCH$_3$, —OC(O)N(CH$_3$)$_2$, wherein the $C_1$-$C_3$ alkyl, $C_1$-$C_3$ alkoxy, $C_1$-$C_3$ haloalkylidenyl or $C_1$-$C_3$ alkylidenyl, is each optionally further substituted with one, two or three $R^{11}$ substituents.

E3b A compound of embodiment E1 or embodiment E2, or a pharmaceutically acceptable salt thereof, wherein L-$R^1$ is:

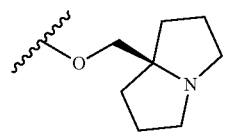

optionally substituted with one, two or three halogen.

E3c A compound of embodiment E1 or embodiment E2, or a pharmaceutically acceptable salt thereof, wherein L-$R^1$ is:

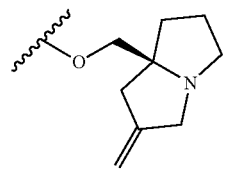 [SMILES: *OC[C@@]12CCCN1CC(=C)C2]

optionally substituted with one or two substituents independently selected from the group consisting of —OH, —CN, halogen, $C_1$-$C_3$ alkyl, wherein the alkylidenyl is optionally further substituted with one or two $R^{11}$ substituents.

E3d A compound of embodiment E1 or embodiment E2, or a pharmaceutically acceptable salt thereof, wherein L-$R^1$ is:

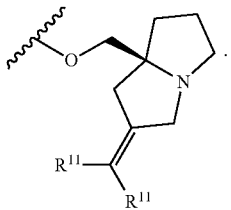

optionally substituted with one or two substituents independently selected from the group consisting of —OH, —CN, halogen, $C_1$-$C_3$ alkyl; and $R^{11}$ are each independently selected from the group consisting of H, —CN, —OH, methyl, —OCH$_3$, $C_1$-$C_3$alkoxy, -cyclopropyl, -oxetane, —C(O)NR$^7$R$^8$, —SO$_2$R$^9$ and halogen, or alternately the $R^{11}$ together with the carbon they are attached form a $C_3$-$C_6$ cycloalkyl ring or a 3-6 membered heterocycloalkyl ring.

E3e A compound of embodiment E3d, or a pharmaceutically acceptable salt thereof, wherein L-$R^1$ is:

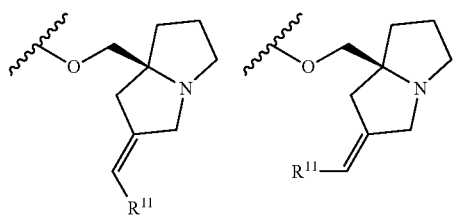

optionally substituted with one or two substituents independently selected from the group consisting of —OH, —CN, halogen, $C_1$-$C_3$ alkyl.

E4 A compound of embodiment E3, or a pharmaceutically acceptable salt thereof, wherein L-$R^1$ is selected from the group consisting of:

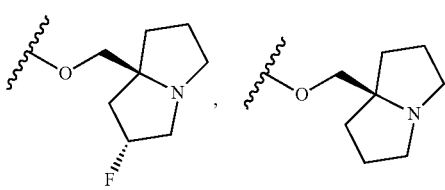

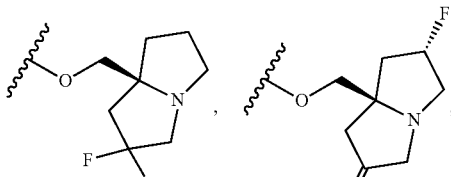

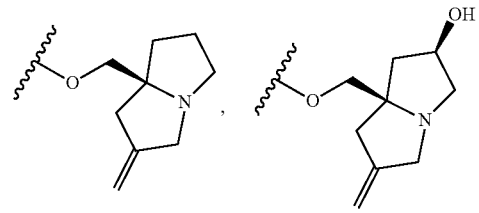

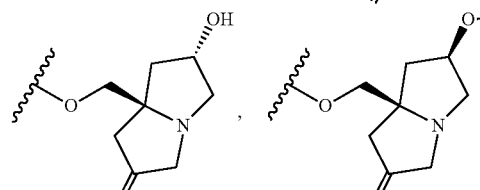

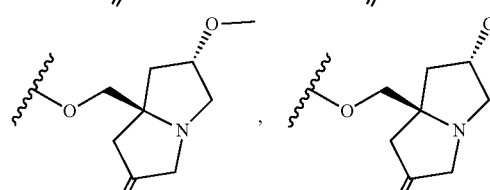

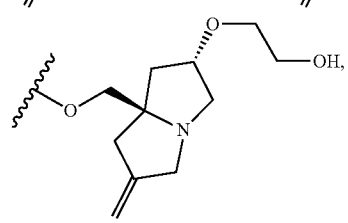

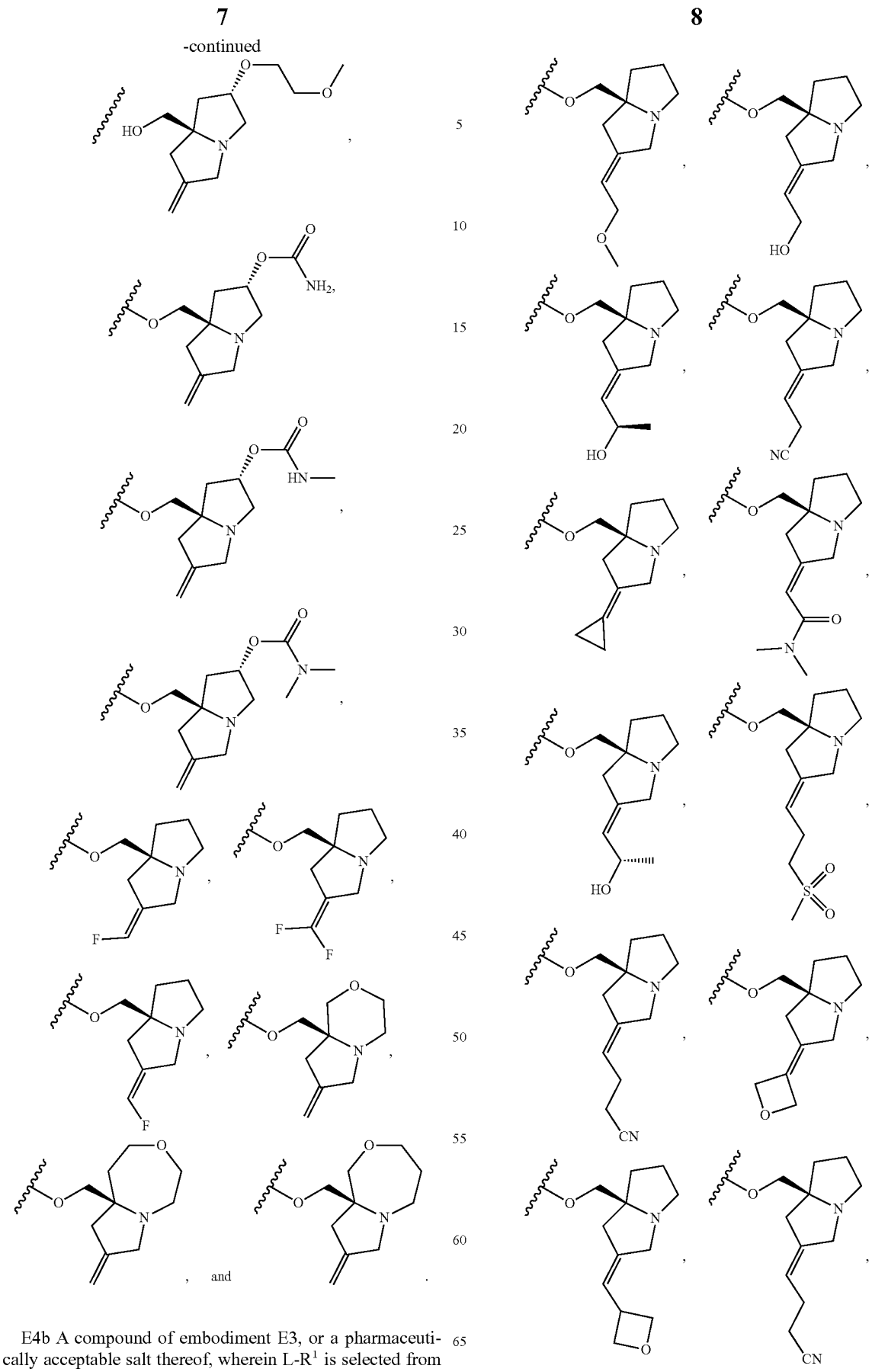
E4b A compound of embodiment E3, or a pharmaceutically acceptable salt thereof, wherein L-R¹ is selected from the group consisting of:

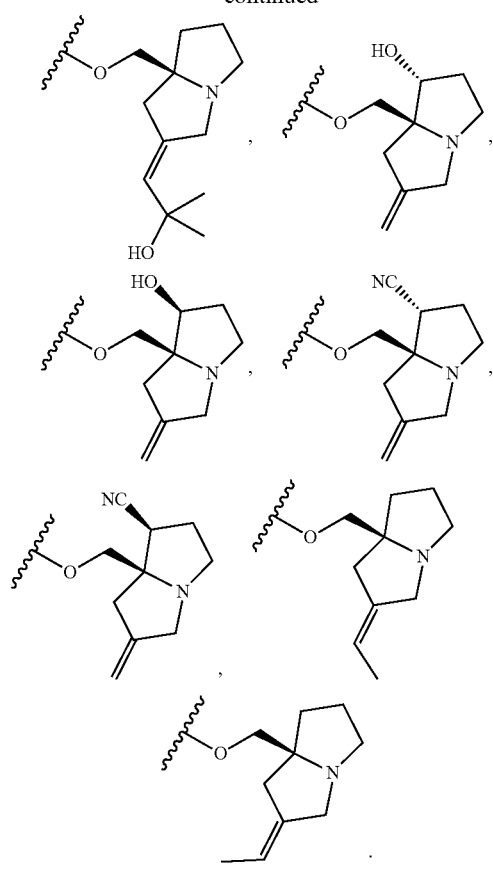

E5 A compound of embodiment E3, or a pharmaceutically acceptable salt thereof, wherein L-R$^1$ is selected from the group consisting of:

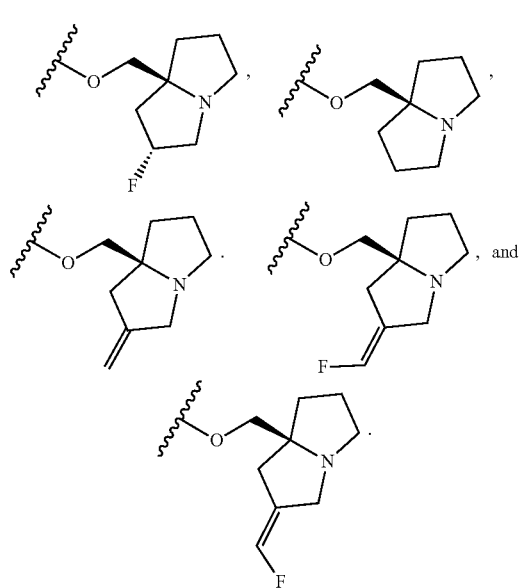

E6 A compound of embodiment E3, or a pharmaceutically acceptable salt thereof, wherein L-R$^1$ is selected from the group consisting of:

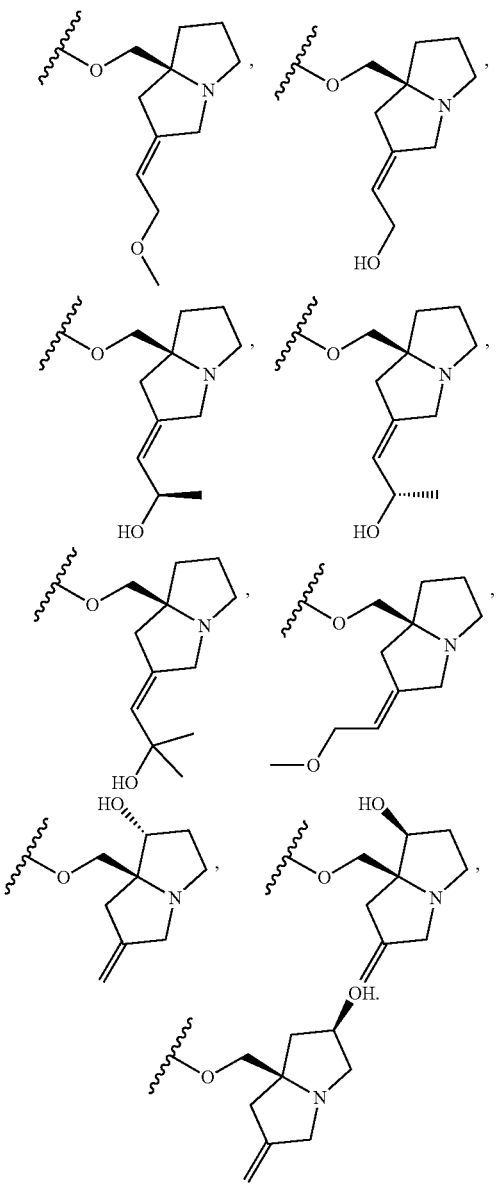

E7 A compound of any one of embodiments E1 to E6, or a pharmaceutically acceptable salt thereof, wherein R$^2$ is H or is selected from the group consisting of —(C$_1$-C$_5$ alkylene)-OH and C$_1$-C$_5$ alkyl, each optionally substituted with one, two or three substituents independently selected from the group consisting of —OH, —CN, and halogen.

E8 A compound of any one of embodiments E1 to E7, or a pharmaceutically acceptable salt thereof, wherein R$^3$ is:

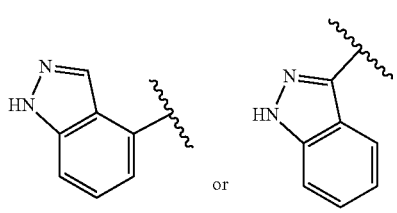 [SMILES: *c1cccc2[nH]ncc12 ; *c1n[nH]c2ccccc12]

optionally substituted with one, two or three R$^{10}$.

E9 A compound of any one of embodiments E1 to E8, or a pharmaceutically acceptable salt thereof, wherein R³:

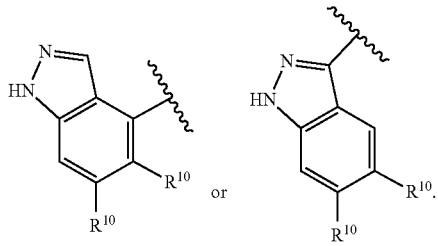

E9a A compound of any one of embodiments E1 to E8, or a pharmaceutically acceptable salt thereof, wherein R³:

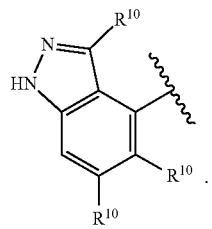

E9b A compound of any one of embodiments E1 to E8 or E9a, or a pharmaceutically acceptable salt thereof, wherein R³:

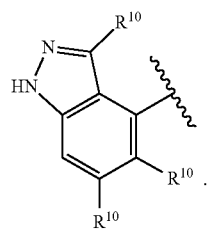

wherein R¹⁰ are each independently selected from the group consisting of —NH₂, halogen, —CN, C₁-C₃ alkyl, C₁-C₃ fluoroalkyl, C₁-C₃ alkoxy, C₂-C₃ alkynyl, C₃-C₅ cycloalkyl, and 4-6 membered heterocycloalkyl comprising one or two heteroatoms selected from the group consisting of N, O, and S, wherein the C₁-C₃ alkyl, C₃-C₅ cycloalkyl or 4-6 membered heterocycloalkyl is further optionally substituted with one or two substituents independently selected from the group consisting of —OH, C₁-C₃ alkoxy, —C₁-C₃ alkyl and halogen.

E10 A compound of any one of embodiments E1 to E9, or a pharmaceutically acceptable salt thereof, wherein R³ is:

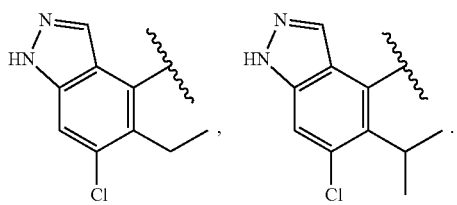

-continued

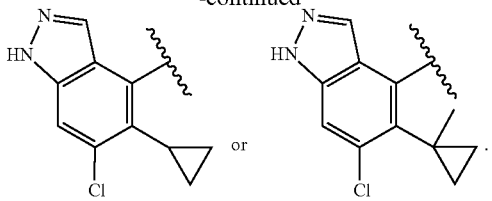

E10a A compound of anyone of embodiments of E9a to E9b, or a pharmaceutically salt thereof, wherein R³ is:

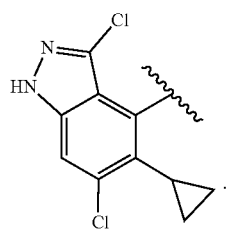 [SMILES: *c1c(C2CC2)c(Cl)cc2[nH]nc(Cl)c12]

E11 A compound of any one of embodiments E1 to E9a, or a pharmaceutically acceptable salt thereof, wherein R³ is:

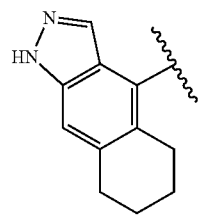 [SMILES: *c1c2c(cc3[nH]ncc13)CCCC2]

further optionally substituted with one R¹⁰ or one, two or three R¹².

E11a A compound of embodiment E11, or a pharmaceutically acceptable salt thereof, wherein R³ is:

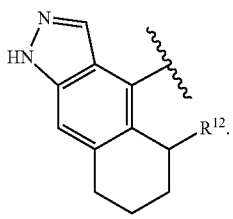

E11b A compound of embodiment E11, or a pharmaceutically acceptable salt thereof, wherein R³ is

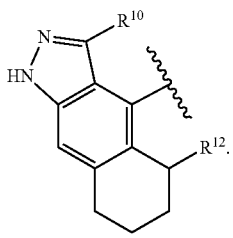

E11c A compound of embodiment E11, or a pharmaceutically acceptable salt thereof, wherein $R^3$ is:

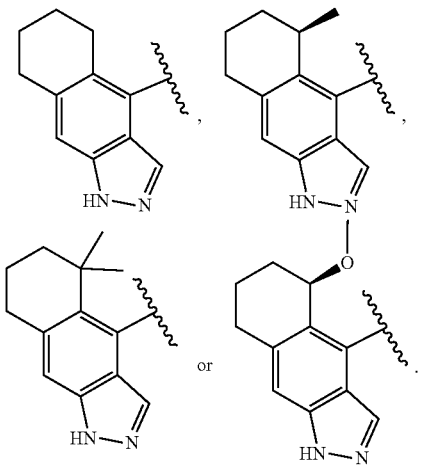

E11d A compound of embodiment E11, or a pharmaceutically acceptable salt thereof, wherein $R^3$ is:

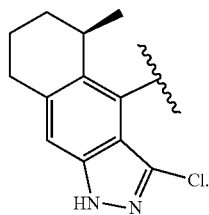 [SMILES: *c1c2c(cc3[nH]nc(Cl)c13)CCC[C@H]2C]

E11e A compound of embodiment E11 or E11b, or a pharmaceutically acceptable salt thereof, wherein $R^3$ is

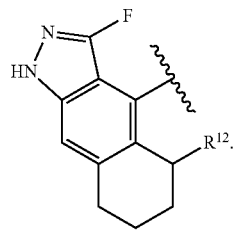

E11f A compound of embodiment E11 or E11b, or a pharmaceutically acceptable salt thereof, wherein $R^3$ is:

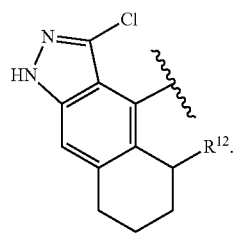

E11g A compound of embodiment E11 or E11b, or a pharmaceutically acceptable salt thereof, wherein $R^3$ is

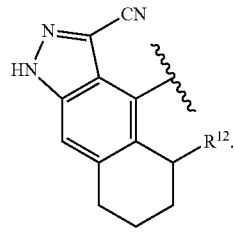

E11h A compound of embodiment E11 or E11b, or a pharmaceutically acceptable salt thereof, wherein $R^3$ is:

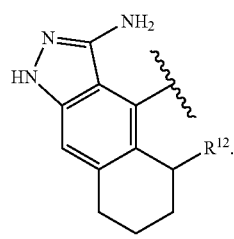

E12 A compound of any one of embodiments E1 to E11h, or a pharmaceutically acceptable salt thereof, wherein $R^4$ is Cl or F.

E13 A compound of any one of embodiments E1 to E12, or a pharmaceutically acceptable salt thereof, wherein $R^5$ and $R^6$ at each occurrence are each independently selected from the group consisting of H, —OH, —CN, and halogen, or $R^5$ and $R^6$ at each occurrence is independently selected from the group consisting of —($C_1$-$C_5$ alkylene)-OH and $C_1$-$C_5$ alkyl, each —($C_1$-$C_5$ alkylene)-OH and $C_1$-$C_5$ alkyl is optionally substituted with one, two or three substituents independently selected from the group consisting of —OH, —CN, and halogen.

E14 A compound of any one of embodiments E1 to E13, or a pharmaceutically acceptable salt thereof, wherein the compound has Formula (II):

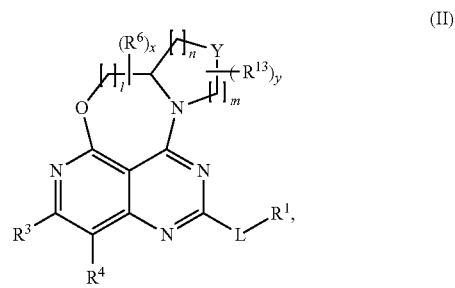

(II)

wherein Y is selected from the group consisting of $CH_2$, O, N($C_1$-$C_6$ alkyl), S, (S=O), and ($SO_2$), $R^{13}$ at each occurrence is independently selected from the group consisting of —OH, —CN, halogen, $C_1$-$C_3$ alkyl, —($C_1$-$C_6$ alkylene)-CN, and —($C_1$-$C_6$ alkylene)-OH; and m and n are each independently 0, 1, 2 or 3, y is 1, 2, or 3, and m plus n is 1, 2, 3, 4, or 5.

E15 A compound of embodiment E14, or a pharmaceutically acceptable salt thereof, wherein Y is —$CH_2$— or O.

E16 A compound of embodiment E15, or a pharmaceutically acceptable salt thereof, wherein Y is O.

E17 A compound of any one of embodiments E1 to E8 or E14 to E16, or a pharmaceutically acceptable salt thereof, wherein R³ is selected from the group consisting of:

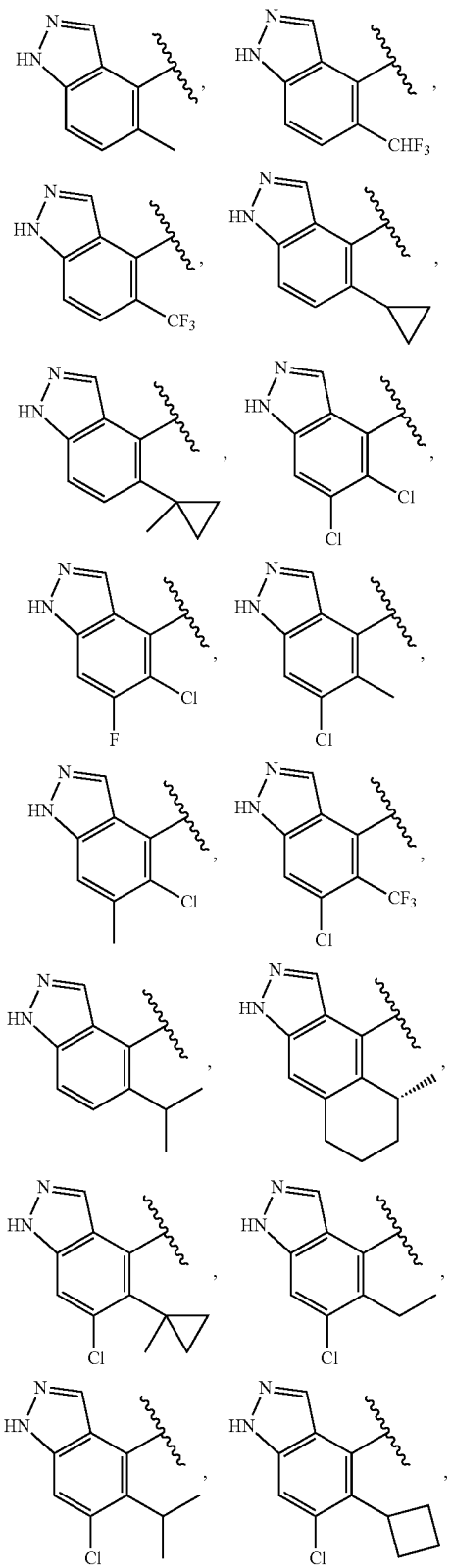

-continued

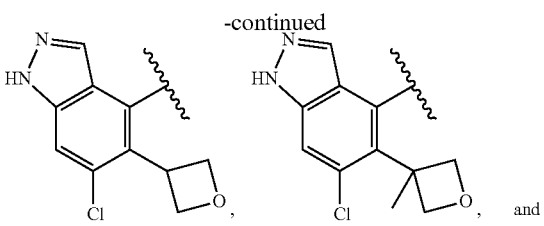

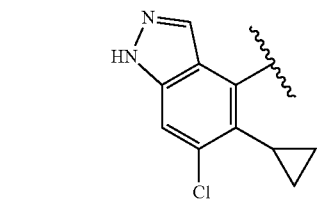

E17a A compound of any one of embodiments E1 to E8 or E14 to E16, or a pharmaceutically acceptable salt thereof, wherein R³ is selected from the group consisting of:

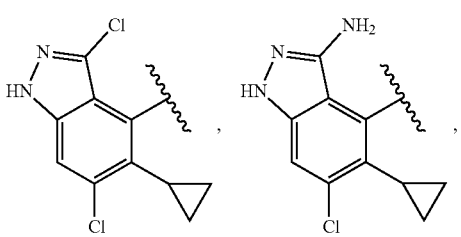

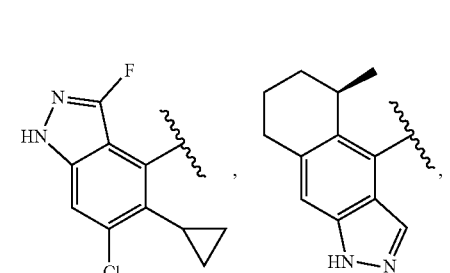

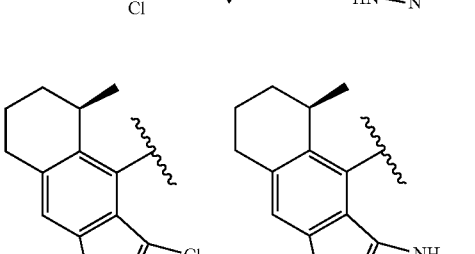

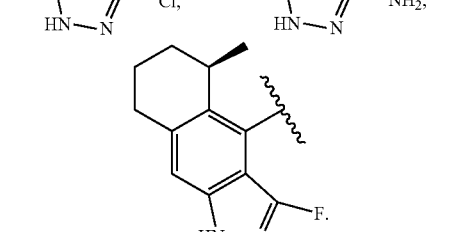

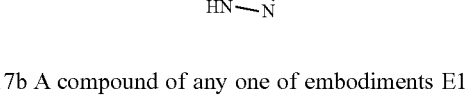

E17b A compound of any one of embodiments E1 to E8 or E14 to E16, or a pharmaceutically acceptable salt thereof, wherein R³ is selected from the group consisting of:

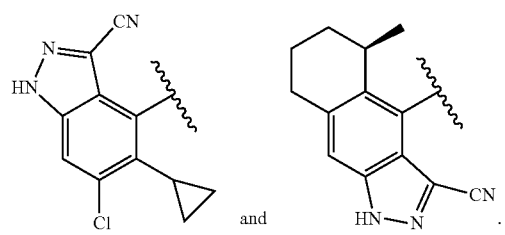 [SMILES: *c1c(C2CC2)c(Cl)cc2[nH]nc(C#N)c12 ; *c1c2c(cc3[nH]nc(C#N)c13)CCC[C@H]2C] and .

E18 A compound of any one of embodiments E1 to E17b, or a pharmaceutically acceptable salt thereof, wherein the compound has Formula (III):

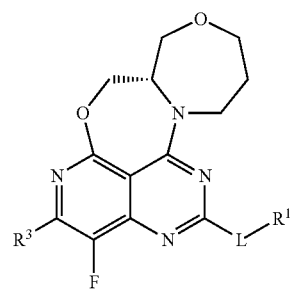

(III)

E18a A compound of anyone of embodiments E1 to E17, or a pharmaceutically acceptable salt thereof, wherein the compound is not:

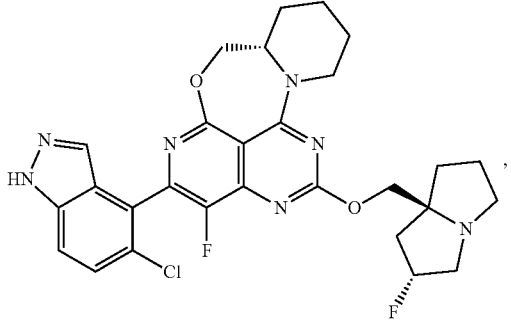

,

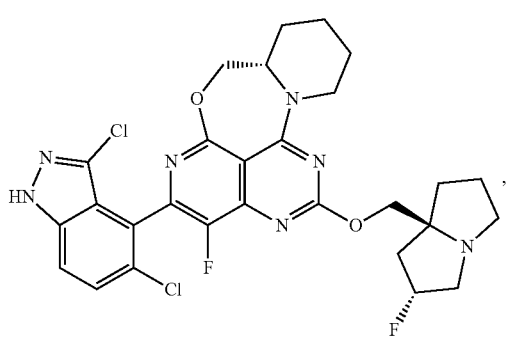

,

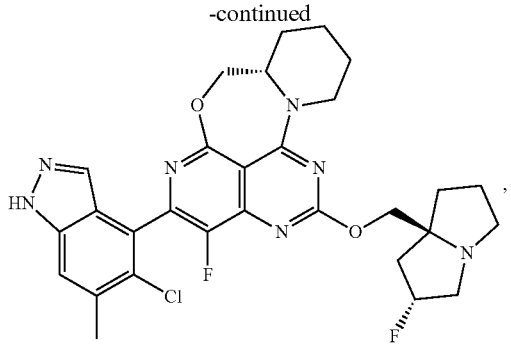

,

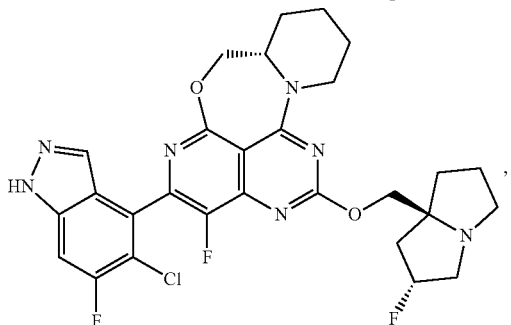

,

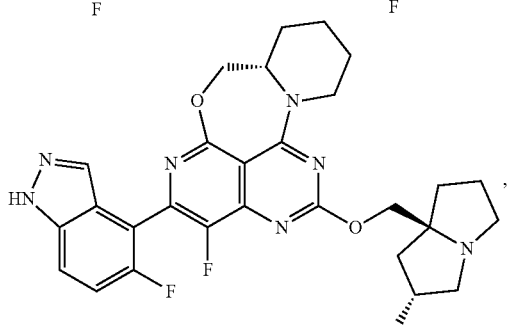

,

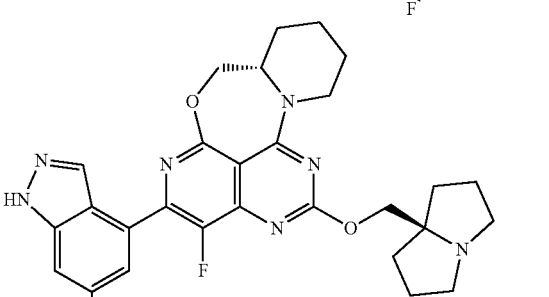

, or

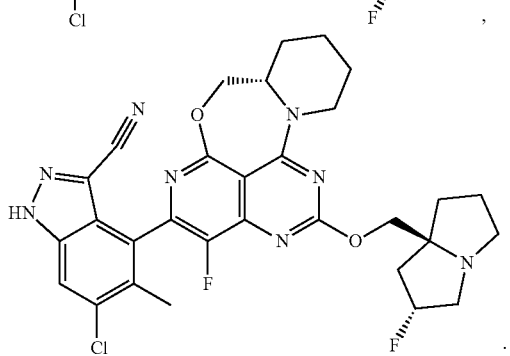

.

E19 A compound of embodiment E1, or a pharmaceutically acceptable salt thereof, wherein the compound is selected from the group consisting of

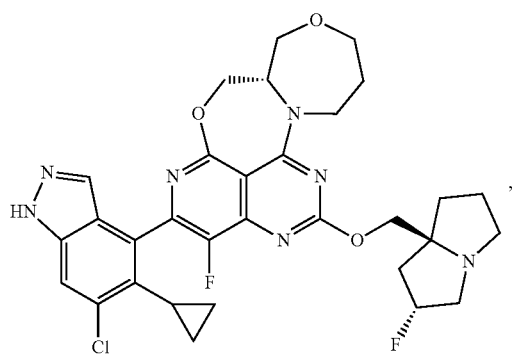
,
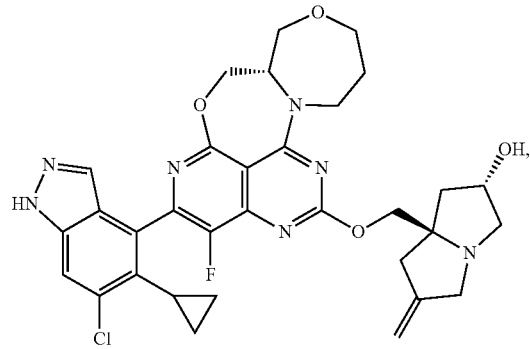
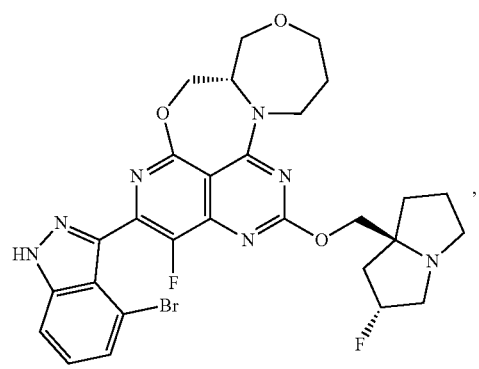
,
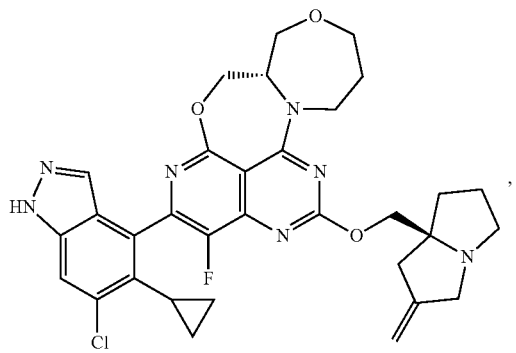 [SMILES: C=C1CN2CCC[C@@]2(COc2nc3c4c(nc(-c5c(C6CC6)c(Cl)cc6[nH]ncc56)c(F)c4n2)OC[C@@H]2COCCCN32)C1]
,
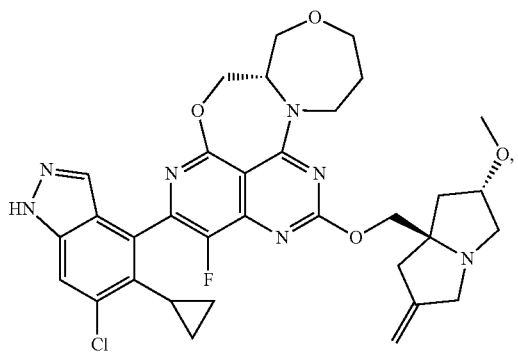
,
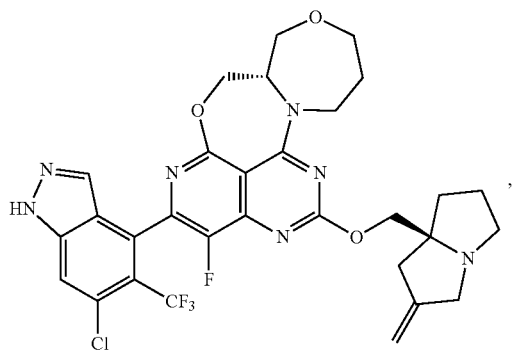
,
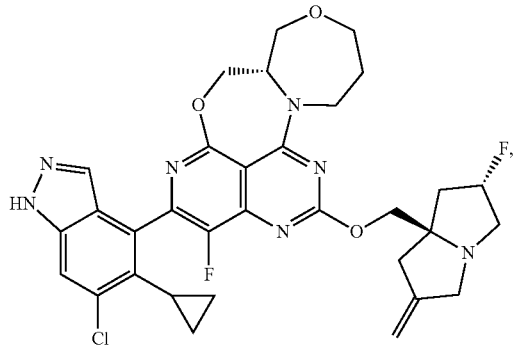
,
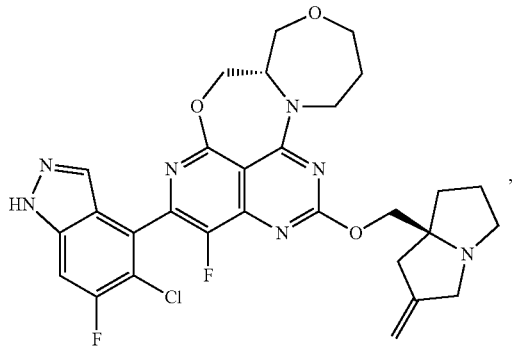
,

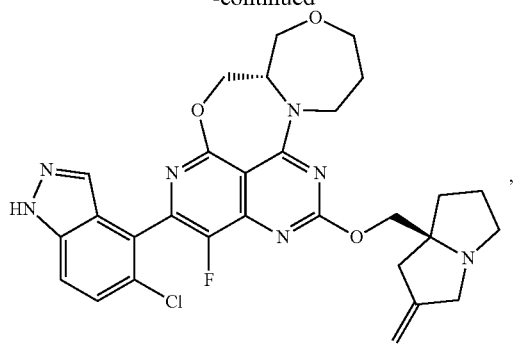
,
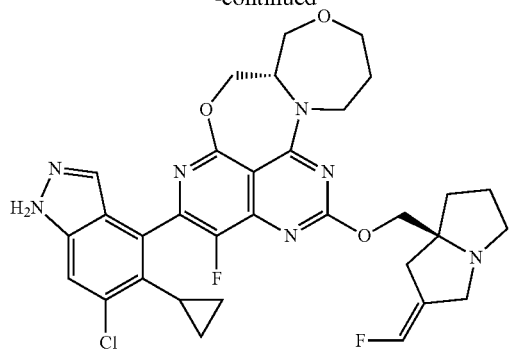
.
E20 A compound of embodiment E1, or a pharmaceutically acceptable salt thereof, wherein the compound is selected from the group consisting of
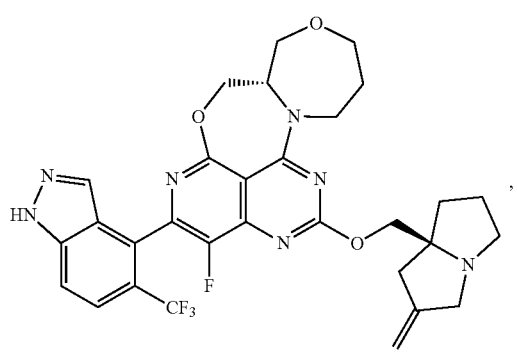
,
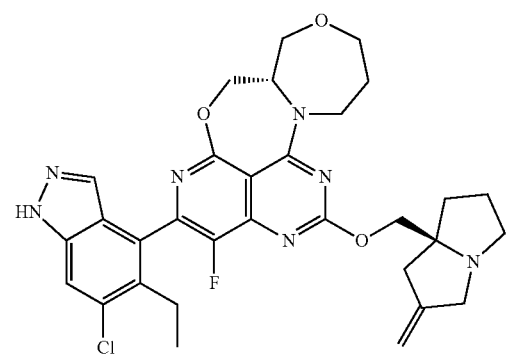
,
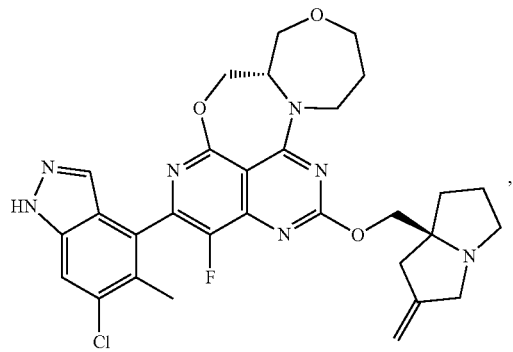 [SMILES: C=C1CN2CCC[C@@]2(COc2nc3c4c(nc(-c5c(C6CC6)c(Cl)cc6[nH]ncc56)c(F)c4n2)OC[C@@H]2COCCCN32)C1]
,
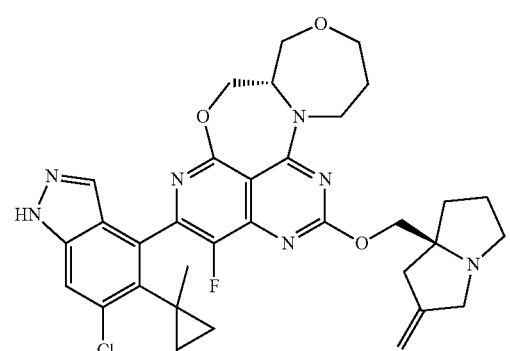
,
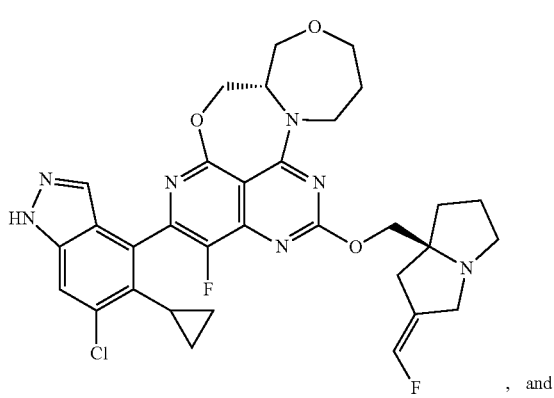
, and
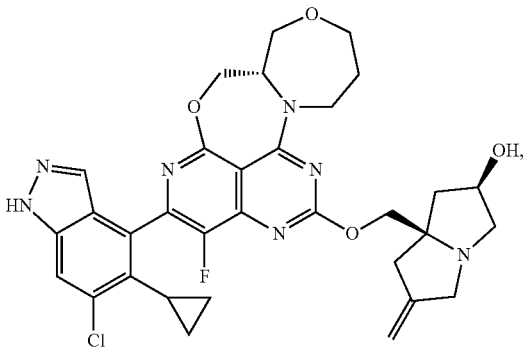
, -continued
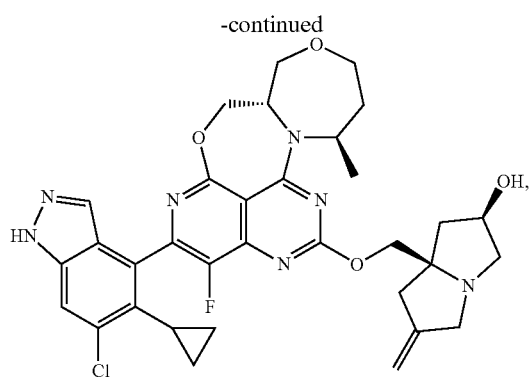
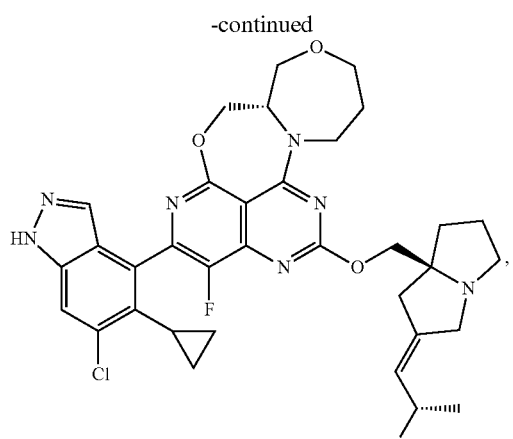
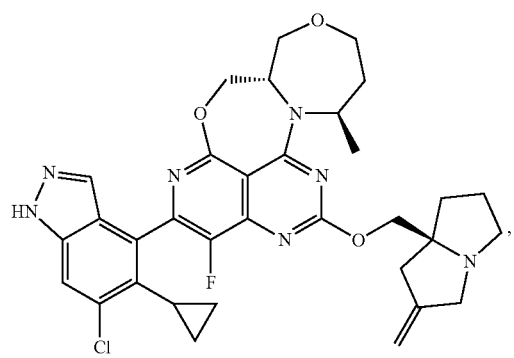
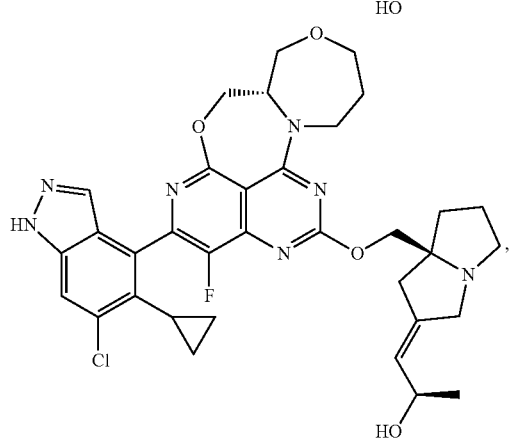
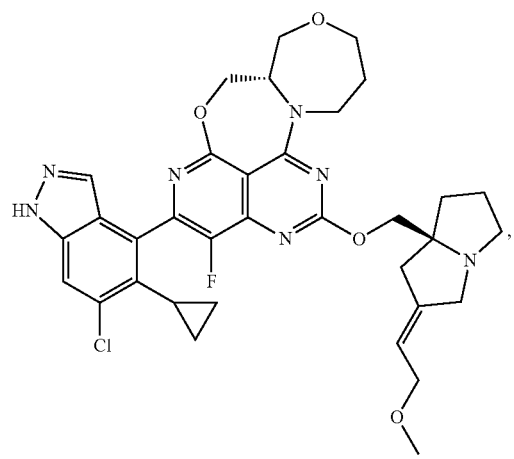
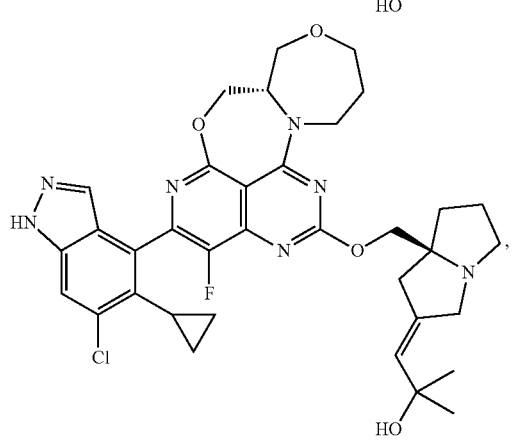
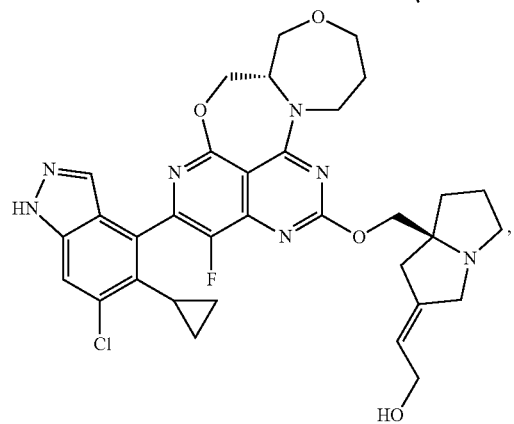
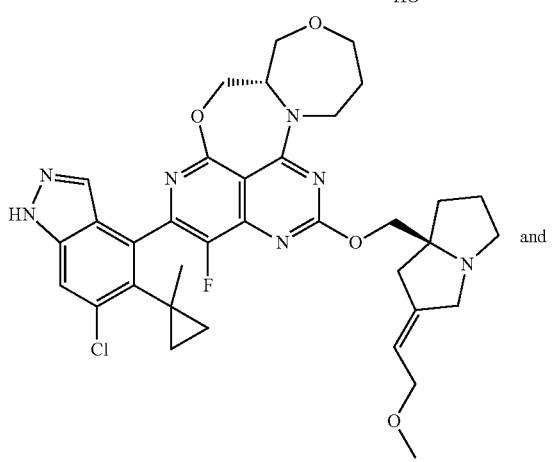
and

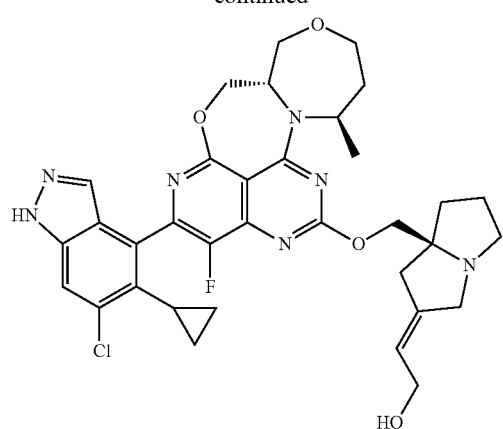
E21 A compound of embodiment E1, or a pharmaceutically acceptable salt thereof, wherein the compound is selected from the group consisting of:
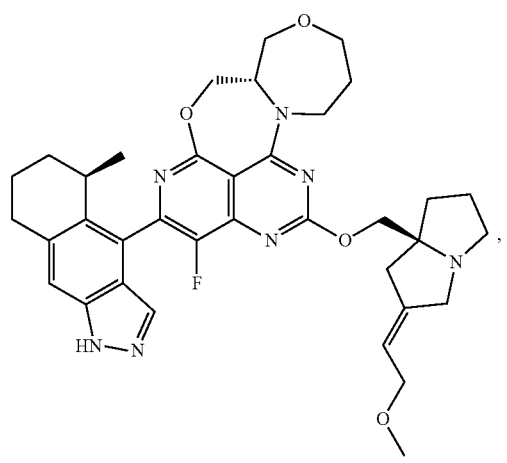
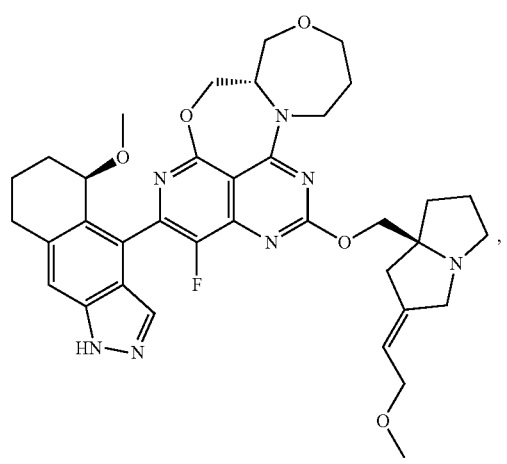
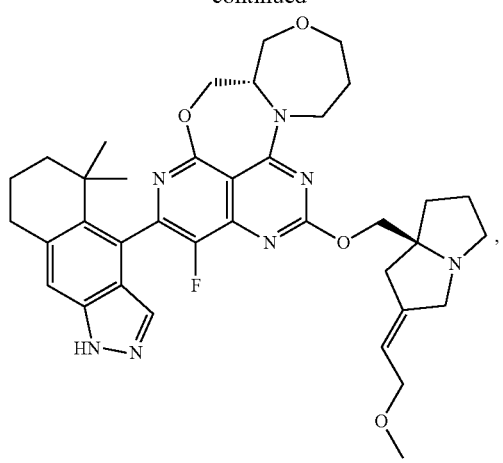
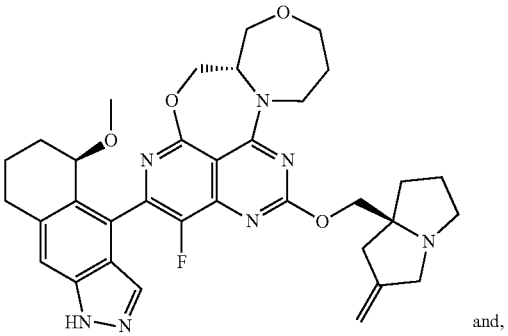
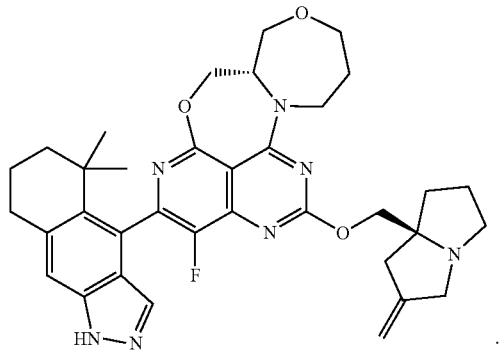
E21a A compound of embodiment E1, or a pharmaceutically acceptable salt thereof, wherein the compound is selected from the group consisting of:
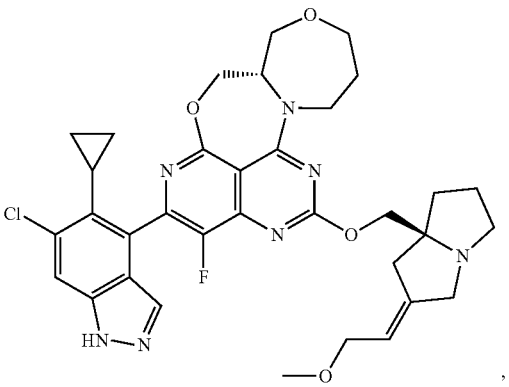

-continued
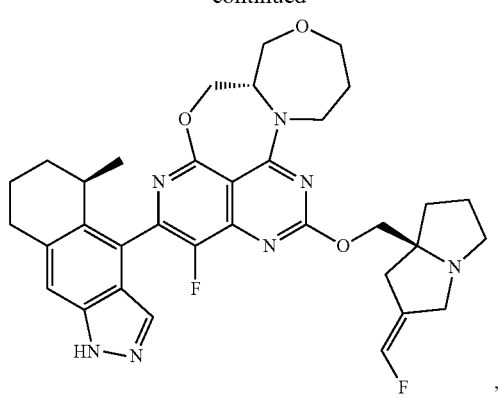
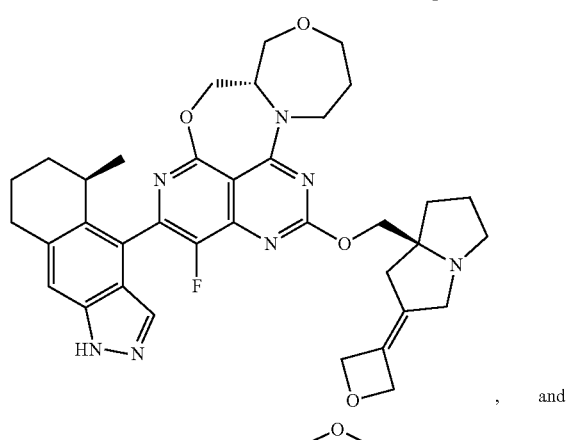
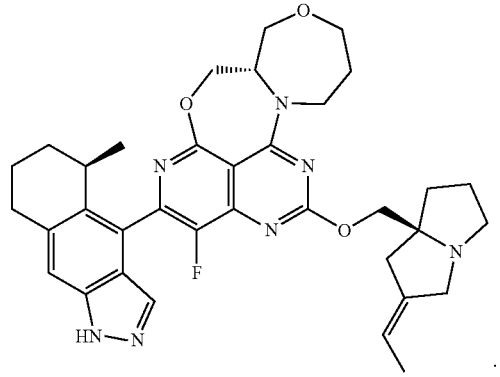
E21 b A compound of embodiment E1, or a pharmaceutically acceptable salt thereof, wherein the compound is selected from the group consisting of
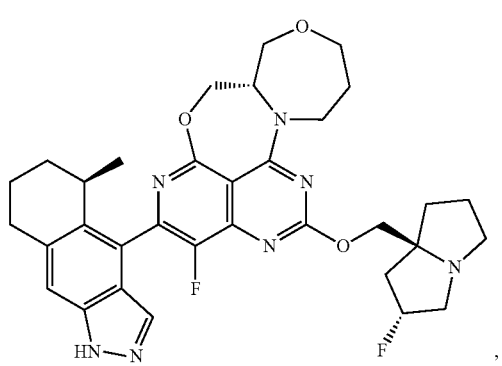
-continued
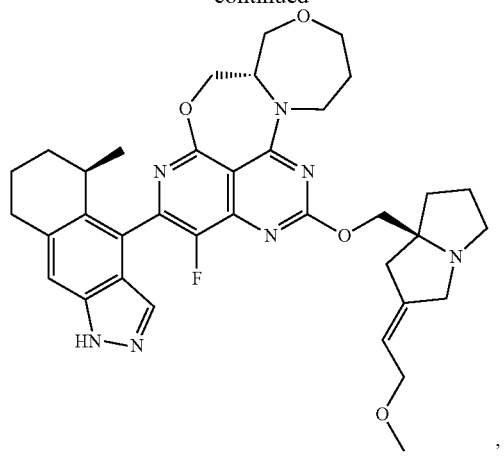
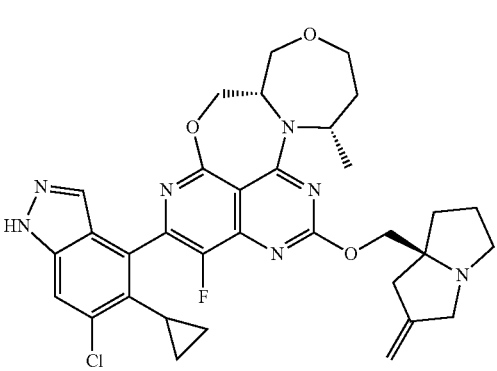
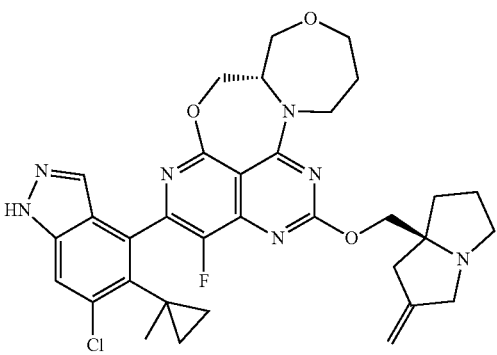
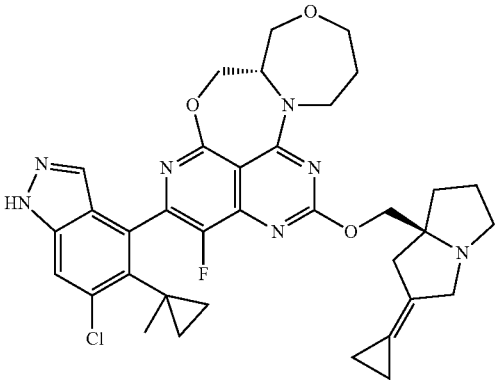

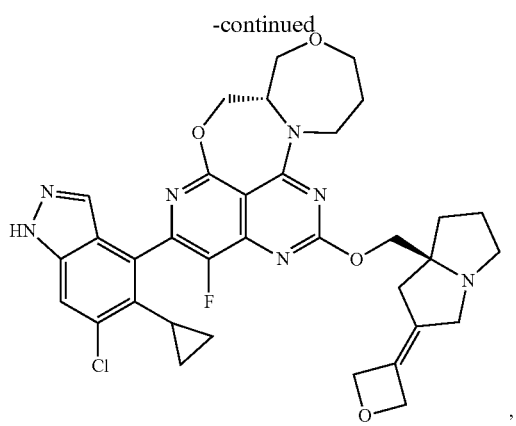
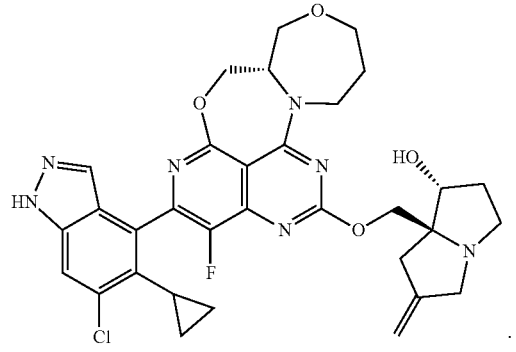
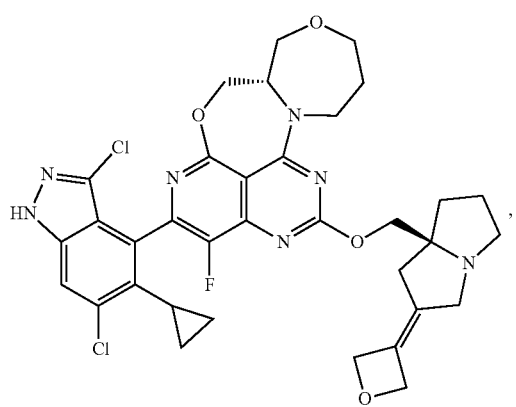
E21 c A compound of embodiment E1, or a pharmaceutically acceptable salt thereof, wherein the compound is selected from the group consisting of:
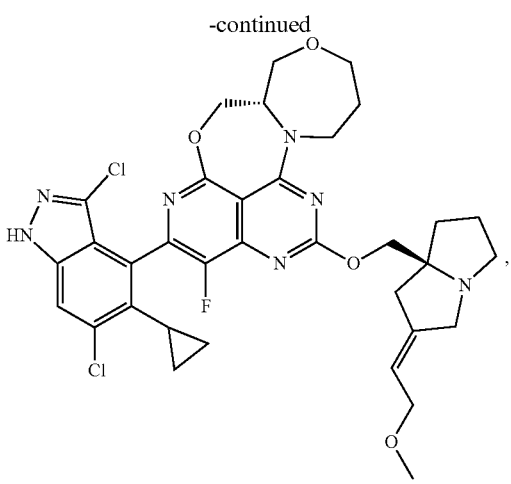
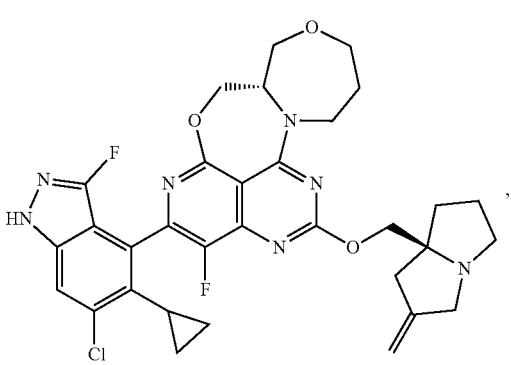
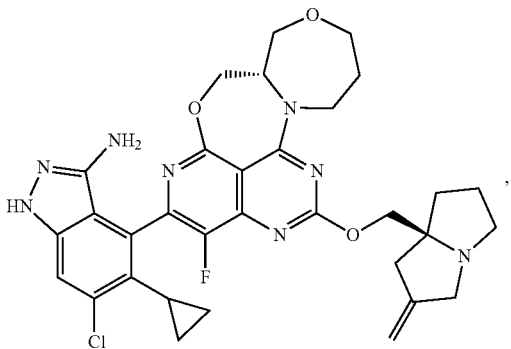

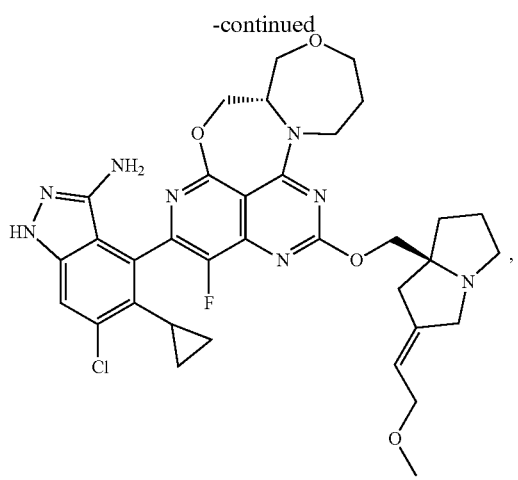
,
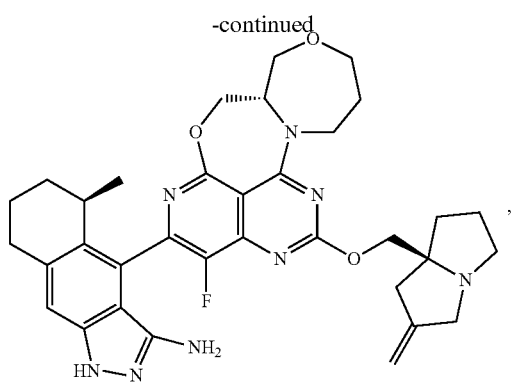
,
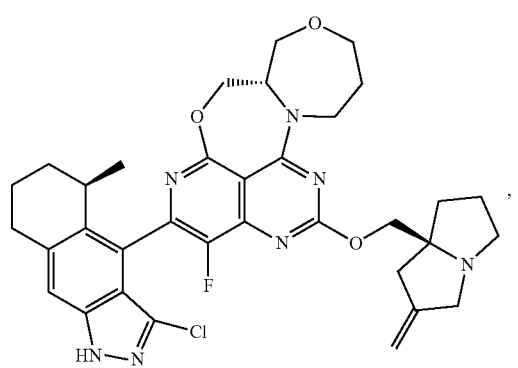
,
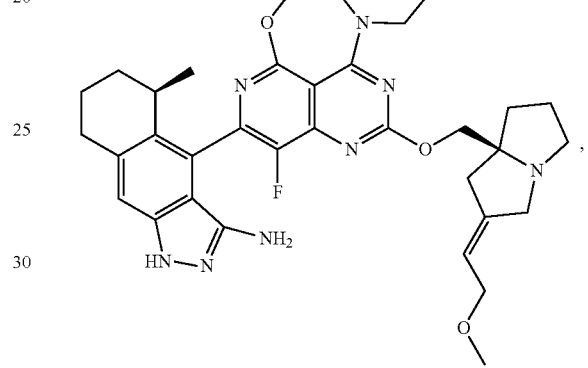
,
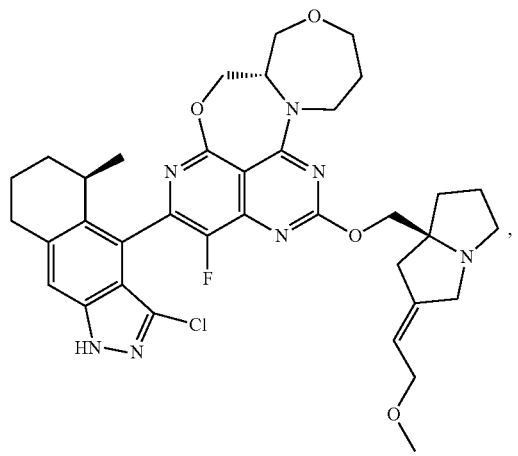
,
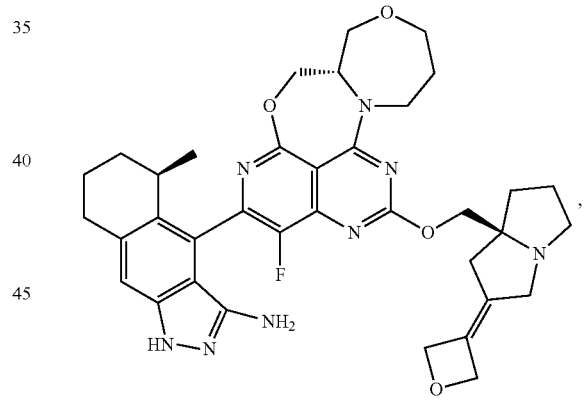
,
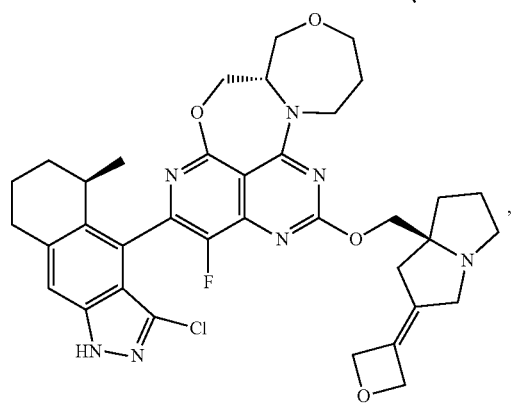
,
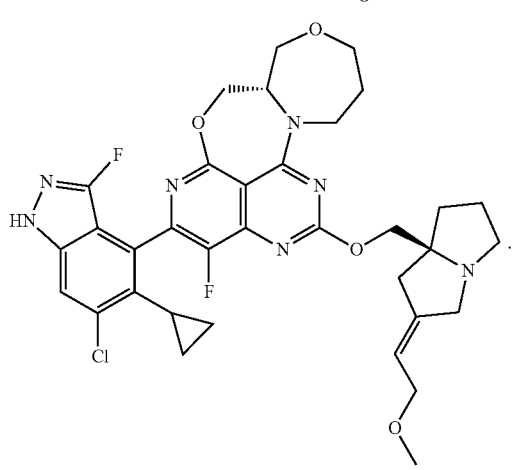

-continued
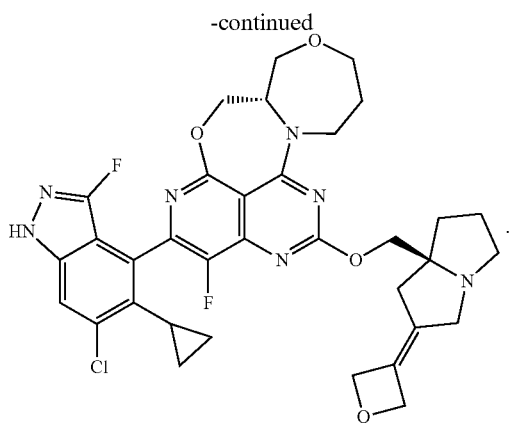
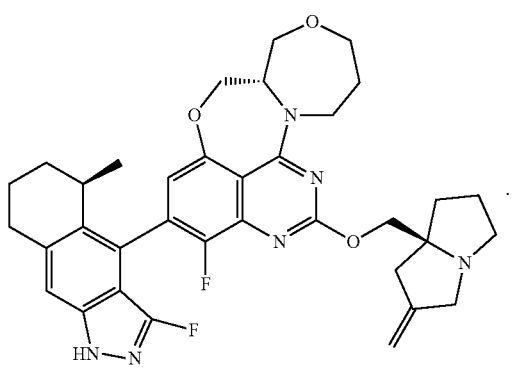
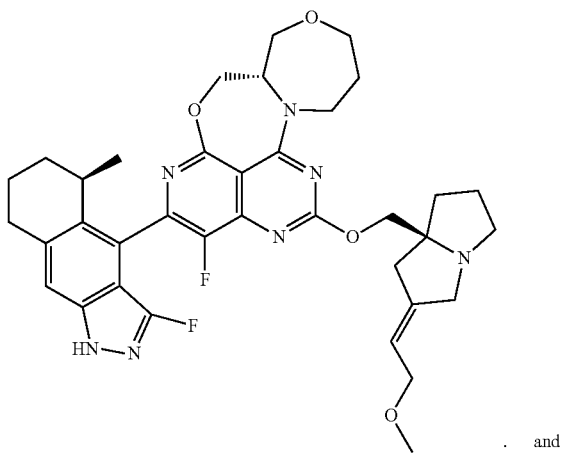
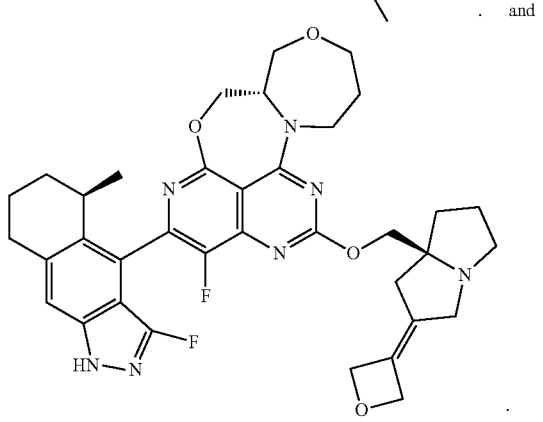
E21 d A compound of embodiment E1, or a pharmaceutically acceptable salt thereof, wherein the compound is selected from the group consisting of:
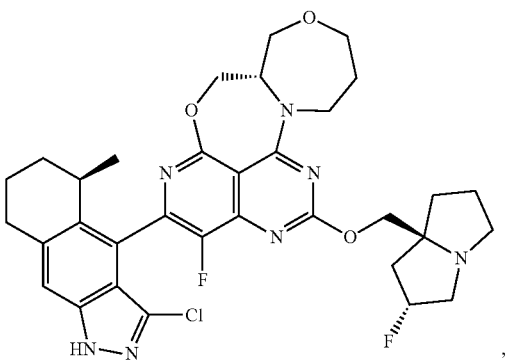
,
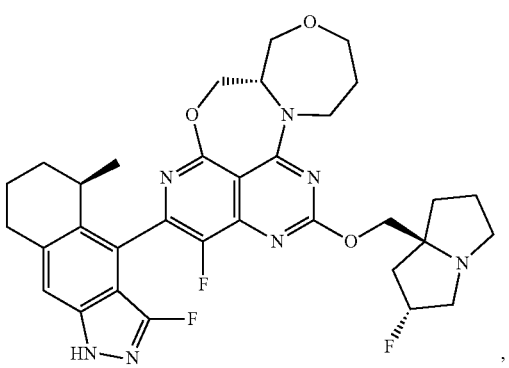
,
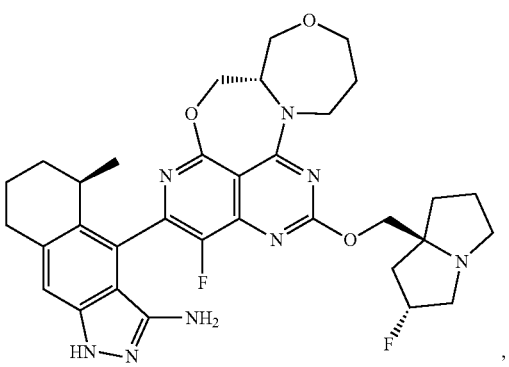
,
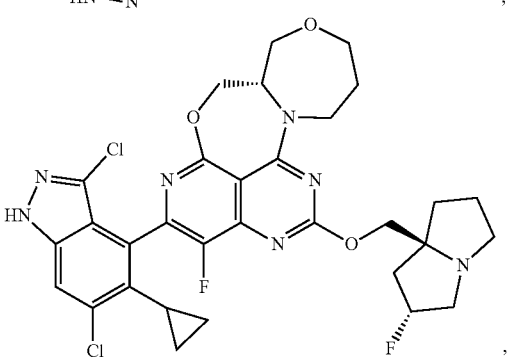
,
and -continued
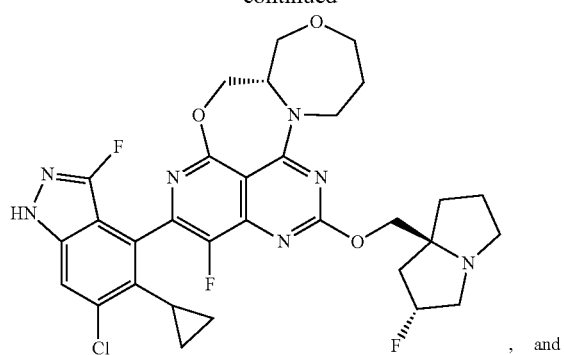
, and
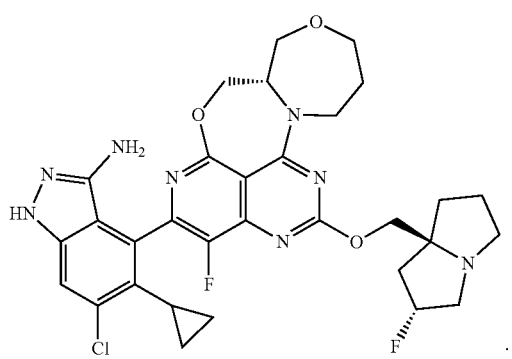
.
E21e A compound of embodiment E1, or a pharmaceutically acceptable salt thereof, wherein the compound is selected from the group consisting of:
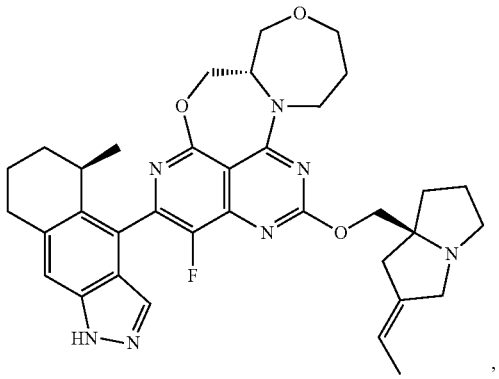
,
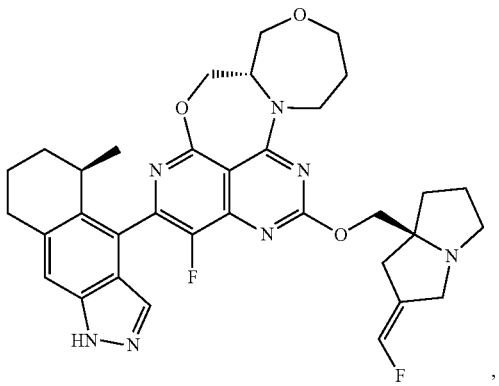
,
-continued
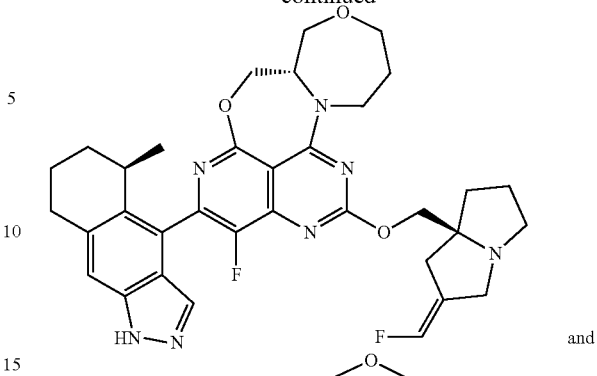
and
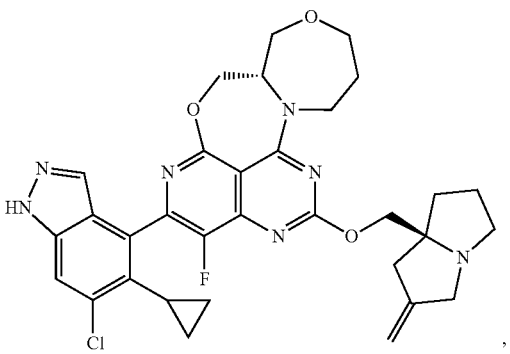 [SMILES: C=C1CN2CCC[C@@]2(COc2nc3c4c(nc(-c5c(C6CC6)c(Cl)cc6[nH]ncc56)c(F)c4n2)OC[C@@H]2COCCCN32)C1]
E22 A compound that is:
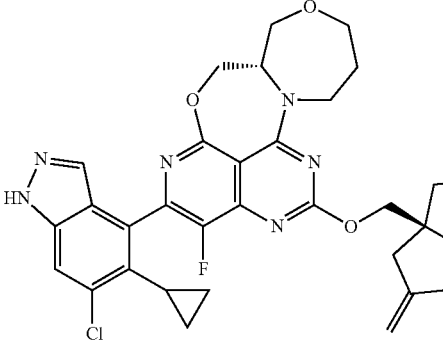
,
or a pharmaceutically acceptable salt thereof.
E23 A compound that is:

E24 A pharmaceutically acceptable salt of a compound, wherein the compound is:
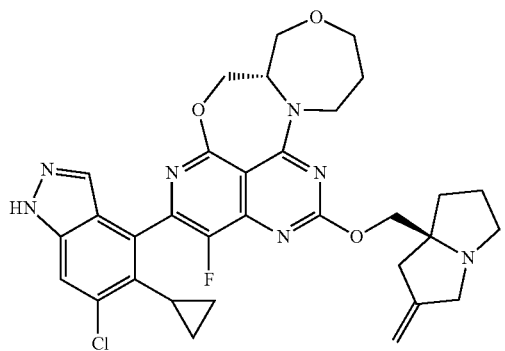
E25 A compound that is:
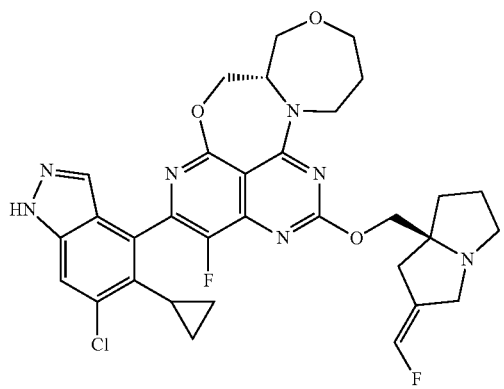
or a pharmaceutically acceptable salt thereof.
E26 A compound that is:
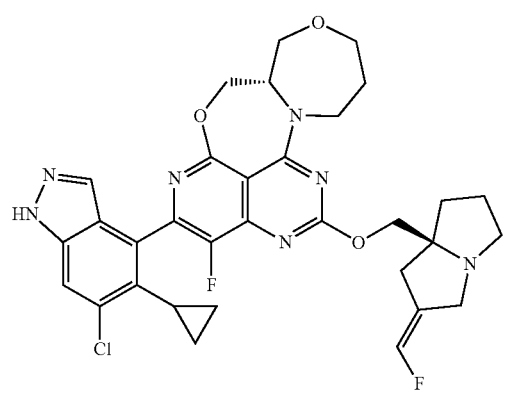 [SMILES: F/C=C1\CN2CCC[C@@]2(COc2nc3c4c(nc(-c5c(C6CC6)c(Cl)cc6[nH]ncc56)c(F)c4n2)OC[C@@H]2COCCCN32)C1]
E27 A pharmaceutically acceptable salt of a compound, wherein the compound is:
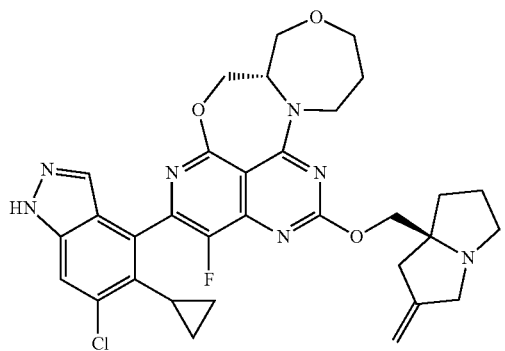
E28 A compound that is:
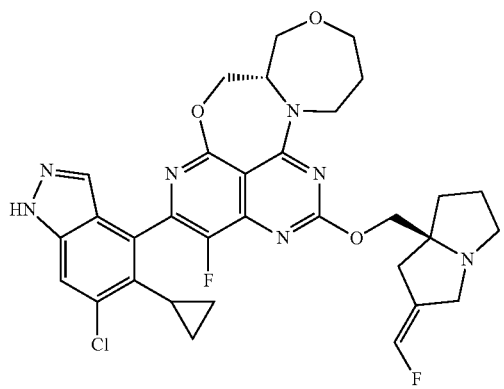
or a pharmaceutically acceptable salt thereof.
E29 A compound that is:
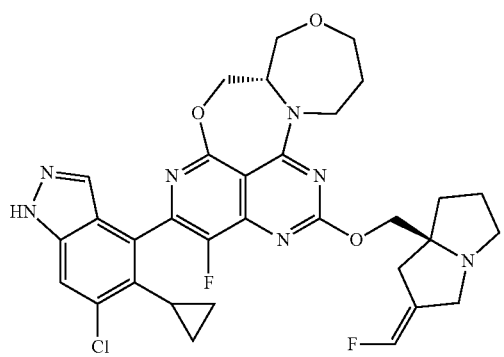 [SMILES: F/C=C1/CN2CCC[C@@]2(COc2nc3c4c(nc(-c5c(C6CC6)c(Cl)cc6[nH]ncc56)c(F)c4n2)OC[C@@H]2COCCCN32)C1]

E30 A pharmaceutically acceptable salt of a compound, wherein the compound is:
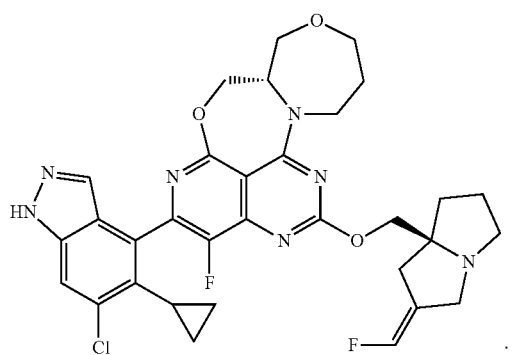 [SMILES: F/C=C1/CN2CCC[C@@]2(COc2nc3c4c(nc(-c5c(C6CC6)c(Cl)cc6[nH]ncc56)c(F)c4n2)OC[C@@H]2COCCCN32)C1]
E31 A compound that is:
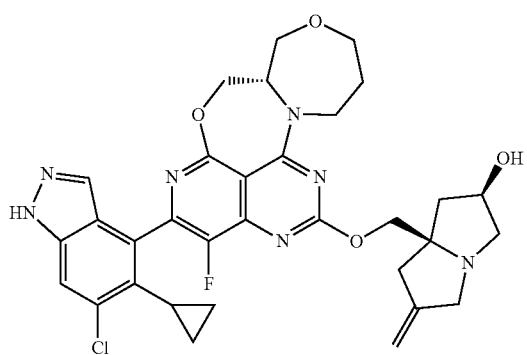 [SMILES: C=C1CN2C[C@H](O)C[C@@]2(COc2nc3c4c(nc(-c5c(C6CC6)c(Cl)cc6[nH]ncc56)c(F)c4n2)OC[C@@H]2COCCCN32)C1]
or a pharmaceutically acceptable salt thereof.
E32 A compound that is:
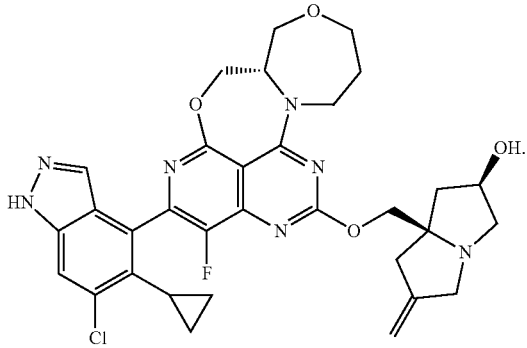
E33 A pharmaceutically acceptable salt of a compound, wherein the compound is:
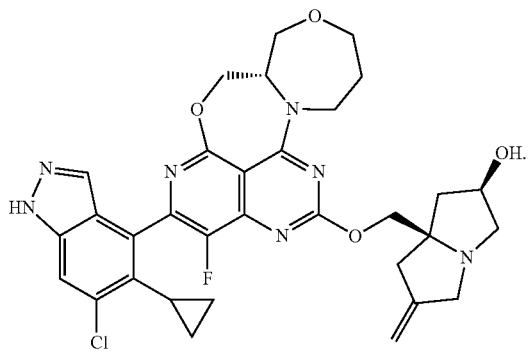 [SMILES: C=C1CN2C[C@H](O)C[C@@]2(COc2nc3c4c(nc(-c5c(C6CC6)c(Cl)cc6[nH]ncc56)c(F)c4n2)OC[C@@H]2COCCCN32)C1]
E34 A compound that is:
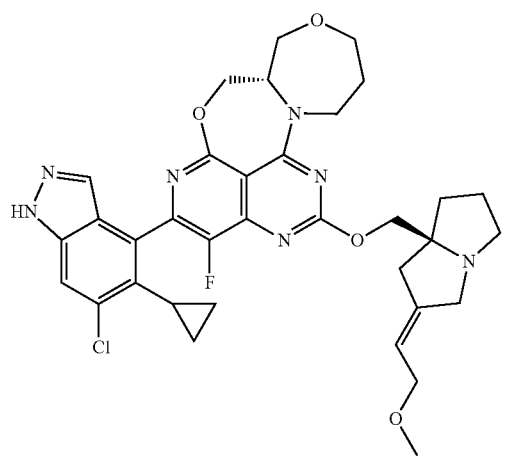 [SMILES: COC/C=C1\CN2CCC[C@@]2(COc2nc3c4c(nc(-c5c(C6CC6)c(Cl)cc6[nH]ncc56)c(F)c4n2)OC[C@@H]2COCCCN32)C1]
or a pharmaceutically acceptable salt thereof.
E35 A compound that is:
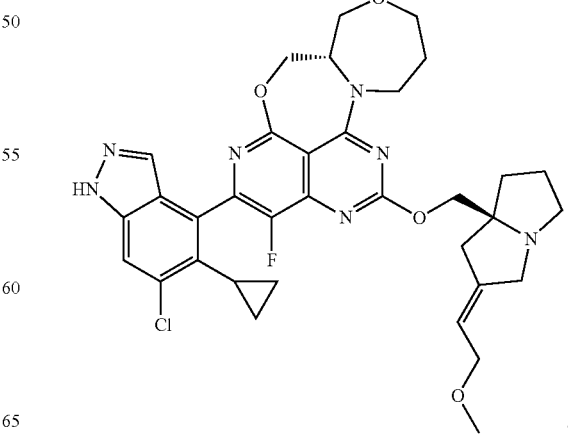

E36 A pharmaceutically acceptable salt of a compound, wherein the compound is:
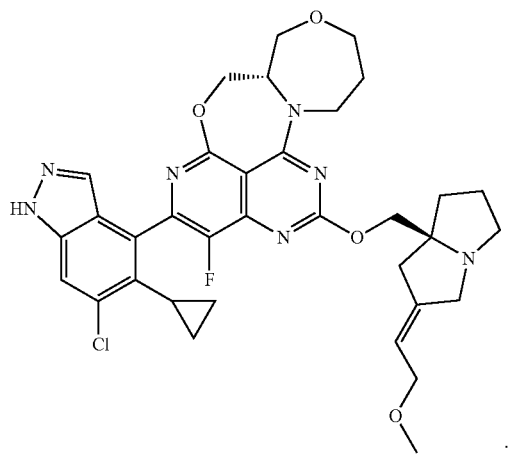 [SMILES: COC/C=C1\CN2CCC[C@@]2(COc2nc3c4c(nc(-c5c(C6CC6)c(Cl)cc6[nH]ncc56)c(F)c4n2)OC[C@@H]2COCCCN32)C1]
E37 A compound that is:
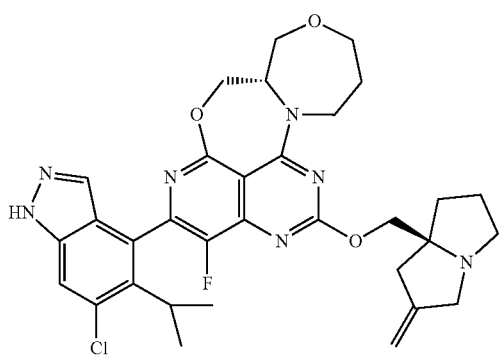 [SMILES: C=C1CN2CCC[C@@]2(COc2nc3c4c(nc(-c5c(C(C)C)c(Cl)cc6[nH]ncc56)c(F)c4n2)OC[C@@H]2COCCCN32)C1]
or a pharmaceutically acceptable salt thereof.
E38 A compound that is:
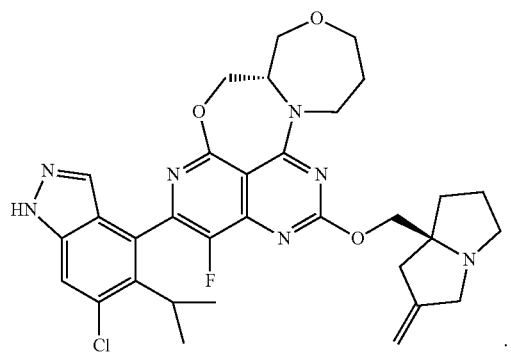 [SMILES: C=C1CN2CCC[C@@]2(COc2nc3c4c(nc(-c5c(C(C)C)c(Cl)cc6[nH]ncc56)c(F)c4n2)OC[C@@H]2COCCCN32)C1]
E39 A pharmaceutically acceptable salt of a compound, wherein the compound is:
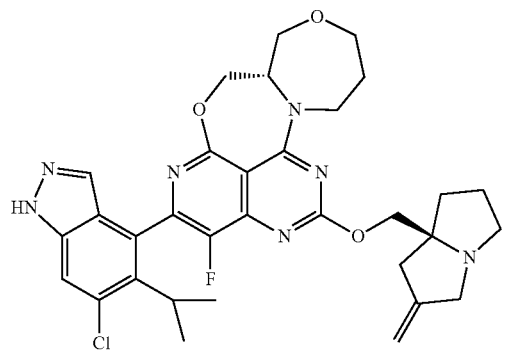
E40 A compound that is:
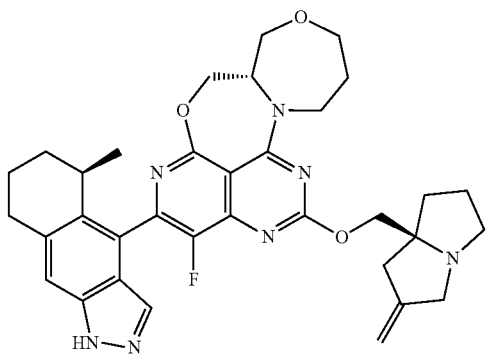 [SMILES: C=C1CN2CCC[C@@]2(COc2nc3c4c(nc(-c5c6c(cc7[nH]ncc57)CCC[C@H]6C)c(F)c4n2)OC[C@@H]2COCCCN32)C1]
or a pharmaceutically acceptable salt thereof.
E41 A compound that is:
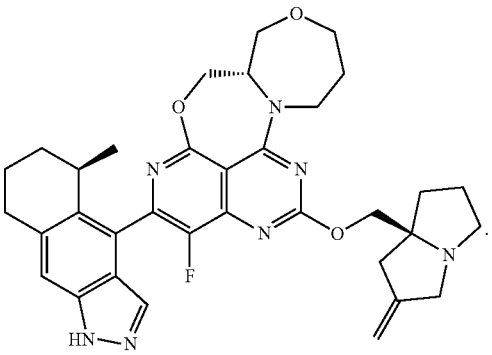 [SMILES: C=C1CN2CCC[C@@]2(COc2nc3c4c(nc(-c5c6c(cc7[nH]ncc57)CCC[C@H]6C)c(F)c4n2)OC[C@@H]2COCCCN32)C1]

E42 A pharmaceutically acceptable salt of a compound that is:
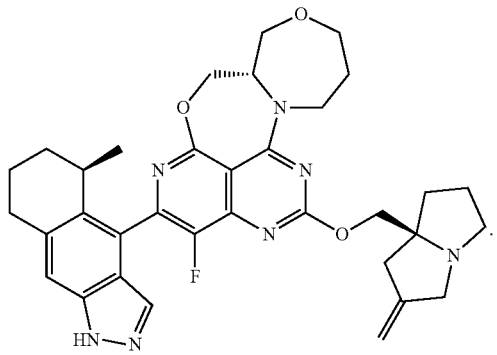 [SMILES: C=C1CN2CCC[C@@]2(COc2nc3c4c(nc(-c5c6c(cc7[nH]ncc57)CCC[C@H]6C)c(F)c4n2)OC[C@@H]2COCCCN32)C1]
E42a A compound that is
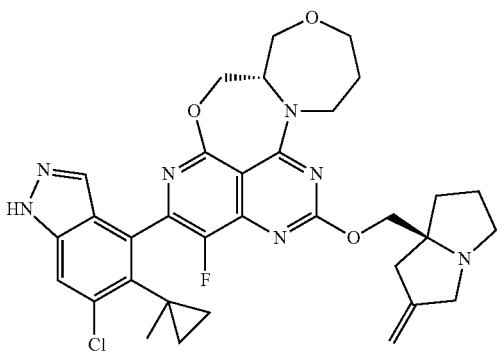 [SMILES: C=C1CN2CCC[C@@]2(COc2nc3c4c(nc(-c5c(C6(C)CC6)c(Cl)cc6[nH]ncc56)c(F)c4n2)OC[C@@H]2COCCCN32)C1]
or a pharmaceutically acceptable salt thereof.
E42b A compound that is
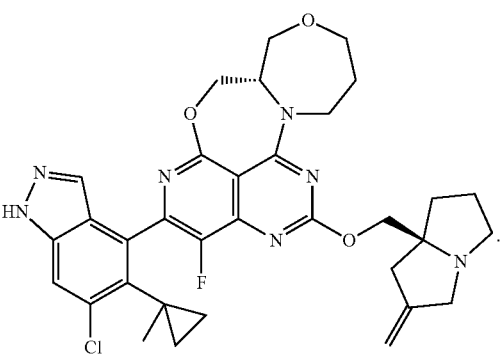 [SMILES: C=C1CN2CCC[C@@]2(COc2nc3c4c(nc(-c5c(C6(C)CC6)c(Cl)cc6[nH]ncc56)c(F)c4n2)OC[C@@H]2COCCCN32)C1]
E42c A pharmaceutically acceptable salt of a compound that is:
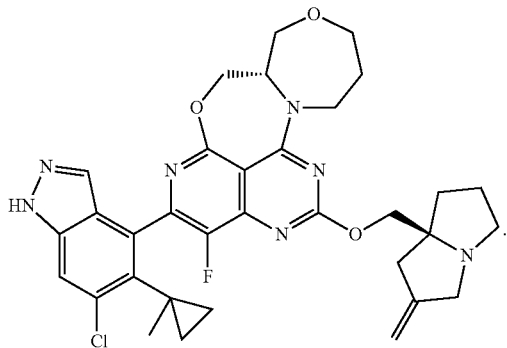 [SMILES: C=C1CN2CCC[C@@]2(COc2nc3c4c(nc(-c5c(C6(C)CC6)c(Cl)cc6[nH]ncc56)c(F)c4n2)OC[C@@H]2COCCCN32)C1]
E42d A compound that is
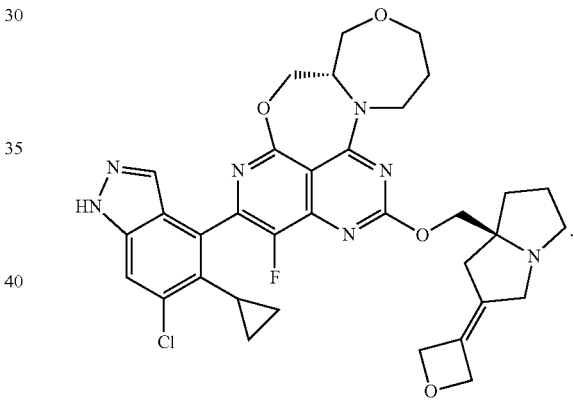
or a pharmaceutically acceptable salt thereof.
E42e A compound that is
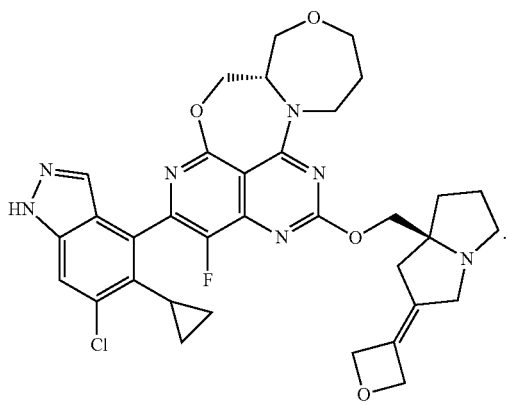 [SMILES: Fc1c(-c2c(C3CC3)c(Cl)cc3[nH]ncc23)nc2c3c(nc(OC[C@@]45CCCN4CC(=C4COC4)C5)nc13)N1CCCOC[C@H]1CO2]

E42f A pharmaceutically acceptable salt of a compound that is:
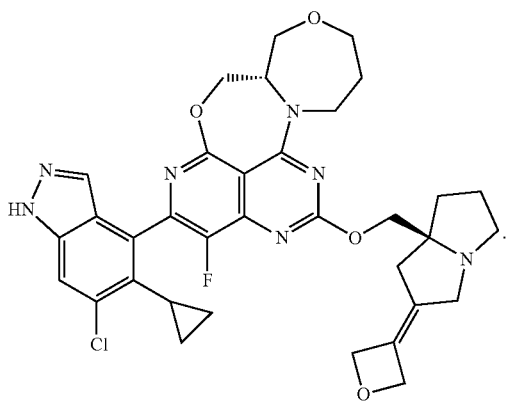 [SMILES: Fc1c(-c2c(C3CC3)c(Cl)cc3[nH]ncc23)nc2c3c(nc(OC[C@@]45CCCN4CC(=C4COC4)C5)nc13)N1CCCOC[C@H]1CO2]
E42g A compound that is
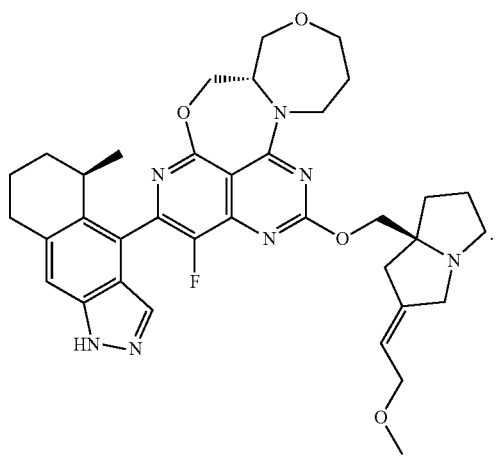 [SMILES: COC/C=C1\CN2CCC[C@@]2(COc2nc3c4c(nc(-c5c6c(cc7[nH]ncc57)CCC[C@H]6C)c(F)c4n2)OC[C@@H]2COCCCN32)C1]
or a pharmaceutically acceptable salt thereof.
E42h A compound that is
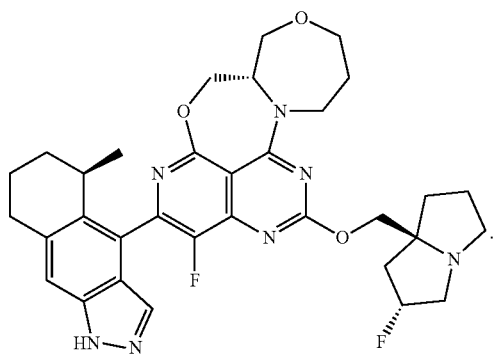 [SMILES: C[C@@H]1CCCc2cc3[nH]ncc3c(-c3nc4c5c(nc(OC[C@@]67CCCN6C[C@H](F)C7)nc5c3F)N3CCCOC[C@H]3CO4)c21]
E42i A pharmaceutically acceptable salt of a compound that is:
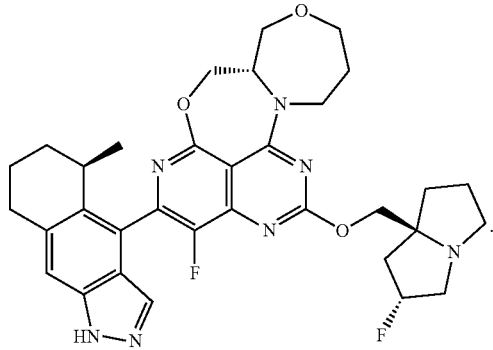 [SMILES: C[C@@H]1CCCc2cc3[nH]ncc3c(-c3nc4c5c(nc(OC[C@@]67CCCN6C[C@H](F)C7)nc5c3F)N3CCCOC[C@H]3CO4)c21]
E42j A compound that is:
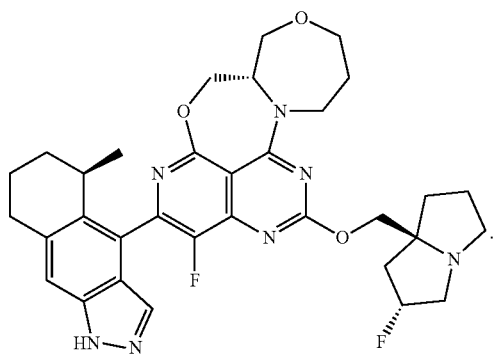 [SMILES: C[C@@H]1CCCc2cc3[nH]ncc3c(-c3nc4c5c(nc(OC[C@@]67CCCN6C[C@H](F)C7)nc5c3F)N3CCCOC[C@H]3CO4)c21]
or a pharmaceutically acceptable salt thereof.
E42k A compound that is
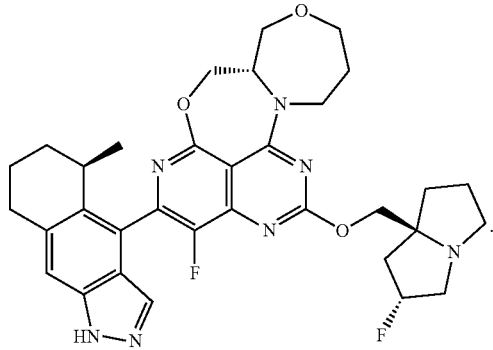 [SMILES: C[C@@H]1CCCc2cc3[nH]ncc3c(-c3nc4c5c(nc(OC[C@@]67CCCN6C[C@H](F)C7)nc5c3F)N3CCCOC[C@H]3CO4)c21]

E42l A pharmaceutically acceptable salt of a compound that is:
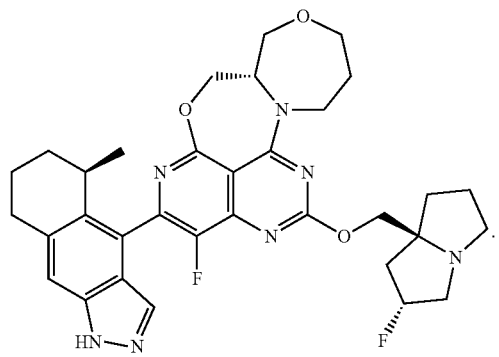 [SMILES: C[C@@H]1CCCc2cc3[nH]ncc3c(-c3nc4c5c(nc(OC[C@@]67CCCN6C[C@H](F)C7)nc5c3F)N3CCCOC[C@H]3CO4)c21]
E42m A compound that is:
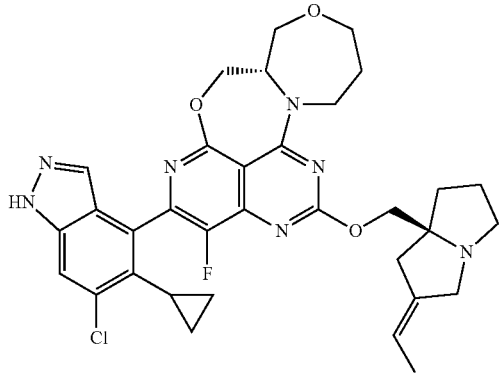 [SMILES: C/C=C1\CN2CCC[C@@]2(COc2nc3c4c(nc(-c5c(C6CC6)c(Cl)cc6[nH]ncc56)c(F)c4n2)OC[C@@H]2COCCCN32)C1]
or a pharmaceutically acceptable salt thereof.
E42n A compound that is:
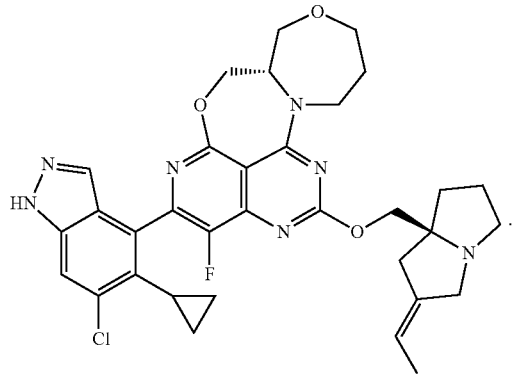 [SMILES: C/C=C1\CN2CCC[C@@]2(COc2nc3c4c(nc(-c5c(C6CC6)c(Cl)cc6[nH]ncc56)c(F)c4n2)OC[C@@H]2COCCCN32)C1]
E42o A pharmaceutically acceptable salt of a compound that is:
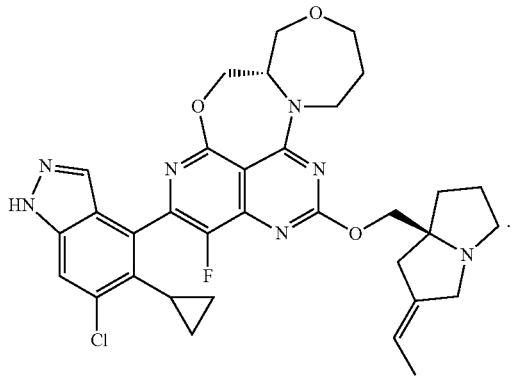 [SMILES: C/C=C1\CN2CCC[C@@]2(COc2nc3c4c(nc(-c5c(C6CC6)c(Cl)cc6[nH]ncc56)c(F)c4n2)OC[C@@H]2COCCCN32)C1]
E42p A compound that is:
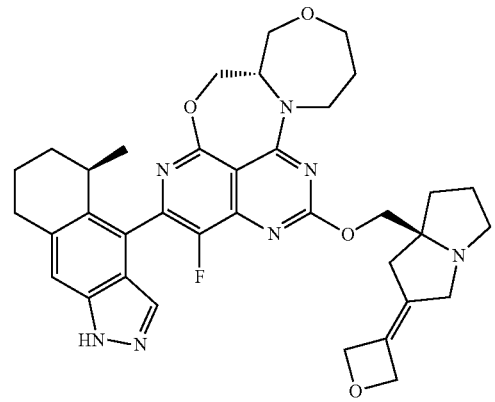 [SMILES: C[C@@H]1CCCc2cc3[nH]ncc3c(-c3nc4c5c(nc(OC[C@@]67CCCN6CC(=C6COC6)C7)nc5c3F)N3CCCOC[C@H]3CO4)c21]
or a pharmaceutically acceptable salt thereof.
E42q A compound that is
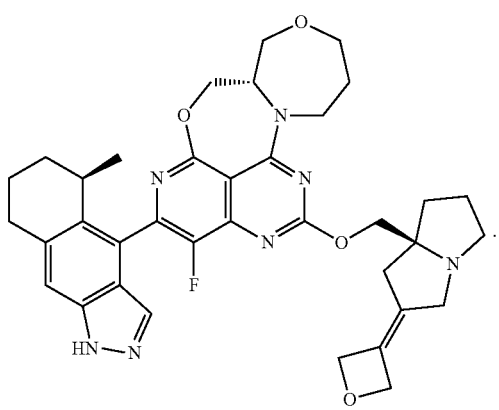 [SMILES: C[C@@H]1CCCc2cc3[nH]ncc3c(-c3nc4c5c(nc(OC[C@@]67CCCN6CC(=C6COC6)C7)nc5c3F)N3CCCOC[C@H]3CO4)c21]

E42r A pharmaceutically acceptable salt of a compound that is:
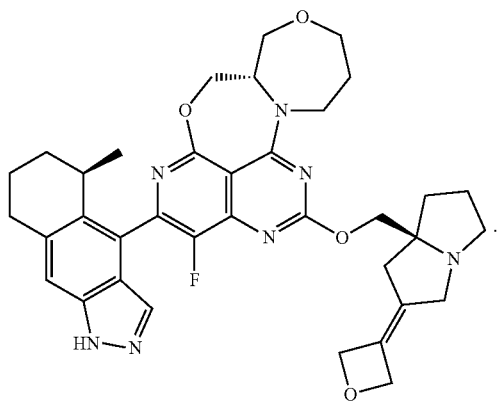 [SMILES: C[C@@H]1CCCc2cc3[nH]ncc3c(-c3nc4c5c(nc(OC[C@@]67CCCN6CC(=C6COC6)C7)nc5c3F)N3CCCOC[C@H]3CO4)c21]
E42s A compound that is
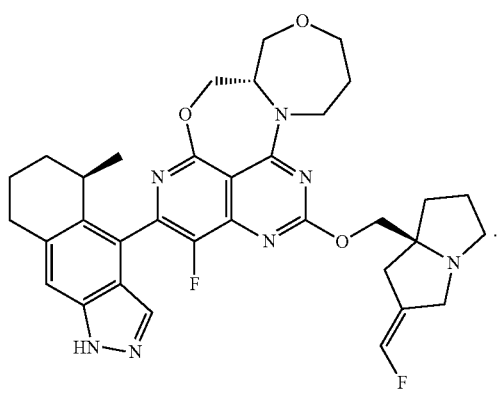 [SMILES: C[C@@H]1CCCc2cc3[nH]ncc3c(-c3nc4c5c(nc(OC[C@@]67CCCN6C/C(=C\F)C7)nc5c3F)N3CCCOC[C@H]3CO4)c21]
or a pharmaceutically acceptable salt thereof.
E42t A compound that is
E42u A pharmaceutically acceptable salt of a compound that is:
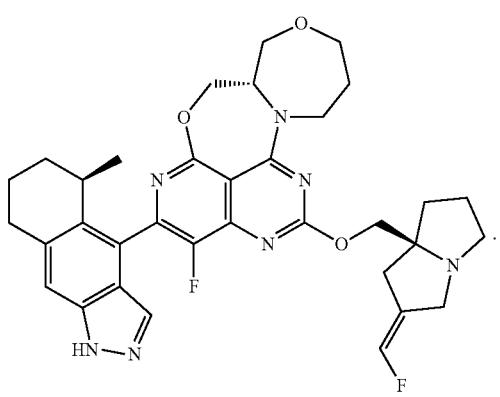 [SMILES: C[C@@H]1CCCc2cc3[nH]ncc3c(-c3nc4c5c(nc(OC[C@@]67CCCN6C/C(=C\F)C7)nc5c3F)N3CCCOC[C@H]3CO4)c21]
E42v A compound that is
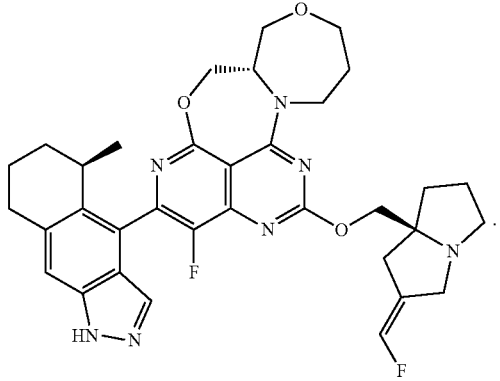 [SMILES: C[C@@H]1CCCc2cc3[nH]ncc3c(-c3nc4c5c(nc(OC[C@@]67CCCN6C/C(=C\F)C7)nc5c3F)N3CCCOC[C@H]3CO4)c21]
or a pharmaceutically acceptable salt thereof.
E42w A compound that is
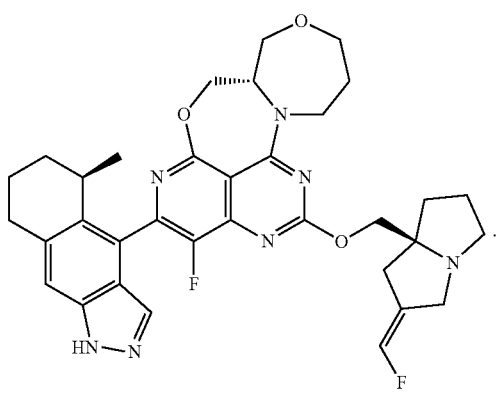 [SMILES: C[C@@H]1CCCc2cc3[nH]ncc3c(-c3nc4c5c(nc(OC[C@@]67CCCN6C/C(=C\F)C7)nc5c3F)N3CCCOC[C@H]3CO4)c21]

E42x A pharmaceutically acceptable salt of a compound that is:

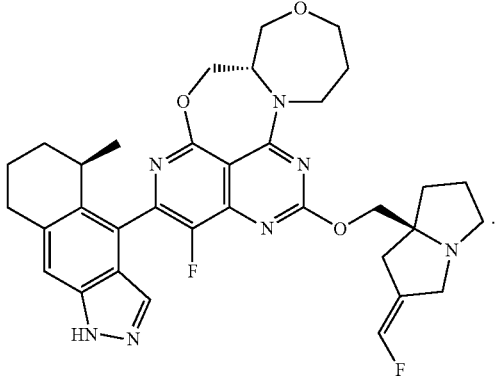 [SMILES: C[C@@H]1CCCc2cc3[nH]ncc3c(-c3nc4c5c(nc(OC[C@@]67CCCN6C/C(=C\F)C7)nc5c3F)N3CCCOC[C@H]3CO4)c21]

E42y A compound that is

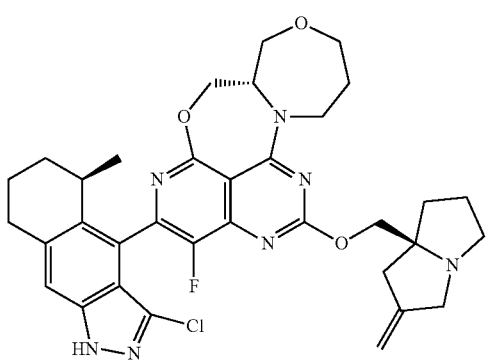 [SMILES: C=C1CN2CCC[C@@]2(COc2nc3c4c(nc(-c5c6c(cc7[nH]nc(Cl)c57)CCC[C@H]6C)c(F)c4n2)OC[C@@H]2COCCCN32)C1]

or a pharmaceutically acceptable salt thereof.

E42a1 A compound that is

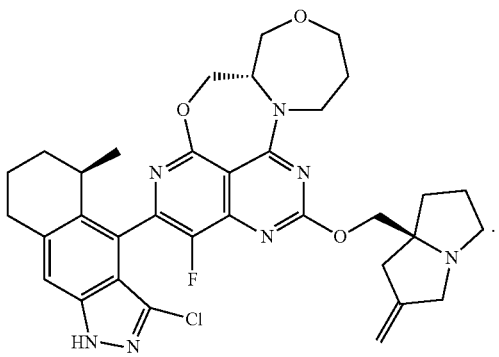 [SMILES: C=C1CN2CCC[C@@]2(COc2nc3c4c(nc(-c5c6c(cc7[nH]nc(Cl)c57)CCC[C@H]6C)c(F)c4n2)OC[C@@H]2COCCCN32)C1]

E42a2 A pharmaceutically acceptable salt of a compound that is

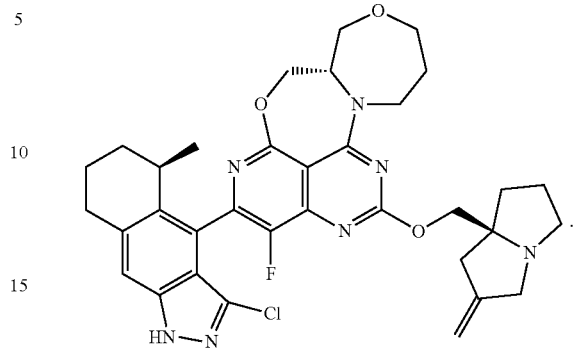

E43 A pharmaceutical composition comprising a compound of any one of embodiments E1 to E42, or a pharmaceutically acceptable salt thereof, and at least one pharmaceutically acceptable excipient.

E44 A method for treating cancer, comprising administering to a subject in need thereof a therapeutically effective amount of a compound of any one of embodiments E1 to E42, or a pharmaceutically acceptable salt thereof.

E45 A method for treating cancer, comprising administering to a subject in need thereof a therapeutically effective amount of a compound of any one of embodiments E1 to E42, or a pharmaceutically acceptable salt thereof, as a single agent.

E46 A method for treating cancer, comprising administering to a subject in need thereof a therapeutically effective amount of a compound of any one of embodiments E1 to E42, or a pharmaceutically acceptable salt thereof, and further comprising administering a therapeutically effective amount of an additional anticancer therapeutic agent.

E47 A method for treating cancer of any one of embodiments E22 to E42, wherein the cancer is small cell lung cancer (NSCLC), pancreatic cancer, or colorectal cancer.

E48 A compound of any one of embodiments E1 to E42, or a pharmaceutically acceptable salt thereof, for use as a medicament.

E49 A compound of any one of embodiments E1 to E42, or a pharmaceutically acceptable salt thereof, for use in the treatment of cancer.

E50 A compound or pharmaceutically acceptable salt thereof for use in the treatment of cancer according to any one of embodiments E22 to E42, wherein said cancer is small cell lung cancer (NSCLC), pancreatic cancer, or colorectal cancer.

E51 Use of a compound of any one of embodiments E1 to E42, or a pharmaceutically acceptable salt thereof, for the manufacture of a medicament for the treatment of cancer.

E52 Use of a compound, or a pharmaceutically acceptable salt thereof, for the manufacture of a medicament for the treatment of cancer according to any one of embodiments E22 to E42, wherein the cancer is small cell lung cancer (NSCLC), pancreatic cancer, or colorectal cancer.

E53 A method for the treatment of a disorder mediated by inhibition of KRAS G12C, KRAS G12D, and KRAS G12V receptors in a subject, comprising administering to the subject in need thereof a compound of any one of embodiments E1 to E42, or a pharmaceutically acceptable salt thereof, in an amount that is effective for treating the disorder.

E54 A pharmaceutical combination comprising a compound of any one of embodiments E1 to E42, or a pharmaceutically acceptable salt thereof, and at least one additional therapeutic agent or a pharmaceutically acceptable salt thereof, wherein said pharmaceutical combination is a fixed or non-fixed combination.

E55 A pharmaceutical composition comprising the pharmaceutical combination of embodiment E54 and at least one excipient.

Each of the embodiments described herein may be combined with any other embodiment(s) described herein not inconsistent with the embodiment(s) with which it is combined. In addition, any of the compounds described in the Examples, or pharmaceutically acceptable salts thereof, may be claimed individually or grouped together with one or more other compounds of the Examples, or a pharmaceutically acceptable salt thereof.

Furthermore, each of the embodiments described herein envisions within its scope pharmaceutically acceptable salts of the compounds, stereoisomers of the compounds, hydrates of the compounds, and pharmaceutically acceptable salts of the stereoisomers described herein.

DEFINITIONS

Unless otherwise defined herein, scientific, and technical terms used in connection with the present invention have the meanings that are commonly understood by those of ordinary skill in the art.

The invention described herein suitably may be practiced in the absence of any element(s) not specifically disclosed herein.

"Compounds of the invention" include compounds of Formula (I), (II) or (III) and the novel intermediates used in the preparation thereof. One of ordinary skill in the art will appreciate that compounds of the invention include conformational isomers (e.g., cis and trans isomers) and all optical isomers (e.g., enantiomers and diastereomers), racemic, diastereomeric and other mixtures of such isomers, tautomers thereof, where they may exist. One of ordinary skill in the art will also appreciate that compounds of the invention include solvates, hydrates, isomorphs, polymorphs, esters, salt forms, prodrugs, and isotopically labelled versions thereof, where they may be formed.

As used herein, the singular form "a", "an", and "the" include plural references unless indicated otherwise. For example, "a" substituent includes one or more substituents.

As used herein, the term "about" when used to modify a numerically defined parameter (e.g., the dose of 5 mg) means that the parameter may vary by as much as 10% below or above the stated numerical value for that parameter. For example, a dose of about 5 mg means 5%±10%, i.e., may vary between 4.5 mg and 5.5 mg.

If substituents are described as being "independently selected" from a group, each substituent is selected independent of the other. Each substituent therefore may be identical to or different from the other substituent(s).

"Optional" or "optionally" means that the subsequently described event or circumstance may, but need not occur, and the description includes instances where the event or circumstance occurs and instances in which it does not.

The terms "optionally substituted" and "substituted or unsubstituted" are used interchangeably to indicate that the particular group being described may have no non-hydrogen substituents (i.e., unsubstituted), or the group may have one or more non-hydrogen substituents (i.e., substituted). If not otherwise specified, the total number of substituents that may be present is equal to the number of H atoms present on the unsubstituted form of the group being described. Where an optional substituent is attached via a double bond, such as an oxo (=O) substituent, the group occupies two available valences, so the total number of other substituents that are included is reduced by two. In the case where optional substituents are selected independently from a list of alternatives, the selected groups may be the same or different. Throughout the disclosure, it will be understood that the number and nature of optional substituent groups will be limited to the extent that such substitutions make chemical sense to one of ordinary skill in the art. For the sake of clarity, "may optionally be substituted" means substituted with zero substituents or more.

"Halogen" refers to fluoro, chloro, bromo and iodo (F, Cl, Br, I).

"Cyano" refers to a substituent having a carbon atom joined to a nitrogen atom by a triple bond, i.e., —C≡N (also depicted herein as "—CN").

"Hydroxy" refers to an —OH group.

"Oxo" refers to a double bonded oxygen (=O).

"Alkyl" refers to a saturated, monovalent aliphatic hydrocarbon radical that has a specified number of carbon atoms, including straight chain or branched chain groups. Alkyl groups may contain, but are not limited to, 1 to 6 carbon atoms ("$C_1$-$C_6$ alkyl"), 1 to 3 carbon atoms ("$C_1$-$C_3$ alkyl"), or 1 to 2 carbon atoms ("$C_1$-$C_2$ alkyl"). Examples include, but are not limited to, methyl, ethyl, n-propyl, isopropyl, and the like.

"Fluoroalkyl" refers to an alkyl group, as defined herein, wherein from one to all of the hydrogen atoms of the alkyl group are replaced by fluoro atoms. Examples include, but are not limited to, fluoromethyl, difluoromethyl, fluoroethyl, difluoroethyl, trifluoroethyl, and tetrafluoroethyl. Examples of fully substituted fluoroalkyl groups (also referred to as perfluoroalkyl groups) include trifluoromethyl (—$CF_3$) and pentafluoroethyl (—$C_2F_5$).

"Alkylene" refers to a bivalent aliphatic hydrocarbon radical that has a specified number of carbon atoms. Alkylene groups may contain, but are not limited to, 1 to 6 carbon atoms ("$C_1$-$C_6$ alkylene"), or 1 to 2 carbon atoms ("$C_1$-$C_2$ alkylene"). Examples include —($CH_2$)— (methylene) and —($CH_2$—$CH_2$)— (ethylene).

"Alkoxy" refers to an alkyl group, as defined herein, that is single bonded to an oxygen atom. The attachment point of an alkoxy radical to a molecule is through the oxygen atom. An alkoxy radical may be depicted as alkyl-O—. Alkoxy groups may contain, but are not limited to, 1 to 6 carbon atoms ("$C_1$-$C_6$ alkoxy"), or 1 to 3 carbon atoms ("$C_1$-$C_3$ alkoxy"). Alkoxy groups include, but are not limited to, methoxy, ethoxy, n-propoxy, and the like.

"Alkynyl" refers to an alkyl group, as defined herein, consisting of at least two carbon atoms and at least one carbon-carbon triple bond. Alkynyl may contain 2-3 carbon atoms ("$C_2$-$C_3$ alkynyl"). Examples include, but are not limited to, ethynyl, 1-propynyl, 2-propynyl, and the like.

"Cycloalkyl" refers to a fully saturated hydrocarbon ring system that has the specified number of carbon atoms, which may be a monocyclic, bridged or fused bicyclic or polycyclic ring system that is connected to the base molecule through a carbon atom of the cycloalkyl ring. Cycloalkyl groups may contain, but are not limited to, 3 to 10 carbon atoms ("$C_3$-$C_{10}$ cycloalkyl"), 3 to 8 carbon atoms ("$C_3$-$C_8$ cycloalkyl"), 3 to 6 carbon atoms ("$C_3$-$C_6$ cycloalkyl"), 3 to 5 carbon atoms ("$C_3$-$C_5$ cycloalkyl") or 3 to 4 carbon atoms ("$C_3$-$C_4$ cycloalkyl"). Examples include, but are not limited to, cyclopropyl, cyclobutyl, cyclopentyl, cyclohexyl, cycloheptyl, adamantanyl, and the like. Cycloalkyl groups may be optionally substituted, unsubstituted or substituted, as further defined herein.

"Alkylidenyl" refers to linear or branched-chain monovalent hydrocarbon radical having formula =CR'R", where R' and R" may be independently selected from H or an alkyl group. Exemplary alkylidenyl radicals include, but are not limited to, methylidenyl (=$CH_2$), ethylidenyl (=$CHCH_3$), iso-propylidenyl (=$C(CH_3)_2$), and propylidenyl (=CH—$CH_2$—$CH_3$). R' and R" may optionally be further substituted as described above.

"Haloalkylidenyl" refers to linear or branched-chain monovalent hydrocarbon radical having formula =CR'R", where R' or R" are as defined for Alkylidenyl and further comprises at least one halogen atom. Exemplary haloalkylidenyl radicals include, but are not limited to, fluoromethylidenyl (=CHF), difluoromethylidenyl (=$CF_2$), fluoroethylidenyl (=$CFCH_3$), and fluoropropylidenyl (=CF—$CH_2$—$CH_3$). R' and R" may optionally be further substituted as described above.

"Alkylidenylcyclopropyl" refers to linear or branched-chain monovalent hydrocarbon radical having formula =CR'R", where R' or R" are as defined for Alkylidenyl and R' and R' together with the carbon they are attached to comprise a cyclopropyl ring.

"Alkylidenyloxetane" refers to linear or branched-chain monovalent hydrocarbon radical having formula =CR'R", where R' or R" are as defined for Alkylidenyl and R' and R' together with the carbon they are attached to comprise an oxetane.

"Fluorocycloalkyl" refers to a cycloalkyl group, as defined herein, wherein from one to all of the hydrogen atoms of the alkyl group are replaced by fluoro atoms. Examples include, but are not limited to, fluorocyclcopropyl, fluorocyclcobutyl, fluorocyclcopentyl and fluorocyclcohexyl, "Heterocycloalkyl" refers to a fully saturated ring system containing the specified number of ring atoms and containing at least one heteroatom selected from N, O and S as a ring member, where ring S atoms are optionally substituted by one or two oxo groups (i.e., $S(O)_q$, where q is 0, 1 or 2) and where the heterocycloalkyl ring is connected to the base molecule via a ring atom, which may be C or N. Heterocycloalkyl rings include monocyclic or polycyclic such as bicyclic rings. Heterocycloalkyl rings also include rings which are spirocyclic, bridged, and/or fused to one or more other heterocycloalkyl or carbocyclic rings, where such spirocyclic, bridged, and/or fused rings may themselves be saturated, partially unsaturated or aromatic to the extent unsaturation or aromaticity makes chemical sense, provided the point of attachment to the base molecule is an atom of the heterocycloalkyl portion of the ring system. Heterocycloalkyl rings may contain 1 to 4 heteroatoms selected from N, O, and $S(O)_q$ as ring members, or 1 to 3 ring heteroatoms, or 1 to 2 ring heteroatoms, provided that such heterocycloalkyl rings do not contain two contiguous oxygen or sulfur atoms.

Heterocycloalkyl rings may be optionally substituted, unsubstituted or substituted, as further defined herein. Such substituents may be present on the heterocyclic ring attached to the base molecule, or on a monocyclic, bicyclic, tricyclic, spirocyclic, bridged or fused ring attached thereto.

Heterocycloalkyl rings may include, but are not limited to, 4-12 membered heterocyclyl groups, for example 5-8 or 4-6 membered heterocycloalkyl groups, in accordance with the definition herein. Examples of heterocycloalkyl ring group of the present invention may include, but are not limited to aziridinyl, azetidinyl, pyrrolidinyl, piperidinyl, piperazinyl, morpholinyl, thiomorpholinyl, azepanyl, oxaazepanyl, thieazepanyl, a radical of hexahydro-1H-pyrrolizine ring, a radical of 8-oxa-3-azabicyclo[3.2.1]octane ring, a radical of 3-azabicyclo[3.2.1]octane ring, a radical of 6-azabicyclo[3.2.1]octane ring, or a radical of 3-azabicyclo[3.2.0]heptane ring.

"Aryl" or "aromatic" refers to monocyclic, bicyclic (e.g., biaryl, fused) or polycyclic ring systems that contain the specified number of ring atoms, in which all carbon atoms in the ring are of $sp^2$ hybridization and in which the pi electrons are in conjugation. Aryl groups may contain, but are not limited to, 6 to 10 carbon atoms ("$C_6$-$C_{10}$ aryl"). Fused aryl groups may include an aryl ring (e.g., a phenyl ring) fused to another aryl ring. Examples include, but are not limited to, phenyl, biphenyl, naphthyl, anthracenyl, phenanthrenyl, indanyl, and indenyl. Aryl groups may be optionally substituted, unsubstituted or substituted, as further defined herein.

Similarly, "heteroaryl" or "heteroaromatic" refer to monocyclic, bicyclic (e.g., heterobiaryl, fused) or polycyclic ring systems that contain the specified number of ring atoms and include at least one heteroatom selected from N, O and S as a ring member in a ring in which all carbon atoms in the ring are of $sp^2$ hybridization and in which the pi electrons are in conjugation. Heteroaryl groups may contain, but are not limited to, 5 to 14 ring atoms ("5-14 membered heteroaryl"), 5 to 12 ring atoms ("5-12 membered heteroaryl"), 5 to 10 ring atoms ("5-10 membered heteroaryl"), 5 to 9 ring atoms ("5-9 membered heteroaryl"), or 5 to 6 ring atoms ("5-6 membered heteroaryl"). Heteroaryl rings are attached to the base molecule via a ring atom of the heteroaromatic ring. Thus, either 5- or 6-membered heteroaryl rings, alone or in a fused structure, may be attached to the base molecule via a ring C or N atom. Examples of heteroaryl groups include, but are not limited to, pyrrolyl, furanyl, thiophenyl, pyrazolyl, imidazolyl, isoxazolyl, oxazolyl, isothiazolyl, thiazolyl, triazolyl, oxadiazolyl, thiadiazolyl, tetrazolyl, pyridinyl, pyridizinyl, pyrimidinyl, pyrazinyl, benzofuranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, quinolinyl, isoquinolinyl, purinyl, triazinyl, naphthyridinyl, cinnolinyl, quinazolinyl, quinoxalinyl, carbazolyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, purinyl, indolininyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, azaquinazolinyl, phthalazinyl, (pyrido[3,2-d]pyrimidinyl, (pyrido[4,3-d]pyrimidinyl, (pyrido[3,4-d]pyrimidinyl, (pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl. Examples of 5- or 6-membered heteroaryl groups include, but are not limited to, pyrrolyl, furanyl, thiophenyl, pyrazolyl, imidazolyl, isoxazolyl, oxazolyl, isothiazolyl, thiazolyl, triazolyl, pyridinyl, pyrimidinyl, pyrazinyl and pyridazinyl rings. Heteroaryl groups may be optionally substituted, unsubstituted or substituted, as further defined herein.

"Amino" refers to a group —$NH_2$, which is unsubstituted. Where the amino is described as substituted or optionally substituted, the term includes groups of the form —NRxRy, where each of Rx and Ry is defined as further described herein. For example, "alkylamino" refers to a group —NRxRy, wherein one of Rx and Ry is an alkyl moiety and the other is H, and "dialkylamino" refers to —NRxRy wherein both of Rx and Ry are alkyl moieties, where the alkyl moieties have the specified number of carbon atoms (e.g., —NH($C_1$-$C_4$ alkyl) or —N($C_1$-$C_4$ alkyl)$_2$).

A wavy line "  " used in a chemical structure in the present disclosure refers to the point of the attachment of a substituent.

The term "pharmaceutically acceptable" means the substance (e.g., the compounds described herein) and any salt thereof, or composition containing the substance or salt of the invention is suitable for administration to a subject or patient.

"Deuterium enrichment factor" as used herein means the ratio between the deuterium abundance and the natural abundance of deuterium, each relative to hydrogen abundance. An atomic position designated as having deuterium typically has a deuterium enrichment factor of, in particular embodiments, at least 1000 (15% deuterium incorporation), at least 2000 (30% deuterium incorporation), at least 3000 (45% deuterium incorporation), at least 3500 (52.5% deuterium incorporation), at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Salts

Salts encompassed within the term "pharmaceutically acceptable salts" refer to the compounds of this invention which are generally prepared by reacting the free base or free acid with a suitable organic or inorganic acid, or a suitable organic or inorganic base, respectively, to provide a salt of the compound of the invention that is suitable for administration to a subject or patient.

In addition, the compounds of Formula (I)-(III) may also include other salts of such compounds which are not necessarily pharmaceutically acceptable salts, which may be useful as intermediates for one or more of the following: 1) preparing compounds of Formula (I); 2) purifying compounds of Formula (I); 3) separating enantiomers of compounds of Formula (I); or 4) separating diastereomers of compounds of Formula (I).

Suitable acid addition salts are formed from acids which form non-toxic salts. Examples include, but are not limited to, acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, 1,5-naphthalenedisulfonic acid and xinofoate salts.

Suitable base salts are formed from bases which form non-toxic salts. Examples include, but are not limited to aluminum, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts.

For a review on suitable salts, see Paulekun, G. S. et al., Trends in Active Pharmaceutical Ingredient Salt Selection Based on Analysis of the Orange Book Database, J. Med. Chem. 2007; 50(26), 6665-6672.

Pharmaceutically acceptable salts of compounds of the invention may be prepared by methods well known to one skilled in the art, including but not limited to the following procedures (i) by reacting a compound of the invention with the desired acid or base;

(ii) by removing an acid- or base-labile protecting group from a suitable precursor of a compound of the invention or by ring-opening a suitable cyclic precursor, for example, a lactone or lactam, using the desired acid or base; or (iii) by converting one salt of a compound of the invention to another. This may be accomplished by reaction with an appropriate acid or base or by means of a suitable ion exchange procedure.

These procedures are typically carried out in solution. The resulting salt may precipitate out and be collected by filtration or may be recovered by evaporation of the solvent.

Solvates

The compounds of the invention, and pharmaceutically acceptable salts thereof, may exist in unsolvated and solvated forms. The term 'solvate' is used herein to describe a molecular complex comprising the compound of the invention, or a pharmaceutically acceptable salt thereof, and one or more pharmaceutically acceptable solvent molecules, for example, ethanol. The term 'hydrate' is employed when said solvent is water.

In addition, the compounds of Formula (I)-(III) may also include other solvates of such compounds which are not necessarily pharmaceutically acceptable solvates, which may be useful as intermediates for one or more of the following: 1) preparing compounds of Formula (I)-(III); 2) purifying compounds of Formula (I)-(III); 3) separating enantiomers of compounds of Formula (I); or 4) separating diastereomers of compounds of Formula (I)-(III).

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Complexes

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, for example, hydrogen bonded complex (co-crystal) may be formed with either a neutral molecule or with a salt. Co-crystals may be prepared by melt crystallization, by recrystallization from solvents, or by physically grinding the components together—see Chem Commun, 17; 1889-1896, by O. Almarsson and M. J. Zaworotko (2004). For a general review of multi-component complexes, see J Pharm Sci, 64(8), 1269-1288, by Haleblian (August 1975).

Solid Form

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may also exist in a mesomorphic state (mesophase or liquid crystal) when subjected to suitable conditions. The mesomorphic state is intermediate between the true crystalline state and the true liquid state (either melt or solution) and consists of two dimensional order on the molecular level. Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see Crystals and the Polarizing Microscope by N. H. Hartshorne and A. Stuart, 4$^{th}$ Edition (Edward Arnold, 1970).

Stereoisomers

Compounds of the invention may exist as two or more stereoisomers. Stereoisomers of the compounds may include cis and trans isomers (geometric isomers), optical isomers such as R and S enantiomers, diastereomers, rotational isomers, atropisomers, and conformational isomers. For example, compounds of the invention containing one or more asymmetric carbon atoms may exist as two or more stereoisomers.

The pharmaceutically acceptable salts of compounds of the invention may also contain a counterion which is optically active (e.g., d-lactate or l-lysine) or racemic (e.g., dl-tartrate or dl-arginine).

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where a compound of the invention contains an acidic or basic moiety, a base or acid such as 1-phenylethylamine or tartaric acid. The resulting diastereomeric mixture may be separated by chromatography, fractional crystallization, or by using both of said techniques, and one or both of the diastereoisomers converted to the corresponding pure enantiomer(s) by means well known to a skilled person. Chiral compounds of the invention (and chiral precursors thereof) may be obtained in enantiomerically-enriched form using chromatography, typically HPLC Concentration of the eluate affords the enriched mixture. Chiral chromatography using sub- and supercritical fluids may be employed. Methods for chiral chromatography useful in some embodiments of the present invention are known in the art (see, for example, Smith, Roger M., Loughborough University, Loughborough, UK; Chromatographic Science Series (1998), 75 (Supercritical Fluid Chromatography with Packed Columns), pp. 223-249 and references cited therein).

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two crystal forms are produced in equimolar amounts each comprising a single enantiomer. While both of the crystal forms present in a racemic mixture have identical physical properties, they may have different physical properties compared to the true racemate. Racemic mixtures may be separated by conventional techniques known to those skilled in the art—see, for example, Stereochemistry of Organic Compounds by E. L. Eliel and S. H. Wilen (Wiley, 1994).

Tautomerism

Where structural isomers are interconvertible via a low energy barrier, tautomeric isomerism ('tautomerism') may occur. This may take the form of proton tautomerism in compounds of the invention containing, for example, an imino/amino, keto/enol, or oxime/nitroso group, lactam/lactim or so-called valence tautomerism in compounds which contain an aromatic moiety. It follows that a single compound may exhibit more than one type of isomerism.

It must be emphasized that while, for conciseness, the compounds of the invention have been drawn herein in a single tautomeric form, all possible tautomeric forms are included within the scope of the invention.

Isotopes

The present invention includes all pharmaceutically acceptable isotopically-labeled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention may include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of the invention, for example those incorporating a radioactive isotope, are useful in one or both of drug or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with deuterium, i.e., $^2$H, may afford certain therapeutic advantages resulting from greater metabolic stability.

Substitution with positron emitting isotopes, such as $^{11}C$, $^{18}F$, $^{15}O$ and $^{13}N$, may be useful in Positron Emission Topography (PET) studies for examining substrate receptor occupancy.

In some embodiments, the disclosure provides deuterium-labeled (or deuterated) compounds and salts, where the formula and variables of such compounds and salts are each and independently as described herein. "Deuterated" means that at least one of the atoms in the compound is deuterium in an abundance that is greater than the natural abundance of deuterium (typically approximately 0.015%). A skilled artisan recognized that in chemical compounds with a hydrogen atom, the hydrogen atom actually represents a mixture of H and D, with about 0.015% being D. The concentration of the deuterium incorporated into the deuterium-labeled compounds and salt of the invention may be defined by the deuterium enrichment factor. It is understood that one or more deuterium may exchange with hydrogen under physiological conditions.

In some embodiments, the deuterium compound is selected from any one of the compounds set forth in Table 2 shown in the Examples section.

In some embodiments, one or more hydrogen atoms on certain metabolic sites on the compounds of the invention are deuterated.

Isotopically-labeled compounds of the invention may generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g., $D_2O$, $d_6$-acetone, $d_6$-DMSO.

Prodrugs

A compound of the invention may be administered in the form of a prodrug. Thus, certain derivatives of a compound of the invention which may have little or no pharmacological activity themselves may, when administered into or onto the body, be converted into a compound of the invention having the desired activity, for example by hydrolytic cleavage, particularly hydrolytic cleavage promoted by an esterase or peptidase enzyme. Such derivatives are referred to as 'prodrugs'. Further information on the use of prodrugs may be found in 'The Expanding Role of Prodrugs in Contemporary Drug Design and Development, Nature Reviews Drug Discovery, 17, 559-587 (2018) (J. Rautio et al.).

Prodrugs in accordance with the invention may, for example, be produced by replacing appropriate functionalities present in compounds of the invention with certain moieties known to those skilled in the art as 'pro-moieties' as described, for example, in 'Design of Prodrugs' by H. Bundgaard (Elsevier, 1985).

Thus, a prodrug in accordance with the invention may be (a) an ester or amide derivative of a carboxylic acid when present in a compound of the invention; (b) an ester, carbonate, carbamate, phosphate or ether derivative of a hydroxyl group when present in a compound of the invention; (c) an amide, imine, carbamate or amine derivative of an amino group when present in a compound of the invention; (d) a thioester, thiocarbonate, thiocarbamate or sulfide derivatives of a thiol group when present in a compound of the invention; or (e) an oxime or imine derivative of a carbonyl group when present in a compound of the invention.

Some specific examples of prodrugs in accordance with the invention include:
(i) when a compound of the invention contains a carboxylic acid functionality (—COOH), an ester thereof, such as a compound wherein the hydrogen of the carboxylic acid functionality of the compound is replaced by $C_1$-$C_8$ alkyl (e.g., ethyl) or ($C_1$-$C_8$ alkyl)C(=O)OCH$_2$— (e.g., $^tBuC(=O)OCH_2$—);
(ii) when a compound of the invention contains an alcohol functionality (—OH), an ester thereof, such as a compound wherein the hydrogen of the alcohol functionality of the compound is replaced by —CO($C_1$-$C_8$ alkyl) (e.g., methylcarbonyl) or the alcohol is esterified with an amino acid;
(iii) when a compound of the invention contains an alcohol functionality (—OH), an ether thereof, such as a compound wherein the hydrogen of the alcohol functionality of the compound is replaced by ($C_1$-$C_8$ alkyl)C(=O)OCH$_2$— or —CH$_2$OP(=O)(OH)$_2$;
(iv) when a compound of the invention contains an alcohol functionality (—OH), a phosphate thereof, such as a compound wherein the hydrogen of the alcohol functionality of the compound is replaced by —P(=O)(OH)$_2$ or —P(=O)(O$^-$Na$^+$)$_2$ or —P(=O)(O$^-$)$_2$Ca$^{2+}$;
(v) when a compound of the invention contains a primary or secondary amino functionality (—NH$_2$ or —NHR where R≠H), an amide thereof, for example, a compound wherein, as the case may be, one or both hydrogens of the amino functionality of the compound is/are replaced by ($C_1$-$C_{10}$)alkanoyl, —COCH$_2$NH$_2$ or the amino group is derivatized with an amino acid;
(vi) when a compound of the invention contains a primary or secondary amino functionality (—NH$_2$ or —NHR where R≠H), an amine thereof, for example, a compound wherein, as the case may be, one or both hydrogens of the amino functionality of the compound is/are replaced by —CH$_2$OP(=O)(OH)$_2$.

Certain compounds of the invention may themselves act as prodrugs of other compounds the invention It is also possible for two compounds of the invention to be joined together in the form of a prodrug. In certain circumstances, a prodrug of a compound of the invention may be created by internally linking two functional groups in a compound of the invention, for instance by forming a lactone.

Metabolites

Also included within the scope of the invention are active metabolites of compounds of the invention, that is, compounds formed in vivo upon administration of the drug, often by oxidation or dealkylation. Some examples of metabolites in accordance with the invention include, but are not limited to:
(i) where the compound of the invention contains an alkyl group, a hydroxyalkyl derivative thereof (—CH>—COH):
(ii) where the compound of the invention contains an alkoxy group, a hydroxy derivative thereof (—OR—>—OH);
(iii) where the compound of the invention contains a tertiary amino group, a secondary amino derivative thereof (—NRR'—>—NHR or —NHR);
(iv) where the compound of the invention contains a secondary amino group, a primary derivative thereof (—NHR—>—NH$_2$);
(v) where the compound of the invention contains a phenyl moiety, a phenol derivative thereof (-Ph->-PhOH);

(vi) where the compound of the invention contains an amide group, a carboxylic acid derivative thereof (—CONH$_2$—>COOH); and (vii) where the compound contains a hydroxy or carboxylic acid group, the compound may be metabolized by conjugation, for example with glucuronic acid to form a glucuronide. Other routes of conjugative metabolism exist. These pathways are frequently known as Phase 2 metabolism and include, for example, sulfation or acetylation. Other functional groups, such as NH groups, may also be subject to conjugation.

Pharmaceutical Compositions

In another embodiment, the invention comprises pharmaceutical compositions. For pharmaceutical composition purposes, the compound per se or pharmaceutically acceptable salt thereof will simply be referred to as the compounds of the invention.

A "pharmaceutical composition" refers to a mixture of one or more of the compounds of the invention, or a pharmaceutically acceptable salt, solvate, hydrate or prodrug thereof as an active ingredient, and at least one pharmaceutically acceptable excipient.

The term "excipient" is used herein to describe any ingredient other than the compound(s) of the invention. The choice of excipient will to a large extent depend on factors such as the mode of administration, the effect of the excipient on solubility and stability, and the nature of the dosage form.

As used herein, "excipient" includes any and all solvents, dispersion media, coatings, antibacterial and antifungal agents, isotonic and absorption delaying agents, carriers, diluents and the like that are physiologically compatible. Examples of excipients include one or more of water, saline, phosphate buffered saline, dextrose, glycerol, ethanol and the like, as well as combinations thereof, and may include isotonic agents, for example, sugars, sodium chloride, or polyalcohols such as mannitol, or sorbitol in the composition. Examples of excipients also include various organic solvents (such as hydrates and solvates). The pharmaceutical compositions may, if desired, contain additional excipients such as flavorings, binders/binding agents, lubricating agents, disintegrants, sweetening or flavoring agents, coloring matters or dyes, and the like. For example, for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of excipients, therefore, also include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with additional excipients such as water, ethanol, propylene glycol, glycerin, or combinations thereof.

Examples of excipients also include pharmaceutically acceptable substances such as wetting agents or minor amounts of auxiliary substances such as wetting or emulsifying agents, preservatives, or buffers, which enhance the shelf life or effectiveness of the compound.

The compositions of this invention may be in a variety of forms. These include, for example, liquid, semi-solid and solid dosage forms, such as liquid solutions (e.g., injectable and infusible solutions), dispersions or suspensions, tablets, capsules, pills, powders, liposomes and suppositories. The form depends on the intended mode of administration and therapeutic application.

Typical compositions are in the form of injectable or infusible solutions, such as compositions similar to those used for passive immunization of humans with antibodies in general. One mode of administration is parenteral (e.g., intravenous, subcutaneous, intraperitoneal, intramuscular). In another embodiment, the compound is administered by intravenous infusion or injection. In yet another embodiment, the compound is administered by intramuscular or subcutaneous injection.

Oral administration of a solid dosage form may be, for example, presented in discrete units, such as hard or soft capsules, pills, cachets, lozenges, or tablets, each containing a predetermined amount of at least one compound of the invention. In another embodiment, the oral administration may be in a powder or granule form. In another embodiment, the oral dosage form is sub-lingual, such as, for example, a lozenge. In such solid dosage forms, the compounds of the invention are ordinarily combined with one or more adjuvants. Such capsules or tablets may comprise a controlled release formulation. In the case of capsules, tablets, and pills, the dosage forms also may comprise buffering agents or may be prepared with enteric coatings.

In another embodiment, oral administration may be in a liquid dosage form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as one or more of wetting, emulsifying, suspending, flavoring (e.g., sweetening), or perfuming agents.

In another embodiment, the invention comprises a parenteral dosage form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using one or more of suitable dispersing, wetting agents, or suspending agents.

In another embodiment, the invention comprises a topical dosage form. "Topical administration" includes, for example, dermal and transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical excipients include alcohol, water, mineral oil, liquid petrolatum, white petrolatum, glycerin, polyethylene glycol and propylene glycol. Penetration enhancers may be incorporated—see, for example, B. C. Finnin and T. M. Morgan, J. Pharm. Sci., vol. 88, pp. 955-958, 1999.

Formulations suitable for topical administration to the eye include, for example, eye drops wherein the compound of this invention is dissolved or suspended in a suitable excipient. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration, the compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the invention comprises a rectal dosage form. Such rectal dosage form may be in the form of, for example, a suppository. Cocoa butter is a traditional suppository base, but various alternatives may be used as appropriate.

Other excipients and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pennsylvania, 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

Acceptable excipients are nontoxic to subjects at the dosages and concentrations employed, and may comprise one or more of the following: 1) buffers such as phosphate, citrate, or other organic acids; 2) salts such as sodium chloride; 3) antioxidants such as ascorbic acid or methionine; 4) preservatives such as octadecyldimethylbenzyl ammonium chloride, hexamethonium chloride, benzalkonium chloride, benzethonium chloride, phenol, butyl or benzyl alcohol; 5) alkyl parabens such as methyl or propyl paraben, catechol, resorcinol, cyclohexanol, 3-pentanol, or m-cresol; 6) low molecular weight (less than about 10 residues) polypeptides; 7) proteins such as serum albumin, gelatin, or immunoglobulins; 8) hydrophilic polymers such as polyvinylpyrrolidone; 9) amino acids such as glycine, glutamine, asparagine, histidine, arginine, or lysine; 10) monosaccharides, disaccharides, or other carbohydrates including glucose, mannose, or dextrins; 11) chelating agents such as EDTA; 12) sugars such as sucrose, mannitol, trehalose or sorbitol; 13) salt-forming counter-ions such as sodium, metal complexes (e.g., Zn-protein complexes), or 14) non-ionic surfactants such as polysorbates (e.g., polysorbate 20 or polysorbate 80), poloxamers or polyethylene glycol (PEG).

For oral administration, the compositions may be provided in the form of tablets or capsules containing 0.01, 0.05, 0.1, 0.5, 1.0, 2.5, 5.0, 10.0, 15.0, 25.0, 50.0, 75.0, 100, 125, 150, 175, 200, 250, 500 or 1000 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Liposome containing compounds of the invention may be prepared by methods known in the art (See, for example, Chang, H. I.; Yeh, M. K.; Clinical development of liposome-based drugs: formulation, characterization, and therapeutic efficacy; Int J Nanomedicine 2012; 7; 49-60). Particularly useful liposomes may be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

Compounds of the invention may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy, 20th Ed., Mack Publishing (2000).

Sustained-release preparations may be used. Suitable examples of sustained-release preparations include semipermeable matrices of solid hydrophobic polymers containing a compound of the invention, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides, copolymers of L-glutamic acid and 7 ethyl-L-glutamate, non-degradable ethylene-vinyl acetate, degradable lactic acid-glycolic acid copolymers such as those used in leuprolide acetate for depot suspension (injectable microspheres composed of lactic acid-glycolic acid copolymer and leuprolide acetate), sucrose acetate isobutyrate, and poly-D-(−)-3-hydroxybutyric acid.

The formulations to be used for intravenous administration must be sterile. This is readily accomplished by, for example, filtration through sterile filtration membranes. Compounds of the invention are generally placed into a container having a sterile access port, for example, an intravenous solution bag or vial having a stopper pierceable by a hypodermic injection needle.

Suitable emulsions may be prepared using commercially available fat emulsions, such as a lipid emulsions comprising soybean oil, a fat emulsion for intravenous administration (e.g., comprising safflower oil, soybean oil, egg phosphatides and glycerin in water), emulsions containing soya bean oil and medium-chain triglycerides, and lipid emulsions of cottonseed oil. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion may comprise fat droplets between 0.1 and 1.0 µm, particularly 0.1 and 0.5 µm, and have a pH in the range of 5.5 to 8.0.

For example, the emulsion compositions may be those prepared by mixing a compound of the invention with a lipid emulsions comprising soybean oil or the components thereof (soybean oil, egg phospholipids, glycerol and water).

Compositions for inhalation or insufflation include solutions and suspensions in pharmaceutically acceptable aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

A drug product intermediate (DPI) is a partly processed material that must undergo further processing steps before it becomes bulk drug product. Compounds of the invention may be formulated into drug product intermediate DPI containing the active ingredient in a higher free energy form than the crystalline form. One reason to use a DPI is to improve oral absorption characteristics due to low solubility, slow dissolution, improved mass transport through the mucus layer adjacent to the epithelial cells, and in some cases, limitations due to biological barriers such as metabolism and transporters. Other reasons may include improved solid state stability and downstream manufacturability. In one embodiment, the drug product intermediate contains a compound of the invention isolated and stabilized in the amorphous state (for example, amorphous solid dispersions (ASDs)). There are many techniques known in the art to manufacture ASD's that produce material suitable for integration into a bulk drug product, for example, spray dried dispersions (SDD's), melt extrudates (often referred to as HME's), co-precipitates, amorphous drug nanoparticles, and nano-adsorbates. In one embodiment amorphous solid dispersions comprise a compound of the invention and a polymer excipient. Other excipients as well as concentrations of said excipients and the compound of the invention are well known in the art and are described in standard textbooks. See, for example, "*Amorphous Solid Dispersions Theory and Practice*" by Navnit Shah et al.

Administration and Dosing

The term "treating", "treat" or "treatment" as used herein embraces both preventative, i.e., prophylactic, and palliative treatment, i.e., relieve, alleviate, or slow the progression of the patient's disease (or condition) or any tissue damage associated with the disease.

As used herein, the terms, "subject, "individual" or "patient," used interchangeably, refer to any animal, including mammals. Mammals according to the invention include canine, feline, bovine, caprine, equine, ovine, porcine, rodents, lagomorphs, primates, humans and the like, and encompass mammals in utero. In an embodiment, humans are suitable subjects. Human subjects may be of any gender and at any stage of development.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which may include one or more of the following:

(1) preventing the disease; for example, preventing a disease, condition or disorder in an individual that may be predisposed to the disease, condition or disorder but does not yet experience or display the pathology or symptomatology of the disease;

(2) inhibiting the disease; for example, inhibiting a disease, condition or disorder in an individual that is experiencing or displaying the pathology or symptomatology of the disease, condition or disorder (i.e., arresting (or slowing) further development of the pathology or symptomatology or both); and (3) ameliorating the disease; for example, ameliorating a disease, condition or disorder in an individual that is experiencing or displaying the pathology or symptomatology of the disease, condition or disorder (i.e., reversing the pathology or symptomatology or both).

Typically, a compound of the invention is administered in an amount effective to treat a condition as described herein. The compounds of the invention may be administered as compound per se, or alternatively, as a pharmaceutically acceptable salt. For administration and dosing purposes, the compound per se or pharmaceutically acceptable salt thereof will simply be referred to as the compounds of the invention.

The compounds of the invention are administered by any suitable route in the form of a pharmaceutical composition adapted to such a route, and in a dose effective for the treatment intended. The compounds of the invention may be administered orally, rectally, vaginally, parenterally, topically, intranasally, or by inhalation.

The compounds of the invention may be administered orally. Oral administration may involve swallowing, so that the compound enters the gastrointestinal tract, or buccal or sublingual administration may be employed by which the compound enters the bloodstream directly from the mouth.

In another embodiment, the compounds of the invention may also be administered parenterally, for example directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors, and infusion techniques.

In another embodiment, the compounds of the invention may also be administered topically to the skin or mucosa, that is, dermally or transdermally. In another embodiment, the compounds of the invention may also be administered intranasally or by inhalation. In another embodiment, the compounds of the invention may be administered rectally or vaginally. In another embodiment, the compounds of the invention may also be administered directly to the eye or ear.

The dosage regimen for the compounds of the invention or compositions containing said compounds is based on a variety of factors, including the type, age, weight, sex and medical condition of the patient; the severity of the condition; the route of administration; and the activity of the particular compound employed. Thus, the dosage regimen may vary widely. In one embodiment, the total daily dose of a compound of the invention is typically from about 0.01 to about 100 mg/kg (i.e., mg compound of the invention per kg body weight) for the treatment of the indicated conditions discussed herein. In another embodiment, total daily dose of the compound of the invention is from about 0.1 to about 50 mg/kg, and in another embodiment, from about 0.5 to about 30 mg/kg. It is not uncommon that the administration of the compounds of the invention will be repeated a plurality of times in a day (typically no greater than 4 times). Multiple doses per day typically may be used to increase the total daily dose, if desired.

Therapeutic Methods and Uses

The compounds of the invention may inhibit the activities of one or more KRAS G12C, KRAS G12D, and KRAS G12V receptors, and may be useful in the treatment, prevention, suppression, and amelioration of diseases such as cancers, disorders and conditions mediated by any of KRAS G12C, KRAS G12D, and KRAS G12V receptors, or a combination thereof.

Cancers to be treated include squamous cell carcinoma, basal cell carcinomas, myeloma, small-cell lung cancer, non-small cell lung cancer, glioma, Hodgkin's lymphoma, non-Hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, uterine cancer, bladder cancer, including non-muscular invasive bladder cancer, hepatoma, breast cancer, and head and neck cancer.

Preferably, the compounds of the present invention may be useful for the treatment of lung cancers such as non-small cell lung cancer (NSCLC), pancreatic cancer, colorectal cancer, breast cancer, blood cancers, gynecological cancers, prostate cancer, or skin cancer. See Mustachio, L., Targeting KRAS in Cancer Promising Therapeutic Strategies, Cancers, 2021, 13, 1204.

More preferably, the compounds of the present invention may be useful for the treatment of non-small cell lung cancer (NSCLC), pancreatic cancer, and colorectal cancer.

Co-Administration

The compounds of the invention may be used alone, or in combination with one or more other therapeutic agents. The invention provides any of the uses, methods or compositions as defined herein wherein the compound of the invention, or pharmaceutically acceptable salt thereof, is used in combination with one or more other therapeutic anticancer agent discussed herein.

The administration of two or more compounds "in combination" means that all of the compounds are administered closely enough in time to affect treatment of the subject. The two or more compounds may be administered simultaneously or sequentially, via the same or different routes of administration, on same or different administration schedules and with or without specific time limits depending on the treatment regimen. Additionally, simultaneous administration may be carried out by mixing the compounds prior to administration or by administering the compounds at the same point in time but as separate dosage forms at the same or different site of administration. Examples of "in combination" include, but are not limited to, "concurrent administration," "co-administration," "simultaneous administration," "sequential administration" and "administered simultaneously".

A compound of the invention and the one or more other therapeutic agents may be administered as a fixed or non-fixed combination of the active ingredients. The term "fixed combination" means a compound of the invention, or a pharmaceutically acceptable salt thereof, and the one or more therapeutic agents, are both administered to a subject simultaneously in a single composition or dosage. The term "non-fixed combination" means that a compound of the invention, or a pharmaceutically acceptable salt thereof, and the one or more therapeutic agents are formulated as separate compositions or dosages such that they may be administered to a subject in need thereof simultaneously or at different times with variable intervening time limits, wherein such administration provides effective levels of the two or more compounds in the body of the subject.

Classes of additional chemotherapeutic agents, which can be administered in combination with a compound of this invention, include, but are not limited to: alkylating agents, antimetabolites, kinase inhibitors, spindle poison plant alkaloids, cytotoxic/antitumor antibiotics, topoisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists; IL-2 receptor agonist (recombinant cytokines or agonists for cytokine receptors); and anti-sense oligonucleotides or oligonucleotides derivatives that inhibit expression of genes implicated in abnormal cell proliferation or tumor growth.

Other additional chemotherapy agents include not only taxanes or platinum agents but also HER2 targeted agents, e.g., trastuzumab.

In another embodiment, such additional anti-cancer therapeutic agents include compounds derived from the following classes: mitotic inhibitors, alkylating agents, antimetabolites, antitumor antibiotics, anti-angiogenesis agents, topoisomerase I and II inhibitors, plant alkaloids, spindle poison plant alkaloids, MCT4 inhibitors; MAT2a inhibitors; alk/c-Met/ROS inhibitors (including crizotinib or lorlatinib); mTOR inhibitors (including temsirolimus or gedatolisib); src/abl inhibitors (including bosutinib); cyclin-dependent kinase (CDK) inhibitors (including palbociclib, PF-06873600); erb inhibitors (including dacomitinib); PARP inhibitors (including talazoparib); SMO inhibitors (including glasdegib); EGFR T790M inhibitors; PRMT5 inhibitors; TGFβR1 inhibitors; growth factor inhibitors; cell cycle inhibitors, biological response modifiers; enzyme inhibitors; and cytotoxics.

In another embodiment, such additional anti-cancer therapeutic agents include compounds derived from an anti-angiogenesis agent, including for example tyrosine kinase/vascular endothelial growth factor (VEGF) receptor (VEGFR) inhibitors (including sunitinib, axitinib, sorafenib, and tivozanib), TIE-2 inhibitors, PDGFR inhibitors, angiopoietin inhibitors, PKCβ inhibitors, COX-2 (cyclooxygenase II) inhibitors, integrins (alpha-v/beta-3), MMP-2 (matrix-metalloproteinase 2) inhibitors, and MMP-9 (matrix-metalloproteinase 9) inhibitors. Preferred anti-angiogenesis agents include sunitinib (Sutent™), bevacizumab (Avastin™), axitinib (Inlyta™), SU 14813 (Pfizer), and AG 13958 (Pfizer). Additional anti-angiogenesis agents include vatalanib (CGP 79787), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™ (AE 941), tetrathiomolybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer). Other anti-angiogenesis agents include enzastaurin (LY 317615), midostaurin (CGP 41251), perifosine (KRX 0401), teprenone (Selbex™) and UCN 01 (Kyowa Hakko). Other examples of anti-angiogenesis agents include celecoxib (Celebrex™), parecoxib (Dynastat™), deracoxib (SC 59046), lumiracoxib (Preige™), valdecoxib (Bextra™), rofecoxib (Vioxx™), iguratimod (Careram™), IP 751 (Invedus), SC-58125 (Pharmacia) and etoricoxib (Arcoxia™). Yet further anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™, Naprosyn™), diclofenac (Voltaren™), indomethacin (Indocin™), sulindac (Clinoril™), tolmetin (Tolectin™), etodolac (Lodine™), ketorolac (Toradol™), and oxaprozin (Daypro™). Yet further anti-angiogenesis agents include ABT 510 (Abbott), apratastat (TMI 005), AZD 8955 (AstraZeneca), incyclinide (Metastat™), and PCK 3145 (Procyon). Yet further anti-angiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™), squalamine (EVIZON™), thalidomide (Thalomid™), Ukrain™ (NSC 631570), Vitaxin™ (MEDI 522), and zoledronic acid (Zometa™).

In another embodiment, such additional anti-cancer therapeutic agents include compounds derived from hormonal agents and antagonists. Examples include where anti-hormonal agents act to regulate or inhibit hormone action on tumors such as anti-estrogens and selective estrogen receptor modulators (SERMs), and a selective estrogen receptor degrader (SERD) including tamoxifen, raloxifene, droloxifene, 4-hydroxytamoxifen, trioxifene, keoxifene, LY117018, onapristone, toremifene (Fareston), and fulvestrant. Examples also include aromatase inhibitors that inhibit the enzyme aromatase, which regulates estrogen production in the adrenal glands, and include compounds like 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, fluridil, apalutamide, enzalutamide, cimetidine and goserelin.

In another embodiment, such additional anti-cancer therapeutic agents include compounds derived from signal transduction inhibitors, such as inhibitors of protein tyrosine kinases and/or serine/threonine kinases: a signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EGF inhibitor, ErbB-1 (EGFR), ErbB-2, pan erb, IGF1R inhibitors, MEK (including binimetinib (Mektovi™)), c-Kit inhibitors, FLT-3 inhibitors, K-Ras inhibitors, PI3 kinase inhibitors, JAK inhibitors, STAT inhibitors, Raf kinase inhibitors, BRAF (including encorafenib (Braftovi™)), Akt inhibitors, mTOR inhibitor, P70S6 kinase inhibitors, inhibitors of the WNT pathway and multi-targeted kinase inhibitors.

In another embodiment, such additional anti-cancer therapeutic agents include docetaxel, paclitaxel, paclitaxel protein-bound particles, cisplatin, carboplatin, oxaliplatin, capecitabine, gemcitabine or vinorelbine.

In another embodiment, such additional anti-cancer therapeutic agents include compounds derived from an epigenetic modulator, where examples include an inhibitor of EZH2 (including PF-06821497), SMARCA4, PBRM1, ARID1A, ARID2, ARID1B, DNMT3A, TET2, MLL1/2/3, NSD1/2, SETD2, BRD4, DOT1L, HKMTsanti, PRMT1-9, LSD1, UTX, IDH1/2 or BCL6.

In another embodiment, such additional anti-cancer therapeutic agents include compounds that are immuno-oncology agents, including immunomodulatory agents.

In another embodiment, combinations with pattern recognition receptors (PRRs) are contemplated. PRRs are receptors that are expressed by cells of the immune system and that recognize a variety of molecules associated with pathogens and/or cell damage or death. PRRs are involved in both the innate immune response and the adaptive immune response. PRR agonists may be used to stimulate the immune response in a subject. There are multiple classes of PRR molecules, including toll-like receptors (TLRs), RIG-I-like receptors (RLRs), nucleotide-binding oligomerization domain (NOD)-like receptors (NLRs), C-type lectin receptors (CLRs), and Stimulator of Interferon Genes (STING) protein.

The STING protein functions as both a cytosolic DNA sensor and an adaptor protein in Type 1 interferon signaling. The terms "STING" and "stimulator of interferon genes" refer to any form of the STING protein, as well as variants, isoforms, and species homologs that retain at least a part of the activity of STING. Unless indicated differently, such as by specific reference to human STING, STING includes all mammalian species of native sequence STING, e.g. human, monkey, and mouse STING is also known as—TMEM173.

"STING agonist" as used herein means, any molecule, which upon binding to STING, (1) stimulates or activates STING, (2) enhances, increases, promotes, induces, or prolongs an activity, function, or presence of STING, or (3) enhances, increases, promotes, or induces the expression of STING. STING agonists useful in the any of the treatment method, medicaments and uses of the present invention include, for example, nucleic acid ligands which bind STING.

Examples of STING agonists that are useful in the treatment methods, medicaments, and uses of the present invention include various immunostimulatory nucleic acids, such as synthetic double stranded DNA, cyclic di-GMP, cyclic-GMP-AMP (cGAMP), synthetic cyclic dinucleotides (CDN) such as MK-1454 and ADU-S100 (MIW815), and small molecules such as WO2019027858, WO20180093964, WO2017175156, WO2017175147.

Therapeutic antibodies may have specificity against a variety of different antigens. For example, therapeutic antibodies may be directed to a tumor associated-antigen, such that binding of the antibody to the antigen promotes death of the cell expressing the antigen. In other example, therapeutic antibodies may be directed to an antigen on an immune cell, such that binding of the antibody prevents downregulation of the activity of the cell expressing the antigen (and thereby promotes activity of the cell expressing the antigen). In some situations, a therapeutic antibody may function through multiple different mechanisms (for example, it may both i) promote death of the cell expressing the antigen, and ii) prevent the antigen from causing down-regulation of the activity of immune cells in contact with the cell expressing the antigen).

In another embodiment, such additional anti-cancer therapeutic agents include antibodies that would be blocking or inhibitory at the target: CTLA-4 (including ipilimumab or tremelimumab), PD-1 or PD-L1 (including atezolizumab, avelumab, cemiplimab, durvalumab, nivolumab, sasanlimab, or pembrolizumab), LAG-3, TIM-3, or TIGIT.

In another embodiment, such additional anti-cancer therapeutic agents include antibodies that are agonists of 4-1BB, OX40, GITR, ICOS, or CD40.

In another embodiment the anti-cancer therapy may be a CAR-T-cell therapy.

Examples of a therapeutic antibody include: an anti-OX40 antibody, an anti-4-1BB antibody, an anti-HER2 antibody (including an anti-HER2 antibody-drug conjugate (ADC)), a bispecific anti-CD47/anti-PD-L1 antibody, and a bispecific anti-P-cadherin/anti-CD3 antibody. Examples of cytotoxic agents that may be incorporated in an ADC include an anthracycline, an auristatin, a dolastatin, a combretastatin, a duocarmycin, a pyrrolobenzodiazepine dimer, an indolinobenzodiazepine dimer, an enediyne, a geldanamycin, a maytansine, a puromycin, a taxane, a vinca alkaloid, a camptothecin, a tubulysin, a hemiasterlin, a spliceostatin, a pladienolide, and stereoisomers, isosteres, analogs, or derivatives thereof. Exemplary immunomodulating agents that may be incorporated in an ADC include gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, cytokines, stem cell growth factors, lymphotoxins, tumor necrosis factor (TNF), hematopoietic factors, interleukins (e.g., interleukin-1 (IL-1), IL-2, IL-3, IL-6, IL-10, IL-12, IL-15, IL-18, and IL-21), colony stimulating factors (e.g., granulocyte-colony stimulating factor (G-CSF) and granulocyte macrophage-colony stimulating factor (GM-CSF)), interferons (e.g., interferons-.alpha., -.beta. and -.gamma.), the stem cell growth factor designated "S 1 factor," erythropoietin and thrombopoietin, or a combination thereof.

Additional examples of therapeutic antibodies may include the following antigens where exemplary antibodies directed to the antigen are also included below (in brackets/parenthesis after the antigen). The antigens as follow may also be referred to as "target antigens" or the like herein. Target antigens for therapeutic antibodies herein include, for example: 4-1BB (e.g. utomilumab); 5T4; A33; alpha-folate receptor 1 (e.g. mirvetuximab soravtansine); Alk-1; BCMA [e.g. see U.S. Pat. No. 9,969,809]; BTN1A1 (e.g. see WO2018222689); CA-125 (e.g. abagovomab); Carboanhydrase IX; CCR2; CCR4 (e.g. mogamulizumab); CCR5 (e.g. leronlimab); CCR8; CD3 [e.g. blinatumomab (CD3/CD19 bispecific), CD3/P-cadherin bispecific, CD3/BCMA bispecific] CD19 (e.g. blinatumomab, MOR208); CD20 (e.g. ibritumomab tiuxetan, obinutuzumab, ofatumumab, rituximab, ublituximab); CD22 (inotuzumab ozogamicin, moxetumomab pasudotox); CD25; CD28; CD30 (e.g. brentuximab vedotin); CD33 (e.g. gemtuzumab ozogamicin); CD38 (e.g. daratumumab, isatuximab), CD40; CD-40L; CD44v6; CD47 (e.g. Hu5F9-G4, CC-90002, SRF231, B6H12); CD52 (e.g. alemtuzumab); CD56; CD63; CD79 (e.g. polatuzumab vedotin); CD80; CD123; CD276/B7-H3 (e.g. omburtamab); CDH17; CEA; CIhCG; CTLA-4 (e.g. ipilimumab, tremelimumab), CXCR4; desmoglein 4; DLL3 (e.g. rovalpituzumab tesirine); DLL4; E-cadherin; EDA; EDB; EFNA4; EGFR (e.g. cetuximab, depatuxizumab mafodotin, necitumumab, panitumumab); EGFRvIII; Endosialin; EpCAM (e.g. oportuzumab monatox); FAP; Fetal Acetylcholine Receptor; FLT3 (e.g. see WO2018/220584); GD2 (e.g. dinutuximab, 3F8); GD3; GITR; GloboH; GM1; GM2; HER2/neu [e.g. margetuximab, pertuzumab, trastuzumab; ado-trastuzumab emtansine, trastuzumab duocarmazine, [see U.S. Pat. No. 8,828,401]; HER3; HER4; ICOS; IL-10; ITG-AvB6; LAG-3 (e.g. relatlimab); Lewis-Y; LG; Ly-6; M-CSF [see U.S. Pat. No. 7,326,414]; MCSP; mesothelin; MUC1; MUC2; MUC3; MUC4; MUC5AC; MUC5B; MUC7; MUC16; Notch1; Notch3; Nectin-4 (e.g. enfortumab vedotin); OX40 [see U.S. Pat. No. 7,960,515]; P-Cadherin [see WO2016/001810]; PCDHB2; PDGFRA (e.g. olaratumab); Plasma Cell Antigen; PolySA; PSCA; PSMA; PTK7 [see U.S. Pat. No. 9,409,995]; Ror1; SAS; SCRx6; SLAMF7 (e.g. elotuzumab); SHH; SIRPa (e.g. ED9, EffiDEM); STEAP; TGF-beta; TIGIT; TIM-3; TMPRSS3; TNF-alpha precursor; TROP-2 (e.g sacituzumab govitecan); TSPAN8; VEGF (e.g. bevacizumab, brolucizumab); VEGFR1 (e.g. ranibizumab); VEGFR2 (e.g. ramucirumab, ranibizumab); Wue-1.

Exemplary imaging agents that may be included in an ADC include fluorescein, rhodamine, lanthanide phosphors, and their derivatives thereof, or a radioisotope bound to a chelator. Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5,-TAMRA), tetramethylrhodamine (TMR), and sulforhodamine (SR) (e.g., SR101). Examples of chelators include, but are not limited to, 1,4,7,10-tetraazacyclododecane-N,N',N",N'"-tetraacetic acid (DOTA), 1,4,7-triazacyclononane-1,4,7-triacetic acid (NOTA), 1,4,7-triazacyclononane, 1-glutaric acid-4,7-acetic acid (deferoxamine), diethylenetriaminepentaacetic acid (DTPA), and 1,2-bis(o-aminophenoxy)ethane-N,N,N',N'-tetraacetic acid) (BAPTA).

Exemplary therapeutic proteins that may be included in an ADC include a toxin, a hormone, an enzyme, and a growth factor.

Exemplary biocompatible polymers that may be incorporated in an ADC include water-soluble polymers, such as polyethylene glycol (PEG) or its derivatives thereof and zwitterion-containing biocompatible polymers (e.g., a phosphorylcholine containing polymer).

Exemplary biocompatible polymers that may be incorporated in an ADC include anti-sense oligonucleotides.

The invention also concerns the use of radiation in combination with any anti-cancer therapeutic agent administered herein. More specifically, compounds of the invention can be administered in combination with additional therapies, such as radiation therapy and/or chemotherapy.

These agents and compounds of the invention may be combined with pharmaceutically acceptable vehicles such as saline, Ringer's solution, dextrose solution, and the like. The particular dosage regimen, i.e., dose, timing and repetition, will depend on the particular individual and that individual's medical history.

Kits

Another aspect of the invention provides kits comprising the compound of the invention or pharmaceutical compositions comprising the compound of the invention. A kit may include, in addition to the compound of the invention or pharmaceutical composition thereof, diagnostic or therapeutic agents. A kit may also include instructions for use in a diagnostic or therapeutic method. In some embodiments, the kit includes the compound or a pharmaceutical composition thereof and a diagnostic agent. In other embodiments, the kit includes the compound or a pharmaceutical composition thereof and one or more therapeutic agents.

In yet another embodiment, the invention comprises kits that are suitable for use in performing the methods of treatment described herein. In one embodiment, the kit contains a first dosage form comprising one or more of the compounds of the invention in quantities sufficient to carry out the methods of the invention. In another embodiment, the kit comprises one or more compounds of the invention in quantities sufficient to carry out the methods of the invention and a container for the dosage and a container for the dosage.

Synthetic Methods

Compounds of the present invention may be synthesized by synthetic routes that include processes analogous to those well-known in the chemical arts, particularly in light of the description contained herein. The starting materials are generally available from commercial sources or may be prepared using methods well known to those skilled in the art. Many of the compounds used herein, are related to, or may be derived from compounds in which one or more of the scientific interest or commercial need has occurred. Accordingly, such compounds may be one or more of 1) commercially available; 2) reported in the literature or 3) prepared from other commonly available substances by one skilled in the art using materials which have been reported in the literature.

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are discussed below, other starting materials and reagents may be substituted to provide one or more of a variety of derivatives or reaction conditions. In addition, many of the compounds prepared by the methods described below may be further modified in light of this disclosure using conventional chemistry well known to those skilled in the art.

The skilled person will appreciate that the experimental conditions set forth in the schemes that follow are illustrative of suitable conditions for effecting the transformations shown, and that it may be necessary or desirable to vary the precise conditions employed for the preparation of compounds of the invention. It will be further appreciated that it may be necessary or desirable to carry out the transformations in a different order from that described in the schemes, or to modify one or more of the transformations, to provide the desired compound of the invention.

In the preparation of compounds of the invention it is noted that some of the preparation methods useful for the preparation of the compounds described herein may require protection of remote functionality (e.g., a primary amine, secondary amine, carboxyl, etc. in a precursor of a compound of the invention). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see March's Advanced Organic Chemistry: Reactions, Mechanisms, and Structure 8th Edition.

For example, if a compound contains an amine or carboxylic acid functionality, such functionality may interfere with reactions at other sites of the molecule if left unprotected. Accordingly, such functionalities may be protected by an appropriate protecting group (PG) which may be removed in a subsequent step. Suitable protecting groups for amine and carboxylic acid protection include those protecting groups commonly used in peptide synthesis (such as N-tert-butoxycarbonyl (Boc), benzyloxycarbonyl (Cbz), and 9-fluorenylmethylenoxycarbonyl (Fmoc) for amines and lower alkyl or benzyl esters for carboxylic acids) which are generally not chemically reactive under the reaction conditions described and may typically be removed without chemically altering other functionality in a compound of the invention.

General Experimental Details $^1$H and $^{19}$F Nuclear Magnetic Resonance (NMR) spectra were recorded on Bruker XWIN-NMR (400 or 700 MHz) spectrometer. $^1$H and $^{19}$F resonances are reported in parts per million (ppm) downfield from tetramethylsilane. $^1$H NMR data are reported as multiplicity (e.g. s, singlet; d, doublet; t, triplet; q, quartet; quint, quintuplet; dd, doublet of doublets; dt, doublet of triplets; br s, broad singlet). For spectra obtained in CDCl$_3$, DMSO-d$_6$, and CD$_3$OD, the residual protons (7.27, 2.50, and 3.31 ppm, respectively) were used as the internal reference. All observed coupling constants, J, are reported in Hertz (Hz). Exchangeable protons are not always observed.

Optical rotations were determined on a Jasco P-2000 or a RUDOLPH AUTOPOL® IV polarimeter. All final compounds were purified to ≥95% purity, unless otherwise specified. When absolute stereochemistry is not known, the software-generated names are modified to include (+)- and (−)-prefixes according to the optical rotations, and (R*/S*) labels are used to show relative configuration.

Mass spectra, MS (m/z), were recorded using either electrospray ionization (ESI) or atmospheric pressure chemical ionization (APCI). Where relevant and unless otherwise stated, the m/z data provided are for isotopes $^{19}$F, $^{35}$Cl, $^{79}$Br and $^{127}$I.

The nomenclature is written as described by IUPAC (International Union of Pure and Applied Chemistry generated within Perkin Elmers CHEMDRAW® 18.0.0.231. The naming convention provided with Perkin Elmers CHEMDRAW® 18.0.0.231 is well known by those skilled in the art and it is believed that the naming convention provided with Perkin Elmers CHEMDRAW® 18.0.0.231 generally comports with the IUPAC (International Union for Pure and Applied Chemistry) recommendations on Nomenclature of Organic Chemistry and the CAS Index rules.

Abbreviations

CH3CN is acetonitrile,
aq is aqueous;
Bn is benzyl;
Boc is tert-butoxycarbonyl;
Boc$_2$O is di-tert-butyl dicarbonate;
br is broad;

tBu is tert-butyl;
° C. is degrees celcius;
CDCl₃ is deutero-chloroform;
δ is chemical shift;
d is doublet;
dd is doublet of doublets;
ddd is doublet of doublet of doublets;
dt is doublet of triplets;
DCM is dichloromethane; methylene chloride;
DHP is dihydropyran,
DIPEA is N-ethyldiisopropylamine, also known as N,N-diisopropylethylamine;
DMAP is 4-dimethylaminopyridine;
DMF is N,N-dimethylformamide;
DMSO is dimethyl sulfoxide;
DMSO-d₆ is deuterodimethylsulfoxide;
EA is Ethyl Acetate,
ee is enantiomeric excess;
ESI is electrospray ionization;
Et₂O is diethyl ether;
EtOAc is ethyl acetate;
EtOH is ethanol;
Et₃N is triethylamine;
g is gram;
HPLC is high pressure liquid chromatography;
hr(s) is hour(s);
L is liter;
LCMS is liquid chromatography mass spectrometry;
m is multiplet;
M is molar;
m-CPBA is 3-chloroperbenzoic acid;
MeOD_d₄ is deuterated methanol;
MeOH is methanol;
2-MeTHF is 2-methyl tetrahydrofuran;
mg is milligram;
MHz is mega Hertz;
min(s) is minute(s);
mL is milliliter;
mmol is millimole;
mol is mole;
MOM is methoxymethyl ether group;
MS (m/z) is mass spectrum peak;
NMR is nuclear magnetic resonance;
Pd/C is palladium on carbon;
Pd(dppf)Cl₂ is [1,1'-bis(diphenylphosphino)ferrocene]dichloropalladium(II);
PE is petroleum-ether
pH is power of hydrogen;
ppm is parts per million;
psi is pounds per square inch;
q is quartet;
rpm is revolutions per minute;
rt is room temperature;
RT is retention time;
RuPhos Pd G3 is (2-dicyclohexylphosphino-2',6'-diisopropoxy-1,1'-biphenyl)[2-(2'-amino-1,1'-biphenyl)]palladium(II) methanesulfonate (CAS Number 1445085-77-7);
s is singlet;
SEMCl is 2-(trimethylsilyl)ethoxymethyl chloride;
SEM is 2-(trimethylsilyl)ethoxymethyl;
SFC is supercritical fluid chromatography;
t is triplet;
TBAF is tert-butyl ammonium fluoride;
TFA is trifluoroacetic acid;
THF is tetrahydrofuran;
THP is tetrahydropyran,
TLC is thin layer chromatography;
TMSCN is trimethylsilyl cyanide;
TsOH is p-toluenesulfonic acid
TsCl is p-toluenesulfonyl chloride;
μL is microliter; and
μmol is micromole.

The schemes described below are intended to provide a general description of the methodology employed in the preparation of the compounds of the present invention. Some of the compounds of the present invention contain a single chiral center. In the following schemes, the general methods for the preparation of the compounds are shown either in racemic or enantioenriched form. It will be apparent to one skilled in the art that all of the synthetic transformations may be conducted in a precisely similar manner whether the materials are enantioenriched or racemic. Moreover, the resolution to the desired optically active material may take place at any desired point in the sequence using well known methods such as described herein and in the chemistry literature.

General Methods

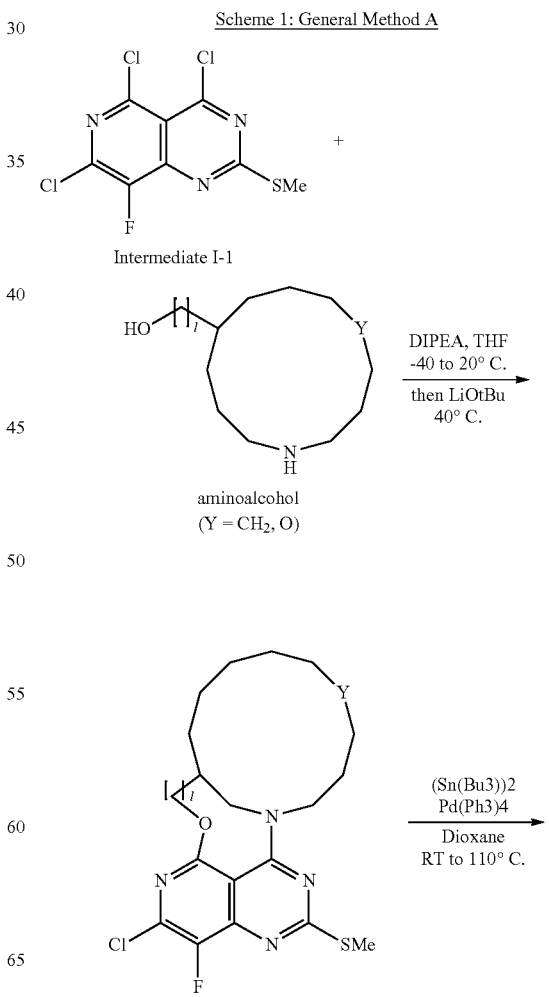

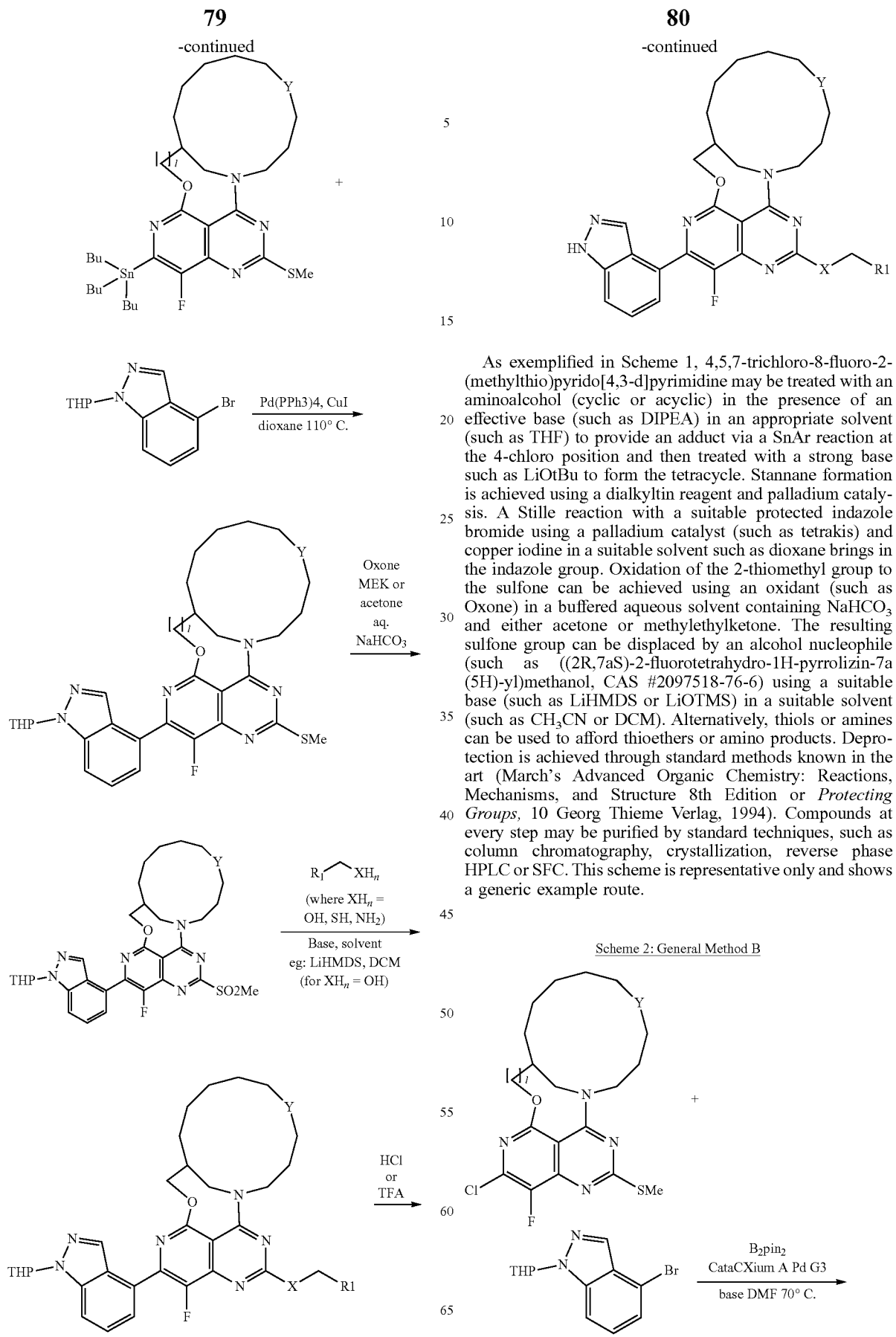

As exemplified in Scheme 1, 4,5,7-trichloro-8-fluoro-2-(methylthio)pyrido[4,3-d]pyrimidine may be treated with an aminoalcohol (cyclic or acyclic) in the presence of an effective base (such as DIPEA) in an appropriate solvent (such as THF) to provide an adduct via a SnAr reaction at the 4-chloro position and then treated with a strong base such as LiOtBu to form the tetracycle. Stannane formation is achieved using a dialkyltin reagent and palladium catalysis. A Stille reaction with a suitable protected indazole bromide using a palladium catalyst (such as tetrakis) and copper iodine in a suitable solvent such as dioxane brings in the indazole group. Oxidation of the 2-thiomethyl group to the sulfone can be achieved using an oxidant (such as Oxone) in a buffered aqueous solvent containing $NaHCO_3$ and either acetone or methylethylketone. The resulting sulfone group can be displaced by an alcohol nucleophile (such as ((2R,7aS)-2-fluorotetrahydro-1H-pyrrolizin-7a(5H)-yl)methanol, CAS #2097518-76-6) using a suitable base (such as LiHMDS or LiOTMS) in a suitable solvent (such as $CH_3CN$ or DCM). Alternatively, thiols or amines can be used to afford thioethers or amino products. Deprotection is achieved through standard methods known in the art (March's Advanced Organic Chemistry: Reactions, Mechanisms, and Structure 8th Edition or *Protecting Groups,* 10 Georg Thieme Verlag, 1994). Compounds at every step may be purified by standard techniques, such as column chromatography, crystallization, reverse phase HPLC or SFC. This scheme is representative only and shows a generic example route.

Scheme 2: General Method B

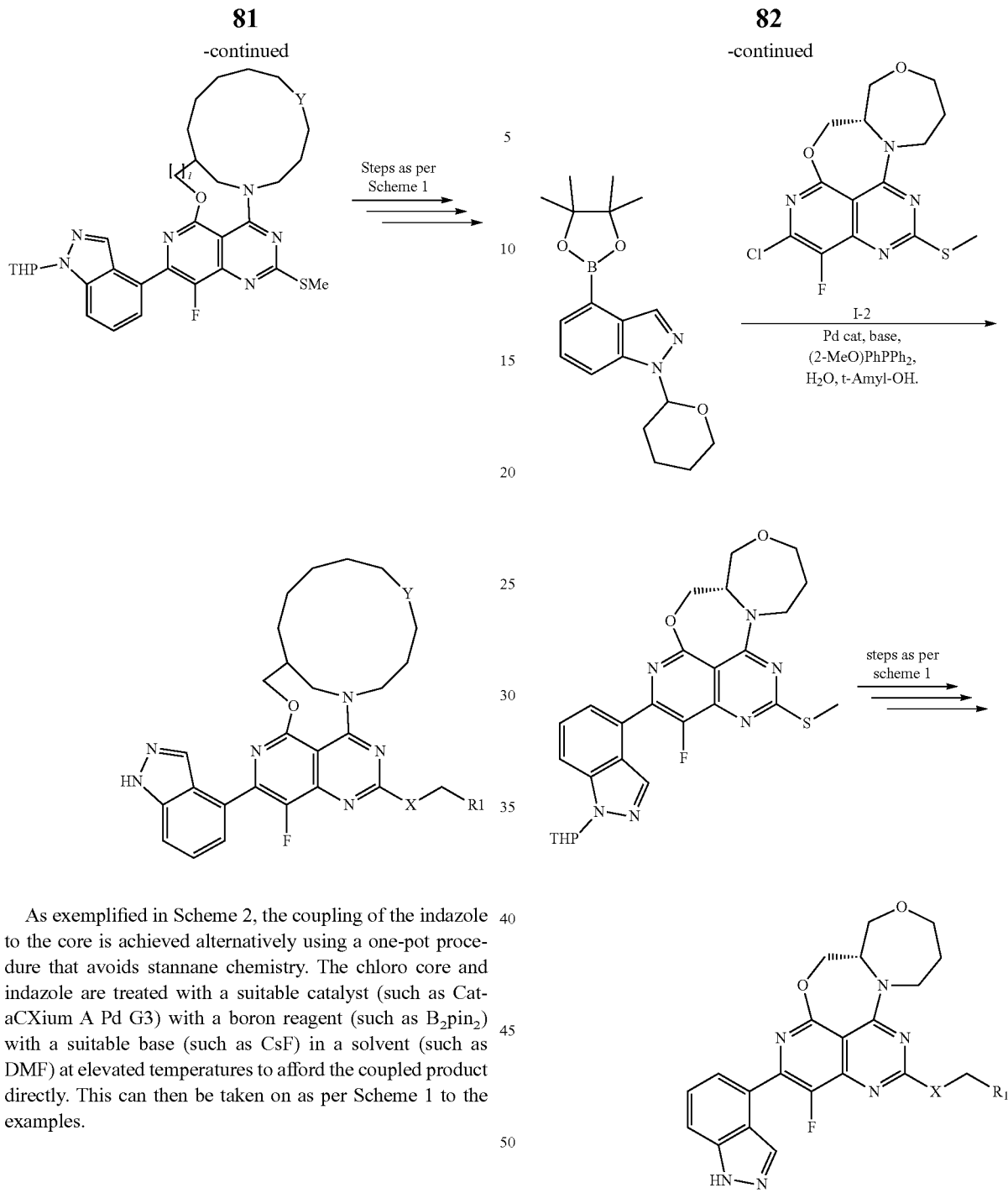

As exemplified in Scheme 2, the coupling of the indazole to the core is achieved alternatively using a one-pot procedure that avoids stannane chemistry. The chloro core and indazole are treated with a suitable catalyst (such as Cat-aCXium A Pd G3) with a boron reagent (such as B₂pin₂) with a suitable base (such as CsF) in a solvent (such as DMF) at elevated temperatures to afford the coupled product directly. This can then be taken on as per Scheme 1 to the examples.

As exemplified in Scheme 3, the coupling of an indazole to the tetracyclic core is achieved alternatively using Suzuki methodology. Conversion of an aryl bromide to the boronate ester is achieved under standard conditions known in the art, such as treatment with B₂Pin₂ with a palladium catalyst (such as palladium acetate) with a base (such as potassium phosphate) with additional phosphine ligand (such as triphenylphosphine) in a suitable solvent (such as tert-amyl alcohol). Coupling of the boronate ester to the chloro-tetracycle is achieved using a palladium catalyst with a phosphine ligand and a suitable base in a suitable solvent with water. The resulting intermediate can then be taken on to the corresponding examples as detailed per Scheme 1.

Scheme 3: General Method C

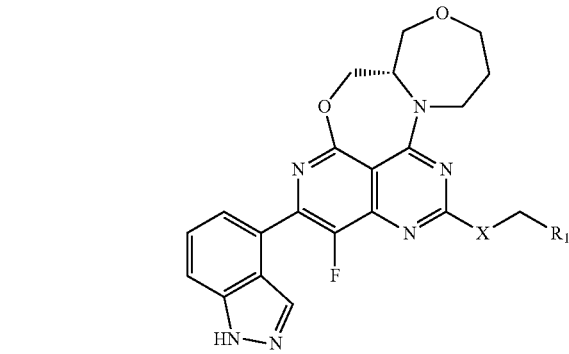

Scheme 4: General Method D

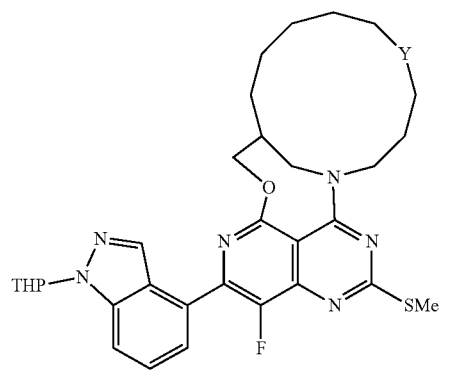

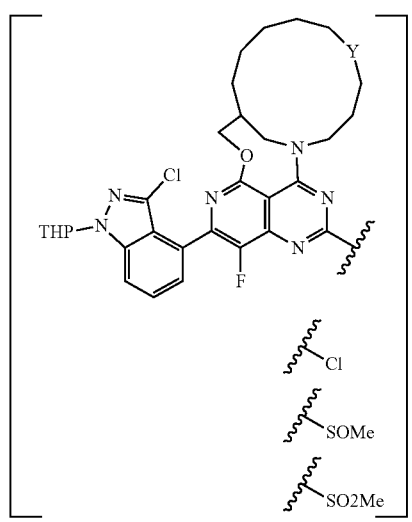

As exemplified in Scheme 4, treatment of the indazole intermediate with a chlorinating oxidant (such as N-chloro succinimide, NCS) affords the 3-chloro indazole derivative as a mixture of oxidized thioether and 2-chloro core products. This crude mixture can then be taken on as per Scheme 1 to the examples through SnAr and deprotection as described.

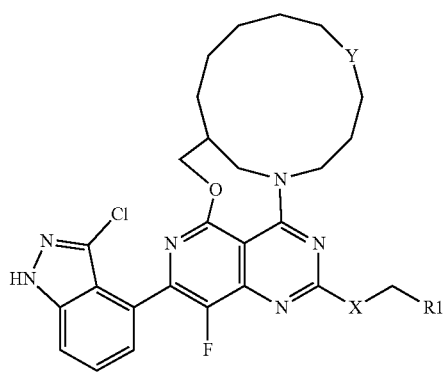

Scheme 5: General Method E

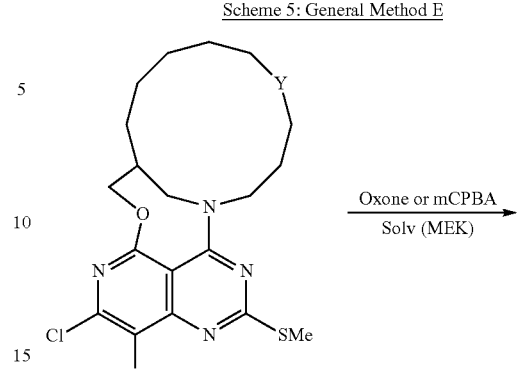

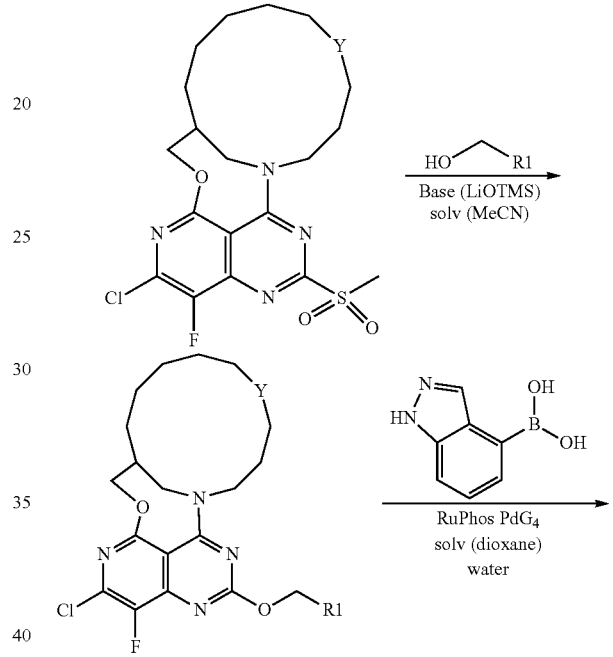

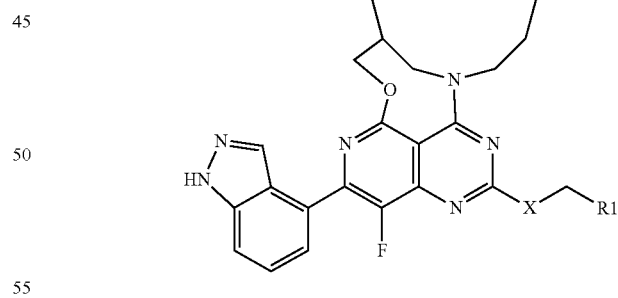

As exemplified in Scheme 5, oxidation of the thioether with either Oxone or mCPBA afforded the sulphone which was then treated with a nucleophile (alcohol) and a suitable base (such as LIOTMS) in a solvent (such as acetonitrile) to afford the adduct via a SnAr reaction. Subsequent coupling of an indazole boronic acid or boronate was achieved through Suzuki chemistry via palladium catalysis under conditions known in the art.

Variables and substituents in Scheme 1, Scheme 2, Scheme 3, Scheme 4 and Scheme 5 are the same as defined in Formula (I), (II) and (III) embodiments herein.

The synthetic intermediates as generally defined in the above schemes are useful for preparing compounds of the invention and synthesis of such non-commercial intermediates are provided as further aspects of this invention.

Synthesis of Intermediates:

Intermediate 1 (I-1): 4,5,7-trichloro-4-fluoro-2-(methylthio)pyrido[4,3-d]pyrimidine

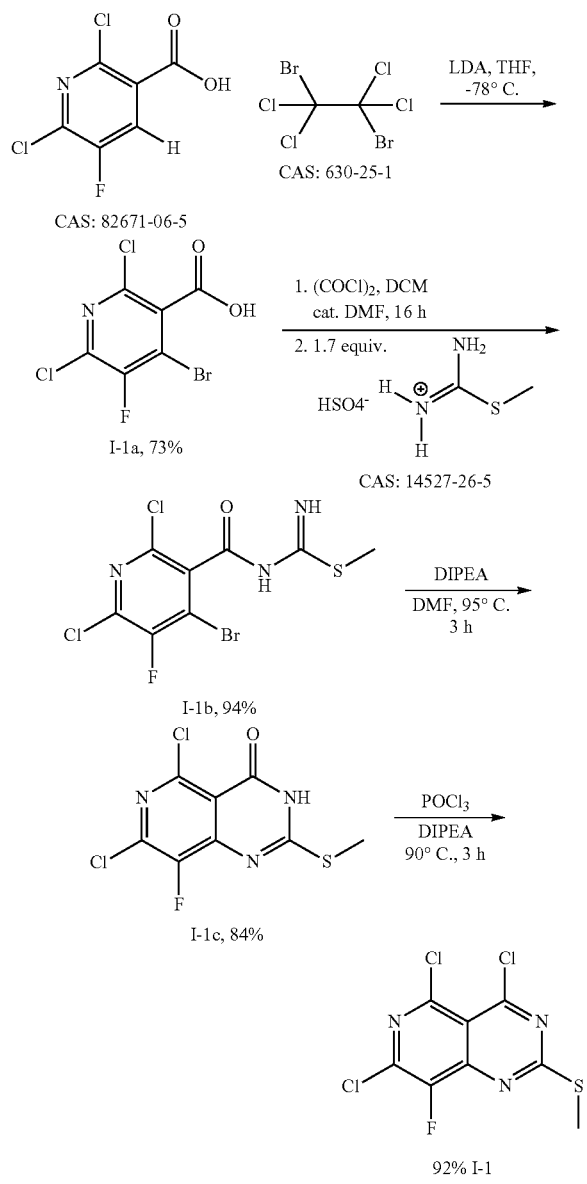

Step 1: Synthesis of 4-bromo-2,6-dichloro-5-fluoropyridine-3-carboxylic Acid, I-1a Diisopropyl amine (44.1 mL, 314 mmol) was dissolved in THF (300 mL) and the solution cooled to −78° C. n-BuLi (114 mL of 2.5 M in hexanes, 286 mmol) was added over 15 min. The mixture was stirred for 45 min. and 2,6-dichloro-5-fluoropyridine-3-carboxylic acid (CAS: 82671-06-5, 30 g, 143 mmol) was added as a solution in THF (75 mL) over 6 min. The mixture was stirred for 30 min at −78° C. 1,2-dibromo-1,1,2,2-tetrachloroethane (CAS: 630-25-1, 69.8 g, 214 mmol) was added as a solution in THF (120 mL) over 10 min. The reaction was held at −78° C. for 2 h and the reaction was checked by LCMS. A new peak with M−H=242 (product—CO$_2$H) was observed (negative ion mode). The mixture was quenched by adding water (120 mL). After stirring for 10 min, at −78° C., the cold bath was removed and 6 N HCl (90 mL) was added. The pH=1 aqueous layer was extracted with EtOAc (×3). The combined organic extract was washed with brine (×2) and dried over MgSO$_4$. Removal of the solvent afforded a solid that was stirred in heptane (250 mL) for 1 h to remove tetrachloroethylene byproduct. After filtration, the solid was washed with heptane (3×100 mL) and dried to afford 4-bromo-2,6-dichloro-5-fluoropyridine-3-carboxylic acid, I-1a, 30.3 g (73%) as a cream colored solid. $^{19}$F NMR (376 MHz, DMSO) d −114.17.

Step 2: Synthesis of methyl N-(4-bromo-2,6-dichloro-5-fluoropyridine-3-carbonyl)carbamimidothioate, I-1b A solution of 4-bromo-2,6-dichloro-5-fluoropyridine-3-carboxylic acid, I-1a (30.2 g, 104 mmol) was suspended in DCM (420 mL). Oxalyl chloride (25.0 mL, 300 mmol) was added followed by DMF (40 mg). After 2 h of stirring, solids were still present and bubbles could still be seen forming. So, the mixture was allowed to stir overnight (16 h). After stirring for 16 h at RT, the solids had dissolved and the mixture became a yellow solution. The solvents were removed in vacuo to afford 33.3 g of the acid chloride as a tan solid. In a separate 500 mL r.b. flask methylimidothiocarbamate sulfate (33.2 g, 177 mmol) was stirred with half-satd. Na$_2$CO$_3$ (80 mL) affording a clear solution. Et$_2$O (60 mL) was added to this solution which was cooled to 10° C. Then, the acid chloride of I-1a added slowly as a solution in EtOAc (120 mL), monitoring the temperature with an internal thermometer. A very slight exotherm was observed and the ice bath was removed after the addition was complete. After warming to RT, the mixture was stirred for an 30 min, while monitoring the consumption of the acid chloride using neg. mode ionization and looking for no more I-1a present (hydrolysis occurs during LCMS giving the acid). After the reaction was complete, clean product formation was observed and a new peak with M+H=360 with multi-halogen pattern was observed. The mixture was partitioned between water (100 mL) and EtOAc (150 mL) and the aq. layer was extracted with EtOAc (×2). The combined organic extracts were washed with satd. NaHCO$_3$ (×1), dried over MgSO$_4$ and concentrated to afford 35 g of methyl N-(4-bromo-2,6-dichloro-5-fluoropyridine-3-carbonyl)carbamimidothioate, I-1b (93%) as a tan solid which was used in the next reaction without further purification. $^1$H NMR (400 MHz, DMSO-d6) δ 9.03 (br s, 1H), 9.53 (br s, 1H), 2.40 (s, 3H).

Step 3: Synthesis of 5,7-dichloro-8-fluoro-2-(methylsulfanyl)pyrido[4,3-d]pyrimidin-4(3H)-one, I-1c N-(4-bromo-2,6-dichloro-5-fluoropyridine-3-carbonyl)carbamimidothioate, I-1b (14.7 g, 40.7 mmol) was dissolved in DMF (45 mL) and DIEA (14.2 mL, 81.4 mmol) was added. The reaction was heated to 95° C. under N$_2$ for 3 h at which time LCMS analysis showed clean conversion to product. After cooling to RT, the mixture solution was poured into an aqueous pH 5 buffer and 100 g ice and the resulting solution was adjusted to pH 3 using 6 N HCl. After addition to the cold aqueous solution, a pale-yellow solid precipitated from solution. This precipitate was collected in a Buchner funnel and washed with water (×3) to afford, after drying, 9.6 g of 5,7-dichloro-8-fluoro-2-(methylsulfanyl) pyrido[4,3-d]pyrimidin-4(3H)-one, I-1c (84%). $^{19}$F NMR (376 MHz, DMSO) d 135.4.

Step 4: Synthesis of 4,5,7-trichloro-8-fluoro-2-(methylsulfanyl)pyrido[4,3-d]pyrimidine, I-1

To a flask containing 5,7-dichloro-8-fluoro-2-(methylsulfanyl)pyrido[4,3-d]pyrimidin-4(3H)-one, I-1c (5.6 g, 20 mmol) was added DIEA (7.1 mL, 28.6 mmol) and the suspension was cooled to 0° C. under $N_2$. POCl$_3$ (30 mL, 320 mmol) was added in one portion and the ice bath was removed. The mixture was then heated to 90° C. for 4 h. LCMS analysis (sample dissolved in MeOH) showed two mono-methanol adducts with M+H=294 with Cl$_2$ isotope pattern. The POCl$_3$ was removed in vacuo chasing the excess POCl$_3$ with a mixture of toluene and DCM (×2). After removing all the volatiles, the resulting orange solid was dry loaded on an 80 g ISCO silica column and purified using a gradient of 0-100% EtOAc in heptane, maintaining 100% EtOAc for 7 column volumes as the product bleeds off the column slowly. Concentration of the fractions afforded 4,5,7-trichloro-8-fluoro-2-(methylsulfanyl)pyrido[4,3-d]pyrimidine, I-1 (5.7 g, 95%) as an orange solid. $^{13}$C NMR (101 MHz, DMSO-d6) δ ppm 165.5, 157.2, 148.6, 146.7, 146.0, 143.2, 137.4, 137.3, 114.8, 12.9; $^{19}$F NMR (376 MHz, DMSO) d −135.5.

Intermediate 2 (I-2): (S)-2-chloro-1-fluoro-12-(methylthio)-5a,6,9,10-tetrahydro-5H,8H-4,7-dioxa-3,10a,11,13-tetraazanaphtho[1,8-ab]heptalene 4,5,7-trichloro-8-fluoro-2-(methylsulfanyl)pyrido[4,3-d] pyrimidine (I-1, 450 mg, 1.51 mmol) was suspended in CH$_3$CN (10 mL). DIPEA (276 uL, 1.59 mmol) was added and the suspension cooled to 0° C. under N$_2$. In a separate vial, [(3R)-1,4-oxazepan-3-yl]methanol hydrochloride (CAS 1262409-55-1-HCl salt, 232 mg, 1.39 mmol) was suspended in DCM (1 mL) and DIPEA (276 uL, 1.59 mmol) was added to dissolve the amine-HCl salt. THF (6 mL) was added to the resulting solution to give a milky mixture. This solution was added to the flask containing the cold solution of I-1. After about 45 m at 0° C., LCMS analysis showed that the initial reaction was complete. LiOtBu (4.5 mL of 1 M in THF, 4.5 mmol) was added dropwise and the ice bath was removed. The ice bath was replaced with an oil bath and the reaction was heated at 50° C. for 30 min. LCMS analysis showed the cyclization step to be complete. The solution was cooled to rt and evaporated. Saturated aqueous NaHCO$_3$ (10 mL) was added and the mixture was extracted with DCM (3×30 mL). The combined organic extract was dried over Na$_2$SO$_4$ and evaporated. The process described above was repeated a second time on the same scale with the same observations and results. The crude material from both reactions was combined and purified using flash chromatography eluting with a gradient of 0-100% EtOAc in heptane and using DCM to load the crude material onto the silica cartridge. Fractions containing the desired product were pooled and concentrated to afford 483 mg of (S)-2-chloro-1-fluoro-12-(methylthio)-5a,6,9,10-tetrahydro-5H, 8H-4,7-dioxa-3,10a,11,13-tetraazanaphtho[1,8-ab]heptalene, I-2 (70%) as a tan solid. $^1$H NMR (400 MHz, CHLOROFORM-d) δ=5.22 (ddd, J=2.9, 6.8, 13.8 Hz, 1H), 4.65 (dd, J=4.6, 13.4 Hz, 1H), 4.42 (d, J=13.4 Hz, 1H), 4.22-4.17 (m, 1H), 4.09-3.98 (m, 2H), 3.72 (dd, J=9.8, 12.6 Hz, 1H), 3.43-3.24 (m, 2H), 2.62 (s, 3H), 2.26-2.12 (m, 1H), 2.05-1.92 (m, 1H). $^{19}$F NMR (376 MHz, CHLOROFORM-d) δ=−140.51 (s, 1F).

Intermediate 3 (I-3): (8aS)-5-chloro-4-fluoro-2-(methylsulfanyl)-8,8a,9,10,11,12-hexahydro-7-oxa-1,3,6,12a-tetraazabenzo[4,5]cyclohepta[1,2,3-de]naphthalene

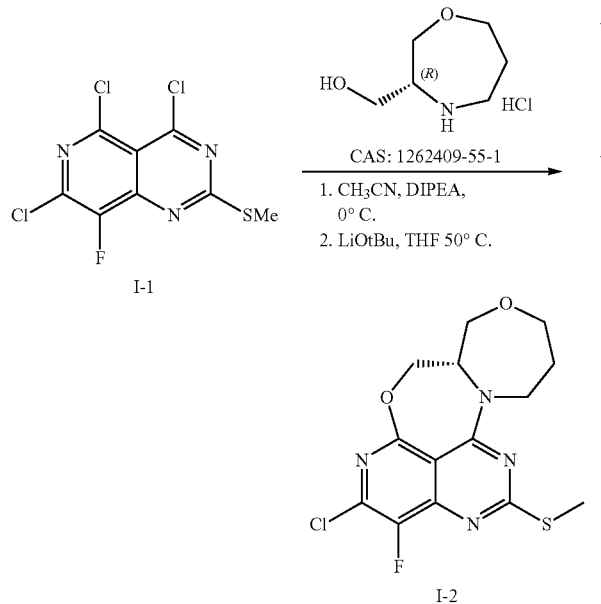

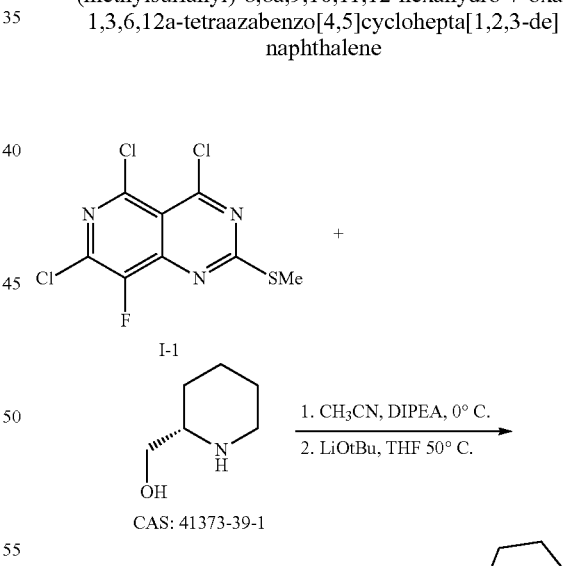

4,5,7-trichloro-8-fluoro-2-(methylsulfanyl)pyrido[4,3-d]pyrimidine (I-1, 1.25 g, 3.70 mmol) was suspended in CH₃CN (24 mL) and DIEA (0.668 mL, 3.83 mmol) was added. The mixture was cooled to 0° C. and (S)-piperidin-2-yl methanol (421 mg, 3.65 mmol) was added as a solution in THF (18 mL). After 8 minutes, the first nitrogen-carbon bond was formed as observed by LCMS. LiOtBu (877 mg, 11.0 mmol) was added as a solution in THF (22 mL) and the mixture was warmed to 50° C. After 4 h at 50° C., LCMS analysis showed conversion to product. The reaction mixture was then diluted with 200 mL water and the product was extracted with DCM (50 mL×4). The combined organic extract was dried over Na₂SO₄, filtered, and evaporated to afford a crude solid. Purification was accomplished via flash chromatography eluting with a gradient of 0-10% MeOH in DCM to afford (8aS)-5-chloro-4-fluoro-2-(methylsulfanyl-8,8a,9,10,11,12-hexahydro-7-oxa-1,3,6,12a-tetraazabenzo[4,5]cyclohepta[1,2,3-de]naphthalene, I-3 (1.13 g, 91%). ¹H NMR (CHLOROFORM-d, 400 MHz) d 4.8-4.9 (m, 1H), 4.4-4.5 (m, 2H), 3.7-3.8 (m, 1H), 2.97 (dt, 1H, J=2.5, 12.8 Hz), 2.7-2.7 (m, 1H), 2.6-2.7 (m, 2H), 2.0-2.1 (m, 1H), 1.7-1.8 (m, 3H), 1.5-1.7 (m, 2H), MS: 341.1 [M+H]⁺.

Intermediate 4 (I-4): (S)-4-fluoro-2-(methylthio)-5-(tributylstannyl)-8a,9,12,13-tetrahydro-8H,11H-7,10-dioxa-1,3,6,13a-tetraazanaphtho[1,8-ab]heptalene

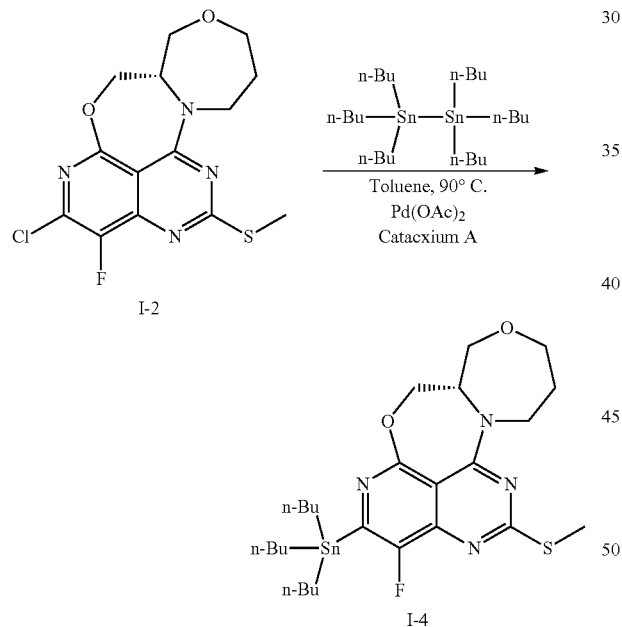

To a solution of (S)-2-chloro-1-fluoro-12-(methylthio)-5a,6,9,10-tetrahydro-5H,8H-4,7-dioxa-3,10a,11,13-tetraazanaphtho[1,8-ab]heptalene (I-2, 7.0 g, 19.6 mmol) in toluene (980 mL) was added 1,1,1,2,2,2-hexabutyldistannane (11.38 g, 9.9 mL, 19.6 mmol), CataCXium A (880 mg, 2.454 mmol) and Pd(OAc)₂ (276 mg, 1.226 mmol) at 20° C. The reaction was stirred at 90° C. for 16 h under N₂ atmosphere. LCMS showed the desired product was formed. The reaction mixture was concentrated under reduced pressure. The residue was purified by flash column chromatography (CombiFlash, 80 g silica gel, 0%-30% EtOAc in Petroleum ether) to afford (S)-4-fluoro-2-(methylthio)-5-(tributylstannyl)-8a,9,12,13-tetrahydro-8H,11H-7,10-dioxa-1,3,6,13a-tetraazanaphtho[1,8-ab]heptalene, 1-4 (5.65 g, 47.1%) as yellow oil. ¹H NMR (400 MHz, CDCl₃) δ 5.20 (ddd, J=13.7, 6.9, 2.6 Hz, 1H), 4.64 (dd, J=13.4, 4.4 Hz, 1H), 4.37 (d, J=13.3 Hz, 1H), 4.20 (dd, J=12.6, 3.5 Hz, 1H), 4.06-3.97 (m, 2H), 3.74 (dd, J=12.6, 9.9 Hz, 1H), 3.39-3.24 (m, 2H), 2.60 (s, 3H), 2.26-2.14 (m, 1H), 2.03-1.90 (m, 1H), 1.63-1.51 (m, 6H), 1.38-1.19 (m, 12H), 0.87 (t, J=7.3 Hz, 9H). ¹⁹F NMR (376 MHz, CDCl₃) δ −132.84. MS: 613.2 [M+H]⁺.

Intermediate 5i and 5ii (I-5i and I-5ii): 4-bromo-8-chloro-5-cyclopropyl-2-(tetrahydro-2H-pyran-2-yl)-2H-indazole and 4-bromo-8-chloro-1-cyclopropyl-1-(tetrahydro-2H-pyran-2-yl)-3a,7a-dihydro-1H-indazole

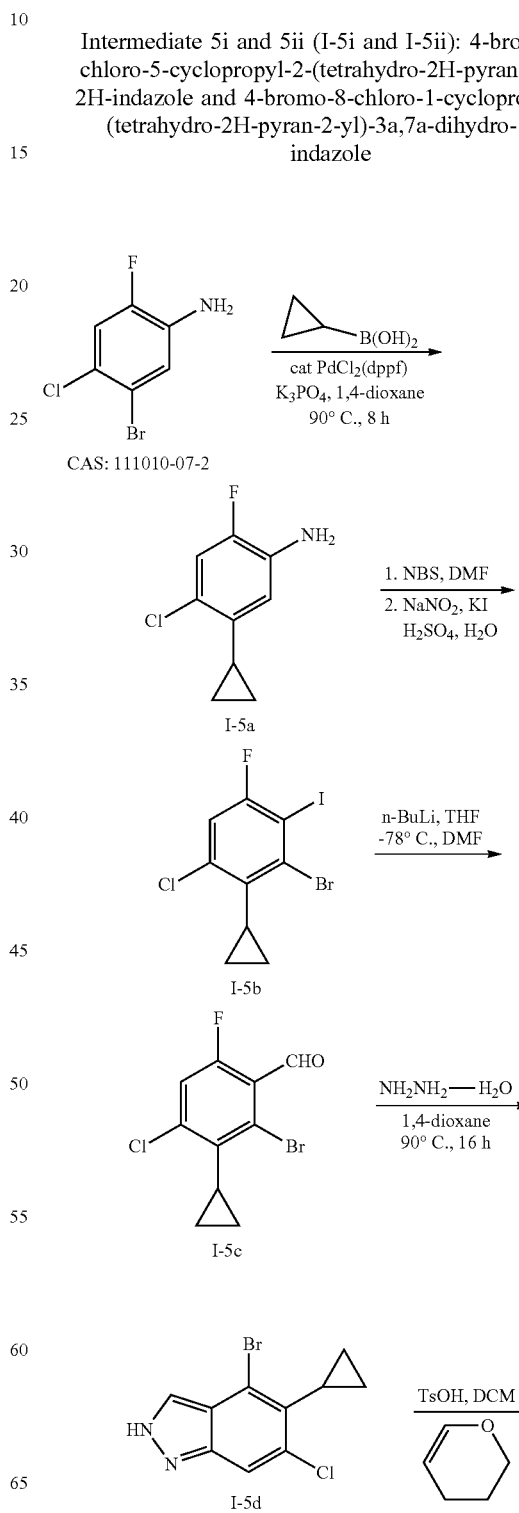

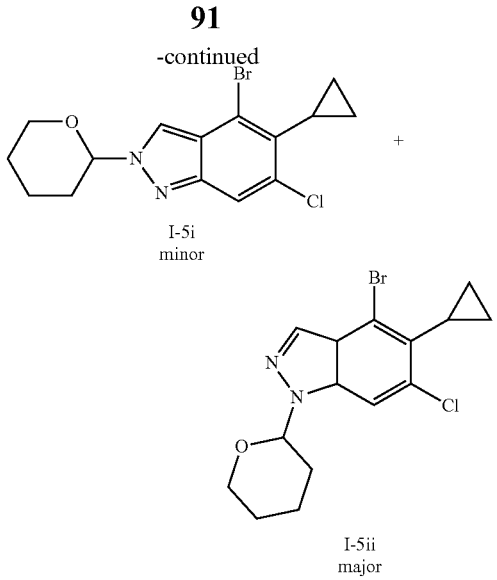

I-5i
minor

I-5ii
major

Step 1: Synthesis of 4-chloro-5-cyclopropyl-2-fluoroaniline (I-5a)

To a solution of 5-bromo-4-chloro-2-fluoroaniline (CAS 111010-07-2, 8.06 g 35.9 mmol) in 1,4-dioxane (200 mL) was added cyclopropylboronic acid (4.63 g, 53.9 mmol), $K_3PO_4$ (15.2 g, 71.8 mmol), and $PdCl_2(dppf)$ (3.15 g, 4.31 mmol). The mixture was stirred at 90° C. under $N_2$ for 8 h. Analysis by TLC showed that the reaction was complete. Water (100 mL) was added and the product extracted into EtOAc (2×150 mL). The combined organic extract was washed with brine and the organic solvents were concentrated. The crude product was purified by flash chromatography eluting with a gradient of 0-40% EtOAc in petroleum ether to afford 4-chloro-5-cyclopropyl-2-fluoroaniline, I-5a (5.4 g, 81%) as a yellow oil. $^1$H NMR (400 MHz, CDCl3) δ 7.02 (d, J=10.5 Hz, 1H), 6.38 (d, J=9.3 Hz, 1H), 4.24-2.95 (m, 2H), 2.13-2.01 (m, 1H), 1.01-0.89 (m, 2H), 0.64-0.48 (m, 2H).

Step 2: Synthesis of 3-bromo-1-chloro-2-cyclopropyl-5-fluoro-4-iodobenzene (I-5b)

A solution of 4-chloro-5-cyclopropyl-2-fluoroaniline (I-5a, 5.40 g 29.1 mmol) in DMF (50 mL) was cooled to 0° C. and NBS (5.18 g 29.1 mmol) was added in portions under $N_2$. The mixture was warmed to rt and allowed to stir for 1h. Analysis by TLC showed consumption of starting material. The mixture was diluted with sat. aq. $NaHCO_3$, and the product was extracted into EtOAc (2×150 mL). The combined organic extract was washed with brine, dried, and filtered to give the crude bromoaniline intermediate that was purified by flash chromatography eluting with a gradient of 0-40% EtOAc in petroleum ether to afford the bromoaniline intermediate (7.2 g, 93.6%) as a brown oil. To a solution of con. $H_2SO_4$ (17 mL) in water (65 mL) was added the bromoaniline (6.55 g, 24.8 mmol) and the solution was cooled to 5° C. $NaNO_2$ (1.88 g, 27.2 mmol) in water (6 mL) was added dropwise. The resulting mixture was stirred at 5° C. for 20 min. The resulting diazo solution was added to a solution of KI (16.4 g 99.0 mmol) in water (14 mL) at 5° C. The reaction was stirred at 5° C. for 20 min and then warmed to rt. Stirring was continued at rt for 18 h. Analysis by TLC indicated that the bromoaniline was almost consumed. The mixture was quenched with water (100 mL) and the product extracted into EtOAc (2×110 mL). The combined organic extract was washed with satd. aq. $Na_2SO_3$, brine, dried over $Na_2SO_4$, filtered, and concentrated under reduced pressure. Purification by flash chromatography gave 3-bromo-1-chloro-2-cyclopropyl-5-fluoro-4-iodobenzene, I-5b (6.03 g, 65%) as an oil. $^1$H NMR (400 MHz, CHLOROFORM-d) d 7.14 (d, J=7.5 Hz, 1H), 1.86-1.74 (m, 1H), 1.30-1.21 (m, 2H), 0.78-0.72 (m, 2H).

Step 3: Synthesis of 2-bromo-4-chloro-3-cyclopropyl-8-fluorobenzaldehyde (I-5c)

To a solution of 3-bromo-1-chloro-2-cyclopropyl-5-fluoro-4-iodobenzene (I-5b, 5.0 g 13 mmol) in THF (25 mL) was added n-BuLi (5.3 mL of 2.5 M, 13.3 mmol) dropwise at −78° C. under argon. The mixture was stirred for 30 min and dry DMF (1.07 g 14.7 mmol) was added while stirring was continued at −78° C. for 20 min. Analysis by TLC showed the consumption of starting material and a new spot was formed. The mixture was quenched with 1N HCl (2 mL) and slowly warmed to rt. The reaction mixture was diluted with water (20 mL), and the product was extracted into EtOAc (2×150 mL). The combined organic extract was washed with water, dried, filtered, and concentrated. Purification by flash chromatography using a gradient of 0-40% EtOAc in petroleum ether afforded 2-bromo-4-chloro-3-cyclopropyl-8-fluorobenzaldehyde, I-5c (2.55 g, 69%) as a yellow solid plus recovered 3-bromo-1-chloro-2-cyclopropyl-5-fluoro-4-iodobenzene (I-5b, 1.03 g, 21%). $^1$H NMR (400 MHz, DMSO-d6) δ 10.19 (s, 1H), 7.71 (d, J=10.3 Hz, 1H), 1.88-1.76 (m, 1H), 1.28-1.19 (m, 2H), 0.74-0.65 (m, 2H); LCMS (ESI) m/z: 277.0 [M+H]+.

Step 4: Synthesis of 4-bromo-6-chloro-5-cyclopropyl-2H-indazole (I-5d)

To a mixture of 2-bromo-4-chloro-3-cyclopropyl-8-fluorobenzaldehyde (I-5c, 2.05 g, 7.38 mmol) in 1,4-dioxane (25 mL) at 10° C. was added 85% $N_2H_4\cdot H_2O$ (2.21 g, 37.6 mmol). The reaction was heated to 90° C. for 16 h. The mixture was combined with the crude product of the same reaction ran separately. The combined reaction mixtures were slowly added to water (50 mL) giving a cream suspension that was filtered and washed water. The filtrate was dissolved in MTBE (150 mL) and the organic layer was dried over $Na_2SO_4$. After concentration the material was purified by flash chromatography eluting with a gradient of 0-30% EtOAc in petroleum ether to give 4-bromo-6-chloro-5-cyclopropyl-2H-indazole, I-5d (1.88 g, 83%) as a yellow solid. $^1$H NMR (400 MHz, DMSO-d6) δ 13.43 (br s, 1H), 8.02 (s, 1H), 7.69 (s, 1H), 1.84 (tt, J=5.6, 8.3 Hz, 1H), 1.22-1.17 (m, 2H), 0.73-0.68 (m, 2H); LCMS (ESI) m/z: 271.9 [M+H]+.

Step 5: Synthesis of 4-bromo-8-chloro-5-cyclopropyl-2-(oxan-2-yl)-2H-indazole (I-5l) and 4-bromo-8-choro-5-cyclopropyl-2-(oxan-2-yl)-2H-indazole (I-5ii)

To a solution of 4-bromo-6-chloro-5-cyclopropyl-2H-indazole I-5d (2.1 g, 7.9 mmol) in DCM (40 mL) was added dihydropyran (999 mg 11.9 mmol) p-TsOH (136 mg, 0.792 mmol). The reaction mixture was stirred at 30° C. for 16 h. LCMS analysis showed the formation of 2 products with the same mass. The reaction mixture was diluted with DCM (40 mL) and washed with satd. aq. $NaHCO_3$ (50 mL) and brine (50 mL). The organic extract was dried, and concentrated to give the crude mixture which was purified by flash chromatography eluting with a gradient of 0-10% EtOAc in petroleum ether to afford 4-bromo-6-chloro-5-cyclopropyl-2-(oxan-2-yl)-2H-indazole (I-5i, 1.9 g, 68%) as a yellow gum and 4-bromo-6-chloro-5-cyclopropyl-2-(oxan-2-yl)-2H-indazole (I-5ii, 335 mg, 12%) as a yellow gum. $^1$H NMR I-5I (400 MHz, CHLOROFORM-d) d 8.21-8.12 (m, 1H), 7.73 (s, 1H), 5.65 (dd, J=3.0, 9.0 Hz, 1H), 4.20-4.12 (m, 1H), 3.80 (dt, J=3.1, 11.0 Hz, 1H), 2.29-2.12 (m, 2H), 2.09-2.01 (m, 1H), 1.88-1.82 (m, 1H), 1.80-1.69 (m, 3H), 1.25-1.19 (m, 2H), 0.85-0.79 (m, 2H), MS: 313.9 [M+H-cyclopropyl]$^+$.

$^1$H NMR I-5ii (400 MHz, CDCl$_3$) δ 7.98 (s, 1H), 7.62 (s, 1H), 5.62 (dd, J=9.1, 2.7 Hz, 1H), 4.06-3.95 (m, 1H), 3.80-3.67 (m, 1H), 2.54-2.41 (m, 1H), 2.19-2.01 (m, 2H), 1.89-1.65 (m, 5H), 1.24-1.17 (m, 2H), 0.81-0.72 (m, 2H). MS: 354.9, 356.9 [M+H]$^+$.

Intermediate 6 (I6): 4-bromo-8-chloro-5-isopropyl-1-(tetrahydro-2H-pyran-2-yl)-1H-indazole

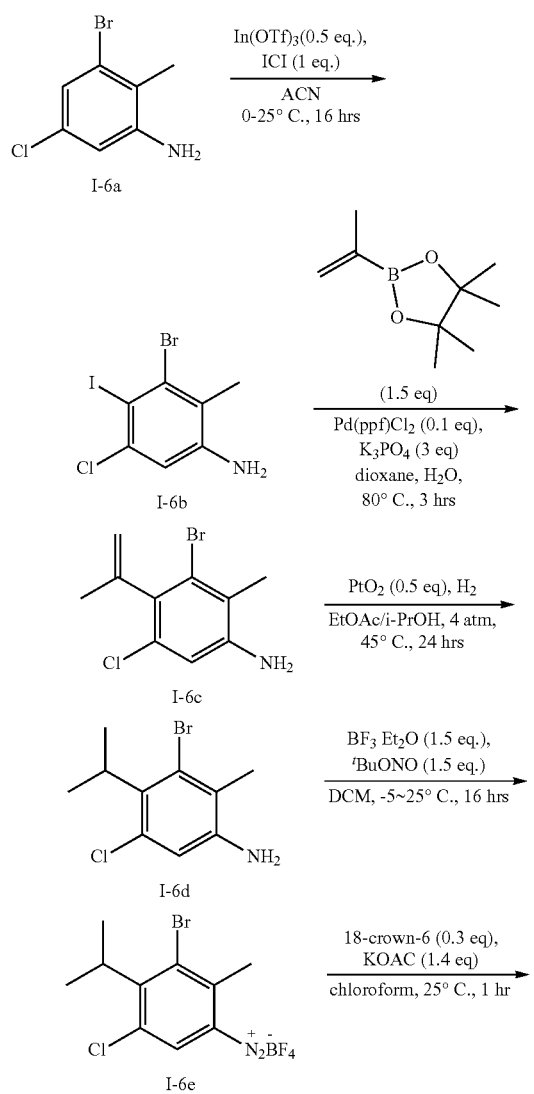

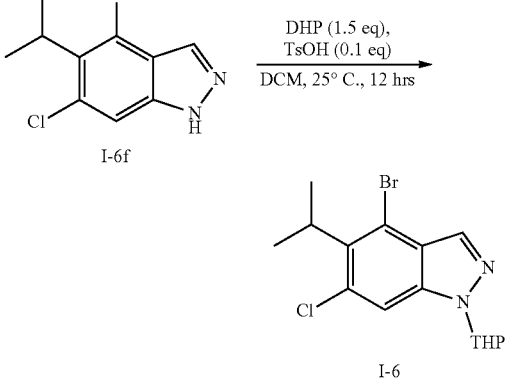

Step 1: Synthesis of 3-bromo-5-chloro-4-iodo-2-methylaniline (I-6b)

To a stirred solution of 3-bromo-5-chloro-2-methylaniline (10 g, 45 mmol) in CH3CN (113 mL) was added indium(III) trifluoromethanesulfonate (12.7 g, 22.7 mmol) followed by ICl (7.36 g, 45.4 mmol) dropwise at 0° C. The reaction was stirred at 0° C. for 2 h. Then warmed to 25° C. and stirred at 25° C. for 16 h. LCMS showed the desired product was detected. The reaction was quenched with TEA (9.48 mL, 68 mmol) then stirred for 15 min. Solids were removed by filtration over celite. The filter cake was rinsed with EtOAc (100 mL). The filtrate was collected, washed with sat. NaCl (70 mL), dried over Na$_2$SO$_4$, filtered and concentrated under reduced pressure. The crude product was purified by flash column chromatography (Combi-Flash, 120 g silica gel, 0-5% EtOAc in Petroleum ether) to give the title intermediate (9.5 g, 60%) as a solid. $^1$H NMR (400 MHz, CDCl$_3$) δ 6.85 (s, 1H), 3.82 (5, 2H), 2.38 (m, 31H). MS: 345.9, 347.8 [M+H]$^+$.

Step 2: Synthesis of 3-bromo-5-chloro-2-methyl-4-(prop-1-en-2-yl)aniline (I-6c)

To a mixture of 3-bromo-5-chloro-4-iodo-2-methylaniline (1.4 g, 4.0 mmol), 4,4,5,5-tetramethyl-2-(prop-1-en-2-yl)-1,3,2-dioxaborolane (1.02 g, 6.06 mmol), and K$_3$PO$_4$ (2.57 g, 12.1 mmol) in 1,4-dioxane (20 mL) and H$_2$O (4 mL) was added Pd(dppf)Cl$_2$ (296 mg, 0.404 mmol). The mixture was stirred at 80° C. under nitrogen for 3 h. LCMS showed starting material was consumed and desired compound was found. The mixture was concentrated under reduced pressure. The residue was purified by flash column chromatography (Combi-Flash, 10 g silica gel, 0~7% EtOAc in Petroleum ether) to afford the title intermediate (820 mg, 78%) as a yellow solid. $^1$H NMR (400 MHz, DMSO) δ 6.73 (s, 1H), 5.41 (s, 2H), 5.31-5.23 (m, 1H), 4.80-4.68 (m, 1H), 2.15 (s, 3H), 1.90 (s, 3H). MS: 260.0, 262.0 [M+H]$^+$.

Step 3: Synthesis of 3-bromo-5-chloro-4-isopropyl-2-methylaniline (I-6d)

To a solution of 3-bromo-5-chloro-2-methyl-4-(prop-1-en-2-yl)aniline (500 mg, 1.92 mmol) in EtOAc (14 mL) and isopropyl alcohol (14 mL) was added PtO$_2$ (218 mg, 0.959 mmol) at 25° C. The reaction was stirred at 45° C. under hydrogen atmosphere at 4 atm for 24 h. LCMS showed 40% of desired compound was found. The reaction was filtered and the filtrate was concentrated under reduced pressure. The residue was purified by flash column chromatography (Combi-Flash, 10 g silica gel, 0-12% EtOAc in Petroleum ether) to afford the title intermediate (300 mg, 60% crude) as a brown oil. $^1$H NMR (400 MHz, CDCl$_3$) δ 6.67 (s, 1H), 3.95-3.82 (m, 3H), 2.28 (s, 3H), 1.37 (d, J=7.1 Hz, 6H). MS: 262.0, 264.0 [M+H]$^+$.

Step 4: Synthesis of 3-bromo-5-chloro-4-isopropyl-2-methylbenzenediazonium Tetrafluoroborate (I-6e)

BF$_3$·Et$_2$O (243 mg, 1.71 mmol, 0.217 mL) was dissolved in DCM (8 mL) and cooled to −5° C. under nitrogen atmosphere. A solution of 3-bromo-5-chloro-4-isopropyl-2-methylaniline (300 mg, 1.14 mmol) in DCM (1 mL) was added to above reaction mixture and stirred for 0.5 hr at −5° C. tert-Butyl nitrite (177 mg, 1.71 mmol) in DCM (1 mL) was added dropwise. The reaction mixture was slowly warmed to 25° C. and stirred at the same temperature for 16 hrs. LCMS showed that the starting material was consumed and the desired product was detected. The reaction mixture was concentrated to 0.5 mL before adding MTBE (10 mL). The suspension was filtered to give the title intermediate (290 mg, 70% crude) as a white solid. MS: 273.0, 275.0 [M]$^+$.

Step 5: Synthesis of 4-bromo-8-chloro-5-isopropyl-1H-indazole (I-6f)

To a mixture of 18-crown-6 (63.6 mg, 0.241 mmol) in chloroform (5 mL) was added KOAc (110 mg, 1.12 mmol) 25° C. Then 3-bromo-5-chloro-4-isopropyl-2-methylbenzenediazonium tetrafluoroborate (290 mg, 0.803 mmol) was added slowly. The reaction mixture was then allowed to stir at 25° C. for 1 h. LCMS showed that the desired product was detected and the starting material was consumed. The reaction mixture was concentrated under reduced pressure. The residue was purified by flash column chromatography (Combi-Flash, 4 g silica gel, 0-70% EtOAc in Petroleum ether) to afford the title intermediate (120 mg, 55%) as a yellow gum. $^1$H NMR (400 MHz, CDCl$_3$) δ 8.05 (s, 1H), 7.51 (s, 1H), 4.07-3.96 (m, 1H), 1.47 (d, J=6.6 Hz, 6H). MS: 273.0, 274.9 [M+H]$^+$.

Step 6: Synthesis of 4-bromo-8-chloro-5-isopropyl-1-(tetrahydro-2H-pyran-2-yl)-1H-indazole (I-6)

To a solution of 4-bromo-6-chloro-5-isopropyl-1H-indazole (120 mg 0.439 mmol) in DCM (7 mL) was added DHP (55.3 mg 0.658 mmol) followed by p-Toluenesulfonic acid monohydrate (8.34 mg, 0.0439 mmol). The reaction mixture was stirred at 25° C. for 12 h. LCMS showed that the starting material was consumed and the desired product was detected. The reaction mixture was diluted with DCM (20 mL), washed with sat. NaHCO$_3$ (30 mL) and brine (30 mL). The organic layer was dried over anhydrous Na$_2$SO$_4$, filtered, and concentrated under reduced pressure. The residue was purified by flash column chromatography (Combi-Flash, 4 g silica gel, 0~4% EtOAc in Petroleum ether) to afford the title intermediate (130 mg, 83%) as a yellow solid. $^1$H NMR (400 MHz, CDCl$_3$) δ 7.96 (s, 1H), 7.60 (s, 1H), 5.62 (dd, J=9.1, 2.5 Hz, 1H), 4.08-3.92 (m, 2H), 3.80-3.69 (m, 1H), 2.54-2.44 (m, 1H), 2.18-2.01 (m, 3H), 1.77-1.71 (m, 2H), 1.46 (d, J=6.9 Hz, 6H). MS: 357.0, 359.0 [M+H]$^+$.

Intermediate 7 (I-7): (2S,7aR)-7a-(hydroxymethyl)-6-methylenehexahydro-1H-pyrrolizin-2-ol

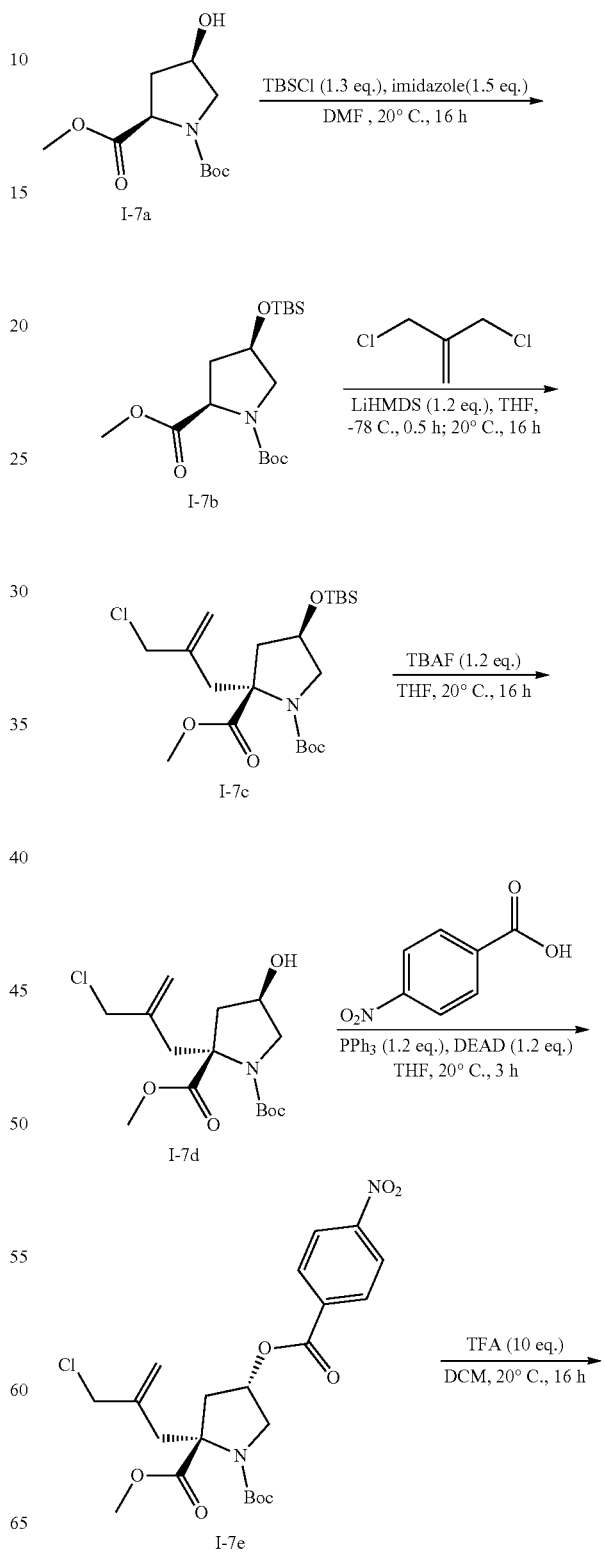

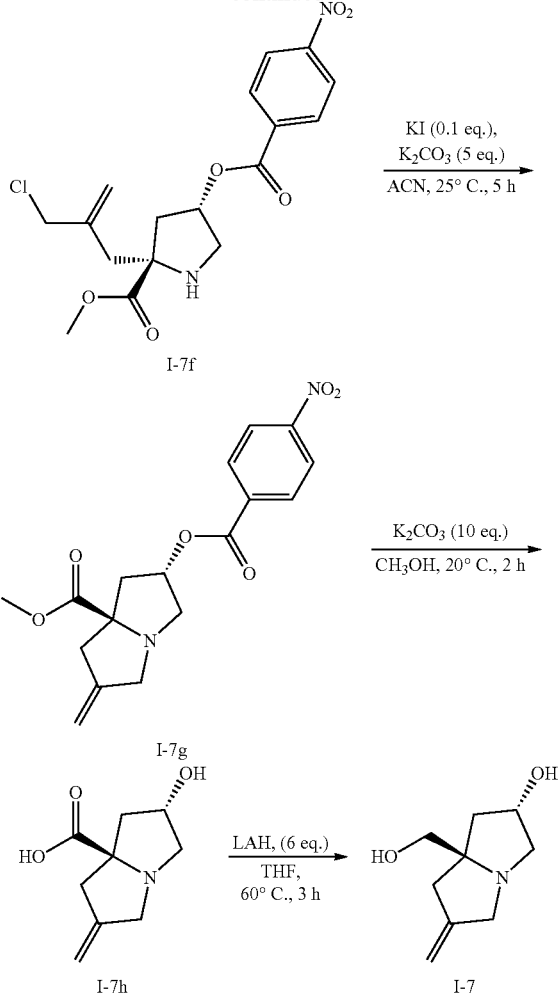

Step 1: Synthesis of 1-(tert-butyl) 2-methyl (2R, 4R)-4-((tert-butyldimethylsilyl)oxy)pyrrolidine-1,2-dicarboxylate (I-7b)

To a solution of 1-(tert-butyl) 2-methyl (2R,4R)-4-hydroxypyrrolidine-1,2-dicarboxylate (I-7a, 22 g, 90 mmol) in DMF (90 mL) was added imidazole (9.16 g, 135 mmol) and TBSCl (17.6 g, 117 mmol) at 0° C. The reaction was stirred at 20° C. for 16 h. LCMS showed that the starting material was consumed and the desired product was detected. The reaction mixture was concentrated in vacuo. The residue was diluted with water (200 mL), extracted with EtOAc (100 mL) and washed with water (20 mL×3). The combined organic layers were concentrated under reduced pressure. The residue was purified by flash column chromatography (Biotage, 120 g silica gel, 0~8% EtOAc in Petroleum ether) to give 1-(tert-butyl) 2-methyl (2R,4R)-4-((tert-butyldimethylsilyl)oxy) pyrrolidine-1,2-dicarboxylate (32 g, 99%) as a colorless oil. $^1$H NMR (400 MHz, CDCl$_3$) δ 4.43-4.25 (m, 2H), 3.70 (s, 3H), 3.60 (ddd, J=27.1, 11.1, 5.4 Hz, 1H), 3.30 (ddd, J=21.3, 11.1, 3.4 Hz, 1H), 2.36-2.20 (m, 1H), 2.14-2.04 (m, 1H), 1.47 and 1.41 (2 s, 9H, minor and major rotamer respectively), 0.85 and 0.84 (2 s, 9H, minor and major rotamer respectively), 0.06-0.01 (m, 6H). MS: 382.1 [M+Na]$^+$.

Step 2: Synthesis of 1-(tert-butyl) 2-methyl (2R, 4R)-4-((tert-butyldimethylsilyl)oxy)-2-(2-(chloromethyl)allyl)pyrrolidine-1,2-dicarboxylate (I-7c)

To a solution of 1-(tert-butyl) 2-methyl (2R,4R)-4-((tert-butyldimethylsilyl)oxy)pyrrolidine-1,2-dicarboxylate (I-7b, 5.00 g, 13.9 mmol) in THF (15 mL) was added LiHMDS (16.7 mL, 1 M in hexane, 16.7 mmol) dropwise at −78° C. The mixture was stirred at −78° C. for 30 min before the addition of 3-chloro-2-(chloromethyl)prop-1-ene (4.35 g, 34.8 mmol) in THF (17.3 mL). The reaction was slowly warmed to 20° C. and stirred at 20° C. for 16 h. LCMS showed that the starting material was consumed and the desired product was detected. The reaction was quenched with sat. NH$_4$Cl (aq.) (10 mL) at 0° C. The resulting mixture was extracted with EtOAc (30 mL×3) and the combined organic layers were washed with water and brine, dried over Na$_2$SO$_4$. After filtration, the filtrate was concentrated in vacuo. The residue was purified by flash column chromatography (Biotage, 80 g silica gel, 0-10% EtOAc in Petroleum ether) to give 1-(tert-butyl) 2-methyl (2R,4R)-4-((tert-butyldimethylsilyl)oxy)-2-(2-(chloromethyl)allyl) pyrrolidine-1,2-dicarboxylate (I-7c, 5.0 g, 80%) as a colorless oil. $^1$H NMR (400 MHz, CDCl$_3$) δ 5.40 (d, J=1.0 Hz, 1H), 5.11 and 5.10 (2 s, 1H, major and minor rotamer respectively), 4.29-4.20 (m, 1H), 4.05-3.93 (m, 2H), 3.75-3.69 (m, 3H), 3.67-3.54 (m, 1H), 3.35-3.13 (m, 2H), 2.65 (dd, J=14.4, 3.0 Hz, 1H), 2.34-2.16 (m, 1H), 2.14-2.01 (m, 1H), 1.45 and 1.44 (2 s, 9H, minor and major rotamer respectively), 0.86 and 0.85 (2 s, 9H, minor and major rotamer respectively), 0.04-0.00 (m, 6H). MS: 470.1 [M+Na]$^+$.

Step 3: Synthesis of 1-(tert-butyl) 2-methyl (2R, 4R)-2-(2-(chloromethyl)allyl)-4-hydroxypyrrolidine-1,2-dicarboxylate (I-7d)

To a solution of 1-(tert-butyl) 2-methyl (2R,4R)-4-((tert-butyldimethylsilyl)oxy)-2-(2-(chloromethyl)allyl)pyrrolidine-1,2-dicarboxylate (I-7c, 5.0 g, 11 mmol) in THF (37.2 mL) was added TBAF (13.4 mL, 1 M in THF, 13.4 mmol) dropwise at 20° C. The reaction was stirred at 25° C. for 20 h. LCMS showed that the starting material was consumed and the desired product was detected. The reaction mixture was concentrated. The residue was dissolved in EtOAc (100 mL) and washed with sat. NaHCO$_3$ (aq.) (30 mL×7). The organic layer was dried over Na$_2$SO$_4$ and filtered. The filtrate was concentrated under reduced pressure and the residue was purified by flash column chromatography (Biotage, 80 g silica gel, 45-55% EtOAc in Petroleum ether) to give 1-(tert-buty) 2-methyl (2R,4R)-2-(2-(chloromethyl)allyl)-4-hydroxypyrrolidine-1,2-dicarboxylate (I-7d, 3.0 g, 80%) as a yellow oil. $^1$H NMR (400 MHz, CDCl$_3$) δ 5.42 (s, 1H), 5.06 (s, 1H), 4.21 (s, 1H), 4.04-3.92 (m, 2H), 3.90-3.73 (m, 4H), 3.43-3.24 (m, 2H), 2.58 (t, J=13.6 Hz, 1H), 2.44 (ddd, J=29.5, 14.5, 5.2 Hz, 1H), 2.11 (d, J=15.2 Hz, 1H), 1.47 (s, 9H). MS: 356.5 [M+Na]$^+$.

Step 4: Synthesis of 1-(tert-butyl) 2-methyl (2R, 4S)-2-(2-(chloromethyl)allyl)-4-((4-nitrobenzoyl) oxy)pyrrolidine-1,2-dicarboxylate (I-7e)

To the solution of 1-(tert-butyl) 2-methyl (2R,4R)-2-(2-(chloromethyl)allyl)-4-hydroxypyrrolidine-1,2-dicarboxylate (I-7d, 6.6 g, 20 mmol), 4-nitrobenzoic acid (3.97 g, 23.7 mmol) and PPh$_3$ (6.22 g, 23.7 mmol) in THF (66 mL) was added DEAD (4.13 g, 23.7 mmol) at 0° C. under nitrogen.

The mixture was stirred at 20° C. for 3 h. LCMS showed that the starting material was consumed and the desired product was detected. The mixture was quenched with sat. NaHCO$_3$ (aq.) solution (15 mL) and extracted with EtOAc (50 mL×3). The combined organic layers were washed with water (100 mL) and brine (100 mL), dried over Na$_2$SO$_4$, filtered and the filtrate was concentrated. The residue was purified by flash column chromatography (Biotage, 120 g silica gel, 15-25% EtOAc in Petroleum ether) to afford methyl (2R,4S)-2-(2-(chloromethyl)allyl)-4-((4-nitrobenzoyl)oxy)pyrrolidine-2-carboxylate (I-7e, 9.0 g, 94%) as a yellow oil. $^1$H NMR (400 MHz, CDCl$_3$) δ 8.31 (d, J=8.8 Hz, 2H), 8.23-8.14 (m, 2H), 5.55-5.41 (m, 1H), 5.32 and 5.24 (2 s, 1H, minor and major rotamer respectively), 5.07 and 5.04 (2 s, 1H, minor and major rotamer respectively), 4.16-4.05 (m, 3H), 3.78 and 3.76 (2 s, 3H, major and minor rotamer respectively), 3.65-3.51 (m, 1H), 3.44-3.21 (m, 1H), 2.81 (dd, J=22.0, 14.7 Hz, 1H), 2.64-2.43 (m, 2H), 1.47 (s, 9H). MS: 505.1 [M+Na]$^+$.

Step 5: Synthesis of methyl (2R,4S)-2-(2-(chloromethyl)allyl)-4-((4-nitrobenzoyl)oxy)pyrrolidine-2-carboxylate (I-7f)

To a solution of methyl (2R,4S)-2-(2-(chloromethyl)allyl)-4-((4-nitrobenzoyl)oxy)pyrrolidine-2-carboxylate (I-7e, 6.0 g, 12 mmol) in DCM (41 mL) was added TFA (9.5 mL) at 0° C. The mixture was stirred at 20° C. for 16 h. LCMS showed that the starting material was consumed and desired product was detected. Then the reaction mixture was concentrated to give the crude product methyl (2R,4S)-2-(2-(chloromethyl)ally)-4-((4-nitrobenzoyl)oxy)pyrrolidine-2-carboxylate (I7f, 8.2 g, crude) as a yellow oil. MS: 383.1 [M+H]$^+$.

Step 6: Synthesis of methyl (6S,7aR)-2-methylene-6(4-nitrobenzoyl)oxy)tetrahydro-1H-pyrrolizine-7a(5H)-carboxylate (I-7g)

To a solution of methyl (2R,4S)-2-(2-(chloromethyl)allyl)-4-((4-nitrobenzoyl)oxy)pyrrolidine-2-carboxylate (I-7f, 200 mg, 0.522 mmol) in CH3CN (5 mL) was added K$_2$CO$_3$ (361 mg, 2.61 mmol) and KI (8.67 mg, 0.0522 mmol) at 25° C. The reaction mixture was stirred at 25° C. for 1 h. LCMS showed starting material was consumed and desired product was detected. The reaction mixture was filtered, and the filtrate was concentrated to give the product methyl (6S,7aR)-2-methylene-6-((4-nitrobenzoyl)oxy)tetrahydro-1H-pyrrolizine-7a(5H)-carboxylate (I-7g, 170 mg, 94%) as a light yellow oil. $^1$H NMR (400 MHz, CDCl$_3$) δ 8.30 (d, J=8.6 Hz, 2H), 8.16 (d, J=8.6 Hz, 2H), 5.58 (s, 1H), 5.02 (s, 1H), 4.98 (s, 1H), 3.94 (d, J=14.4 Hz, 1H), 3.77 (s, 3H), 3.62 (dd, J=12.6, 5.1 Hz, 1H), 3.52 (d, J=14.3 Hz, 1H), 3.15 (d, J=16.2 Hz, 2H), 3.08 (dd, J=12.6, 1.8 Hz, 1H), 2.87 (dd, J=14.6, 6.7 Hz, 1H), 2.75 (d, J=16.2 Hz, 1H), 2.20 (dd, J=14.6, 2.7 Hz, 1H). MS: 347.1 [M+H]$^+$.

Step 7: Synthesis of (2S,7aR)-2-hydroxy-6-methylenetetrahydro-1H-pyrrolizine-7a(5H)-carboxylic Acid (I-7h)

A solution of methyl (6S,7aR)-2-methylene-6-((4-nitrobenzoyl)oxy)tetrahydro-1H-pyrrolizine-7a(5H)-carboxylate (I-7g, 500 mg, 1.44 mmol) and K$_2$CO$_3$ (2000 mg, 14.4 mmol) in methanol (10 mL) was stirred at 20° C. for 2 h. LCMS showed that the starting material was consumed and desired product was detected. The reaction mixture was filtered, and the filtrate was concentrated to give the crude product (2S,7aR)-2-hydroxy-6-methylenetetrahydro-1H-pyrrolizine-7a(5H)-carboxylic acid (I-7h, 300 mg, crude) as a light-yellow oil. MS: 184.1 [M+H]$^+$.

Step 8: Synthesis of (2S,7aR)-7a-(hydroxymethyl)-8-methylenehexahydro-1H-pyrrolizin-2-ol (I-7)

To a stirred solution of (2S,7aR)-2-hydroxy-6-methylenetetrahydro-1H-pyrrolizine-7a(5H)-carboxylic acid (I-7h, 250 mg, 1.36 mmol) in THF (6.8 mL) was added LiAlH$_4$ (8.19 mL, 8.19 mmol, 1M in THF) dropwise at 0° C. The resulting mixture was stirred for 3 h at 60° C. LCMS showed starting material was consumed and desired product was formed. The reaction was quenched with Na$_2$SO$_4$·10H$_2$O solid (0.5 g) and stirred at 20° C. for 2 h. The suspension was filtered through celite, and the filtrate was concentrated in vacuo. The residue was purified by flash column chromatography (Biotage, 4 g, 15-30% MeOH in DCM (1% NH$_4$OH in MeOH)) to afford (2S,7aR)-7a-(hydroxymethyl)-6-methylenehexahydro-1H-pyrrolizin-2-ol (I-7, 70 mg, 30%) as a light-yellow oil. $^1$H NMR (400 MHz, CDCl$_3$) δ 4.98-4.90 (m, 2H), 4.49 (dq, J=10.5, 5.2 Hz, 1H), 3.68 (d, J=15.4 Hz, 1H), 3.46 (dd, J=14.6, 1.3 Hz, 1H), 3.31 (dd, J=10.8, 5.3 Hz, 1H), 3.25 (s, 2H), 2.73 (dd, J=10.8, 5.2 Hz, 1H), 2.63 (dd, J=15.8, 1.4 Hz, 1H), 2.41 (dd, J=15.8, 0.9 Hz, 1H), 2.29 (dd, J=13.4, 6.7 Hz, 1H), 1.77 (dd, J=13.4, 4.9 Hz, 1H). MS: 170.2 [M+H]$^+$.

Intermediate 8 (I-8): [(2Z,7aS)-2-(2-methoxyethylidene)tetrahydro-1H-pyrrolizin-7a(5H)-yl]methanol

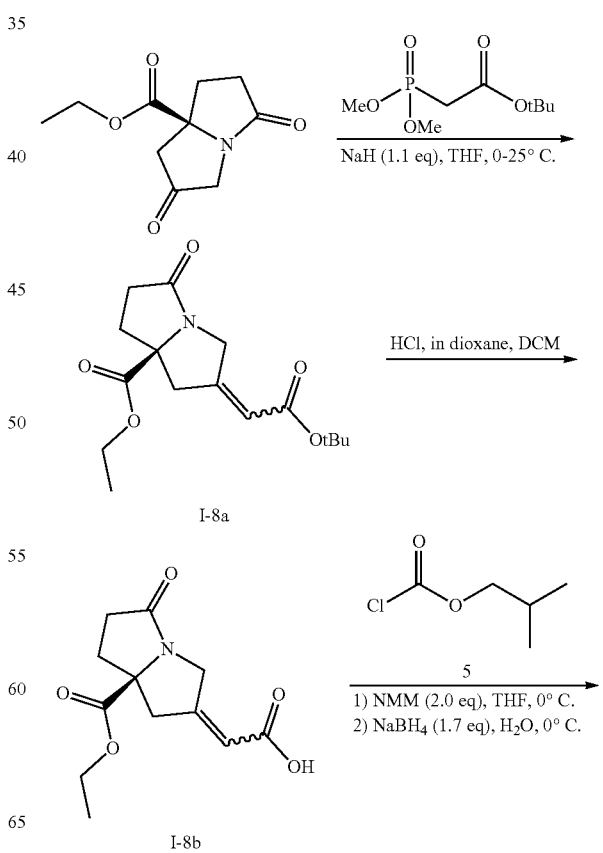

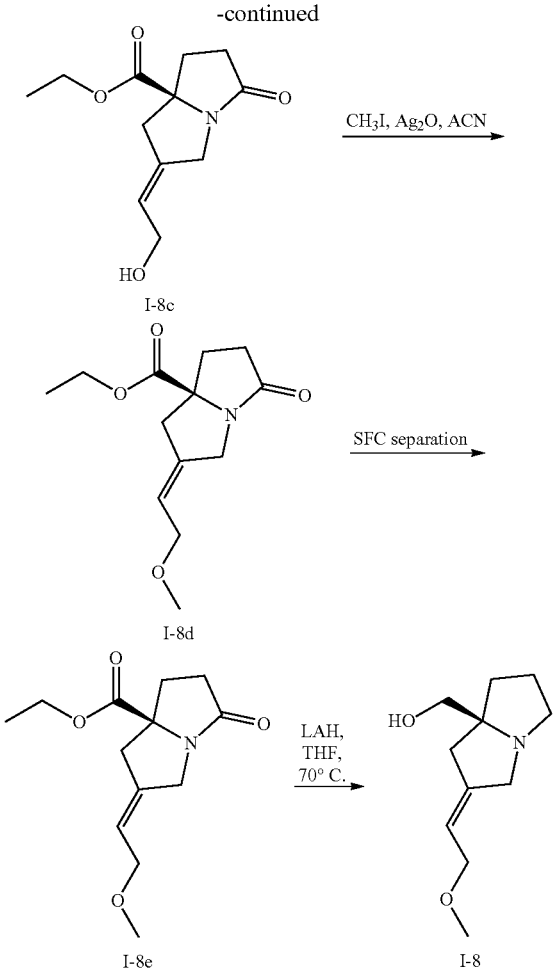

Step 1: Synthesis of ethyl (S)-2-(2-(tert-butoxy)-2-oxoethylidene)-5-oxotetrahydro-1H-pyrrolizine-7a(5H)-carboxylate (I-8a)

To a stirred solution of tert-butyl 2-(dimethoxyphosphoryl)acetate (2340 mg, 10.4 mmol) in THF (40 mL) was slowly added NaH (417 mg, 10.4 mmol) at 0° C. The suspension was stirred at 0° C. for 10 min. Then ethyl (S)-2,5-dioxotetrahydro-1H-pyrrolizine-7a(5H)-carboxylate (2000 mg, 9.47 mmol) in THF (5 mL) was added dropwise at 0° C. The resulting mixture was warmed up to 25° C. gradually and stirred for another 2 h. LCMS showed the starting material was consumed and desired product was formed. The reaction was quenched with water (50 mL) and extracted with EtOAc (50 mL×3). The combined organic layers were washed with brine (150 mL), dried over Na2SO4, filtered and concentrated under reduced pressure. The residue was purified by flash column chromatography (Biotage, 80 g silica gel, 0%-30% EtOAc in Petroleum ether) to give crude ethyl (S)-2-(2-(tert-butoxy)-2-oxoethylidene)-5-oxotetrahydro-1H-pyrrolizine-7a(5H)-carboxylate (1870 mg, crude) as colorless oil. LCMS (ESI) m/z: 310.1 [M+H]+.

Step 2: Synthesis of (S)-2-(7a-(ethoxycarbonyl)-5-oxotetrahydro-1H-pyrrolizin-2(3H)-ylidene)acetic Acid (I-8b)

To a solution of ethyl (S)-2-(2-(tert-butoxy)-2-oxoethylidene)-5-oxotetrahydro-1H-pyrrolizine-7a(5H)-carboxylate (700 mg, 2.26 mmol) in DCM (8 mL) was added HCl (6 mL, 4.0 M in dioxane). Then the mixture was stirred at 25° C. for 16 h. LCMS showed the starting material was consumed and desired product was formed. The solution was concentrated under reduced pressure to give (S)-2-(7a-(ethoxycarbonyl)-5-oxotetrahydro-1H-pyrrolizin-2(3H)-ylidene)acetic acid (550 mg, crude) as light-yellow oil. LCMS (ESI) m/z: 254.1 [M+H]+.

Step 3: Synthesis of ethyl (S)-2-(2-hydroxyethylidene)-5-oxotetrahydro-1H-pyrrolizine-7a(5H)-carboxylate (I-8c)

To a solution of (S)-2-(7a-(ethoxycarbonyl)-5-oxotetrahydro-1H-pyrrolizin-2(3H)-ylidene)acetic acid (970 mg, 3.83 mmol) and NMM (774 mg, 7.65 mmol) in THF (33 mL) was added isobutyl chloroformate (784 mg, 5.74 mmol) in THF (4 mL) dropwise at 0° C. The mixture was stirred at 0° C. for 40 min. Precipitation occurred and LCMS showed the mixed anhydride intermediate was formed. Solid was filtered. NaBH4 (247 mg, 6.53 mmol) in water (5 mL) was added to the filtrate at 0° C. The resulting mixture was stirred at 0° C. for 15 min. LCMS showed the desired product was formed. The solution was concentrated under reduced pressure. The residue was purified by flash column chromatography (Biotage, 25 g silica gel, 0-100% EtOAc in Petroleum ether) to give ethyl (S)-2-(2-hydroxyethylidene)-5-oxotetrahydro-1H-pyrrolizine-7a(5H)-carboxylate (220 mg, 24%, E/Z mixture) as colorless oil. $^1$H NMR (400 MHz, CDCl$_3$) δ 5.71-5.57 (m, 1H), 4.33 (d, J=16.0 Hz, 1H), 4.21 (q, J=7.1 Hz, 2H), 4.16-4.08 (m, 2H), 3.78 (d, J=17.0 Hz, 1H), 3.24 (d, J=15.7 Hz, 0.2H, minor isomer), 3.07 (d, J=15.8 Hz, 0.8H, major isomer), 2.84-2.73 (m, 1H), 2.67-2.57 (m, 1H), 2.55-2.37 (m, 2H), 2.18-2.06 (m, 1H), 1.28 (t, J=7.1 Hz, 3H). LCMS (ESI) m/z 240.1 [M+H]+.

Step 4: Synthesis of ethyl (S)-2-(2-methoxyethylidene)-5-oxotetrahydro-1H-pyrrolizine-7a(5H)-carboxylate (I-8d)

To a solution of ethyl (S)-2-(2-hydroxyethylidene)-5-oxotetrahydro-1H-pyrrolizine-7a(5H)-carboxylate (180 mg, 0.752 mmol) and Ag$_2$O (872 mg, 3.76 mmol) in CH3CN (10 mL) was added iodomethane (1070 mg, 7.52 mmol). The reaction mixture was stirred at 25° C. for 16 h. LCMS showed ~50% of the starting material remained and ~50% of the desired product was formed. Another portion of Ag$_2$O (436 mg, 1.88 mmol) was added and the mixture was stirred for another 16 h. LCMS showed the starting material was consumed and desired product was formed. The mixture was filtered. The filtrate was concentrated under reduced pressure to give crude ethyl (S)-2-(2-methoxyethylidene)-5-oxotetrahydro-1H-pyrrolizine-7a(SH)-carboxylate (200 mg, crude, E/Z mixture) as a light yellow solid. $^1$H NMR (400 MHz, CDCl$_3$) δ 5.54-5.45 (m, 1H), 4.31-4.21 (m, 1H), 4.13 (q, J=7.1 Hz, 2H), 3.86-3.77 (m, 2H), 3.71 (d, J=15.6 Hz, 1H), 3.24 (s, 3H), 3.15 (d, J=16.7 Hz, 0.2H, minor isomer), 3.00 (d, J=15.8 Hz, 0.8H, major isomer), 2.79-2.66 (m, 1H), 2.61-2.50 (m, 1H), 2.49-2.33 (m, 2H), 2.11-2.00 (m, 1H), 1.20 (t, J=7.1 Hz, 3H). LCMS (ESI) m/z: 254.1 [M+H]+.

Step 5: Separation of ethyl (S,Z)-2-(2-methoxyethylidene)-5-oxotetrahydro-1H-pyrrolizine-7a(5H)-carboxylate (I-8e)

The E/Z mixture of ethyl (S)-2-(2-methoxyethylidene)-5-oxotetrahydro-1H-pyrrolizine-7a(5SH-carboxylate    (200 mg, 0.79 mmol) was separated by chiral SFC (Apparatus: SFC 150; Column: Daicel CHIRALPAK IC, 250 mm×30 mm I.D., 10 μm; Mobile phase: CO$_2$/MeOH [0.2% NH$_3$ (7M Solution in MeOH)]=90/10; Flow rate: 120 g/min; Wave length: UV 214 nm; Temperature: 35° C.) to give ethyl (S,Z)-2-(2-methoxyethylidene)-5-oxotetrahydro-1H-pyrrolizine-7a(5H)-carboxylate (91 mg, 46%, Rt: 2.406 min, Peak 1) as a light-yellow oil. $^1$H NMR (400 MHz, CDCl$_3$) δ 5.63-5.52 (m, 1H), 4.32 (d, J=16.0 Hz, 1H), 4.20 (q, J=7.1 Hz, 2H), 3.87 (d, J=6.5 Hz, 2H), 3.78 (d, J=15.9 Hz, 1H), 3.31 (s, 3H), 3.07 (d, J=15.8 Hz, 1H), 2.78 (dt, J=16.7, 9.7 Hz, 1H), 2.61 (ddd, J=13.2, 9.1, 1.8 Hz, 1H), 2.56-2.40 (m, 2H), 2.18-2.05 (m, 1H), 1.27 (t, J=7.1 Hz, 3H). LCMS (ESI) m/z: 254.1 [M+H]$^+$.

Step 6: Synthesis of (S,Z)-(2-(2-methoxyethylidene) tetrahydro-1H-pyrrolizin-7a(5H)-yl)methanol (Compound I-8)

To a solution of ethyl (S,Z)-2-(2-methoxyethylidene)-5-oxotetrahydro-1H-pyrrolizine-7a(5H)-carboxylate (80 mg, 0.32 mmol) in THF (3.2 mL) was added LAH (0.63 mL, 1 M in THF) at 0° C. under nitrogen. The resulting mixture was warmed to 70° C. and stirred at 70° C. for 1 h. TLC (DCM/MeOH=10:1, iodine stain) showed the starting material was consumed and a new point was observed. The mixture was quenched with Na$_2$SO$_4$·10 H$_2$O, and the suspension was stirred at 25° C. for 2 h. The mixture was filtered and the filtrate concentrated to give crude (S,Z)-(2-(2-methoxyethylidene)tetrahydro-1H-pyrrolizin-7a(5H)-yl) methanol (58 mg, 93%) as yellow oil. $^1$H NMR (400 MHz, CDCl$_3$) δ 5.52-5.42 (m, 1H), 3.88-3.81 (m, 2H), 3.68 (d, J=15.6 Hz, 1H), 3.36-3.21 (m, 6H), 3.15-3.05 (m, 1H), 2.67 (dt, J=10.1, 7.1 Hz, 1H), 2.50 (d, J=16.1 Hz, 1H), 2.38 (d, J=16.3 Hz, 1H), 1.93-1.78 (m, 3H), 1.72-1.65 (m, 1H). LCMS (ESI) m/z 198.3 [M+H]$^+$.

(Note: separately, the E isomer was also prepared from the pure E-ester through LAH reduction in a similar fashion)

Intermediate(s) 9 (I9-i and I9-ii): (5R)-4-bromo-5-methyl-1-(tetrahydro-2H-pyran-2-yl)-5,6,7,8-tetrahydro-1H-benzo[f]indazole and (5S)-4-bromo-5-methyl-1-(tetrahydro-2H-pyran-2-yl)-5,6,7,8-tetrahydro-1H-benzo[f]indazole

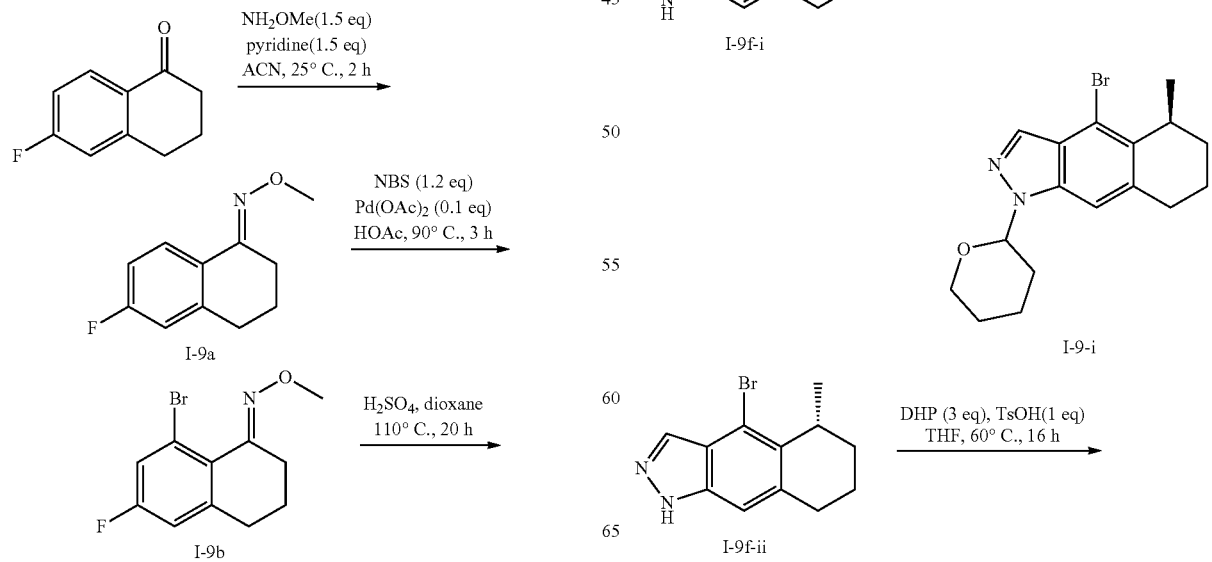

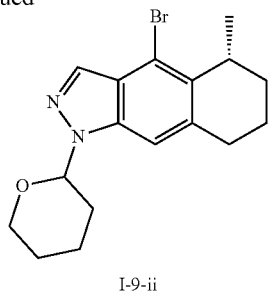

I-9-ii

Step 1: Synthesis of (E)-6-fluoro-3,4-dihydronaphthalen-1(2H)-one O-methyl Oxime (I-9a)

A solution of 6-fluoro-1-tetralone (4.00 g, 24.4 mmol), methoxylamine hydrochloride (3.05 g, 36.5 mmol) and pyridine (2.89 g, 36.5 mmol) in CH3CN (20 mL) was stirred at 25° C. for 2 h. LCMS showed the desired product was formed. The reaction mixture was diluted with water (100 mL) and extracted with EtOAc (100 mL×3). The organic layers were combined, washed with 2 M aqueous HCl (100 mL×2) and brine (200 mL), dried over Na$_2$SO$_4$, filtered, and concentrated under reduced pressure to give (E)-6-fluoro-3,4-dihydronaphthalen-1(2H)-one O-methyl oxime (4.90 g, crude) as a yellow oil. $^1$H NMR (400 MHz, CDCl$_3$) δ 7.96 (dd, J=8.8, 6.0 Hz, 1H), 6.88 (td, J=8.6, 2.7 Hz, 1H), 6.82 (dd, J=9.3, 2.6 Hz, 1H), 3.97 (s, 3H), 2.76-2.67 (m, 4H), 1.88-1.77 (m, 2H). LCMS (ESI) m/z: 194.1 [M+H]$^+$.

Step 2: Synthesis of (E)-8-bromo-6-fluoro-3,4-dihydronaphthalen-1(2H)-one O-methyl Oxime (I-9b)

To a mixture of (E)-6-fluoro-3,4-dihydronaphthalen-1(2H)-one O-methyl oxime (4.90 g, 25.4 mmol) and NBS (5.42 g, 30.4 mmol) in acetic acid (121 mL) was added palladium acetate (422 mg, 2.54 mmol) under nitrogen. Then the reaction was stirred at 90° C. for 3 h. LCMS showed the starting material was consumed and the desired compound was found. The mixture was filtered through a Celite pad, and the filtrate was concentrated to give the crude product. The crude product was purified by flash column chromatography (Combi-Flash, 80 g silica gel, 0~5% EtOAc in Petroleum ether) to afford (E)-8-bromo-6-fluoro-3,4-dihydronaphthalen-1(2H)-one O-methyl oxime (5.60 g, 81%) as a yellow oil. $^1$H NMR (400 MHz, CDCl$_3$) δ 7.27 (dd, J=8.5, 2.7 Hz, 1H), 6.84 (dd, J=8.3, 2.6 Hz, 1H), 4.02 (s, 3H), 2.75 (t, J=6.9 Hz, 2H), 2.65-2.57 (m, 2H), 1.81-1.70 (m, 2H). LCMS (ESI) m/z: 272.1, 274.0 [M+H]$^+$.

Step 3: Synthesis of 8-bromo-8-fluoro-3,4-dihydronaphthalen-1(2H)-one (I-9c)

To a solution of (E)-8-bromo-6-fluoro-3,4-dihydronaphthalen-1(2H)-one O-methyl oxime (5.00 g, 18.3 mmol) in 1,4-dioxane (80 mL) was added diluted sulfuric acid (92 mL, 4 M) at 25° C. The mixture was stirred at 110° C. for 20 h. LCMS showed that the starting material was consumed and the desired product was formed. The reaction mixture was basified to pH 8 with aqueous NaOH (1 M) and extracted with EtOAc (100 mL). The organic layers were combined, washed with brine (30 mL), dried over Na$_2$SO$_4$, filtered, and concentrated in vacuo to give the crude product. The crude product was purified by flash column chromatography (Combi-Flash, 80 g silica gel, 0~5% gradient of EtOAc in petroleum ether) to give 8-bromo-8-fluoro-3,4-dihydronaphthalen-1(2H)-one (3.00 g, 67%) as a yellow oil. $^1$H NMR (400 MHz, CDCl$_3$) δ 7.31 (dd, J=8.3, 2.5 Hz, 1H), 6.96-6.91 (m, 1H), 2.98 (t, J=6.2 Hz, 2H), 2.72-2.65 (m, 2H), 2.15-2.06 (m, 2H). LCMS (ESI) m/z: 243.0, 245.0 [M+H]$^+$.

Step 4: Synthesis of 8-bromo-8-fluoro-1-methyl-1,2,3,4-tetrahydronaphthalene (I-9d)

A solution of MeMgBr in THF (3 M, 12.3 mL, 37.0 mmol) was added dropwise to a solution of 8-bromo-8-fluoro-3,4-dihydronaphthalen-1(2H)-one (3.00 g, 12.3 mmol) in THF (50 mL) at 0° C. After completion of the addition, the solution was stirred at 25° C. for an additional 30 minutes. LCMS showed most starting material was almost consumed and the alcohol intermediate was detected. The reaction mixture was quenched by saturated aqueous NH4Cl solution (25 mL). The mixture was extracted with EtOAc (100 mL). The combined organic extracts were dried over MgSO$_4$ and concentrated. The residue was dissolved in DCM (50 mL). Triethylsilane (5.01 g, 43.2 mmol) and trifluoroacetic acid (3.3 mL) were added at −60° C. The reaction mixture was stirred for 3 h at 25° C. LCMS showed the intermediate was consumed and a desired MS was detected. The reaction mixture was quenched by the addition of saturated aqueous NaHCO$_3$ and extracted with DCM (100 mL). The combined organic extracts were dried over MgSO$_4$ and concentrated in vacuo. The residue was purified by flash column chromatography (Combi-Flash, 80 g silica gel, 0~2% gradient of EtOAc in petroleum ether) to give 8-bromo-8-fluoro-1-methyl-1,2,3,4-tetrahydronaphthalene (2.25 g, 75%) as a colorless oil. $^1$H NMR (400 MHz, CDCl$_3$) δ 7.12 (dd, J=8.1, 2.6 Hz, 1H), 6.77-6.72 (m, 1H), 3.23-3.14 (m, 1H), 2.84-2.67 (m, 2H), 1.91-1.72 (m, 4H), 1.21 (d, J=7.0 Hz, 3H).

Step 5: Synthesis of 1-bromo-3-fluoro-8-methyl-5,6,7,8-tetrahydronaphthalene-2-carbaldehyde (I-9e)

A solution of 2,2,6,6-tetramethylpiperidine (2.09 g, 14.8 mmol) in THF (20 mL) was cooled to −78° C. Then n-BuLi (2.5 M, 4.3 mL, 10.9 mmol) was added to the above solution. The reaction mixture was stirred for 30 mins at −60° C. Then a solution of 8-bromo-6-fluoro-1-methyl-1,2,3,4-tetrahydronaphthalene (1.2 g, 4.9 mmol) in THF (20 mL) was added to the above solution and stirring was continued at −60° C. for 30 mins. Then DMF (1.1 mL, 14.8 mmol) was added to the above solution at −60° C. The mixture was allowed to warm to 15° C. and stirred at 15° C. for 3 h. LCMS showed the starting material was consumed and the desired MS was detected. The mixture was quenched with saturated aqueous NH$_4$Cl (50 mL) and extracted with EtOAc (50 mL×2). The combined organic layer was washed with brine (50 mL), dried and concentrated to give the crude product. The crude product was combined with another batch and purified by flash column chromatography (Combi-Flash, 12 g silica gel, 0-15% petroleum ether in DCM) to provide 1-bromo-3-fluoro-8-methyl-5,6,7,8-tetrahydronaphthalene-2-carbaldehyde (900 mg, 40%) as a yellow oil. $^1$H NMR (400 MHz, CDCl$_3$) δ 10.38 (s, 1H), 6.86 (d, J=11.0 Hz, 1H), 3.41-3.32 (m, 1H), 2.93-2.73 (m, 2H), 1.96-1.76 (m, 4H), 1.24 (d, J=7.0 Hz, 3H). LCMS (ESI) m/z: 271.1, 273.0 [M+H]$^+$.

Step 6: Synthesis of 4-bromo-5-methyl-5,6,7,8-tetrahydro-1H-benzo[f]indazole (I-9f)

To the mixture of 1-bromo-3-fluoro-8-methyl-5,6,7,8-tetrahydronaphthalene-2-carbaldehyde (700 mg, 2.58 mmol) in ethylene glycol (10 mL) was added hydrazine hydrate (1.62 g, 25.8 mmol) at 10° C., then the mixture was stirred at 130° C. for 48 h. LCMS showed that the starting material was consumed and the desired product was formed. Water (10 mL) was added. The aqueous phase was extracted with EtOAc (20 mL), dried over $Na_2SO_4$, and filtered. The solvent was evaporated and the residue was purified by flash column chromatography (Combi-Flash, 4 g silica gel, petroleum ether/EtOAc=90:10) to afford 4-bromo-5-methyl-5,6,7,8-tetrahydro-1H-benzo[f]indazole (330 mg, 48%) as a yellow oil. $^1$H NMR (400 MHz, $CDCl_3$) δ 8.02 (s, 1H), 7.16 (s, 1H), 3.48-3.40 (m, 1H), 3.04-2.88 (m, 2H), 1.90-1.80 (m, 4H), 1.28 (d, J=7.0 Hz, 3H). LCMS (ESI) m/z: 265.1, 267.0 $[M+H]^+$.

Step 7: Chiral Separation of 4-bromo-5-methyl-5,6,7,8-tetrahydro-1H-benzo[f]indazole (to Afford I-9f-i and I-9f-ii)

Racemic 4-bromo-5-methyl-5,6,7,8-tetrahydro-1H-benzo[f]indazole (300 mg, 1.13 mmol) was separated by chiral SFC (Apparatus: SFC 80; Column: Daicel CHIRALCEL® AD, 250 mm×30 mm I.D., 10 µm; Mobile phase: $CO_2$/MeOH [0.2% $NH_3$ (7 M solution in MeOH)]=80/20; Flow rate: 70 g/min; Wave length: UV 214 nm; Temperature: 35° C.) to give two isomers: (R)-4-Bromo-5-methyl-5,6,7,8-tetrahydro-1H-benzo[f]indazole (I9f-i) (90 mg, 30%, Rt: 1.487 min, Peak 1) as a white solid. $^1$H NMR (400 MHz, $CDCl_3$) δ 8.03 (s, 1H), 7.18 (s, 1H), 3.50-3.40 (m, 1H), 3.04-2.84 (m, 2H), 2.01-1.74 (m, 4H), 1.28 (d, J=7.0 Hz, 3H). LCMS (ESI) m/z: 265.0, 267.0 [M+H]+. $[α]_D^{25}$=−29.09 (c 0.11, MeOH). This isomer was taken on to deliver Example 29.

(S)-4-Bromo-5-methyl-5,6,7,8-tetrahydro-1H-benzo[f]indazole (I9f-ii)(80 mg, 27%, Rt: 1.860 min, Peak 2) as a white solid. $^1$H NMR (400 MHz, $CDCl_3$) δ 8.01 (s, 1H), 7.16 (s, 1H), 3.48-3.39 (m, 1H), 3.04-2.82 (m, 2H), 1.98-1.79 (m, 4H), 1.27 (d, J=7.0 Hz, 3H). LCMS (ESI) m/z: 265.0, 266.9 [M+H]+. $[α]_D^{25}$=+17.00 (c 0.1, MeOH). This isomer was taken on to deliver example 32.

Step 8: Synthesis of (5R)-4-bromo-5-methyl-1-(tetrahydro-2H-pyran-2-yl)-5,6,7,8-tetrahydro-1H-benzo[f]indazole (I-9-i)

To a solution of (R)-4-Bromo-5-methyl-5,6,7,8-tetrahydro-1H-benzo[f]indazole (I-9f-i) (50 mg, 0.19 mmol) in THF (3.0 mL) was added DHP (47 mg 0.56 mmol) followed by p-toluenesulfonic acid monohydrate (36 mg, 0.19 mmol). The reaction mixture was stirred at 60° C. for 16 hours. LCMS showed that the desired product was formed. The mixture was cooled and washed with saturated aqueous $NaHCO_3$ (10 mL) and brine (10 mL). The organic layer was dried and concentrated. The residue was combined with the crude product of another batch and purified by flash column chromatography (Combi-flash, 4 g silica gel, EtOAc in petroleum ether from 0 to 10%) to give (5R)-4-bromo-5-methyl-1-(tetrahydro-2H-pyran-2-yl)-5,6,7,8-tetrahydro-1H-benzo[f]indazole (70 mg, 89%) as a light-yellow oil. $^1$H NMR (400 MHz, $CDCl_3$) δ 7.96 (s, 1H), 7.25 (s, 1H), 5.63 (dt, J=9.3, 2.8 Hz, 1H), 4.04-3.94 (m, 1H), 3.77-3.69 (m, 1H), 3.54-3.41 (m, 1H), 3.07-2.88 (m, 2H), 2.60-2.46 (m, 1H), 2.20-1.75 (m, 9H), 1.26-1.24 (m, 3H). LCMS (ESI) m/z: 349.1, 351.1 $[M+H]^+$.

Step 9: Synthesis of (5S)-4-bromo-5-methyl-1-(tetrahydro-2H-pyran-2-yl)-5,6,7,8-tetrahydro-1H-benzo[f]indazole (I-9-ii)

To a solution of (S)-4-Bromo-5-methyl-5,6,7,8-tetrahydro-1H-benzo[f]indazole (19f-ii) (80 mg 0.30 mmol) in THF (4.0 mL) was added DHP (76 mg 0.905 mmol) followed by p-toluenesulfonic acid monohydrate (57 mg, 0.302 mmol). The reaction mixture was stirred at 60° C. for 16 hours. LCMS showed that the desired product was formed. The mixture was cooled and washed with saturated aqueous $NaHCO_3$ (10 mL) and brine (10 mL). The organic layer was dried, concentrated, and the residue was purified by flash column chromatography (Combi-flash, 4 g silica gel, EtOAc in petroleum ether from 0 to 10%) to give (5S*)-4-bromo-5-methyl-1-(tetrahydro-2H-pyran-2-yl)-5,6,7,8-tetrahydro-1H benzo[f]indazole) (72 mg, 68%), as a light yellow oil. $^1$H NMR (400 MHz, $CDCl_3$) δ 7.96 (s, 1H), 7.25 (s, 1H), 5.64 (dt, J=9.3, 2.9 Hz, 1H), 4.04-3.99 (m, 1H), 3.76-3.69 (m, 1H), 3.46-3.39 (m, 1H), 3.04-2.91 (m, 2H), 2.59-2.45 (m, 1H), 2.18-1.77 (m, 9H), 1.26-1.24 (m, 3H). LCMS (ESI) m/z: 349.0, 351.0 $[M+H]^+$.

Intermediate 10 (I-10): rac-4-bromo-6-chloro-5-(cis-2-methylcyclopropyl)-1-(tetrahydro-2H-pyran-2-yl)-1H-indazole

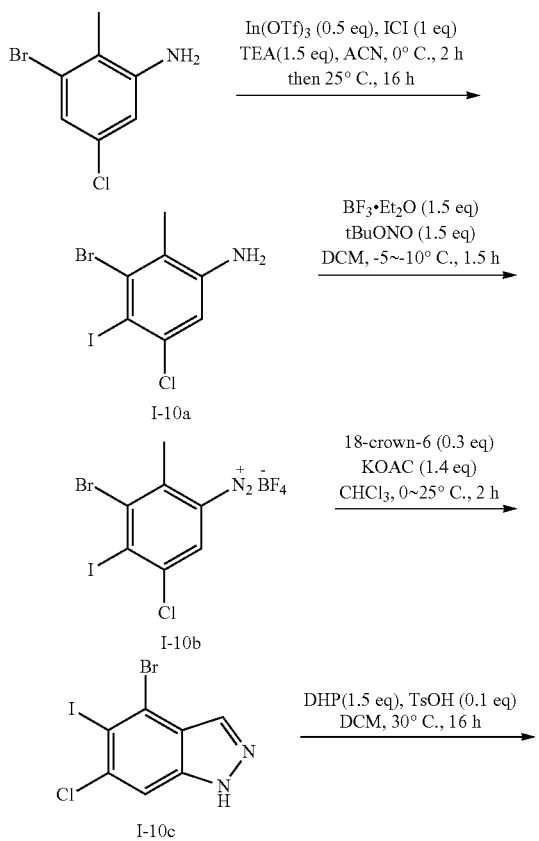

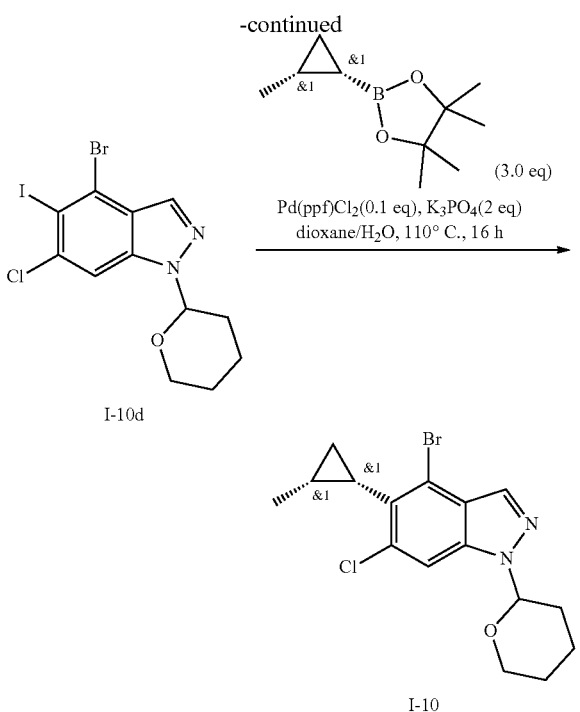

I-10d

I-10

Step 1: Synthesis of 3-bromo-5-chloro-4-iodo-2-methylaniline (I-10a)

To a stirred solution of 3-bromo-5-chloro-2-methylaniline (10 g, 45 mmol) in CH3CN (113 mL) was added indium(III) trifluoromethanesulfonate (12.7 g, 22.7 mmol) followed by iodine monochloride (7.36 g, 45.4 mmol) dropwise at 0° C. The reaction was stirred at 0° C. for 2 h. It was then warmed to 25° C. and stirred at 25° C. for 16 h. LCMS showed that most starting material was consumed, and the desired product was formed. The reaction was quenched with triethylamine (9.5 mL, 68 mmol) and then stirred for 15 mins. Solids were removed by filtration over celite. The filter cake was rinsed with EtOAc (100 mL). The filtrate was collected, washed with brine (70 mL), dried over Na$_2$SO$_4$, filtered, and concentrated under reduced pressure. The residue was purified by flash column chromatography (120 g silica gel, 0-5% EtOAc in petroleum ether) to give 3-bromo-5-chloro-4-iodo-2-methylaniline (9.5 g, 60%) as a solid. $^1$H NMR (400 MHz, CDCl$_3$) δ 6.85 (s, 1H), 3.82 (s, 2H), 2.38 (s, 3H). LCMS (ESI) m/z: 345.9, 347.8 [M+H]$^+$.

Step 2: Synthesis of 3-bromo-5-chloro-4-iodo-2-methylbenzenediazonium Tetrafluoroborate (I-10b)

Boron trifluoride diethyl etherate (2.46 g, 17.3 mmol) was dissolved in DCM (35 mL) and cooled to −5 to −10° C. under nitrogen atmosphere. A solution of 3-bromo-5-chloro-4-iodo-2-methylaniline (4 g, 11.6 mmol) in DCM (5 mL) was added to the above reaction mixture and stirred for 0.5 h. Then tert-butyl nitrite (1.79 g, 17.3 mmol) was added dropwise, and the reaction mixture was stirred at −5 to −10° C. for 1.5 h. TLC (petroleum ether/EtOAc=5:1, UV 254 nm) showed the starting material (Rf=0.15) was consumed completely. MTBE (50 mL) was added to the reaction mixture to form a precipitate, which was vacuum filtered and washed with cold MTBE (10 mL×2) to give 3-bromo-5-chloro-4-iodo-2-methylbenzenediazonium tetrafluoroborate (4.6 g, 90%) as a white solid. $^1$H NMR (400 MHz, MeOD) δ 8.79 (s, 1H), 2.94 (s, 3H).

Step 3: Synthesis of 4-bromo-8-chloro-5-iodo-1H-indazole (I-10c)

To a solution of 18-crown-6 (819 mg, 3.1 mmol) in chloroform (50 mL) was added KOAc (1.42 g, 14.5 mmol) and the mixture was cooled to 0° C. Then 3-bromo-5-chloro-4-iodo-2-methylbenzenediazonium tetrafluoroborate (4.6 g, 10.3 mmol) was added slowly. The reaction mixture was then allowed to stir at 25° C. for 2 h. LCMS showed that the desired product was formed. The reaction mixture was poured into ice-cold water (100 mL) and extracted with DCM (50 mL×3). The combined organic layers were washed with saturated aqueous NaHCO$_3$ (50 mL) and brine (50 mL), dried over Na$_2$SO$_4$, filtered, and concentrated. The residue was purified by flash column chromatography (40 g silica gel, 9% EtOAc in petroleum ether) to give 4-bromo-6-chloro-5-iodo-1H-indazole (1.95 g, 53%) as a yellow solid. $^1$H NMR (400 MHz, CDCl3) δ 8.02 (s, 1H), 7.68 (d, J=0.9 Hz, 1H). LCMS (ESI) m/z: 356.8, 358.7 [M+H]+.

Step 4: Synthesis of 4-bromo-8-chloro-5-iodo-1-(tetrahydro-2H-pyran-2-yl)-1H-indazole (I-10d)

To a solution of 4-bromo-8-chloro-5-iodo-1H-indazole (1.95 g, 5.45 mmol) in DCM (50 mL) was added DHP (688 mg, 8.18 mmol) followed by p-toluenesulfonic acid monohydrate (104 mg, 0.546 mmol) and the reaction mixture was stirred at 30° C. for 16 h. LCMS showed that the starting material was consumed. The mixture was sequentially washed with saturated aqueous NaHCO$_3$ (30 mL) and brine (30 mL). The organic layer was dried, concentrated, and purified by flash column chromatography (12 g silica gel, EtOAc in PE from 0-5%) to give 4-bromo-6-chloro-5-iodo-1-(tetrahydro-2H-pyran-2-yl)-1H-indazole (2.1 g, 87%) as a yellow solid. $^1$H NMR (400 MHz, CDCl$_3$) δ 7.92 (s, 1H), 7.78 (d, J=0.7 Hz, 1H), 5.65 (dd, J=8.9, 2.7 Hz, 1H), 4.04-3.92 (m, 1H), 3.84-3.62 (m, 1H), 2.55-2.38 (m, 1H), 2.16-2.02 (m, 2H), 1.80-1.67 (m, 3H). LCMS (ESI) m/z: 356.8 and 358.9 [M-THP+H]+.

Step 5: Synthesis of rac-4-bromo-6-chloro-5-((1R,2S)-2-methylcyclopropyl)-1-(tetrahydro-2H-pyran-2-yl)-1H-indazole (I-10)

To a mixture of 4-bromo-6-chloro-5-iodo-1-(tetrahydro-2H-pyran-2-yl)-1H-indazole (217 mg, 0.49 mmol), potassium phosphate tribasic (209 mg, 0.98 mmol) and rac-cis-4,4,5,5-tetramethyl-2-(cis-2-methylcyclopropyl)-1,3,2-dioxaborolane (268 mg, 1.47 mmol) in 1,4-dioxane (5 mL) and water (0.5 mL) was added Pd(dppf)Cl$_2$ (36 mg, 0.05 mmol). The mixture was degassed with nitrogen for 2 mins and then stirred at 110° C. for 16 h. Another 3 reactions on the same scale were set up in parallel. LCMS showed the starting material was consumed and about 25% of the desired product was detected (UV 214 nm). The mixture of all 4 reactions were combined, diluted with water (100 mL), and extracted with EtOAc (50 mL×3). The combined organic layer was dried over Na$_2$SO$_4$ and concentrated under reduced pressure. The residue was purified by flash column chromatography (12 g silica gel, eluted with 3% EtOAc in petroleum ether) followed by flash reversed-phase column chromatography (40 g C18, eluted with a gradient of 0-70% CH3CN in water (0.1% FA)) to give rac-4-bromo-6-chloro- 5-(cis)-2-methylcyclopropyl)-1-(tetrahydro-2H-pyran-2-yl)-1H-indazole (200 mg, 27%) as an oil. $^1$H NMR (400 MHz, CDCl3) δ 7.98 (s, 1H), 7.64 (s, 1H), 5.63 and 5.62 (2 dd, J=9.2, 2.7 Hz, 1H, major and minor diastereomer respectively), 4.08-3.93 (m, 1H), 3.81-3.66 (m, 1H), 2.59-2.40 (m, 1H), 2.18-2.03 (m, 2H), 1.95 (td, J=8.5, 6.7 Hz, 1H), 1.82-1.63 (m, 3H), 1.46-1.32 (m, 2H), 1.31-1.21 (m, 1H), 0.89-0.84 (m, 1H), 0.81 and 0.81 (2 d, J=6.0 Hz, 3H, major and minor diastereomer respectively). LCMS (ESI) m/z: 369.0, 370.9 [M+H]+.

Note: this intermediate was taken on to final products according to scheme A. Separation of the final analogs was achieved by chiral-HPLC (Column: CHIRALPAK IK 2.5 cm I.D.×25 cm L, 10 μm; mobile phase: CH3CN/DEA=100/0.1 (V/V); flow rate: 30 mL/min) followed by prep-HPLC purification to afford examples 30 and 31.

Intermediate 11 (I-11): 4-bromo-6-chloro-5-ethyl-1-(tetrahydro-2H-pyran-2-yl)-1H-indazole

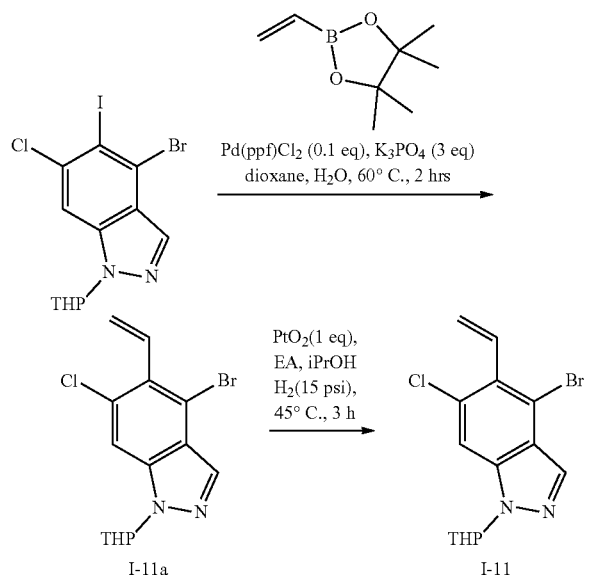

Step 1: Synthesis of 4-bromo-6-chloro-1-(tetrahydro-2H-pyran-2-yl)-5-vinyl-1H-indazole (I-11a)

To a solution of 4-bromo-6-chloro-5-iodo-1-(tetrahydro-2H-pyran-2-yl)-1H-indazole (450 mg, 1.02 mmol) and 4,4,5,5-tetramethyl-2-vinyl-1,3,2-dioxaborolane (314 mg, 2.04 mmol) in 1,4-dioxane (10 mL) and water (1 mL) were added Pd(dppf)Cl$_2$ (75 mg, 0.102 mmol) and potassium phosphate tribasic (649 mg, 3.06 mmol). Then the mixture was degassed by nitrogen and stirred at 60° C. for 2 h. LCMS showed that the starting material was consumed and the desired product was formed. The reaction mixture was poured into EtOAc (50 mL) and layers were partitioned. The organic layer was washed with water (30 mL), dried over Na$_2$SO$_4$. After filtration, the filtrate was concentrated in vacuo. The residue was purified flash column chromatography (Combi-Flash, 12 g silica gel, 0-10% EtOAc in Petroleum ether) to give 4-bromo-6-chloro-1-(tetrahydro-2H-pyran-2-yl)-5-vinyl-1H-indazole (220 mg, 63%) as a white solid. LCMS (ESI) m/z: 340.9, 343.0 [M+H]$^+$.

Step 2: Synthesis of 4-bromo-6-chloro-5-ethyl-1-(tetrahydro-2H-pyran-2-yl)-1H-indazole (I-11)

To a solution of 4-bromo-6-chloro-1-(tetrahydro-2H-pyran-2-yl)-5-vinyl-1H-indazole (220 mg, 0.644 mmol) in EtOAc (5 mL) and isopropanol (5 mL) was added platinum (IV) oxide (146 mg, 0.644 mmol). Then the reaction mixture was stirred at 45° C. under hydrogen (15 psi) atmosphere for 3 h. LCMS showed that the starting material was consumed and the desired product was formed. The mixture was filtered and the filter cake was washed with EtOAc (30 mL). The filtrate was concentrated in vacuo. The residue was purified by Prep-TLC (EtOAc/petroleum ether=1/15, UV 254 nm) to give 4-bromo-6-chloro-5-ethyl-1-(tetrahydro-2H-pyran-2-yl)-1H-indazole (80 mg, 36%) as a white solid. $^1$H NMR (400 MHz, CDCl$_3$) δ 7.89 (d, J=3.0 Hz, 1H), 7.56 (d, J=3.0 Hz, 1H), 5.61-5.53 (m, 1H), 3.93 (d, J=8.2 Hz, 1H), 3.67 (t, J=10.0 Hz, 1H), 3.00 (dt, J=14.7, 5.4 Hz, 2H), 2.41 (dd, J=11.1, 8.5 Hz, 1H), 2.07 (s, 1H), 1.77-1.60 (m, 4H), 1.12 (td, J=7.4, 3.8 Hz, 3H). LCMS (ESI) m/z: 343.0, 345.0 [M+H]$^+$.

Intermediate 12 (I-12): (8aS,13S)-5-chloro-4-fluoro-13-methyl-2-(methylthio)-8a,9,12,13-tetrahydro-8H,11H-7,10-dioxa-1,3,6,13a-tetraazanaphtho[1,8-ab]heptalene

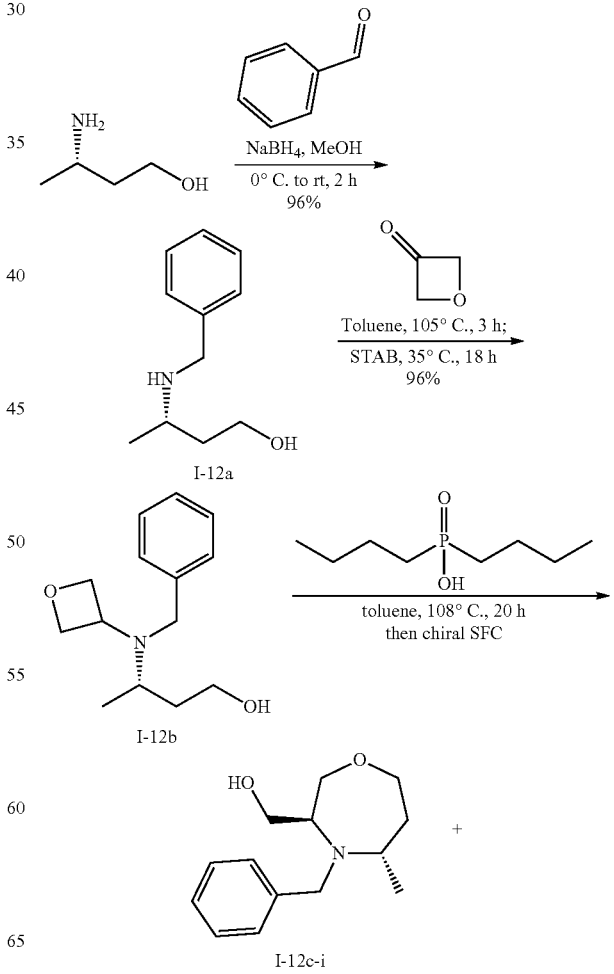

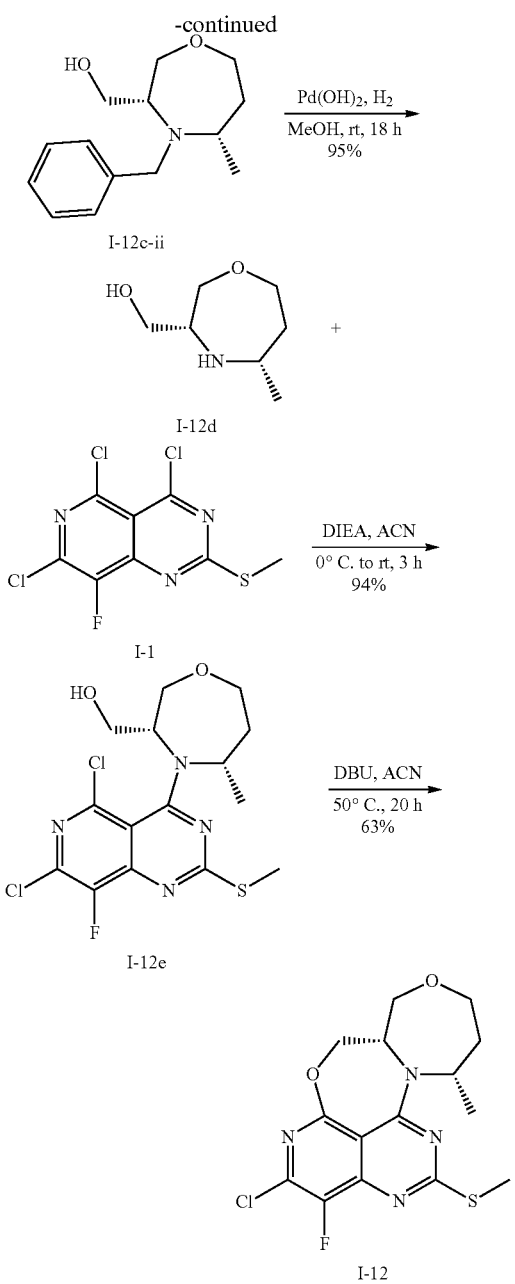

Step 1: Synthesis of (S)-3-(benzylamino)butan-1-ol (I-12a)

To a solution of (3S)-3-aminobutan-1-ol (1.765 g, 1.90 mL, 1.00 Eq, 19.80 mmol) in methanol (30 mL) was added benzaldehyde (2.10 g, 2.01 mL, 1 Eq, 19.8 mmol). The mixture was stirred at rt for 1 h. The reaction was then cooled in an ice bath, and sodium borohydride (749 mg, 1 eq, 19.8 mmol) was added in portions to keep the bubbling under control. After 20 minutes, the reaction was removed from the ice bath and stirred at rt for 2 h. LCMS shows desired mass and no benzaldehyde peak remaining. Water was added, and the reaction was concentrated under vacuum. The white solid was taken up in water (40 mL) and extracted with DCM (2×40 mL). The combined DCM layers were dried over $Na_2SO_4$, filtered and concentrated to give (S)-3-(benzylamino)butan-1-ol (3.41 g, 96%) as a clear oil. $^1$H NMR (400 MHz, METHANOL-$d_4$) δ=7.38-7.28 (m, 4H), 7.28-7.21 (m, 1H), 3.84-3.79 (m, 1H), 3.75-3.58 (m, 3H), 2.87 (sxt, J=6.4 Hz, 1H), 1.76 (tdd, J=6.2, 7.8, 14.0 Hz, 1H), 1.56 (qd, J=5.8, 14.0 Hz, 1H), 1.13 (d, J=6.3 Hz, 3H). LCMS (ES-API) m/z: 180.1 [M+H]$^+$.

Step 2: Synthesis of (S)-3-(benzyl(oxetan-3-yl)amino)butan-1-ol (I-12b)

A solution of (S)-3-(benzylamino)butan-1-ol (3.28 g, 1 Eq, 18.3 mmol) in Toluene (30 mL) was treated with Oxetan-3-on (1.52 g, 1.35 mL, 1.15 Eq, 21.1 mmol) and heated to 105° C. for 3 h. The reaction was cooled to 35° C. and sodium triacetoxyborohydride (6.21 g, 1.60 Eq, 29.3 mmol) was added. The reaction was continued overnight at 35° C. The reaction was quenched with 2N $Na_2CO_3$ (40 mL) and stirred vigorously at rt for 1 h. The layers were separated. The aqueous layer was extracted a second time with toluene. The combined toluene layers were concentrated under vacuum at 40° C. to give (S)-3-(benzyl(oxetan-3-yl)amino)butan-1-ol (4.14 g, 96%) as a clear oil. $^1$H NMR (400 MHz, METHANOL-$d_4$) δ=7.37-7.33 (m, 2H), 7.32-7.26 (m, 2H), 7.25-7.20 (m, 1H), 4.68-4.63 (m, 1H), 4.56 (t, J=6.6 Hz, 1H), 4.45-4.35 (m, 2H), 4.30-4.20 (m, 1H), 3.92 (d, J=14.0 Hz, 1H), 3.66-3.52 (m, 3H), 2.89-2.78 (m, 1H), 1.79 (qd, J=7.1, 14.5 Hz, 1H), 1.41 (qd, J=6.1, 13.9 Hz, 1H), 0.99 (d, J=6.6 Hz, 3H). LCMS (APCI) m/z: 236.1 [M+H]$^+$.

Step 3: Synthesis of ((3R,5S)-4-benzyl-5-methyl-1,4-oxazepan-3-yl)methanol (I-12c-ii)

To a solution of (S)-3-(benzyl(oxetan-3-yl)amino)butan-1-ol (3.916 g, 1 Eq, 16.64 mmol) in Toluene (40 mL) was added Dibutylhydrogenphosphate (3.8 g, 3.5 mL, 1.1 Eq, 18 mmol). The reaction was heated to 108° C. (oil bath temp.) for 20 h. The reaction was cooled to rt and 2N $Na_2CO_3$ (40 mL) was added. The mixture was stirred vigorously for 1 h. The layers were separated, and the toluene layer was concentrated under vacuum. Crude $^1$H NMR shows a 2.1 to 1 mixture of diastereomers as a light-yellow oil (3.61 g, 15.3 mmol, 92%).

The diastereomers were separated via chiral SFC (Column: Chiralpak IG SFC Sum 30 mm×250 mm, Mobile phase A: $CO_2$, Mobile phase B: MeOH+10 mm $NH_3$ 12% B isocratic, 120 bar, 120 mL/min.) to give ((3S,5S)-4-benzyl-5-methyl-1,4-oxazepan-3-yl)methanol (1.53 g, 6.50 mmol, 39%) (I-12c-i, trans product) >99.0% de, [á]D22=−70.7° (C 0.1, MeOH). $^1$H NMR (400 MHz, METHANOL-$d_4$) δ=7.38-7.33 (m, 2H), 7.32-7.25 (m, 2H), 7.23-7.17 (m, 1H), 4.06 (dd, J=5.0, 12.9 Hz, 1H), 4.00-3.90 (m, 2H), 3.70 (d, J=14.0 Hz, 1H), 3.67-3.59 (m, 2H), 3.43-3.33 (m, 2H), 2.94 (dq, J=5.1, 7.5 Hz, 1H), 1.97 (dtd, J=5.3, 9.3, 14.7 Hz, 1H), 1.79-1.70 (m, 1H), 1.24 (d, J=6.9 Hz, 3H) 1H under solvent peak. LCMS (APCI): 236.1 [M+H]$^+$ and ((3R,5S)-4-benzyl-5-methyl-1,4-oxazepan-3-yl)methanol (0.739 g, 3.14 mmol, 19%) (I-12c-ii, cis Product) >99.0% de, [á]D22=−14.8° (C 0.1, MeOH). $^1$H NMR (400 MHz, METHANOL-$d_4$) δ=7.39 (d, J=7.6 Hz, 2H), 7.30-7.23 (m, 2H), 7.20-7.13 (m, 1H), 3.90-3.76 (m, 5H), 3.68 (ddd, J=2.6, 9.8, 12.6 Hz, 1H), 3.40-3.34 (m, 1H), 3.29-3.21 (m, 2H), 3.20-3.12 (m, 1H), 1.97-1.86 (m, 1H), 1.75 (qdd, J=2.6, 3.5, 15.0 Hz, 1H), 1.12 (d, J=6.6 Hz, 3H). LCMS (APCI): 236.1 [M+H]$^+$.

Step 4: Synthesis of ((3R,5S)-5-methyl-1,4-oxazepan-3-yl)methanol (I-12d)

To a solution of ((3R,5S)-4-benzyl-5-methyl-1,4-oxazepan-3-yl)methanol (737 mg, 1 Eq, 3.13 mmol) in Methanol (20 mL) was added Palladium(II) dihydroxide (44.0 mg, 0.1 Eq, 313 μmol).

The reaction was stirred vigorously under H₂ for 18 h. The reaction was filtered and concentrated under vacuum. The resulting clear oil ((3R,5S)-5-methyl-1,4-oxazepan-3-yl)methanol (433 mg, 2.98 mmol, 95%) was used without further purification. $^1$H NMR (400 MHz, METHANOL-$d_4$) δ=5.41 (t, J=5.4 Hz, 1H), 4.50 (dd, J=3.4, 11.7 Hz, 1H), 4.47-4.42 (m, 2H), 4.07-3.91 (m, 3H), 3.73-3.58 (m, 2H), 2.61-2.50 (m, 2H), 2.25 (dddd, J=5.7, 7.1, 9.4, 14.2 Hz, 1H), 1.85 (d, J=6.4 Hz, 3H). LCMS (APCI): 146.2 [M+H]⁺.

Step 5: Synthesis of ((3R,5S)-4-(5,7-dichloro-8-fluoro-2-(methylthio)pyrido[4,3-d]pyrimidin-4-yl)-5-methyl-1,4-oxazepan-3-yl)methanol (I-12e)

To a solution of ((3R,5S)-5-methyl-1,4-oxazepan-3-yl)methanol (430 mg, 1 eq, 2.96 mmol) in Acetonitrile (50 mL) in an ice bath was added Hunig's base (1.53 g, 2.06 mL, 4 eq, 11.8 mmol) and then 4,5,7-trichloro-8-fluoro-2-(methylthio)pyrido[4,3-d]pyrimidine (I-1, 884 mg, 1 eq, 2.96 mmol). The reaction was stirred in the ice bath which was allowed to warm to rt. After 3 h, the reaction was complete by LCMS. The CH3CN was removed under vacuum, and the resulting bright orange solid was purified by flash column chromatography (Isco Gold, 80 g silica gel column, gradient of 0 to 5.5% MeOH in DCM and then hold at 5.5% MeOH until product elutes) to give ((3R,5S)-4-(5,7-dichloro-8-fluoro-2-(methylthio)pyrido[4,3-d]pyrimidin-4-yl)-5-methyl-1,4-oxazepan-3-yl)methanol (1.23 g, 94%) as an orange solid. $^1$H NMR (400 MHz, METHANOL-d4) δ=4.57 (dd, J=5.5, 11.0 Hz, 1H), 4.45 (dd, J=6.6, 11.0 Hz, 1H), 4.01 (dd, J=3.8, 12.3 Hz, 1H), 3.88-3.65 (m, 4H), 3.54-3.46 (m, 1H), 3.19-3.08 (m, 1H), 2.66 (s, 3H), 1.93-1.83 (m, 1H), 1.76-1.64 (m, 1H), 1.20 (d, J=6.4 Hz, 3H). $^{19}$F NMR (377 MHz, CHLOROFORM-d) δ=−137.17 (s, 1F). LCMS (APCI): 407.0 [M+H]⁺.

Step 6: Synthesis of (8aS,13S)-5-chloro-4-fluoro-13-methyl-2-(methylthio)-8a,9,12,13-tetrahydro-8H,11H-7,10-dioxa-1,3,6,13a-tetraazanaphtho[1,8-ab]heptalene (I-12)

To a cloudy solution of ((3R,5S)-4-(5,7-dichloro-8-fluoro-2-(methylthio)pyrido[4,3-d]pyrimidin-4-yl)-5-methyl-1,4-oxazepan-3-yl)methanol (1.07 g, 1 Eq, 2.62 mmol) in Acetonitrile (65 mL) was added DBU (1.198 g, 1.186 mL, 3.0 Eq, 7.867 mmol). The reaction was stirred at 50° C. for 20 h. The CH3CN was removed under vacuum to give a thick oil which solidified upon standing. The solids were triturated with CH3CN at 50° C. After stirring the slurry for 1 h, it was removed from the oil bath and cooled to rt. The solids were collected by filtration, washed with MTBE, and dried under vacuum to give (8aS,13S)-5-chloro-4-fluoro-13-methyl-2-(methylthio)-8a,9,12,13-tetrahydro-8H,11H-7,10-dioxa-1,3,6,13a-tetraazanaphtho[1,8-ab]heptalene (0.614 g, 63%) as an off white powder. $^1$H NMR (400 MHz, CHLOROFORM-d) δ=4.60 (dd, J=5.1, 13.3 Hz, 1H), 4.38 (dd, J=1.1, 13.3 Hz, 1H), 4.32-4.19 (m, 2H), 4.14-4.02 (m, 2H), 3.65 (dd, J=10.4, 12.8 Hz, 1H), 3.28 (ddd, J=4.6, 11.6, 12.8 Hz, 1H), 2.63 (s, 3H), 2.53-2.43 (m, 1H), 2.10 (dddd, J=5.5, 6.5, 11.7, 14.0 Hz, 1H), 1.76 (d, J=6.9 Hz, 3H). $^{19}$F NMR (377 MHz, CHLOROFORM-d) δ=−140.42 (s, 1F). LCMS (APCI): 371.0 [M+H]⁺.

Intermediate 13 (I-13): 4-bromo-8-chloro-5-(1-methylcyclopropyl)-1-(tetrahydro-2H-pyran-2-yl)-1H-indazole

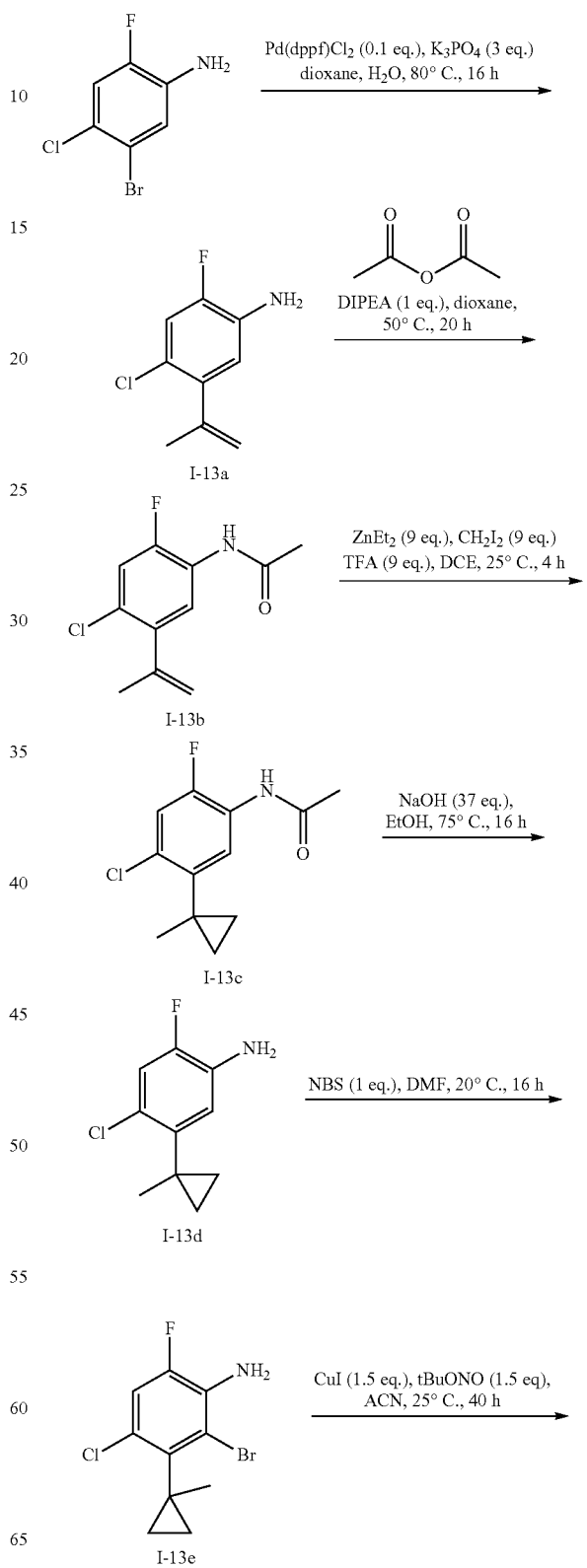

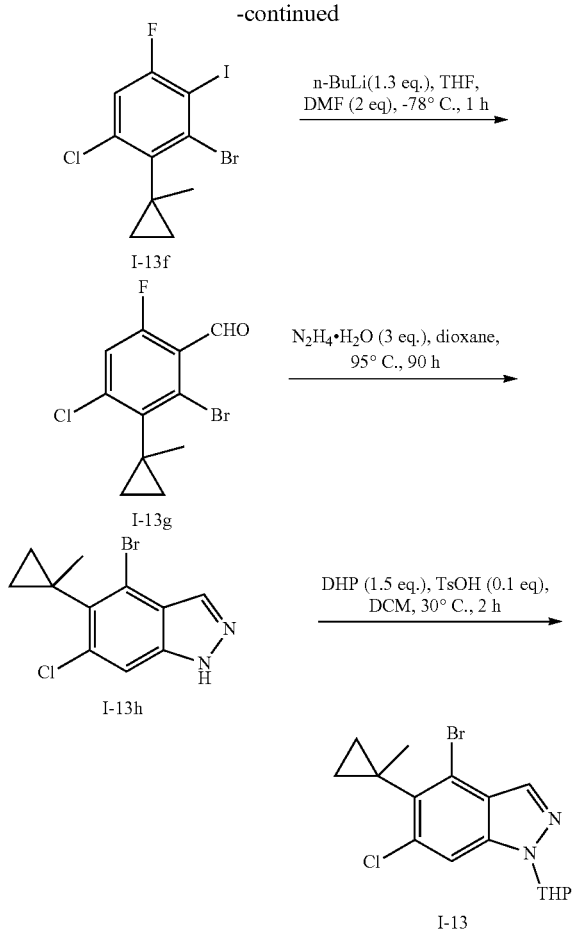

Step 1: Synthesis of 4-chloro-2-fluoro-5-(prop-1-en-2-yl) aniline (I-13a)

To a 5-bromo-4-chloro-2-fluoroaniline (2500 mg, 11.14 mmol, 4,4,5,5-tetramethyl-2-(prop-1-en-2-yl)-1,3,2-dioxaborolane (2810 mg, 16.7 mmol) and K₃PO₄ (7090 mg, 33.4 mmol) in 1,4-dioxane (90 mL) and water (9 mL) was added Pd(dppf)Cl₂ (815 mg 1.11 mmol). The mixture was stirred at 80° C. for 16 h under nitrogen atmosphere. LCMS showed that the starting material was consumed. The reaction was diluted with water (30 mL) and extracted with EtOAc (3×20 mL). The organic layers were combined, washed with brine (15 mL), dried over Na₂SO₄, filtered, and concentrated in vacuo to give crude product. The crude product was purified by flash column chromatography (40 g silica gel, 0-5% gradient of EtOAc in PE) to give the title intermediate (1500 mg, 73%) as a yellow oil. $^1$H NMR (400 MHz, CDCl3) δ 7.00 (d, J=10.7 Hz, 1H), 6.62 (d, J=9.4 Hz, 1H), 5.19-5.17 (m, 1H), 4.94-4.91 (m, 1H), 3.65 (br, 2H), 2.06-2.05 (m, 3H). LCMS (ESI) m/z: 186.1 [M+H]+.

Step 2: Synthesis of N-(4-chloro-2-fluoro-5-(prop-1-en-2-yl) phenyl) acetamide (I-13b)

To a solution of 4-chloro-2-fluoro-5-(prop-1-en-2-yl) aniline (1500 mg, 8.08 mmol) in 1,4-dioxane (40 mL) was added acetic anhydride (1150 mg, 11.3 mmol) and DIPEA (1040 mg, 8.08 mmol) at 25° C. The mixture was stirred at 50° C. for 20 h. LCMS showed that the SM was consumed. The mixture was extracted with EtOAc (3×40 mL), and the organic layers were combined, washed with brine (15 mL), dried over Na2SO4, filtered and concentrated in vacuo to give N-(4-chloro-2-fluoro-5-(prop-1-en-2-yl) phenyl) acetamide (1700 mg, 92%) as a yellow solid. $^1$H NMR (400 MHz, CDCl3) δ 8.20 (d, J=8.5 Hz, 1H), 7.12 (d, J=10.7 Hz, 1H), 5.26-5.21 (m, 1H), 4.97 (d, J=0.7 Hz, 1H), 2.22 (s, 3H), 2.08-2.05 (m, 3H). LCMS (ESI) m/z: 228 [M+H]+.

Step 3: Synthesis of N-(4-chloro-2-fluoro-5-(1-methylcyclopropyl) phenyl) acetamide (Compound I-13c)

To a solution of diethylzinc (8300 mg, 67.2 mmol, 67.2 mL, 1.0 M) in DCE (40 mL) was added a solution of TFA (7660 mg, 67.2 mmol, 5.15 mL) in DCE (15 mL) at 0° C. under nitrogen atmosphere. After 30 min, a solution of CH₂I₂ (18000 mg, 67.2 mmol, 5.41 mL) in DCE (10 mL) was added to the mixture and stirred for 30 min. Then a solution of N-(4-chloro-2-fluoro-5-(prop-1-en-2-yl) phenyl) acetamide (1700 mg, 7.467 mmol) in DCE (15 mL) was added to the mixture. The reaction was stirred at 25° C. for 4 h. LCMS showed that the starting material was almost consumed. The solvent was removed under reduced pressure. The crude product was purified by flash column chromatography (40 g silica gel, 0-10% EtOAc in petroleum ether) to give N-(4-chloro-2-fluoro-5-(1-methylcyclopropyl) phenyl) acetamide (1500 mg, 83%) as a light-yellow solid. $^1$H NMR (400 MHz, CDCl3) δ 8.28 (d, J=8.6 Hz, 1H), 7.09 (d, J=10.6 Hz, 1H), 2.24 (s, 3H), 1.32 (s, 3H), 0.83-0.79 (m, 2H), 0.78-0.73 (m, 2H). LCMS (ESI) m/z: 242.1 [M+H]+.

Step 4: Synthesis of 4-chloro-2-fluoro-5-(1-methylcyclopropyl) aniline (I-13d)

To a solution of N-(4-choro-2-fluoro-5-(1-methylcyclopropyl) phenyl) acetamide (1500 mg, 6.206 mmol) in EtOH (50 mL) was added NaOH (9190 mg, 230 mmol) and the mixture was stirred at 75° C. for 16 h. LCMS showed the starting material was consumed. A majority of the EtOH was removed under reduced pressure. The residue was diluted with ice water (50 mL) and adjusted to pH=5 with 2M HCl. The mixture was extracted with EtOAc (3×30 mL). The organic layers were combined, washed with brine, dried over Na₂SO₄, filtered and concentrated under reduced pressure to give crude product. The crude product was purified by flash column chromatography (25 g silica gel, 0-10% EtOAc in petroleum ether) to give 4-chloro-2-fluoro-5-(1-methylcyclopropyl) aniline (870 mg, 70%) as a light-yellow oil. $^1$H NMR (400 MHz, CDCl3) δ 6.97 (d, J=10.6 Hz, 1H), 6.77 (d, J=9.5 Hz, 1H), 1.30 (s, 3H), 0.78-0.74 (m, 2H), 0.72-0.68 (m, 2H). LCMS (ESI) m/z: 200.1 [M+H]+.

Step 5: Synthesis of 2-bromo-4-chloro-8-fluoro-3-(1-methylcyclopropyl) aniline (I-13e)

To a solution of 4-chloro-2-fluoro-5-(1-methylcyclopropyl) aniline (1040 mg, 5.209 mmol) in DMF (35 mL) was added NBS (927 mg 5.21 mmol) in portions at 0° C. under nitrogen atmosphere. The mixture was stirred at 20° C. for 16 h. LCMS showed that the starting material was consumed. The mixture was diluted with saturated aqueous NaHCO₃ (5 mL), extracted with EtOAc (25 mL×3). The organic layers were combined, washed with brine (10 mL), dried over Na₂SO₄, filtered and concentrated under reduced pressure to give 2-bromo-4-chloro-6-fluoro-3-(1-methylcyclopropyl) aniline (1320 mg, 91%) as a brown oil. $^1$H NMR (400 MHz, CDCl$_3$) δ 7.02 (d, J=10.4 Hz, 1H), 1.29 (s, 3H), 0.96-0.87 (m, 4H). LCMS (ESI) m/z: 278 [M+H]+.

Step 6: Synthesis of 3-bromo-1-chloro-fluoro-4-Iodo-2-(1-methylcyclopropyl) benzene (I-13f)

To a flask containing CH3CN (20 mL) were added CuI (1130 mg, 5.92 mmol) and tert-Butyl nitrite (611 mg, 5.92 mmol. The mixture was stirred at 25° C. for 30 min. 2-bromo-4-chloro-6-fluoro-3-(1-methylcyclopropyl) aniline (1100 mg, 3.95 mmol) in CH3CN (10 mL) was added drop-wise, which was stirred at 5° C. for 20 minutes and then warmed to 25° C. for 40 h. LCMS showed that the starting material was almost consumed. The mixture was quenched with HCl (5 mL, 1 M) and extracted with EtOAc (3×20 mL). The combined organic layers were washed with saturated aqueous Na$_2$SO$_3$ (20 mL), brine, dried over Na$_2$SO$_4$, filtered, concentrated under reduced pressure. The residue was purified by flash column chromatography (4 g silica gel, petroleum ether) to provide 3-bromo-1-chloro-5-fluoro-4-iodo-2-(1-methylcyclopropyl) benzene (1150 mg, 75%) as a light-yellow oil. $^1$H NMR (400 MHz, CDCl$_3$) δ 7.11 (d, J=7.4 Hz, 1H), 1.31 (s, 3H), 0.98-0.85 (m, 4H).

Step 7: Synthesis of 2-bromo-4-chloro-4-fluoro-3-(1-methylcyclopropyl) benzaldehyde (I-13g)

To a solution of 3-bromo-1-chloro-5-fluoro-4-iodo-2-(1-methylcyclopropyl) benzene (1050 mg, 2.696 mmol) in THF (40 mL) was added dropwise n-BuLi (225 mg, 3.51 mmol) at −78° C. under nitrogen atmosphere. The mixture was stirred at that temperature for 10 min. Then dry DMF (394 mg, 5.39 mmol) was added into the above mixture and the mixture was stirred at −78° C. for 1 h. LCMS showed that starting material was consumed and a new peak was formed. The mixture was quenched with 1N HCl (3 mL) and slowly warmed to 20° C. Then the reaction mixture was diluted with water, extracted with EtOAc (3×15 mL). The organic layers were combined, washed with water, dried over Na$_2$SO$_4$, filtered and concentrated under reduced pressure to give crude product. The crude product was purified by flash column chromatography (12 g silica gel, PE) to give 2-bromo-4-chloro-6-fluoro-3-(1-methylcyclopropyl) benzaldehyde (440 mg, 56%) as a light-yellow oil. $^1$H NMR (400 MHz, DMSO-d6) δ 10.18 (s, 1H), 7.70 (d, J=10.4 Hz, 1H), 1.30 (s, 3H), 1.06-1.00 (m, 2H), 0.92-0.84 (m, 2H).

Step 8: Synthesis of 4-bromo-4-chloro-5-(1-methylcyclopropyl)-1H-indazole (I-13h)

To the mixture of 2-bromo-4-chloro-6-fluoro-3-(1-methylcyclopropyl) benzaldehyde (480 mg 1.65 mmol) in 1,4-Dioxane (16 mL) was added 85% N$_2$H$_4$·H$_2$O (291 mg 4.94 mmol) at 0° C., then the mixture was stirred at 95° C. for 90 h. LCMS showed that the starting material was consumed. The reaction was cooled to 25° C. and then slowly poured into water (10 mL). The mixture was extracted with MTBE (3×10 mL). The organic layer was dried over Na$_2$SO$_4$, filtered and concentrated to give crude product. The crude product was purified by flash column chromatography (4 g silica gel, PE) to give 4-bromo-6-chloro-5-(1-methylcyclopropyl)-1H-indazole (300 mg, 58%) as a light-yellow oil. $^1$H NMR (400 MHz, CDCl$_3$) δ 8.06 (s, 1H), 7.51 (s, 1H), 1.37 (s, 3H), 1.02-0.90 (m, 4H). LCMS (ESI) m/z: 285.0 [M+H]+.

Step 9: Synthesis of 4-bromo-4-chloro-5-(1-methyl-cyclopropyl)-1-(tetrahydro-2H-pyran-2-yl)-1H-indazole (Intermediate I-13)

To a solution of 4-bromo-6-chloro-5-(1-methylcyclopropyl)-1H-indazole (270 mg 0.945 mmol) in DCM (9 mL) was added DHP (119 mg 1.42 mmol) followed by p-toluenesulfonic acid monohydrate (18 mg 0.0945 mmol). The reaction mixture was stirred at 30° C. for 2 hours. LCMS showed that the starting material was consumed. The reaction was washed with saturated aqueous NaHCO$_3$ (10 mL) and brine (10 mL). The organic layer was dried over Na2SO4, filtered under concentrated under reduced pressure. The residue was purified by flash column chromatography (4 g silica gel, EtOAc in PE from 0% to 5%) to give 4-bromo-8-chloro-5-(1-methylcyclopropyl)-1-(tetrahydro-2H-pyran-2-yl)-1H-indazole (300 mg, 77%) as a yellow oil. $^1$H NMR (400 MHz, CDCl$_3$) δ 7.98 (s, 1H), 7.63-7.60 (m, 1H), 5.63-5.61 (m, 1H), 4.03-3.95 (m, 1H), 3.73 (ddd, J=15.2, 7.2, 3.9 Hz, 1H), 2.53-2.42 (m, 1H), 2.18-2.05 (m, 2H), 1.78-1.68 (m, 3H), 1.36 (s, 3H), 1.00-0.88 (m, 4H). LCMS (ESI) m/z: 369.0 [M+H]+.

Intermediate 14 (I-14): ethyl (S)-(2-cyclopropylidenetetrahydro-1H-pyrrolizin-7a(5H)-yl)methanol

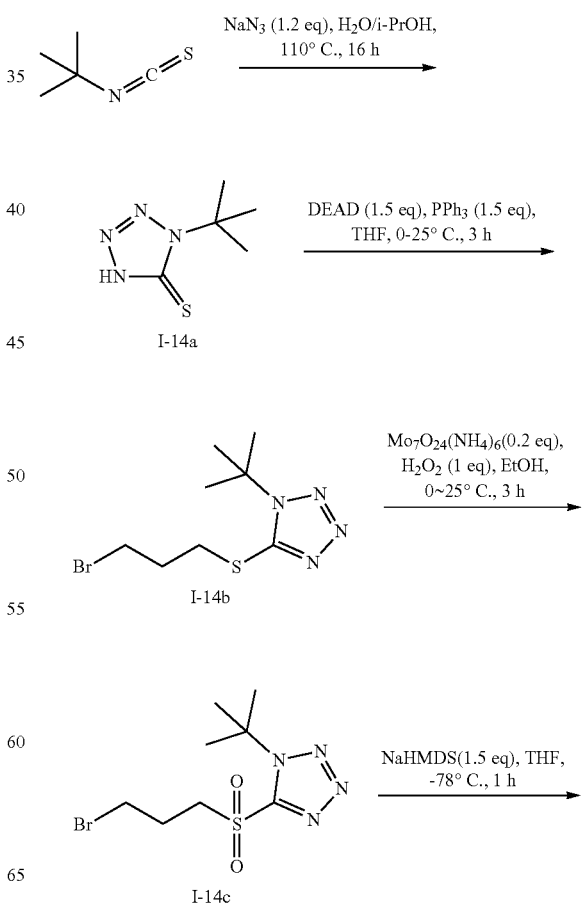

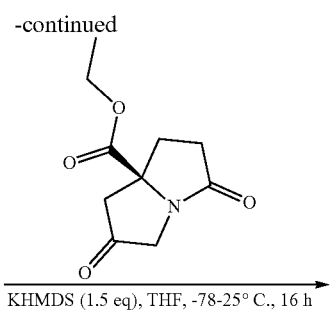

I-14d

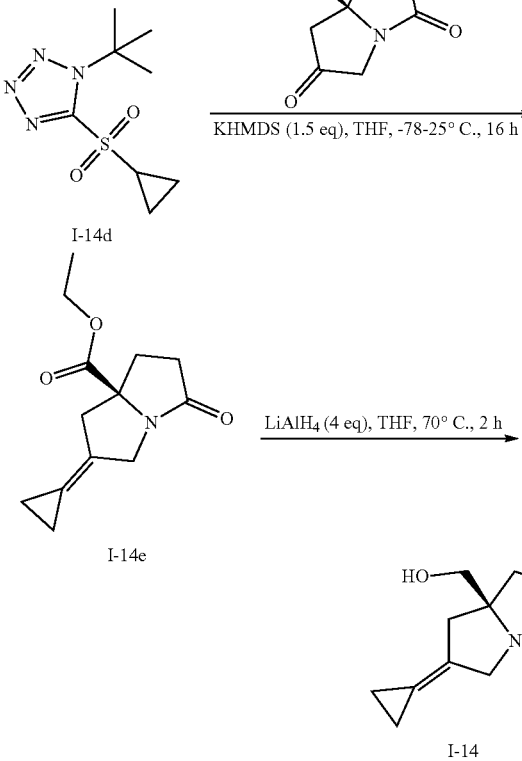

I-14e

I-14

Step 1: Synthesis of 1-(tert-butyl)-1,4-dihydro-5H-tetrazole-5-thione (I-14a)

To a solution of 2-isothiocyanato-2-methylpropane (2300 mg, 19.97 mmol) in 2-propanol (30 mL) was added sodium azide (1630 mg, 24.0 mmol) in H₂O (20 mL) at 25° C. The reaction was stirred at 110° C. for 16 h under nitrogen atmosphere. LCMS showed the desired product was formed. The reaction was quenched by dropwise addition of conc. HCl and stirred at 25° C. for 1 h. The mixture was neutralized by addition of solid NaHCO₃ and extracted with EtOAc (5×50 mL), dried over Na₂SO₄, filtered and concentrated under reduced pressure. The residue was purified by flash column chromatography (12 g silica gel, 0-20% EtOAc in petroleum ether) to give 1-(tert-butyl)-1,4-dihydro-5H-tetrazole-5-thione (850 mg, 27%) as colorless oil. ¹H NMR (400 MHz, DMSO-d₆) δ 5.62 (s, 1H), 1.76 (s, 9H). LCMS (ESI) m/z 159.1 (M+H)⁺.

Step 2: Synthesis of 5-((3-bromopropyl)thio)-1-(tert-butyl)-1H-tetrazole (I-14b)

To a solution of 1-(tert-butyl)-1,4-dihydro-5H-tetrazole-5-thione (700 mg, 4.42 mmol) in THF (40 mL) was added DEAD (1160 mg, 6.64 mmol) and PPh₃ (1740 mg, 6.64 mmol). Cooled the mixture to 0° C. and added 3-bromopropan-1-ol (738 mg, 6.64 mmol). The resulting reaction mixture was stirred at 25° C. for 3 h. LCMS showed the desired product was formed. The reaction mixture was concentrated under reduced pressure, purified by flash column chromatography (12 g silica gel, 0-10% EtOAc in petroleum ether) to give 5-((3-bromopropyl)thio)-1-(tert-butyl)-1H-tetrazole (500 mg, 35%) as colorless oil. ¹H NMR (400 MHz, CDCl₃) δ 3.59-3.49 (m, 4H), 2.49-2.36 (m, 2H), 1.73 (s, 9H). LCMS (ESI) m/z 279.0, 281.0 (M+H)⁺.

Step 3: Synthesis of 5-((3-bromopropyl)sulfonyl)-1-(tert-butyl)-1H-tetrazole (I-14c)

To a solution of 5-((3-bromopropyl)thio)-1-(tert-butyl)-1H-tetrazole (400 mg 1.43 mmol) in EtOH (10 mL) was added a solution of Mo₇O₂₄(NH₄)₆·xH₂O (334 mg, 0.287 mmol) in H₂O₂ (30%, 5 mL) at 0° C. The resulting reaction mixture was stirred at 25° C. for 3 h. LCMS showed the desired product was formed. The reaction mixture was poured into saturated aqueous Na₂SO₃ (30 mL), extracted with EA (30 mL×3). The combined organic layer was dried over Na₂SO₄, filtered and concentrated under reduced pressure. The residue was purified by flash column chromatography (12 g silica gel, 0-10% EtOAc in petroleum ether) to give 5-((3-bromopropyl)sulfonyl)-1-(tert-butyl)-1H-tetrazole (500 mg, 90%) as colorless oil. ¹H NMR (400 MHz, CDCl₃) δ 4.04-3.96 (m, 2H), 3.59 (t, J=6.3 Hz, 2H), 2.63-2.53 (m, 2H), 1.86 (s, 9H). LCMS (ESI) m/z 311.0, 313.0 (M+H)+.

Step 4: Synthesis of 1-(tert-butyl)-5-(cyclopropylsulfonyl)-1H-tetrazole (I-14d)

To a solution of 5-((3-bromopropyl)sulfonyl)-1-(tert-butyl)-1H-tetrazole (450 mg 1.45 mmol) in THF (15 mL) was added NaHMDS (1.08 mL, 2.0 M in THF, 2.17 mmol,) at −78° C. The resulting reaction mixture was stirred at −78° C. for 1 h. LCMS showed the desired product was formed. The reaction mixture was poured into saturated aqueous NH₄Cl (30 mL), extracted with EA (30 mL×3). The combined organic layer was dried over Na₂SO₄, filtered and concentrated under reduced pressure. The residue was purified by flash column chromatography (12 g silica gel, 0-2% MeOH in DCM) to give 1-(tert-butyl)-5-(cyclopropylsulfonyl)-1H-tetrazole (340 mg, 92%) as colorless oil. ¹H NMR (400 MHz, CDCl₃) δ 3.28 (tt, J=7.9, 4.9 Hz, 1H), 1.85 (s, 9H), 1.53-1.48 (m, 2H), 1.42-1.35 (m, 2H). LCMS (ESI) m/z 231.1 (M+H)⁺.

Step 5: Synthesis of ethyl (S)-2-cyclopropylidene-5-oxotetrahydro-1H-pyrrolizine-7a(5H)-carboxylate (I-14e)

To a solution of 1-(tert-butyl)-5-(cyclopropylsulfonyl)-1H-tetrazole (260 mg 1.13 mmol) and ethyl (S)-2,5-dioxotetrahydro-1H-pyrrolizine-7a(5H)-carboxylate (238 mg 1.13 mmol) in THF (15 mL) was added KHMDS (1.69 mL, 1.0 M in THF, 1.69 mmol) at −78° C. The resulting reaction mixture was stirred at 25° C. for 16 h. LCMS showed the desired product was formed. The reaction mixture was poured into saturated aqueous NH₄Cl (30 mL), extracted with EA (3×30 mL), dried over Na₂SO₄ and concentrated under reduced pressure. The residue was purified by flash column chromatography (12 g silica gel, 0-2% MeOH in DCM) to give (S)-2-cyclopropylidene-5-oxotetrahydro-1H-pyrrolizine-7a(5H)-carboxylate (160 mg, 52%) as colorless oil. ¹H NMR (400 MHz, CDCl₃) δ 4.36 (d, J=15.2 Hz, 1H), 4.27-4.13 (m, 3H), 3.78 (dd, J=14.9, 7.7 Hz, 1H), 3.17 (d, J=15.5 Hz, 1H), 3.04-2.94 (m, 1H), 2.86-2.75

(m, 1H), 2.67-2.41 (m, 4H), 2.25-2.10 (m, 2H), 1.33-1.26 (m, 3H). LCMS (ESI) m/z 236.1 (M+H)+.

Step 6: Synthesis of ethyl (S)-(2-cyclopropylidenetetrahydro-1H-pyrrolizin-7a(5H)-yl)methanol (Intermediate I-14)

To a solution of (S)-2-cyclopropylidene-5-oxotetrahydro-1H-pyrrolizine-7a(5H)-carboxylate (140 mg 0.595 mmol) in THF (10 mL) was added LiAlH$_4$ (90 mg, 2.38 mmol) at 25° C. The resulting reaction mixture was stirred at 70° C. for 2 h. LCMS showed the desired product was formed. The reaction mixture was added Na$_2$SO$_4$.10H$_2$O (2 g), stirred at 25° C. for 10 min, filtrated and concentrated under reduced pressure. The residue was purified by flash column chromatography (12 g silica gel, 0-10% MeOH in DCM) to give (S)-(2-cyclopropylidenetetrahydro-1H-pyrrolizin-7a(5H)-yl)methanol (40 mg, 33%) as colorless oil. $^1$H NMR (400 MHz, CDCl$_3$) δ 4.33 (d, J=14.0 Hz, 1H), 3.94-3.79 (m, 3H), 3.59 (d, J=13.8 Hz, 1H), 2.95 (d, J=15.3 Hz, 1H), 2.91-2.79 (m, 1H), 2.56 (d, J=15.2 Hz, 1H), 2.40-2.27 (m, 1H), 2.24-1.99 (m, 6H), 1.91-1.77 (m, 1H). LCMS (ESI) m/z 180.1 (M+H)+.

Intermediate 15 (I-15): (S)-2-(oxetan-3-ylidene)tetrahydro-1H-pyrrolizin-7a(5H)-yl)methanol

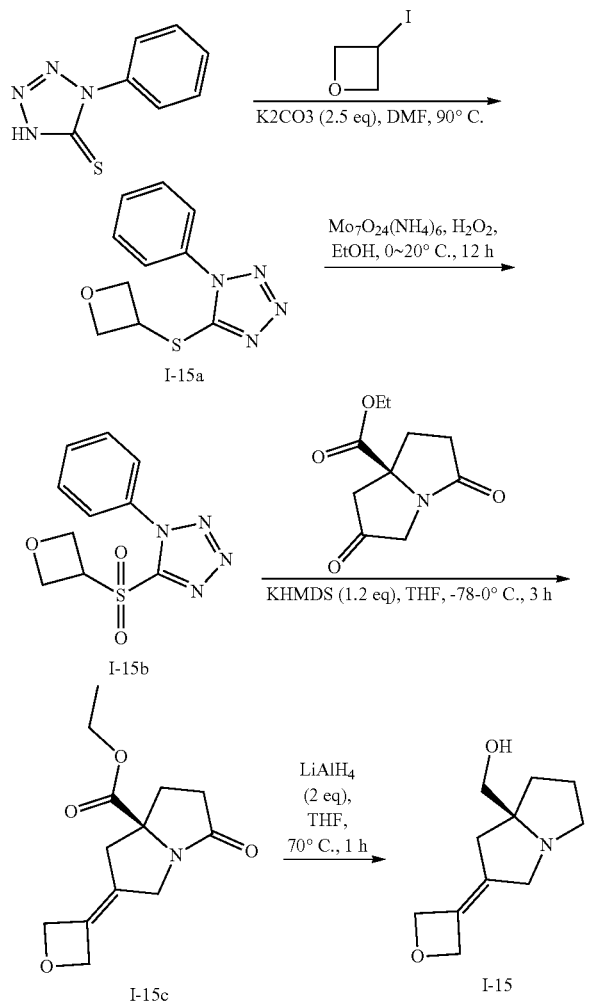

Step 1: Synthesis of 5-(oxetan-3-ylthio)-1-phenyl-1H-tetrazole (I-15a)

To a solution of 1-phenyl-1,4-dihydro-5H-tetrazole-5-thione (500 mg 2.81 mmol) in DMF (10 mL) was added K$_2$CO$_3$ (968 mg, 7.01 mmol) and 3-iodooxetane (1040 mg, 14.0 mmol). The resulting reaction mixture was stirred at 90° C. for 2 h. The reaction was poured into H$_2$O (10 mL), extracted with EA (2×10 mL). The combined organic layer was concentrated under reduced pressure and purified by flash column chromatography (24 g silica gel, 0-30% of EtOAc in petroleum ether) to give 5-(oxetan-3-ylthio)-1-phenyl-1H-tetrazole (710 mg, 98%) as yellow solid. $^1$H NMR (400 MHz, CDCl$_3$) δ 7.66-7.51 (m, 5H), 5.22 (t, J=7.3 Hz, 2H), 5.08-4.97 (m, 1H), 4.76-4.64 (m, 2H). LCMS (ESI) m/z: 235.2 [M+H]+.

Step 2: Synthesis of 5-(oxetan-3-ylsulfonyl)-1-phenyl-1H-tetrazole (I-15b)

To a solution of 5-(oxetan-3-ylthio)-1-phenyl-1H-tetrazole (650 mg, 2.77 mmol) in EtOH (36 mL) at 0° C. was added a solution of Mo$_7$O$_{24}$(NH$_4$)$_6$ (596 mg, 0.56 mmol) in H$_2$O$_2$ (18 mL) over 5 min. The reaction mixture was allowed to stir at 20° C. for 12 h. The reaction mixture was quenched with aq. Na$_2$SO$_3$ (10 mL) and then extracted with EA (20 mL×3). The combined organic phase was washed with brine (3×20 mL), dried over sodium sulfate and filtered. The filtrate was concentrated under reduced pressure. The residue was purified by flash column chromatography (24 g silica gel, 0-20% of EtOAc in petroleum ether) to afford 5-(oxetan-3-ylsulfonyl)-1-phenyl-1H-tetrazole (650 mg, 88%) as a white solid. $^1$H NMR (400 MHz, CDCl$_3$) δ 7.74 (dd, J=4.0, 2.0 Hz, 2H), 7.67-7.61 (m, 3H), 5.30-5.22 (m, 1H), 5.09 (d, J=6.8 Hz, 4H). LCMS (ESI) m/z: 267.0 [M+H]+.

Step 3: Synthesis of ethyl (S)-2-(oxetan-3-ylidene)-5-oxotetrahydro-1H-pyrrolizine-7a(5H)-carboxylate (I-15c)

To a solution of 5-(oxetan-3-ylsulfonyl)-1-phenyl-1H-tetrazole (250 mg, 0.94 mmol) in THF (15 mL) at −78° C. was added KHMDS (1.13 mL, 1.13 mmol, 1 M in THF) over 5 min. The reaction mixture was stirred at −78° C. for 50 min under nitrogen atmosphere. Then ethyl (S)-2,5-dioxotetrahydro-1H-pyrrolizine-7a(5H)-carboxylate (198 mg, 0.94 mmol) in THF (5 mL) was added to the mixture and stirred at 0° C. for 2 h. The reaction mixture was quenched with saturated aqueous NH$_4$Cl (30 mL) and then extracted with EtOAc (3×50 mL). The combined organic phase was washed with brine (3×20 mL), dried over sodium sulfate and filtered. The filtrate was concentrated under reduced pressure. The residue was purified by flash column chromatography (12 g silica gel, 0-80% of EtOAc in petroleum ether) to afford ethyl (S)-2-(oxetan-3-ylidene)-5-oxotetrahydro-1H-pyrrolizine-7a(5H)-carboxylate (155 mg, 66%) as a colorless oil. $^1$H NMR (400 MHz, CDCl$_3$) δ 5.14 (s, 4H), 4.23 (q, J=7.1 Hz, 2H), 4.15 (d, J=15.3 Hz, 1H), 3.54 (d, J=15.4 Hz, 1H), 2.88 (d, J=15.7 Hz, 1H), 2.83-2.74 (m, 1H), 2.66-2.57 (m, 1H), 2.46 (dd, J=16.7, 9.4 Hz, 1H), 2.27 (d, J=15.9 Hz, 1H), 2.18-2.07 (m, 1H), 1.29 (t, J=7.1 Hz, 3H). LCMS (ESI) m/z: 252.1 [M+H]+.

Step 4: Synthesis of (S)-(2-(oxetan-3-ylidene)tetrahydro-1H-pyrrolizin-7a(5H)-yl)methanol (I-15)

To a solution of ethyl (S)-2-(oxetan-3-ylidene)-5-oxotetrahydro-1H-pyrrolizine-7a(5H)-carboxylate (110 mg, 0.44 mmol) in THF (8 mL) was added LiAlH₄ (0.88 mL, 0.88 mmol, 1 M in THF). The mixture was stirred at 70° C. for 1 h under nitrogen atmosphere. Then reaction was quenched with Na₂SO₄·10H₂O and filtered. The filtrate was concentrated under reduced pressure to afford (S)-(2-(oxetan-3-ylidene)tetrahydro-1H-pyrrolizin-7a(5H)-yl)methanol (85 mg, 99%) as a white oil. ¹H NMR (400 MHz, MeOD) δ 5.18-5.14 (m, 4H), 3.58-3.55 (m, 2H), 3.48-3.40 (m, 1H), 3.18-3.10 (m, 1H), 3.05-2.98 (m, 1H), 2.67-2.60 (m, 1H), 2.49-2.37 (m, 1H), 2.20-2.08 (m, 1H), 1.98-1.87 (m, 2H), 1.78-1.67 (m, 2H). LCMS (ESI) m/z: 196.1 [M+H]⁺.

Intermediate 16 (I-16): (S)-(2-(tetrahydro-4H-pyran-4-ylidene)tetrahydro-1H-pyrrolizin-7a(5H)-yl)methanol

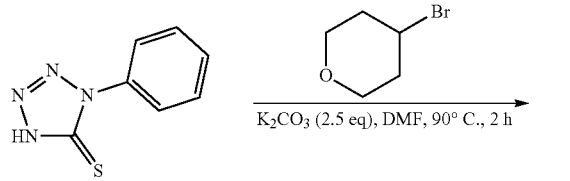

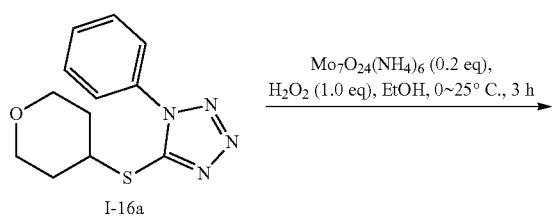

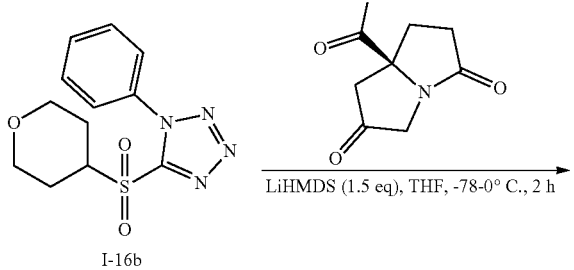

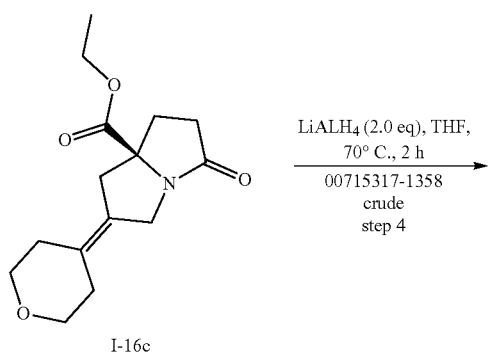

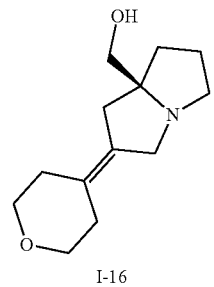

I-16

Step 1: Synthesis of 1-phenyl-5-((tetrahydro-2H-pyran-4-yl)thio)-1H-tetrazole (I-16a)

To a solution of 1-phenyl-1,4-dihydro-5H-tetrazole-5-thione (500 mg, 2.81 mmol) in DMF (5 mL) were added K₂CO₃ (968 mg, 7.01 mmol) and 4-bromotetrahydro-2H-pyran (1160 mg, 7.01 mmol). The resulting mixture was stirred at 90° C. for 3 h. LCMS showed the desired product was formed. The reaction was combined with a batch from 50 mg of starting material 1, poured into H₂O (20 mL) and extracted with EA (2×10 mL). The combined organic layer was concentrated under reduced pressure and purified by flash column chromatography (24 g silica gel, 0-30% gradient of EtOAc in petroleum ether) to give 1-phenyl-5-((tetrahydro-2H-pyran-4-yl)thio)-1H-tetrazole (630 mg, 78%) as yellow solid. ¹H NMR (400 MHz, CDCl3) δ 7.63-7.49 (m, 5H), 4.25-4.16 (m, 1H), 3.99 (dt, J=12.0, 3.8 Hz, 2H), 3.59 (td, J=11.9, 2.3 Hz, 2H), 2.23 (dd, J=11.6, 1.6 Hz, 2H), 1.91-1.77 (m, 2H). LCMS (ESI) m/z: 263.2 [M+H]⁺.

Step 2: Synthesis of 1-phenyl-5-((tetrahydro-2H-pyran-4-yl)sulfonyl)-1H-tetrazole (I-16b)

To a solution of 1-phenyl-5-((tetrahydro-2H-pyran-4-yl)thio)-1H-tetrazole (630 mg 2.4 mmol) in EtOH (16 mL) was added a solution of Mo₇O₂₄(NH₄)₆·xH₂O (559 mg, 0.480 mmol) in H₂O₂ (30%, 8 mL) at 0° C. The resulting mixture was stirred at 25° C. for 3 h. LCMS showed that most starting material was consumed, and the desired product was formed. The reaction mixture was poured into saturated aqueous Na₂SO₃ (30 mL) and extracted with EtOAc (3×30 mL). The combined organic layer was dried over Na₂SO₄, filtered and concentrated under reduced pressure. The residue was purified by flash column chromatography (12 g silica gel, 0-10% of EtOAc in petroleum ether) to give 1-phenyl-5-((tetrahydro-2H-pyran-4-yl)sulfonyl)-1H-tetrazole (524 mg, 74%) as white solid. ¹H NMR (400 MHz, CDCl₃) δ 7.72-7.56 (m, 5H), 4.22-4.10 (m, 3H), 3.52 (t, J=11.8 Hz, 2H), 2.21-2.13 (m, 2H), 2.05 (td, J=12.1, 4.5 Hz, 2H). LCMS (ESI) m/z: 295.2 [M+H]⁺.

Step 3: Synthesis of ethyl (S)-5-oxo-2-(tetrahydro-4H-pyran-4-ylidene)tetrahydro-1H-pyrrolizine-7a(5H)-carboxylate (116c)

To a solution of 1-phenyl-5-((tetrahydro-2H-pyran-4-yl)sulfonyl)-1H-tetrazole (200 mg, 0.680 mmol) in THF (20 mL) at −78° C. was added LiHMDS (1M in THF, 1.02 mL, 1.02 mmol) over 5 min. The reaction mixture was stirred at −78° C. for 50 min under nitrogen atmosphere. Then ethyl (S)-2,5-dioxotetrahydro-1H-pyrrolizine-7a(5H)-carboxylate (172 mg, 0.815 mmol) in THF (5 mL) was added to the mixture and stirred at 0° C. for 2 h. LCMS showed that most starting material was consumed, and the desired product was formed. The reaction was quenched with saturated aqueous NH₄Cl (30 mL) and then extracted with EA (3×50 mL). The combined organic phase was washed with brine (3×20 mL), dried over sodium sulfate and filtered. The filtrate was concentrated under reduced pressure. The residue was purified by flash column chromatography (4 g silica gel, 0-100% of EtOAc in petroleum ether) to give ethyl (S)-5-oxo-2-(tetrahydro-4H-pyran-4-ylidene)tetrahydro-1H-pyrrolizine-7a(5H)-carboxylate (52 mg, crude) as a colorless oil. $^1$H NMR (400 MHz, CDCl₃) δ 4.32 (d, J=15.3 Hz, 1H), 4.25-4.18 (m, 2H), 3.74-3.66 (m, 3H), 3.65-3.58 (m, 2H), 3.14 (d, J=15.8 Hz, 1H), 2.83-2.75 (m, 1H), 2.66-2.58 (m, 1H), 2.50-2.42 (m, 2H), 2.35 (d, J=16.0 Hz, 1H), 2.23-2.14 (m, 4H), 1.30-1.27 (m, 3H). LCMS (ESI) m/z: 280.3 [M+H]⁺.

Step 4: Synthesis of (S)-(2-(tetrahydro-4H-pyran-4-ylidene)tetrahydro-1H-pyrrolizin-7a(5H)-yl)methanol (Intermediate I-16)

To a solution of ethyl (S)-5-oxo-2-(tetrahydro-4H-pyran-4-ylidene)tetrahydro-1H-pyrrolizine-7a(5H)-carboxylate (52 mg, 0.19 mmol) in THF (5 mL) was added LiAlH₄ (0.372 mL, 0.372 mmol) under nitrogen atmosphere. Then the reaction was stirred at 70° C. for 2 h. LCMS showed that the desired product was formed. The mixture was quenched with Na₂SO₄·10 H₂O and stirred at 25° C. for 1 h. The mixture was filtered and concentrated to give (S)-(2-(tetrahydro-4H-pyran-4-ylidene)tetrahydro-1H-pyrrolizin-7a(5H)-yl)methanol (43 mg) as oil, which was used for next step without further purification. LCMS (ESI) m/z: 224.3 [M+H]⁺.

Intermediate 17 (I-17): (S, Z)-2-(7a-(hydroxymethyl)tetrahydro-1H-pyrrolizin-2(3H)-ylidene)-N,N-dimethylacetamide

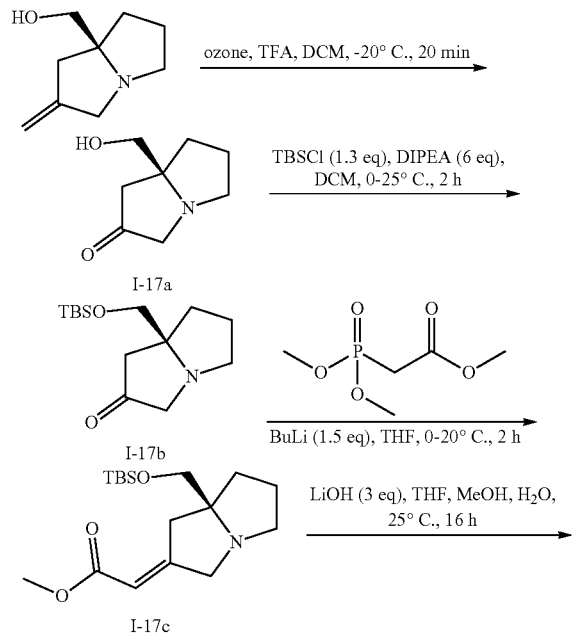

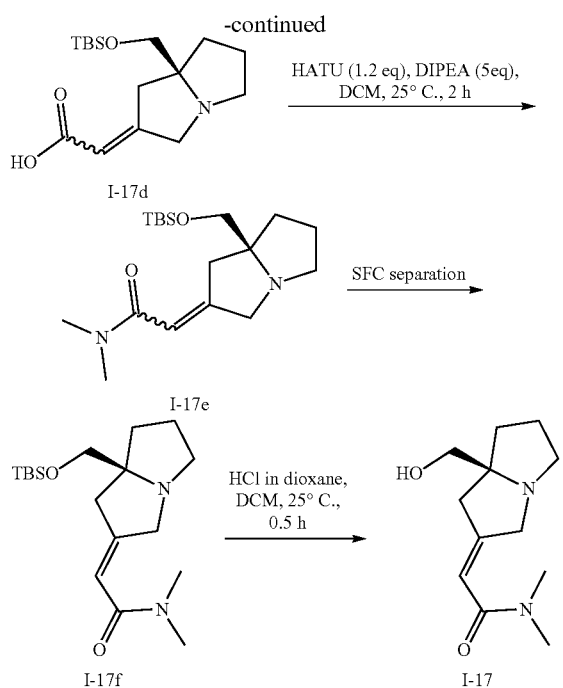

Step 1: Synthesis of (S)-7a-(hydroxymethyl)tetrahydro-1H-pyrrolizin-2(3H)-one (I-17a)

To (S)-(2-methylenetetrahydro-1H-pyrrolizin-7a(5H)-yl)methanol (800 mg, 5.22 mmol) was dissolved in a mixture of TFA (22 mL) and DCM (22 mL, c=0.2 M) and cooled to −20° C. Ozone was bubbled through the mixture at −20° C. for 20 min. −20° C. was achieved through a 1:3 ratio of NaCl to water ice. LCMS showed that most starting material was consumed, and the desired product was formed. Then nitrogen was bubbled through the mixture for 30 min to quench the reaction. The solution was concentrated under reduced pressure to get the crude (S)-7a-(hydroxymethyl)tetrahydro-1H-pyrrolizin-2(3H)-one (2.4 g, crude) as light-yellow oil. $^1$H NMR (400 MHz, CDCl₃) δ 4.31 (d, J=17.8 Hz, 1H), 4.17-4.04 (m, 2H), 3.84 (d, J=12.7 Hz, 1H), 3.52 (d, J=17.9 Hz, 1H), 3.21-3.08 (m, 2H), 2.63 (d, J=18.9 Hz, 1H), 2.34-2.23 (m, 3H), 2.18-2.10 (m, 1H). LCMS(ESI) m/z: 156.1 [M+H]⁺.

Step 2: Synthesis of (S)-7a-(((tert-butyldimethylsilyl)oxy)methyl)tetrahydro-1H-pyrrolizin-2(3H)-one (I-17b)

To a solution of (S)-7a-(hydroxymethyl)tetrahydro-1H-pyrrolizin-2(3H)-one (2.4 g, 8.915 mmol) and DIPEA (6.9 g, 53.5 mmol) in DCM (40 mL) was added TBSCl (1.75 g, 11.6 mmol) in DCM (10 mL) dropwise at 0° C. Then the mixture was stirred at 25° C. for 2 h. LCMS showed the desired product was formed. The reaction was diluted with DCM (50 mL) and washed with water, dried over Na₂SO₄, filtered and concentrated under reduced pressure. The residue was purified by flash column chromatography (40 g silica gel, 0-60% EtOAc in petroleum ether) to give (S)-7a-(((tert-butyldimethylsilyl)oxy)methyl)tetrahydro-1H-pyrrolizin-2(3H)-one (925 mg, 38.5%) as light-yellow oil. $^1$H NMR (400 MHz, CDCl₃) δ 3.60-3.39 (m, 3H), 3.33-3.22 (m, 1H), 3.07 (d, J=18.7 Hz, 1H), 2.69-2.57 (m, 1H), 2.47 (d, J=18.2 Hz, 1H), 2.20 (dd, J=18.2, 1.1 Hz, 1H), 1.85-1.83 (m, 4H), 0.83 (s, 9H), 0.02-0.00 (m, 6H). LCMS(ESI) m/z: 270.2 [M+H]$^+$

Step 3: Synthesis of methyl (S)-2-(7a-(((tert-butyldimethylsilyl)oxy)methyl)tetrahydro-1H-pyrrolizin-2(3H)-ylidene)acetate (I-17c)

To a solution of methyl 2-(dimethoxyphosphoryl)acetate (1050 mg, 5.79 mmol) in THF (20 mL) was added n-BuLi (1.74 mL, 4.34 mmol, 1.2 M in hexane) at 0° C. The mixture was stirred at 0° C. for 10 min. Then (S)-7a-(((tert-butyldimethylsilyl)oxy)methyl)tetrahydro-1H-pyrrolizin-2(3H)-one (780 mg, 2.89 mmol) in THF (5 mL) was added dropwise at 0° C. The resulting mixture was stirred at 20° C. for 2 h. LCMS showed the desired product was formed. The reaction was quenched with water (2 mL) and diluted with EA (80 mL). The solution was washed with brine, dried over Na$_2$SO$_4$, filtered and concentrated under reduced pressure. The residue was purified by flash column chromatography (40 g silica gel, 0-60% EtOAc in petroleum ether) to give methyl(S)-2-(7a-(((tert-butyldimethylsilyl)oxy)methyl)tetrahydro-1H-pyrrolizin-2(3H) ylidene)acetate (560 mg, 59%) as light-yellow oil. $^1$H NMR (400 MHz, CDCl$_3$) δ 5.82 and 5.74 (2s, 1H, the minor and major isomer), 3.71 and 3.69 (2s, 3H, the major and minor isomer), 3.48-3.39 (m, 2H), 3.33-3.03 (m, 2H), 2.88-2.52 (m, 2H), 1.96-1.82 (m, 3H), 1.78-1.57 (m, 3H), 0.87 and 0.86 (2s, 9H, the minor and major isomer), 0.03 and 0.02 (2s, 6H, the major and minor isomer). LCMS(ESI) m/z: 326.1 [M+H]$^+$

Step 4: Synthesis of (S)-2-(7a-(((tert-butyldimethylsilyl)oxy)methyl)tetrahydro-1H-pyrrolizin-2(3H)-ylidene)acetic Acid (I-17d)

A solution of methyl (S)-2-(7a-(((tert-butyldimethylsilyl)oxy)methyl)tetrahydro-1H-pyrrolizin-2(3H)-ylidene)acetate (480 mg, 1.47 mmol) and LiOH (106 mg, 4.42 mmol) in THF/MeOH/H$_2$O (6 mL/6 mL/6 mL) was stirred at 25° C. for 16 h. LCMS showed the desired product was formed. The reaction was diluted with water (30 mL) and adjusted PH to 6 with 0.3 M HCl. The solution was lyophilized to get the crude (S)-2-(7a-(((tert-butyldimethylsilyl)oxy)methyl) tetrahydro-1H-pyrrolizin-2(3H)-ylidene)acetic acid (480 mg, crude) as white solid. LCMS(ESI) m/z: 312.1 [M+H]$^+$

Step 5: Synthesis of (S)-2-(7a-(((tert-butyldimethylsilyl)oxy)methyl)tetrahydro-1H-pyrrolizin-2(3H)-ylidene)-N,N-dimethylacetamide (I-17e)

To a solution of (S)-2-(7a-(((tert-butyldimethylsilyl)oxy) methyl)tetrahydro-1H-pyrrolizin-2(3H)-ylidene)acetic acid (480 mg, 1.54 mmol) and DIPEA (996 mg, 7.70 mmol) in DCM (30 mL) were added HATU (703 mg, 1.85 mmol) and Dimethylamine hydrochloride (251 mg, 3.08 mmol). Then the mixture was stirred at 25° C. for 2 h. LCMS showed the desired product was formed. The reaction was diluted with DCM (20 mL) and washed with water (40 mL×3). The organic layer was dried over Na$_2$SO$_4$, filtered and concentrated under reduced pressure. The residue was purified by flash column chromatography (12 g silica gel, 0-50% EtOAc in petroleum ether in 15 min, holding for 5 min, and then MeOH in DCM from 0 to 20% in 15 min) to give (S)-2-(7a-(((tert-butyldimethylsilyl)oxy)methyl)tetrahydro-1H-pyrrolizin-2(3H)-ylidene)-N,N dimethylacetamide (197 mg, 38%) as yellow oil. $^1$H NMR (400 MHz, CDCl$_3$) δ 5.48 (s, 1H), 3.73-3.70 (m, 4H), 3.30 (d, J=16.5 Hz, 1H), 3.11-3.01 (m, 5H), 2.99-2.95 (m, 4H), 2.09-1.99 (m, 3H), 1.86 (s, 1H), 0.89 (d, J=2.9 Hz, 9H), 0.10 (d, J=4.0 Hz, 6H). LCMS(ESI) m/z: 339.2 [M+H]$^+$

Step 6: Chiral Separation of (S,Z)-2-(7a-(((tert-butyldimethylsilyl)oxy)methyl)tetrahydro-1H-pyrrolizin-2(3H)-ylidene)-N,N-dimethylacetamide (I-17f)

(S)-2-(7a-(((tert-butyldimethylsilyl)oxy)methyl)tetrahydro-1H-pyrrolizin-2(3H)-ylidene)-N,N-dimethylacetamide (197 mg, 0.270 mmol) was purified by chiral separation (SFC 150; Column: Daicel CHIRALCEL® IC, 250 mm*30 mm I.D., 10 µM; Mobile phase: CO$_2$/MeOH[0.2% NH$_3$ (7M Solution in MeOH)]=70/30; Flow rate: 780 g/min; Wave length UV 214 nm; Temperature: 35° C.) to give (S,Z)-2-(7a-(((tert-butyldimethylsilyl)oxy)methyl)tetrahydro-1H-pyrrolizin-2(3H)-ylidene)-N,N dimethylacetamide (95 mg, 48%, Rt: 2.997 min, Peak 2) as yellow oil. $^1$H NMR (400 MHz, CDCl3) δ 5.50 (s, 1H), 3.81 (d, J=15.2 Hz, 1H), 3.47-3.39 (m, 2H), 3.34 (d, J=15.2 Hz, 1H), 3.19 (d, J=15.8 Hz, 1H), 3.16-3.10 (m, 1H), 3.07 (d, J=15.3 Hz, 1H), 2.98 (s, 3H), 2.93 (s, 3H), 2.56 (dt, J=9.7, 7.1 Hz, 1H), 1.91-1.83 (m, 1H), 1.78-1.69 (m, 2H), 1.64-1.53 (m, 1H), 0.86 (d, J=2.7 Hz, 9H), 0.00 (d, J=2.8 Hz, 6H). LCMS(ESI) m/z: 339.3 [M+H]$^+$

Step 7: Synthesis of (S, Z)-2-(7a-(hydroxymethyl) tetrahydro-1H-pyrrolizin-2(3H)-ylidene)-N,N-dimethylacetamide (Intermediate I-17)

To a solution of (S,Z)-2-(7a-(((tert-butyldimethylsilyl) oxy)methyl)tetrahydro-1H-pyrrolizin-2(3H)-ylidene)-N,N-dimethylacetamide (70 mg, 0.21 mmol) in DCM (5 mL) was added HCl/dioxane (4.0 M, 2 mL) dropwise and the mixture was stirred at 25° C. for 30 min. LCMS showed the desired product was formed. The mixture was diluted with DCM (5 mL) and washed water (10 mL), followed by the extraction with water (10 mL×2). The aqueous phase is lyophilized to obtain (S,Z)-2-(7a-(hydroxymethyl)tetrahydro-1H-pyrrolizin-2(3H)-ylidene)-N,N-dimethylacetamide (55 mg, crude) as yellow oil. $^1$H NMR (400 MHz, MeOD) δ 5.55 (s, 1H), 4.39 (d, J=14.4 Hz, 1H), 3.95 (d, J=15.3 Hz, 1H), 3.75 (dd, J=29.2, 12.1 Hz, 2H), 3.68-3.56 (m, 1H), 3.45-3.34 (m, 2H), 3.29-3.25 (m, 1H), 3.07 (s, 3H), 2.95 (d, J=3.8 Hz, 3H), 2.23-1.97 (m, 4H). LCMS (ESI) m/z 225.1 [M+H]$^+$.

Intermediate 18 (I-18): (S,Z)-(2-(2-((tert-butyldimethylsilyl)oxy)ethylidene)tetrahydro-1H-pyrrolizin-7a(5H)-yl)methanol

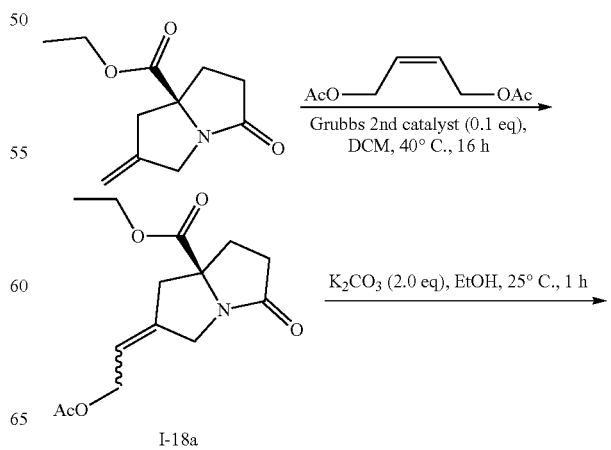

I-18a

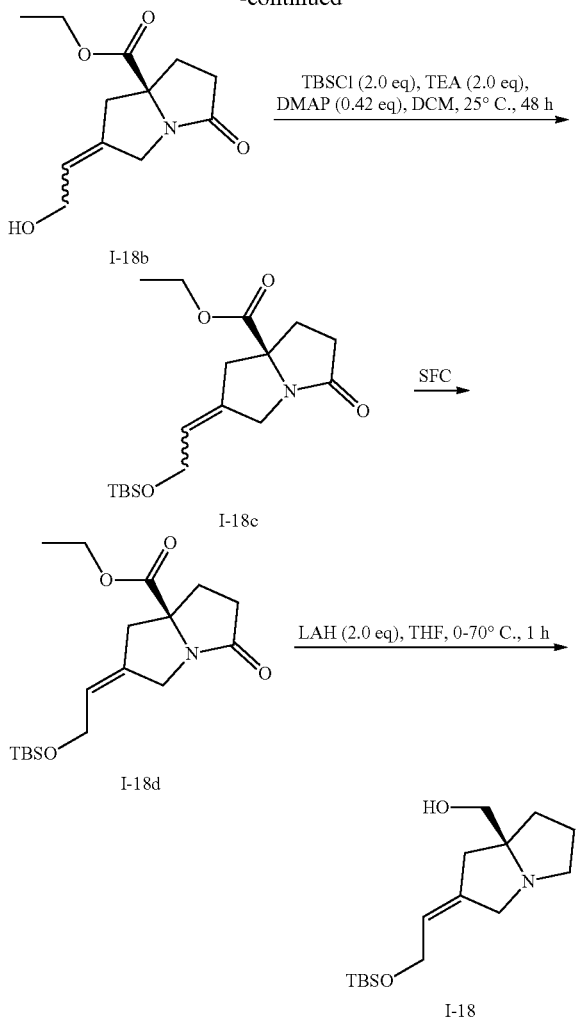

Step 1: Synthesis of ethyl (S)-2-(2-acetoxyethylidene)-5-oxotetrahydro-1H-pyrrolizine-7a(5H)-carboxylate (I-18a)

To a solution of ethyl (S)-2-methylene-5-oxotetrahydro-1H-pyrrolizine-7a(5H)-carboxylate (450 mg, 2.15 mmol) and (Z)-but-2-ene-1,4-diyl diacetate (741 mg, 4.30 mmol) in DCM (13 mL) was added Grubbs second generation catalyst (183 mg, 0.215 mmol). Then the mixture was stirred at 40° C. for 16 h under nitrogen atmosphere. LCMS showed the starting material was consumed and desired product was formed. The solution was concentrated under reduced pressure. The residue was purified by flash column chromatography (12 g silica gel, 0-80% EtOAc in petroleum ether) to give ethyl (S)-2-(2-acetoxyethylidene)-5-oxotetrahydro-1H-pyrrolizine-7a(SH)-carboxylate (373 mg, 62%) as black oil. $^1$H NMR (400 MHz, CDCl$_3$) δ 5.58 (ddd, J=6.8, 5.6, 2.6 Hz, 1H), 4.57-4.45 (m, 2H), 4.42-4.31 (m, 1H), 4.25-4.08 (m, 2H), 3.83 (d, J=16.1 Hz, 0.7H, major isomer), 3.74 (d, J=12.8 Hz, 0.3H, minor isomer), 3.27 (d, J=16.4 Hz, 0.3H, minor isomer), 3.07 (d, J=16.0 Hz, 0.7H, major isomer), 2.85-2.73 (m, 1H), 2.70-2.57 (m, 1H), 2.56-2.37 (m, 2H), 2.19-2.09 (m, 1H), 2.06-2.04 (m, 3H), 1.27 (t, J=7.1 Hz, 3H). LCMS (ESI) m/z: 282.1

Step 2: Synthesis of ethyl (S)-2-(2-hydroxyethylidene)-5-oxotetrahydro-1H-pyrrolizine-7a(5H)-carboxylate (I-18b)

To a solution of ethyl (S)-2-(2-acetoxyethylidene)-5-oxotetrahydro-1H-pyrrolizine-7a(5H)-carboxylate (350 mg, 1.24 mmol) in EtOH (10 mL) was added K$_2$CO$_3$ (344 mg, 2.49 mmol). Then the reaction was stirred at 25° C. for 1 h. LCMS showed the starting material was consumed and desired product was formed. Then the reaction was filtered to remove the base, the filtrate was diluted with H$_2$O (50 mL) and extracted with EtOAc (50 mL×3). Then the organic layers were combined and concentrated under reduced pressure to get the crude ethyl (S)-2-(2-hydroxyethylidene)-5-oxotetrahydro-1H-pyrrolizine-7a(5H)-carboxylate (185 mg, crude) as black oil which was used for next step without further purification. $^1$H NMR (400 MHz, CDCl$_3$) δ 5.70-5.55 (m, 1H), 4.33 (d, J=16.2 Hz, 1H), 4.21 (q, J=7.1 Hz, 2H), 4.17-4.06 (m, 2H), 3.85-3.69 (m, 1H), 3.23 (d, J=16.0 Hz, 0.3H, minor isomer), 3.07 (d, J=15.8 Hz, 0.7H, major isomer), 2.85-2.73 (m, 1H), 2.67-2.57 (m, 1H), 2.55-2.41 (m, 2H), 2.18-2.07 (m, 1H), 1.28 (t, J=7.1 Hz, 3H). LCMS (ESI) m/z: 240.7 [M+H]$^+$.

Step 3: Synthesis of ethyl (S)-2-(2-((tert-butyldimethylsilyl)oxy)ethylidene)-5-oxotetrahydro-1H-pyrrolizine-7a(5H)-carboxylate (I-18c)

To a solution of ethyl (S)-2-(2-hydroxyethylidene)-5-oxotetrahydro-1H-pyrrolizine-7a(5H)-carboxylate (100 mg, 0.418 mmol) in DCM (5 mL) were added TBSCl (126 mg, 0.836 mmol), TEA (84.6 mg, 0.836 mmol) and DMAP (21.4 mg, 0.176 mmol). Then the reaction was stirred at 25° C. for 48 h under nitrogen atmosphere. LCMS showed the starting material was consumed and desired product was formed. The reaction mixture was diluted with H$_2$O (20 mL) and extracted with DCM (20 mL×3). The combined organic layer was washed with brine (100 mL), dried over anhydrous Na$_2$SO$_4$, filtered and concentrated under reduced pressure. The residue was purified by flash column chromatography (4.0 g silica gel, 0%-100% DCM in PE) to give ethyl (S)-2-(2-((tert-butyldimethylsilyl) oxy) ethylidene)-5-oxotetrahydro-1H-pyrrolizine-7a(SH)-carboxylate (141 mg, 95%) as yellow oil. $^1$H NMR (400 MHz, CDCl$_3$) δ 5.52-5.44 (m, 1H), 4.22 (d, J=16.7 Hz, 1H), 4.18-4.04 (m, 4H), 3.73-3.63 (m, 1H), 3.12 (d, J=16.0 Hz, 0.3H, minor isomer), 2.98 (d, J=15.6 Hz, 0.7H, major isomer), 2.72 (dt, J=16.6, 10.0 Hz, 1H), 2.60-2.50 (m, 1H), 2.46-2.34 (m, 2H), 2.11-2.03 (m, 1H), 1.21 (t, J=7.1 Hz, 3H), 0.83 (s, 9H), 0.00 (s, 6H). LCMS (ESI) m/z: 354.3 [M+H]$^+$.

Step 4: Synthesis of ethyl (S,Z)-2-(2-((tert-butyldimethylsilyl)oxy)ethylidene)-5-oxotetrahydro-1H-pyrrolizine-7a(5H)-carboxylate (I-18d)

The ethyl (S)-2-(2-((tert-butyldimethylsilyl) oxy) ethylidene)-5-oxotetrahydro-1H-pyrrolizine-7a(5H)-carboxylate (120 mg) was purified by chiral separation (Apparatus: SFC 150; Column: Daicel CHIRALCEL® AS, 250 mm×30 mm I.D., 10 μm; Mobile phase: CO2/MeOH[0.2% NH$_3$ (7M Solution in MeOH)]=90/10; Flow rate: 80 g/min; Wave length: UV 214 nm; Temperature: 35° C.) to give ethyl (S,Z)-2-(2-((tert-butyldimethylsilyl)oxy)ethylidene)-5-oxotetrahydro-1H-pyrrolizine-7a(5H)-carboxylate (50 mg, peak 1 of 2, Rt: 1.584 min, yield: 43%). $^1$H NMR (400 MHz, CDCl$_3$) δ 5.52-5.43 (m, 1H), 4.21 (d, J=15.9 Hz, 1H), 4.13 (q, J=7.1 Hz, 2H), 4.06 (dd, J=3.8, 1.2 Hz, 2H), 3.69 (d, J=15.8 Hz, 1H), 2.98 (d, J=15.6 Hz, 1H), 2.71 (dt, J=16.7, 10.0 Hz, 1H), 2.53 (ddd, J=13.1, 9.1, 1.7 Hz, 1H), 2.47-2.33 (m, 2H), 2.12-2.01 (m, 1H), 0.83 (s, 9H), −0.00 (s, 6H).

Step 5: Synthesis of (S,Z)-(2-(2-((tert-butyldimethylsilyl)oxy)ethylidene)tetrahydro-1H-pyrrolizin-7a(5H)-yl)methanol (I-18)

To a solution of ethyl (S,Z)-2-(2-((tert-butyldimethylsilyl)oxy)ethylidene)-5-oxotetrahydro-1H-pyrrolizine-7a(5H)-carboxylate (50 mg, 0.14 mmol) in THF (5 mL) was added LAH (0.283 mL, 1 M in THF) at 0° C. under nitrogen atmosphere. The resulting mixture was allowed to warm up to 70° C. and stirred at 70° C. for 1 h. LCMS showed the starting material was consumed and the desired product was detected. The mixture was quenched with Na$_2$SO$_4$·10 H$_2$O and stirred at 25° C. for 2 h. The mixture was filtered and concentrated under reduced pressure to give product (S,Z)-(2-(2-((tert-butyldimethylsilyl)oxy)ethylidene)tetrahydro-1H-pyrrolizin-7a(5H)-yl)methanol (60 mg, crude) as pale-yellow oil, which was used for next step without further purification. LCMS (ESI) m/z: 298.3 [M+H]$^+$. This was carried through steps as per general scheme A with a final global deprotection step using HCl in dioxane at 25° C.

Intermediate 19 (I-19): (1R,7aS*)-7a-(hydroxymethyl)-6-methylenehexahydro-1H-pyrrolizin-1-ol

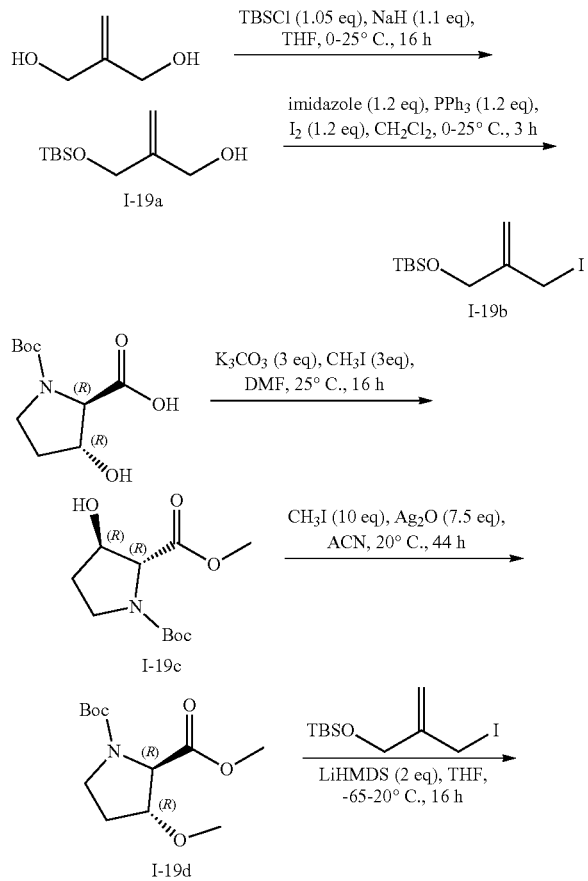

Step 1: Synthesis of 2-(((tert-butyldimethylsilyl)oxy)methyl)prop-2-on-1-ol (I-19a)

To a mixture of 2-Methylene-1,3-propanediol (10 g, 113.5 mmol) in THF (400 mL) was added Sodium hydride (4.99 g, 125 mmol) at 0° C. The mixture was stirred at 0° C. for 1 h under nitrogen atmosphere. tert-Butyldimethylsilyl chloride (18.0 g, 119 mmol) was added in one batch. The mixture was stirred at 25° C. for 16 h. LCMS showed the starting material was consumed and the desired product was formed (UW 214, R$_t$=1.360 min). Water (200 mL) was added. The mixture was extracted with EtOAc (400 mL×3). The combined organic layer was dried over Na₂SO₄, filtered and concentrated to dryness. The crude was purified by flash column chromatography (CH₂Cl₂ in PE from 0% to 30%) to afford 2-(((tert-butyldimethylsilyl) oxy) methyl) prop-2-en-1-ol (23.2 g, crude) as a colorless oil. $^1$H NMR (400 MHz, CDCl₃) δ 5.11-5.09 (m, 1H), 5.08 (dd, J=2.4, 1.2 Hz, 11H), 4.25 (s, 2H), 4.17 (s, 2H), 0.91 (d, J=2.6 Hz, 9H), 0.10-0.08 (m, 6H). LCMS (m/z)=203.2 (M+H)⁺

Step 2: Synthesis of tert-butyl((2-(iodomethyl) allyl) oxy) dimethyl silane (I-19b)

To a mixture of 2-(((tert-butyldimethylsilyl) oxy) methyl) prop-2-en-1-ol (13.3 g, 65.72 mmol) in CH₂Cl₂ (300 mL) was added imidazole (5.37 g, 78.9 mmol) and PPh₃ (20.7 g, 78.9 mmol) at 0° C. I₂ (20 g, 78.9 mmol) was added in one portion. The reaction was stirred at 0° C. and then allowed to stir at 25° C. for 3 h. TLC (PE=100%, I₂, Rf=0.8) showed that the starting material was consumed and a new spot was detected. The mixture was concentrated under reduced pressure. The residue was diluted with CH₂Cl₂ (50 mL). Then hexane (300 mL) was added. The mixture was filtered by Celite. The filtrate was concentrated to dryness. The residue was purified by flash column chromatography (220 g silica gel, PE=100%) to give tert-butyl((2-(iodomethyl) allyl) oxy) dimethyl silane (15.3 g, 75%) as a light-yellow oil. $^1$H NMR (400 MHz, CDCl₃) δ 5.31 (d, J=0.8 Hz, 1H), 5.19 (dd, J=2.8, 1.4 Hz, 1H), 4.31 (s, 2H), 3.95 (s, 2H), 0.92 (s, 9H), 0.10 (d, J=3.1 Hz, 6H).

Step 3: Synthesis of 1-(tert-butyl) 2-methyl (2R, 3R)-3-hydroxypyrrolidine-1,2-dicarboxylate (I-19c)

To a solution of (2R,3R)-1-(tert-butoxycarbonyl)-3-hydroxypyrrolidine-2-carboxylic acid (2 g, 8.65 mmol) in DMF (50 mL) were added K₂CO₃ (3.6 g, 25.9 mmol) and CH₃I (3.68 g, 25.9 mmol) at 0° C. The reaction mixture was stirred at 25° C. for 16 h. LCMS showed the starting material was consumed and desired product was detected. The reaction mixture was diluted with saturated aqueous LiCl (100 mL) and extracted with EtOAc (50 mL×3). The combined organic layer was washed with water (100 mL) and brine (100 mL), dried over Na₂SO₄. After filtration, the filtrate was concentrated under reduced pressure. The residue was purified by flash column chromatography (24 g silica gel, eluted with EtOAc in PE from 0% to 35%) to give 1-(tert-butyl) 2-methyl (2R,3R)-3-hydroxypyrrolidine-1,2-dicarboxylate (2.3 g, crude) as a light-yellow oil. $^1$H NMR (400 MHz, CDCl₃) δ 4.44 (s, 1H), 4.31-4.22 (m, 1H), 3.74 (s, 3H), 3.69-3.52 (m, 2H), 2.16-2.04 (m, 1H), 1.92-1.90 (m, 1H), 1.44 (m, 9H). LCMS (ESI) m/z 268.1 (M+Na)⁺.

Step 4: Synthesis of 1-(tert-butyl) 2-methyl (2R, 3R)-3-methoxypyrrolidine-1,2-dicarboxylate (I-19d)

A mixture of 1-(tert-butyl) 2-methyl (2R,3R)-3-hydroxypyrrolidine-1,2-dicarboxylate (4.4 g, 17.9 mmol), CH₃I (25.2 g, 179 mmol) and Ag₂O (24.9 g, 108 mmol) in CH3CN (75 mL) was stirred at 20° C. for 20 h. LCMS showed that some starting material was remained and desired product was detected. Ag₂O (6.24 g, 26.9 mmol) was added to the above solution and stirred for another 24 hours. LCMS showed that most starting material was consumed and desired product was detected. The reaction mixture was filtered, and the filter cake was washed with CH3CN (30 mL). The filtrate was concentrated under reduced pressure. The residue was purified by flash column chromatography (24 g silica gel, eluting with EtOAc in PE from 0% to 25%) to give 1-(tert-butyl) 2-methyl (2R,3R)-3-methoxypyrrolidine-1,2-dicarboxylate (3.95 g, 85%) as a colorless oil. $^1$H NMR (400 MHz, CDCl₃) δ 4.42-4.26 (m, 1H), 3.96-3.84 (m, 1H), 3.75 (d, J=2.8 Hz, 3H), 3.70 3.42 (m, 2H), 3.38 (s, 3H), 2.10-1.94 (m, 2H), 1.45-1.43 (m, 9H). LCMS (ESI) m/z 282.0 (M+Na).

Step 5: Synthesis of 1-(tert-butyl) 2-methyl (3R)-2-(2-(((tert-butyldimethylsilyl)oxy)methyl)allyl)-3-methoxypyrrolidine-1,2-dicarboxylate (I-19e)

To a mixture of 1-(tert-butyl) 2-methyl (2S,3S)-3-methoxypyrrolidine-1,2-dicarboxylate (3.9 g, 15.04 mmol) in THF (65 mL) was added LIHMDS (30.1 mL, 30.1 mmol, 1M in THF) at −65° C. The mixture was stirred at −65° C. for 1 h. tert-butyl((2-(iodomethyl) allyl) oxy) dimethyl silane (9.39 g, 30.1 mmol) in THF (5 mL) was added dropwise to above solution at −65° C. The mixture was allowed to warm to 20° C. and stirred at 20° C. for 16 h under nitrogen atmosphere. LCMS showed the starting material was consumed and the desired product was formed. The reaction mixture was quenched with saturated aqueous NH₄Cl (60 mL) and then extracted with EtOAc (50 mL×3). The combined organic phase was washed with brine (60 mL) and dried over sodium sulfate and filtered. The filtrate was concentrated under reduced pressure. The residue was purified by flash column chromatography (40 g silica gel, eluting with EtOAc in PE from 0% to 5%) to afford 1-(tert-butyl) 2-methyl (3R)-2-(2-(((tert-butyldimethylsilyl) oxy) methyl) ally-3-methoxypyrrolidine-1,2-dicarboxylate (2.2 g, 33%) as a yellow oil. $^1$H NMR (400 MHz, CDCl₃) δ 5.39-5.25 (m, 1H), 4.97 (d, J=12.2 Hz, 1H), 4.17-3.97 (m, 3H), 3.75-3.68 (m, 3H), 3.51-3.28 (m, 4H), 3.26-3.08 (m, 1H), 3.02-2.77 (m, 1H), 2.61-2.54 (m, 1H), 2.13-1.87 (m, 2H), 1.45-1.41 (m, 9H), 0.91 (s, 9H), 0.05 (s, 6H).
LCMS(ESI) m/z=466.1 (M+Na)⁺

Step 6: Synthesis of methyl (3R)-2-(2-(chloromethyl)allyl)-3-methoxypyrrolidine-2-carboxylate (I-19f)

SOCl₂ (4.2 mL) was slowly added to a solution of 1-(tert-butyl) 2-methyl (3R)-2-(2-(((tert-butyldimethylsilyl) oxy) methyl) ally-3-methoxypyrrolidine-1,2-dicarboxylate (0.3 g, 0.67 mmol) in CH₂Cl₂ (10 mL). The reaction mixture was stirred at 20° C. for 16 h. LCMS showed the reaction was completed. The mixture was concentrated under reduced pressure to give methyl (3R)-2-(2-(chloromethyl) allyl)-3-methoxypyrrolidine-2-carboxylate (230 mg, crude) as a brown oil, which was used for next step directly. LCMS (ESI) m/z 248.1 (M+H)⁺.

Step 7: Synthesis of methyl (1R,7aS*)-1-methoxy-6-methylenetetrahydro-1H-pyrrolizine-7a(5H)-carboxylate (I-19g and I-19h)

Into a 25 mL round-bottom flask was added crude methyl (3R)-2-(2-(chloromethyl)allyl)-3-methoxypyrrolidine-2-carboxylate (1600 mg, 6.45 mmol), sodium bicarbonate (2.71 g, 32.2 mmol) and potassium iodide (107 mg, 0.64 mmol) in CH3CN (70 mL). The mixture was stirred at 20° C. for 1.5 h. LCMS showed the starting material was consumed and desired product was detected. Concentrated to remove most CAN, then diluted with H₂O (50 mL) and extracted with i-PrOH/CH₂Cl₂ (1/5, 50 mL×3). The combined organic layer was dried over Na₂SO₄, filtered and concentrated under reduced pressure. The residue was purified by flash column chromatography (24 g silica gel, eluting with EtOAc in PE (0.1% NH₄OH) from 0% to 40%) to give methyl (1R,7aS*)-1-methoxy-6-methylenetetrahydro-1H-pyrrolizine-7a(5H)-carboxylate (intermediate I-19g) (150 mg, 15%) as yellow oil. ¹H NMR (400 MHz, MeOD) δ5.06-4.91 (m, 2H), 4.13-4.07 (m, 1H), 3.92-3.86 (m, 1H), 3.75 (s, 3H), 3.46-3.41 (m, 1H), 3.35 (s, J=3.7 Hz, 1H), 3.24-3.18 (m, 1H), 3.16-3.09 (m, 1H), 2.88-2.78 (m, 1H), 2.75-2.68 (m, 1H), 2.11-2.01 (m, 2H). $[\alpha]_D^{25}$=+2.31 (c 0.13, MeOH). And methyl(1R,7aR*)-1-methoxy-6-methylenetetrahydro-1H-pyrrolizine-7a(5H)-carboxylate (intermediate I-19h) (370 mg, 21%) as yellow oil. ¹H NMR (400 MHz, MeOD) δ 5.06-4.93 (m, 2H), 3.97-3.91 (m, 1H), 3.73 (s, 3H), 3.70-3.65 (m, 1H), 3.41-3.34 (m, 2H), 3.30 (s, 3H), 3.09-3.00 (m, 1H), 2.78-2.68 (m, 1H), 2.62-2.56 (m, 1H), 2.24-2.14 (m, 1H), 2.05-1.96 (m, 1H). LCMS(ESI) m/z=212 (M+1). $\alpha]_D^{25}$=-24.62 (c 0.13, MeOH).

Step 8: Synthesis of ((1R,7aS*)-1-methoxy-6-methylenetetrahydro-1H-pyrrolizin-7a(5H)-yl) methanol (I-19j)

To a solution of methyl (1R,7aS*)-1-methoxy-6-methylenetetrahydro-1H-pyrrolizine-7a(5H)-carboxylate (intermediate I-19g) (150 mg, 0.71 mmol) in THF (15 mL) was added DIBALH (4.73 mL, 1.5 M in toluene) at 0° C. under nitrogen atmosphere. The resulting mixture was allowed to warm to 25° C. and stirred at 25° C. for 45 mins. LCMS showed the starting material was consumed and desired product was detected. The mixture was quenched with MeOH (1 mL) at -50° C., then allowed to warm to 20° C. and stirred at 20° C. for 30 mins. Then the mixture was poured into aq. potassium sodium tartrate tetrahydrate (10 mL, 2 M) at 20° C. and stirred at 20° C. for 2 hours. Separated the organic layer and the aqueous layer was extracted with i-PrOH/CH₂Cl₂ (1/5, 15 mL×4). The combined organic layer was dried over Na₂SO₄, filtered and concentrated under reduced pressure to give ((1R,7aS*)-1-methoxy-6-methylenetetrahydro-1H-pyrrolizin-7a(5H)-yl) methanol (Compound 8-1) (130 mg, crude) as oil, which was used for next step without further purification. LCMS (ESI) m/z 184.1 (M+H)⁺.

Synthesis of (1R,7aS*)-7a-(hydroxymethyl)-8-methylenehexahydro-1H-pyrrolizin-1-ol (Intermediate I-19)

To a solution of ((1R,7aS*)-1-methoxy-8-methylenetetrahydro-1H-pyrrolizin-7a(5H)-yl) methanol (Compound 10-1) (130 mg, 0.71 mmol) in CH₂Cl₂ (5 mL) was added BBr₃ (1.78 g, 7.09 mmol) at 0° C. The mixture was allowed to warm to 20° C. and stirred at 20° C. for 16 h. LCMS showed the starting material was consumed and a major peak with desired MS was detected. The mixture was concentrated under reduced pressure. The residue was diluted with CH₂Cl₂ (10 mL), quenched with MeOH (1 mL) and then basified with NaHCO₃ at 0° C. The separated aqueous layer was concentrated and then diluted with MeOH/CH₂Cl₂ (50 mL, 1/20). The mixture was filtered and concentrated under reduced pressure. The residue was purified by flash column chromatography (4 g silica gel, eluting with MeOH in CH₂Cl₂ (0.1% NH₄OH) from 15% to 100%) to give crude product. The crude was diluted with MeOH/CH₂Cl₂ (20 mL, 1/10), then filtered and concentrated under reduced pressure. The residue was diluted with CH3CN (50 mL) and then ultrasonic washing, filtered, and concentrated under reduced pressure to give (1R,7aR*)-7a-(hydroxymethyl)-8-methylenehexahydro-1H-pyrrolizin-1-ol (Compound 11-1) (75 mg, crude) as a yellow oil. LCMS (ESI) m/z: 170.1 [M+H]⁺.

Intermediate 20 (I-20): 6-chloro-5-cyclopropyl-1-(oxan-2-yl)-4-(4,4,5,5-tetramethyl-1,3,2-dioxaborolan-2-yl)-1H-indazole

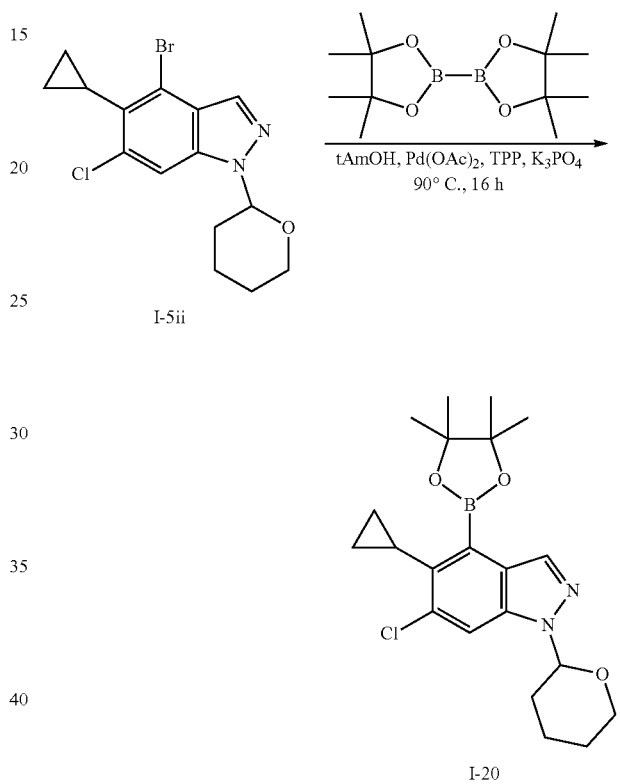

To a solution of 4-bromo-8-chloro-5-cyclopropyl-1-(oxan-2-yl)-1H-indazole (I-5ii, 30.0 g, 81.8 mmol) in tert-Amyl alcohol (401 mL) was added bis(pinacolato)diborane (41.6 g, 163 mmol, palladium acetate (1.15 g, 5.11 mmol, triphenylphosphine (2.68 g, 10.2 mmol) and K₃PO₄ (52.1 g, 245 mmol). The resulting mixture was degassed 3× with Ar, then heated in an oil bath at 90° C. for 16 h. Analysis by LCMS showed the desired product had formed. The mixture was filtered through celite and rinsed with EtOac. The crude product was purified by flash column chromatography (ISCO, 120 g silica gel, EtOAc in heptane 0-10%) to afford the title intermediate, 1-20 (26.3 g, 80%). ¹H NMR (400 MHz, CDCl₃) δ 8.14 (d, J=1.0 Hz, 1H), 7.67 (d, J=1.0 Hz, 1H), 5.64 (dd, J=9.0, 2.9 Hz, 1H), 3.98 (dtd, J=11.5, 3.7, 1.4 Hz, 1H), 3.77-3.60 (m, 1H), 2.57-2.39 (m, 1H), 2.13 (tt, J=8.4, 5.6 Hz, 2H), 2.07-1.97 (m, 1H), 1.83-1.59 (m, 3H), 1.45 (s, 12H), 1.11-1.01 (m, 2H), 0.61-0.50 (m, 2H). MS: 403.2, [M+H]⁺.

(Note: this procedure outlines the general methodology to convert indazole bromides to boronates and can be applied with non-critical changes and/or substitutions to afford requisite boronates from indazole bromides described within.)

Intermediate 21 (I-21): (8aS)-5-chloro-4-fluoro-2-(methanesulfonyl)-8a,9,12,13-tetrahydro-8H,11H-7,10-dioxa-1,3,6,13a-tetraazanaphtho[1,8-ab]heptalene

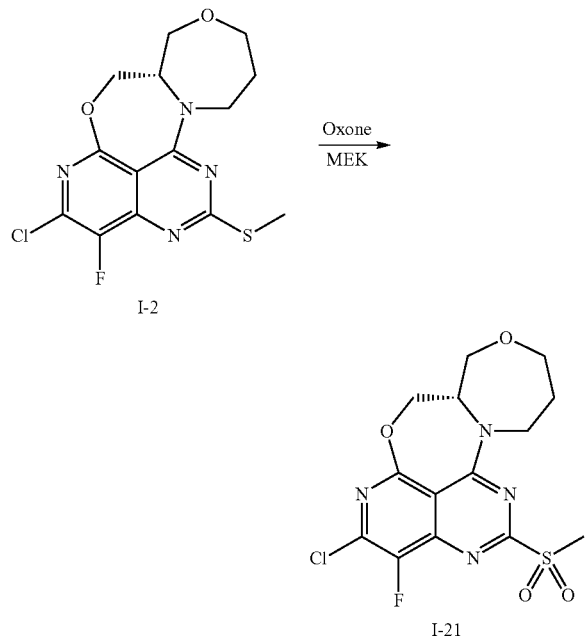

(S)-2-chloro-1-fluoro-12-(methylthio)-5a,6,9,10-tetrahydro-5H,8H-4,7-dioxa-3,10a,11,13-tetraazanaphtho[1,8-ab]heptalene (I-2, 3.0 g, 8.4 mmol, 1 equiv) was dissolved in methyl ethyl ketone (84 mL) and saturated aqueous NaHCO₃ (42 mL), then Oxone (11.6 g, 18.9 mmol) was added at room temperature. Additional Oxone (14.1 g) was added in portions over 2 hours to reach full conversion, at which point the layers were separated, the aqueous layer extracted with EtOAc (3×5 mL), the combined organic layers dried with sodium sulfate, filter, and concentrated. The residue was azeotroped with CH₃CN (2×5 mL), and concentrated again to afford the desired product, which was taken on crude with no purification.

Intermediate 22 (I-22): Synthesis of 4-bromo-1-(tetrahydro-2H-pyran-2-yl)-5,6,7,8-tetrahydro-1H-benzo[f]indazole

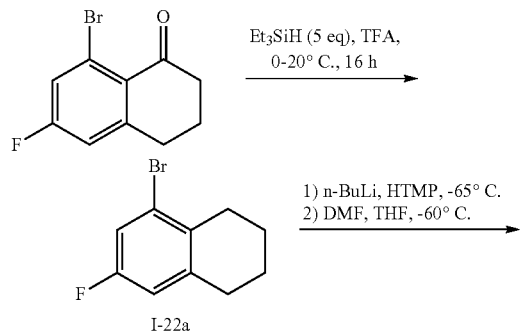

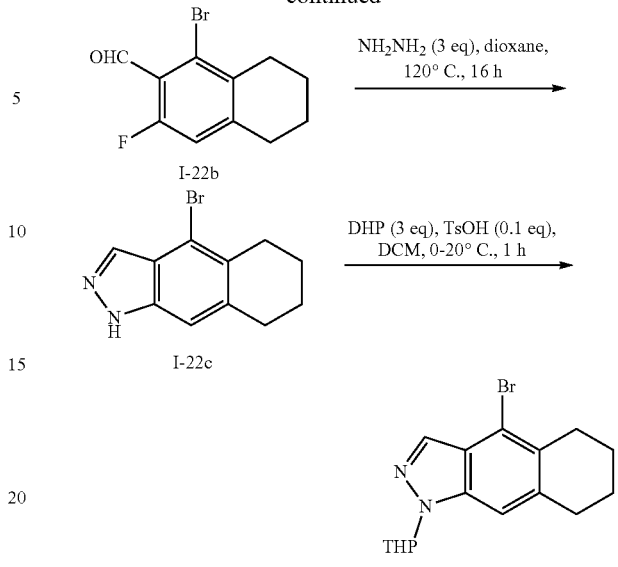

Step 1: Synthesis of 5-bromo-7-fluoro-1,2,3,4-tetrahydronaphthalene (I-22a)

To a stirred solution of 8-bromo-6-fluoro-3,4-dihydronaphthalen-1(2H)-one (500 mg, 2.06 mmol) in TFA (2 mL) was added dropwise Et₃SiH (1200 mg, 10.3 mmol) at 0° C. under nitrogen. The mixture was stirred at 20° C. for 16 h. LCMS showed that the starting material was consumed. The mixture was concentrated under reduced pressure and quenched with saturated aqueous NH₄Cl (10 mL), extracted with EtOAc (10 mL×2). The combined organic layer was washed with brine (10 mL), dried over Na₂SO₄, filtered and concentrated under reduced pressure. The residue was purified by flash column chromatography (12 g silica gel, 0-2% EtOAc in petroleum ether) to give 5-bromo-7-fluoro-1,2,3,4-tetrahydronaphthalene (460 mg, 97.6%) as yellow oil. ¹H NMR (400 MHz, CDCl₃) δ 7.13 (dd, J=8.1, 2.6 Hz, 1H), 6.76 (dd, J=9.1, 2.5 Hz, 1H), 2.75 (t, J=6.2 Hz, 2H), 2.68 (t, J=6.2 Hz, 2H), 1.87-1.78 (m, 2H), 1.77-1.67 (m, 2H).

Step 2: Synthesis of 1-bromo-3-fluoro-5,6,7,8-tetrahydronaphthalene-2-carbaldehyde (I-22b)

To an oven dried vial under an atmosphere of nitrogen and equipped with a magnetic stir bar was added 2,2,6,6-Tetramethylpiperidin (425 mg, 3.01 mmol) dissolve in THF (8 mL) and the solution was cooled to −65° C. Then n-BuLi (0.80 mL, 2.0 mmol) was added to the above solution. The reaction mixture was stirred for 30 mins at −40° C. A solution of 5-bromo-7-fluoro-1,2,3,4-tetrahydronaphthalene (230 mg, 1.0 mmol) in THF (5 mL) was added to above solution at −60° C. And stirring was continued at −60° C. for 1 h. Then DMF (147 mg, 2.0 mmol) was added to above solution at −60° C. The reaction was stirred at −60° C. for 1 h. LCMS showed the starting material was consumed and a new peak was detected. The mixture was quenched with saturated aqueous NH₄Cl (2 mL) and extracted with EtOAc (10 mL×2). The organic layer was washed brine (20 mL), dried over Na₂SO₄, filtered, and concentrated under reduced pressure. The residue was purified by flash column chromatography (12 g silica gel, 0-25% EtOAc in petroleum ether) to give 1-bromo-3-fluoro-5,6,7,8-tetrahydronaphthalene-2-carbaldehyde (230 mg, 89.1%) as yellow oil. $^1$H NMR (400 MHz, CDCl$_3$) δ 10.38 (s, 1H), 6.88 (d, J=11.0 Hz, 1H), 2.82 (t, J=6.2 Hz, 2H), 2.76 (t, J=6.2 Hz, 2H), 1.91-1.81 (m, 2H), 1.80-1.69 (m, 2H).

Step 3: Synthesis of 4-bromo-5,6,7,8-tetrahydro-1H-benzo[f]indazole (I-22c)

To a stirred solution of 1-bromo-3-fluoro-5,6,7,8-tetrahydronaphthalene-2-carbaldehyde (230 mg, 0.895 mmol) in 1,4-dioxane (5 mL) was added N$_2$H$_4$·H$_2$O (158 mg 2.68 mmol), then the mixture was stirred in a sealed tube at 120° C. for 16 h. LCMS showed that the starting material was consumed and the desired product was detected. The mixture was quenched with saturated aqueous NH$_4$Cl (2 mL), extracted with EtOAc (10 mL×2). The organic layer was washed brine (20 mL), dried over Na$_2$SO$_4$, filtered and concentrated under reduced pressure. The residue was purified by flash column chromatography (12 g silica gel, 0-25% EtOAc in petroleum ether) to give 4-bromo-5,6,7,8-tetrahydro-1H-benzo[f]indazole (95 mg, 42%) as a yellow oil. $^1$H NMR (400 MHz, CDCl$_3$) δ 8.03 (s, 1H), 7.18 (s, 1H), 2.94 (t, J=6.2 Hz, 2H), 2.89 (t, J=6.6 Hz, 2H), 1.90-1.84 (m, 2H), 1.83-1.77 (m, 2H). LCMS (ESI) m/z 251, 253 [M+H]$^+$.

Synthesis of 4-bromo-1-(tetrahydro-2H-pyran-2-yl)-5,6,7,8-tetrahydro-1H-benzo[f]indazole (I-22)

To a stirred solution of 4-bromo-5,6,7,8-tetrahydro-1H-benzo[f]indazole (95 mg, 0.38 mmol) in DCM (2 mL) were added p-Toluenesulfonic acid (7.2 mg, 0.038 mmol) and DHP (95 mg, 1.13 mmol) at 0° C. under nitrogen atmosphere. The mixture was stirred at 20° C. for 1 h. LCMS showed that the starting material was consumed and the desired product was detected. The reaction mixture was poured into EtOAc (5 mL), washed with water (5 mL), dried over Na$_2$SO$_4$, filtered, and concentrated under reduced pressure. The residue was purified by flash column chromatography (12 g silica gel, 0-30% EtOAc in petroleum ether) to give 4-bromo-1-(tetrahydro-2H-pyran-2-yl)-5,6,7,8-tetrahydro-1H-benzo[f]indazole (95 mg, yield: 75%) as yellow oil. $^1$HNMR (400 MHz, CDCl$_3$) δ 8.10 (s, 1H), 7.40 (s, 1H), 5.70 (dd, J=9.4, 2.8 Hz, 1H), 3.86 (dd, J=10.7, 8.0 Hz, 1H), 3.55-3.46 (m, 1H), 2.91-2.87 (m, 4H), 1.92-1.80 (m, 4H), 1.80-1.70 (m, 6H). LCMS (ESI) m/z 335, 337 [M+H]$^+$.

Synthesis of Intermediate 23 (I-23i and I-23ii): rel-4-bromo-6-chloro-5-((1R,2R)-2-methylcyclopropyl)-1-(tetrahydro-2H-pyran-2-yl)-1H-indazole

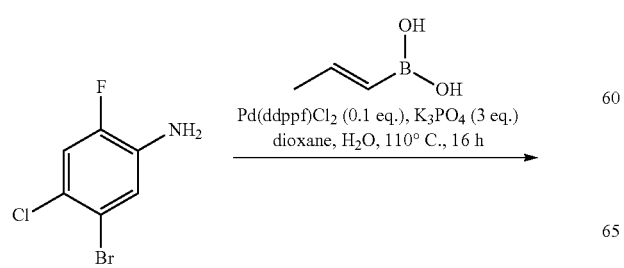

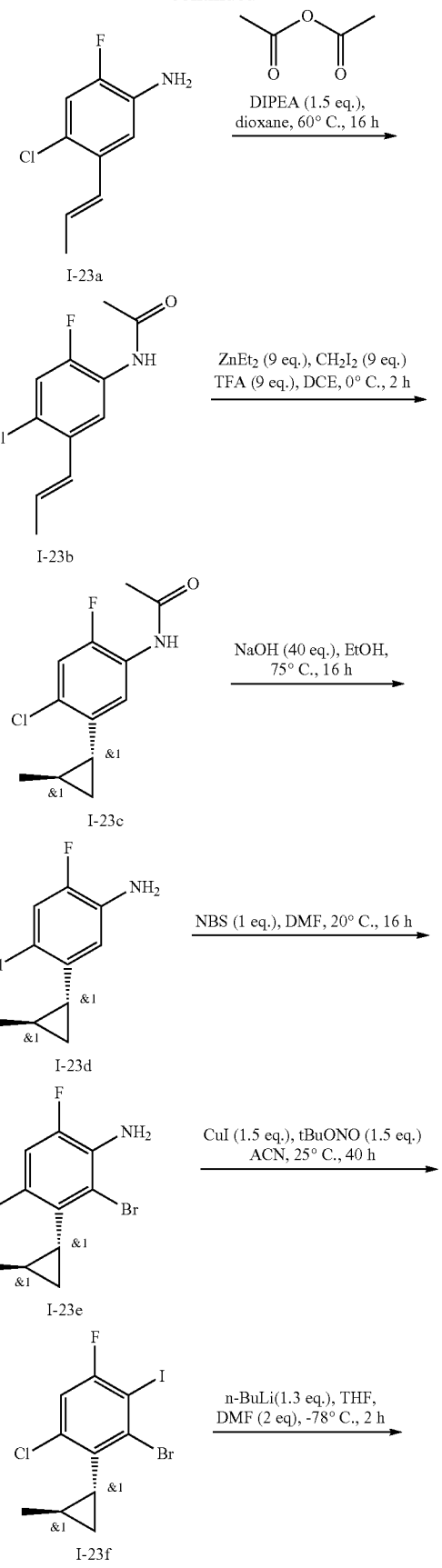

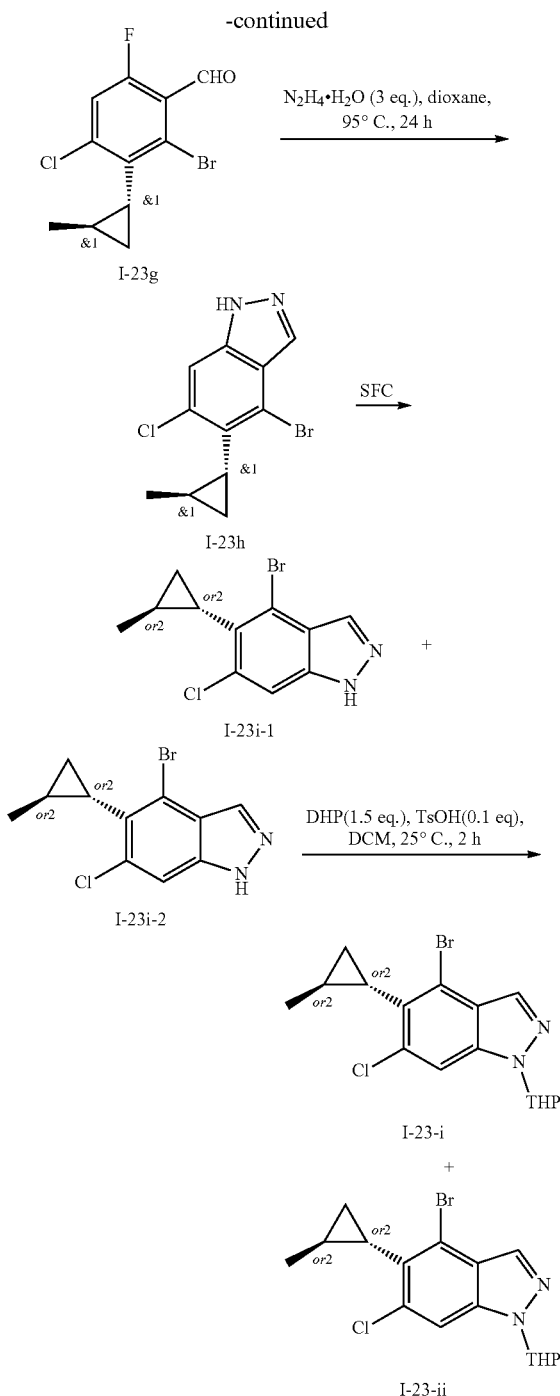

Step 1: Synthesis of (E)-4-chloro-2-fluoro-H-prop-1-en-1-yl)aniline (I-23a)

To a mixture of 5-bromo-4-chloro-2-fluoroaniline (3400 mg, 15.1 mmol), (E)-prop-1-en-1-ylboronic acid (2600 mg, 30.27 mmol), and K₃PO₄ (9640 mg, 45.4 mmol) in 1,4-dioxane (70 mL) and H₂O (14 mL) was added Pd(dppf)Cl₆ (1110 mg, 1.51 mmol). The mixture was stirred at 110° C. for 16 h under nitrogen atmosphere. LCMS showed that the desired product was detected and no starting material was remained. The reaction mixture was filtered. The filtrate was diluted with EtOAc (200 mL) and washed with brine (100 mL*2). The organic layer was dried over Na₂SO₄, filtered and concentrated under reduced pressure. The residue was purified by flash column chromatography (80 g silica gel, 0-10% of EtOAc in petroleum ether) to give (E)-4-chloro-2-fluoro-5-(prop-1-en-1-yl)aniline (3140 mg, 97% yield) as a yellow oil. ¹H NMR (400 MHz, DMSO) δ 7.11 (d, J=11.0 Hz, 1H), 6.97 (d, J=9.6 Hz, 1H), 6.53 (dd, J=15.7, 1.7 Hz, 1H), 6.09-6.05 (m, 1H), 5.41-5.07 (br, 2H), 1.86 (dd, J=6.7, 1.6 Hz, 3H). LCMS (ESI) m/z: 186.0 [M+H]⁺.

Step 2: Synthesis of (E)-N-(4-chloro-2-fluoro-S-(prop-1-on-1-yl)phenyl)acetamide (I-23b)

To a solution of (E)-4-chloro-2-fluoro-5-(prop-1-en-1-yl)aniline (2600 mg, 14.01 mmol) in dioxane (75 mL) was added Acetic anhydride (2140 mg, 21.0 mmol) and DIPEA (2720 mg, 21.0 mmol) at 25° C. The mixture was stirred at 60° C. for 16 h. LCMS showed that the starting material was consumed and the desired product was detected. The reaction was diluted with EtOAc (150 mL) and washed with brine (150 mL×2). The organic was dried over Na₂SO₄, filtered and concentrated under reduced pressure. The residue was dissolved in EtOAc. Then petroleum ether was added dropwise until no solid was formed. Filtration to get the white solid as (E)-N-(4-chloro-2-fluoro-5-(prop-1-en-1-yl)phenyl)acetamide (2200 mg, 58%). ¹H NMR (400 MHz, DMSO-d₆) δ 9.81 (s, 1H), 8.14 (d, J=8.4 Hz, 1H), 7.44 (d, J=10.5 Hz, 1H), 6.61 (dd, J=15.7, 1.7 Hz, 1H), 6.30-6.10 (m, 1H), 2.09 (s, 3H), 1.88 (dd, J=6.6, 1.6 Hz, 3H). LCMS(ESI) (m/z): 228.1 [M+H]⁺.

Step 3: Synthesis of rac-N-(4-chloro-2-fluoro-5-((1R,2R)-2-methylcyclopropyl)phenyl)acetamide (I-23c)

To a solution of ZnEt₂ (67.2 mmol, 67.2 mL, 1.0 M) in DCE (15 mL) was added a solution of TFA (67.2 mmol, 5.15 mL) in DCE (20 mL) at 0° C. under a nitrogen atmosphere. After 30 min, a solution of CH₂I₂ (67.2 mmol, 5.41 mL) in DCE (15 mL) was added to the mixture. After 30 min of stirring, a solution of (E)-N-(4-chloro-2-fluoro-5-(prop-1-en-1-yl)phenyl)acetamide (1700 mg, 7.467 mmol) in DCE (57 mL) was added to the mixture. The reaction was stirred at 0° C. for 2 h. LCMS showed that the starting material was consumed and the desired product was detected. The mixture was concentrated under reduced pressure. The crude product was purified by flash column chromatography (80 g silica gel, 0-10% of EtOAc in petroleum ether) to provide rac-N-(4-chloro-2-fluoro-5-((1R,2R)-2-methylcyclopropyl)phenyl)acetamide (1800 mg, 100%) as a light yellow oil. ¹H NMR (400 MHz, CDCl₃) δ 7.78 (d, J=8.3 Hz, 1H), 7.12 (d, J=10.4 Hz, 1H), 2.29 (s, 3H), 1.80-1.74 (m, 1H), 1.22 (d, J=5.7 Hz, 3H), 0.99-0.93 (m, 2H), 0.77-0.72 (m, 1H). LCMS(ESI) (m/z): 241.9 [M+H]⁺.

Step 4: Synthesis of rac-4-chloro-2-fluoro-5-((1R, 2R)-2-methylcyclopropyl)aniline (I-23d)

To the solution of rac-N-(4-chloro-2-fluoro-5-((1R,2R)-2-methylcyclopropyl)phenyl)acetamide (3200 mg, 13.24 mmol) in EtOH (130 mL) was added NaOH (21200 mg, 530 mmol) and the mixture was stirred at 75° C. for 16 h. LCMS showed the starting material was consumed and the desired product was detected. Evaporate most of the EtOH under reduced pressure. Then the residue was diluted with ice water (50 mL) and adjusted to PH=5 with 2 M HCl. The mixture was extracted with EtOAc (40 mL×3). The organic layers were combined, washed with brine, dried over $Na_2SO_4$, filtered and concentrated under reduced pressure. The crude product was purified by flash column chromatography (40 g silica gel, 0-10% of EtOAc in petroleum ether) to provide rac-4-chloro-2-fluoro-5-((1R,2R)-2-methylcyclopropyl)aniline (1100 mg, 42%) as a light-yellow oil. $^1$H NMR (400 MHz, $CDCl_3$) δ 6.99 (d, J=10.6 Hz, 1H), 6.34 (d, J=9.3 Hz, 1H), 1.76-1.70 (m, 1H), 1.21 (d, J=5.8 Hz, 3H), 0.92-0.85 (m, 1H), 0.83-0.78 (m, 1H), 0.72-0.66 (m, 1H). LCMS (ESI) m/z: 200.2 $[M+H]^+$.

Step 5: Synthesis of rac-2-bromo-4-chloro-6-fluoro-3-((1R,2R)-2-methylcyclopropyl)aniline (I-23e)

To a solution of rac-4-chloro-2-fluoro-5-((1R,2R)-2-methylcyclopropyl)aniline (1100 mg, 5.51 mmol) in DMF (27 mL) was added NBS (981 mg 5.51 mmol) at 0° C. under nitrogen atmosphere. The mixture was stirred at 20° C. for 16 h. LCMS showed that the starting material was consumed and the desired product was detected. The mixture was diluted with saturated aqueous $NaHCO_3$ (15 mL), extracted with EtOAc (25 mL×3). The combined organic layer was washed with brine (15 mL), dried over $Na_2SO_4$, filtered and concentrated to give rac-2-bromo-4-chloro-8-fluoro-3-((1R,2R)-2-methylcyclopropyl)aniline (1400 mg, 91%) as a brown oil. $^1$H NMR (400 MHz, CDCl3) δ 7.02 (d, J=10.4 Hz, 1H), 1.38-1.32 (m, 1H), 1.28 (d, J=5.9 Hz, 3H), 1.06-0.99 (m, 1H), 0.96-0.85 (m, 2H). LCMS (ESI) m/z: 278.0, 280.0 $[M+H]^+$.

Step 6: Synthesis of rac-3-bromo-1-chloro-5-fluoro-4-iodo-2-((1R,2R)-2-methylcyclopropyl)benzene (I-23f)

To a solution of CH3CN (20 mL) were added CuI (1440 mg, 7.54 mmol) and tert-Butyl nitrite (778 mg, 7.54 mmol). The mixture was stirred at 25° C. for 30 min. rac-2-bromo-4-chloro-8-fluoro-3-((1R,2R)-2-methylcyclopropyl)aniline (1400 mg, 5.026 mmol) in CAN (20 mL) was added drop-wise, which was stirred at 5° C. for 20 minutes and then warmed to 25° C. for 40 h. LCMS showed that the starting material was consumed and a new peak was formed. The mixture was quenched with HCl (10 mL, 1 M) and extracted with ethyl acetate (3×25 mL). The combined organic layers were washed with saturated aqueous $Na_2SO_3$ (30 mL), brine, dried over $Na_2SO_4$, filtered and concentrated under reduced pressure. The residue was purified by flash column chromatography (4 g silica gel, petroleum ether) to provide rac-3-bromo-1-chloro-5-fluoro-4-iodo-2-((1R,2R)-2-methylcyclopropyl)benzene (1300 mg, 66%) as a light-yellow oil. $^1$H NMR (400 MHz, $CDCl_3$) δ 7.11 (d, J=7.4 Hz, 1H), 1.46-1.40 (m, 1H), 1.29 (d, J=5.6 Hz, 3H), 1.07-0.98 (m, 2H), 0.90-0.84 (m, 1H).

Step 7: Synthesis of rac-2-bromo-4-chloro-1-fluoro-3-((1R,2R)-2-methylcyclopropyl)benzaldehyde (I-23g)

To a solution of rac-3-bromo-1-chloro-5-fluoro-4-iodo-2-((1R,2R)-2-methylcyclopropyl)benzene (1500 mg 3.852 mmol) in THF (40 mL) was added dropwise n-BuLi (321 mg 5.01 mmol) at −78° C. under nitrogen and stirred for 10 min. Then dry DMF (563 mg, 7.7 mmol) was added into the above mixture and the mixture was stirred at −78° C. for 2 h. LCMS showed that starting material was consumed and a new peak was formed. The mixture was quenched with 1N HCl (10 mL) and slowly warmed to 20° C. Then the mixture was diluted with water, extracted with EA (20*3 mL). The combined organic layer was washed with $H_2O$, dried over $Na_2SO_4$, filtered and concentrated to give crude product. The crude product was purified by flash column chromatography (12 g silica gel, petroleum ether) to provide rac-2-bromo-4-chloro-6-fluoro-3-((1R,2R)-2-methylcyclopropyl)benzaldehyde (510 mg, 45%) as a light yellow oil. $^1$H NMR (400 MHz, $CDCl_3$) δ 10.33 (s, 1H), 7.20 (d, J=10.0 Hz, 1H), 1.41-1.39 (m, 1H), 1.32 (d, J=4.8 Hz, 3H), 1.10-1.01 (m, 2H), 0.95-0.87 (m, 1H).

Step 8: Synthesis of rac-4-bromo-8-chloro-5-((1R, 2R)-2-methylcyclopropyl)-1H-indazole (I-23h)

To the mixture of rac-2-bromo-4-chloro-6-fluoro-3-((1R, 2R)-2-methylcyclopropyl)benzaldehyde (510 mg, 1.75 mmol) in 1,4-dioxane (17 mL) was added 85% $N_2H_4 \cdot H_2O$ (309 mg, 5.25 mmol) at 20° C., then the mixture was stirred at 95° C. for 24 h. LCMS showed that the starting material was consumed and the desired product was detected. The reaction was cooled to 25° C. and slowly added to water (10 mL). The mixture was extracted with MTBE (30 mL). The organic layer was dried over $Na_2SO_4$, filtered and concentrated to give crude product. The crude product was purified by flash column chromatography (4 g silica gel, PE) to give rac-4-bromo-6-chloro-5-((1R,2R)-2-methylcyclopropyl)-1H-indazole (270 mg, 54%) as a light yellow solid. LCMS (ESI) m/z: 285.0, 287.0 $[M+H]^+$.

Step 9: Synthesis of rel-4-bromo-6-chloro-54(1R, 2R)-2-methylcyclopropyl)-1H-indazole (I-23i-1 and I-23i-2)

rac-4-bromo-6-chloro-5-((1R,2R)-2-methylcyclopropyl)-1H-indazole (350 mg, 1.23 mmol) was purified by chiral separation (Apparatus: SFC 150; Column: CHIRALPAK IK, 0.46 cm I.D.*25 cm L, 0.5 ul; Mobile Phase: A/B: Hexane/IPA=95/5; Flow rate: 1 mL/min; Wave length: UV 214 nm; Temp: 35 degree) to give rel-4-bromo-6-chloro-5-((1R,2R)-2-methylcyclopropyl)-1H-indazole PEAK 1 was colorless oil (135 mg, 38.6%), [α]25D=+288.00 (c=0.05, MeOH). LCMS (ESI) m/z: 285.0, 287.0 $[M+H]^+$. $^1$H NMR (400 MHz, $CDCl_3$) δ 8.06 (s, 1H), 7.52 (d, J=0.8 Hz, 1H), 1.49 (dt, J=8.4, 5.4 Hz, 1H), 1.33 (d, J=5.9 Hz, 3H), 1.14-1.06 (m, 1H), 1.03-0.94 (m, 2H). PEAK 2 was colorless oil (142 mg, 40.6%), [α]25D=−226.00 (c=0.05, MeOH). LCMS (ESI) m/z: 285.0, 287.0 $[M+H]^+$. $^1$H NMR (400 MHz, $CDCl_3$) δ 8.06 (s, 1H), 7.52 (d, J=0.7 Hz, 1H), 1.49 (dt, J=8.4, 5.4 Hz, 1H), 1.33 (d, J=5.9 Hz, 3H), 1.14-1.06 (m, 1H), 1.03-0.93 (m, 2H).

Step 10: Synthesis of rel-4-bromo-6-chloro-5-((1R, 2R)-2-methylcyclopropyl)-1-(tetrahydro-2H-pyran-2-yl)-1H-indazole (I-23i and I23ii)

To a solution of rel-4-bromo-6-chloro-5-((1R,2R)-2-methylcyclopropyl)-1H-indazole (100 mg 0.35 mmol, I-23i-1) in DCM (4 mL) was added DHP (44.2 mg 0.525 mmol) followed by p-Toluenesulfonic acid monohydrate (6.66 mg 0.0350 mmol) and the reaction mixture was stirred at 25° C. for 2 h. LCMS showed that the starting material was consumed and the desired product was detected. The reaction was washed with saturated aqueous $NaHCO_3$ (10 mL) and brine (10 mL). The organic layer was dried over $Na_2SO_4$, filtered and concentrated to give rel-4-bromo-6-chloro-5-((1R*,2R*)-2-methylcyclopropyl)-1-(tetrahydro- 2H-pyran-2-yl)-1H-indazole (I-23i, 120 mg, Y: 93%) as a yellow oil. $^1$H NMR (400 MHz, CDCl$_3$) δ 7.97 (s, 1H), 7.62 (d, J=0.6 Hz, 1H), 5.62 (dd, J=9.1, 2.8 Hz, 1H), 4.04-3.95 (m, 1H), 3.78-3.69 (m, 1H), 2.53-2.42 (m, 1H), 2.18-2.10 (m, 1H), 2.09-2.02 (m, 1H), 1.81-1.68 (m, 4H), 1.32 (d, J=5.9 Hz, 3H), 1.11-1.04 (m, 1H), 1.00-0.92 (m, 2H). LCMS (ESI) m/z: 369 [M+H]$^+$.

Similarly, I-23i-2 was treated as above to afford rel-4-bromo-6-chloro-5-((1R*,2R*)-2-methylcyclopropyl)-1-(tetrahydro-2H-pyran-2-yl)-1H-indazole (I-23ii, 90 mg, 70%) as a colorless oil. $^1$H NMR (400 MHz, CDCl$_3$) δ 7.97 (s, 1H), 7.61 (d, J=0.7 Hz, 1H), 5.62 (dd, J=9.1, 2.8 Hz, 1H), 4.04-3.95 (m, 1H), 3.77-3.68 (m, 1H), 2.53-2.41 (m, 1H), 2.17-2.02 (m, 2H), 1.76-1.65 (m, 3H), 1.42 (d, J=3.1 Hz, 1H), 1.33 (d, J=6.1 Hz, 3H), 1.13-1.03 (m, 1H), 1.00-0.92 (m, 2H). LCMS (ESI) m/z: 369 [M+H]$^+$.

Synthesis of Intermediate 24 (I-24i and I-24ii): (R*)-4-bromo-5-methoxy-1-((2-(trimethylsilyl)ethoxy)methyl)-5,6,7,8-tetrahydro-1H-benzo[f]indazole

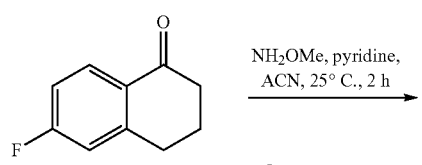
I-24a

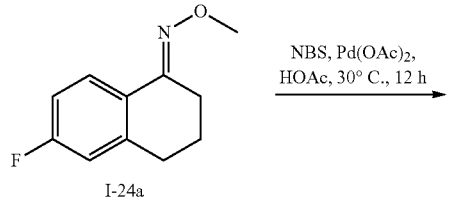
I-24b

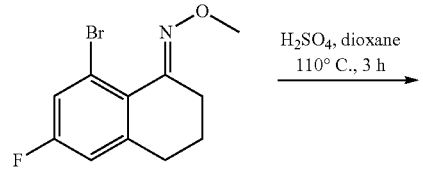
I-24c

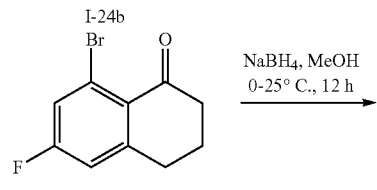
I-24d

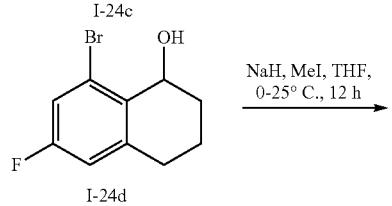
I-24e

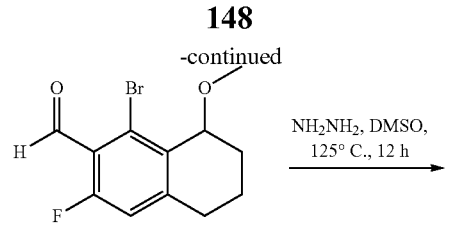
I-24f

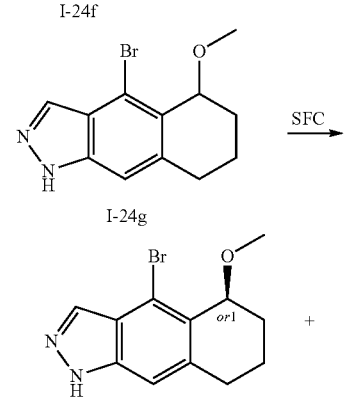
I-24g

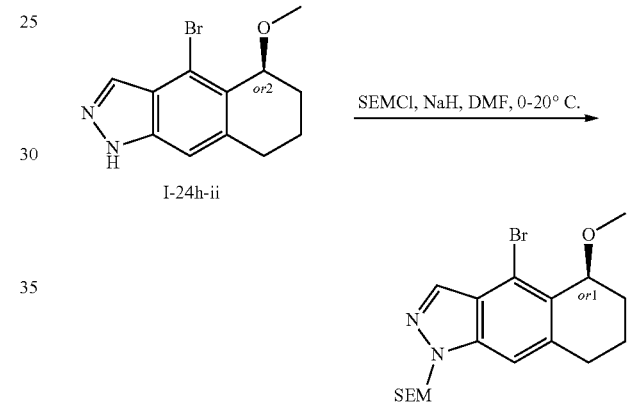
I-24h-i

I-24h-ii

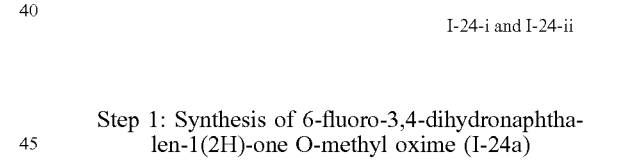
I-24-i and I-24-ii

Step 1: Synthesis of 6-fluoro-3,4-dihydronaphthalen-1(2H)-one O-methyl oxime (I-24a)

A mixture 6-Fluoro-1-tetralone (90 g, 548.19 mmol,), NH$_2$OMe·HCl (68.7 g, 822 mmol), pyridine (65 g, 822 mmol) in CH3CN (500 mL) was stirred at 25° C. for 2 h. TLC (PE, UV) showed that the starting material was consumed and desired spot was detected. The reaction was added H$_2$O (1000 mL) and extracted with MTBE (500 mL×2). Then the combined organic layer was washed with H$_2$O (500 mL) and brine, dried over Na$_2$SO$_4$, filtered and concentrated in vacuo. The brown foam was triturated with toluene (40 mL) to give 6-fluoro-3,4-dihydronaphthalen-1 (2H)-one O-methyl oxime (98 g, 92.5%) as a light brown oil. $^1$H NMR (400 MHz, CDCl$_3$) δ 7.96 (dd, J=8.8, 6.0 Hz, 1H), 6.88 (td, J=8.6, 2.7 Hz, 1H), 6.82 (dd, J=9.2, 2.6 Hz, 1H), 3.97 (s, 3H), 2.77-2.65 (m, 4H), 1.88-1.79 (m, 2H). LCMS (ESI) m/z: 194.1 [M+H]$^+$.

Step 2: Synthesis of 8-bromo-8-fluoro-3,4-dihydronaphthalen-1(2H)-one O-methyl oxime (I-24b)

To a solution of 6-fluoro-3,4-dihydronaphthalen-1(2H)-one O-methyl oxime (98 g, 510 mmol) and NBS (108 g, 609 mmol) in acetic acid (800 mL) was added palladium acetate (8.44 g, 50.7 mmol) under $N_2$. Then the reaction was stirred at 30° C. for 12 h. LCMS showed most starting material was consumed and a major peak with desired mass was detected. The mixture was diluted with water (1000 mL) and TBME (800 mL). The organic phase was dried over sodium sulfate, filtered and concentrated in vacuo. The brown foam was triturated with CH3CN (100 mL) to give crude product 8-bromo-6-fluoro-3,4-dihydronaphthalen-1(2H)-one O-methyl oxime (130 g, 94%) as brown oil, which was used for next step directly. $^1$H NMR (400 MHz, $CDCl_3$) δ 7.30-7.26 (m, 1H), 6.84 (dd, J=8.3, 2.6 Hz, 1H), 4.03 (s, 3H), 2.75 (t, J=6.9 Hz, 2H), 2.65-2.58 (m, 2H), 1.79-1.71 (m, 2H). LCMS (ESI) m/z: 272.0 [M+H]$^+$ Step 3: Synthesis of 8-bromo-8-fluoro-3,4-dihydronaphthalen-1(2H)-one (I-24c)

To a crude 8-bromo-6-fluoro-3,4-dihydronaphthalen-1(2H)-one O-methyl oxime (130 g, 478 mmol) in 1,4-dioxane (2000 mL) was added $H_2SO_4$ (2460 mL, 4 M) at 25° C. The mixture was stirred at 110° C. for 3 h. LCMS showed that the starting material was consumed and the desired product was detected. The reaction was basified to pH=8 with NaOH aq. (1 M, 10 L). The mixture was extracted with EtOAc (1000 mL×2). The organic layers were combined, washed with brine (1000 mL), dried over $Na_2SO_4$, filtered and concentrated in vacuo to give crude product. The crude product was purified by column chromatography ($SiO_2$, 0-3% of EtOAc in petroleum ether) to give 8-bromo-6-fluoro-3,4-dihydronaphthalen-1(2H)-one (66 g, 56.8%) as a yellow solid. $^1$H NMR (400 MHz, $CDCl_3$) δ 7.31 (dd, J=8.3, 2.5 Hz, 1H), 6.94 (dd, J=8.4, 2.5 Hz, 1H), 2.98 (t, J=6.2 Hz, 2H), 2.73-2.66 (m, 2H), 2.10 (dt, J=12.8, 6.5 Hz, 2H). LCMS (ESI) m/z: 243 [M+H]$^+$.

Step 4: Synthesis of 8-bromo-8-fluoro-1,2,3,4-tetrahydronaphthalen-1-ol (I-24d)

A solution of 8-bromo-8-fluoro-3,4-dihydronaphthalen-1(2H)-one (1 g, 4.114 mmol) in MeOH (20 mL) was added $NaBH_4$ (311 mg, 8.23 mmol) at 0° C. The mixture was stirred at 25° C. for 12 h. LCMS showed that the starting material was consumed and the desired product was detected. The mixture was quenched with water (10 mL). The residue was extracted with DCM (20 mL×2). The combined organic phase was dried over $Na_2SO_4$, filtered and concentrated in vacuo. The residue was purified by flash column chromatography (25 g silica gel column, 0-10% of EtOAc in petroleum ether) to give 8-bromo-6-fluoro-1,2,3,4-tetrahydronaphthalen-1-ol (846 mg, 83.9%) as a white solid. $^1$H NMR (400 MHz, $CDCl_3$) δ 7.18 (dd, J=8.0, 2.5 Hz, 1H), 6.82 (dd, J=9.0, 2.5 Hz, 1H), 4.99 (t, J=3.2 Hz, 1H), 2.84 (dd, J=17.2, 5.2 Hz, 1H), 2.76-2.65 (m, 1H), 2.28 (s, 1H), 2.24-2.16 (m, 1H), 2.04-1.91 (m, 1H), 1.81-1.69 (m, 2H). LCMS (ESI) m/z: 227 [M-17]$^+$.

Step 5: Synthesis of 8-bromo-8-fluoro-1-methoxy-1,2,3,4-tetrahydronaphthalene (I-24e)

To a solution of NaH (122 mg, 3.04 mmol) in THF (15 mL) was added 8-bromo-6-fluoro-1,2,3,4-tetrahydronaphthalen-1-ol (745 mg, 3.04 mmol) at 0° C. The mixture was stirred at 0° C. for 1 h. Then $CH_3I$ (647 mg, 4.56 mmol) was added at 0° C. The mixture was stirred at 25° C. for 12 h. LCMS showed that the starting material was consumed and the desired product was detected. The mixture was quenched with $NH_4Cl$ aq. (5 mL) and concentrated under reduced pressure. The residue was extracted with EtOAc (10 mL×2). The combined organic phase was dried over $Na_2SO_4$, filtered and concentrated in vacuo. The residue was purified by flash column chromatography (12 g silica gel column, 0-10% of EtOAc in petroleum ether) to give 8-bromo-6-fluoro-1-methoxy-1,2,3,4-tetrahydronaphthalene (700 mg, 89%) as a yellow oil. $^1$H NMR (400 MHz, DMSO) δ 7.41 (dd, J=8.4, 2.6 Hz, 1H), 7.04 (dd, J=9.5, 2.6 Hz, 1H), 4.29 (t, J=2.8 Hz, 1H), 3.36 (s, 3H), 2.84-2.76 (m, 1H), 2.65 (ddd, J=17.5, 11.1, 6.6 Hz, 1H), 2.30-2.21 (m, 1H), 1.77-1.63 (m, 2H), 1.52-1.42 (m, 1H). LCMS (ESI) m/z: 227[M-31]$^+$.

Step 6: Synthesis of 1-bromo-3-fluoro-8-methoxy-5,6,7,8-tetrahydronaphthalene-2-carbaldehyde (I-24f)

To an oven dried vial under an atmosphere of nitrogen and equipped with a magnetic stir bar were added 2, 2, 6, 6-Tetramethylpiperidin (3590 mg, 25.5 mmol) dissolve in THF (10 mL) and the solution was cooled to −65° C. Then n-BuLi (6.79 mL, 17 mmol) was then added to the above solution. The reaction mixture was stirred for 30 mins at −40° C. Then a solution of 8-bromo-6-fluoro-1-methoxy-1,2,3,4-tetrahydronaphthalene (2200 mg, 8.49 mmol) in THF (40 mL) was added to the above solution. And stirring was continued at −60° C. for 1 h. Then DMF (1240 mg, 17 mmol) was added to the above solution at −60° C. The resulting mixture was stirred at −60° C. for 1 h. LCMS showed the starting material was consumed and a minor peak with desired mass was detected. The mixture was quenched with sat. $NH_4Cl$ (10 mL), extracted with EA (30 mL×2). The organic layer was washed with brine (40 mL), dried over $Na_2SO_4$, filtered and concentrated under reduced pressure. The residue was purified by flash column chromatography (45 g silica gel, 0-25% of EA in petroleum ether) to provide 1-bromo-3-fluoro-8-methoxy-5,6,7,8-tetrahydronaphthalene-2-carbaldehyde (1300 mg, 53.3%) as a yellow oil. $^1$H NMR (400 MHz, $CDCl_3$) δ 10.42-10.36 (m, 1H), 6.90 (d, J=10.9 Hz, 1H), 4.54 (t, J=2.7 Hz, 1H), 3.50 (s, 3H), 2.89 (dd, J=17.8, 5.3 Hz, 1H), 2.81-2.66 (m, 1H), 2.46-2.35 (m, 1H), 1.99-1.86 (m, 1H), 1.80-1.69 (m, 1H), 1.58-1.44 (m, 1H). LCMS (ESI) m/z: 287 [M+H]$^+$.

Step 7: Synthesis of 4-bromo-5-methoxy-5,6,7,8-tetrahydro-1H-benzo[f]indazole (I-24g)

To a solution of 1-bromo-3-fluoro-8-methoxy-5,6,7,8-tetrahydronaphthalene-2-carbaldehyde (1300 mg, 4.528 mmol) in DMSO (10 mL) was added Hydrazine hydrate (2180 mg, 67.9 mmol) at 25° C. Then the reaction was stirred for 12 h at 125° C. LCMS showed the desired product was formed. The mixture was quenched with water (5 mL). The residue was extracted with EA (10 mL×2). The combined organic phase was dried over $Na_2SO_4$, filtered and concentrated. The residue was purified by flash column chromatography (25 g silica gel, 0-40% of EtOAc in petroleum ether) to give 4-bromo-5-methoxy-5,6,7,8-tetrahydro-1H-benzo[f]indazole (700 mg, 55%) as a white solid. $^1$H NMR (400 MHz, $CDCl_3$) δ 8.11 (s, 1H), 7.21 (s, 1H), 4.71 (t, J=2.8 Hz, 1H), 3.49 (s, 3H), 3.10-2.99 (m, 1H), 2.89-2.78 (m, 1H), 2.39 (dd, J=14.2, 3.8 Hz, 1H), 2.10-1.94 (m, 1H), 1.79-1.70 (m, 1H), 1.68-1.56 (m, 1H). LCMS (ESI) m/z 281[M+H]$^+$.

Step 8: SFC Chiral separation of 4-bromo-5-methoxy-5,6,7,8-tetrahydro-1H-benzo[f]indazole (I-24hi and I-24h-ii)

800 mg of crude diastereomeric mixture was purified by SFC; Separation Conditions: Column: Daicel CHIRALCEL® AD, 250 mm' 30 mm I.D., 10 μm; Mobile phase: $CO_2$/MeOH [0.2% $NH_3$ (7M Solution in MeOH)]=80/20; Flow rate: 80 g/min; Wave length: UV 214 nm; Temperature: 35° C. to give two isomers with unknown absolute configuration (denoted as R*).

(R*)-4-bromo-5-methoxy-5,6,7,8-tetrahydro-1H-benzo[f]indazole (I-24-h-i) (380 mg, 47.5%, Rt: 1.418 min, Peak 1) as a white solid. $^1$H NMR (400 MHz, MeOD) δ 7.99 (s, 1H), 7.27 (s, 1H), 4.73 (s, 1H), 3.48 (d, J=0.8 Hz, 3H), 3.04 (d, J=16.5 Hz, 1H), 2.86 (ddd, J=16.9, 11.3, 5.9 Hz, 1H), 2.46-2.37 (m, 1H), 1.95 (td, J=12.6, 6.3 Hz, 1H), 1.80-1.70 (m, 1H), 1.68-1.58 (m, 1H). LCMS (ESI) m/z: 281 [M+H]$^+$. $[\alpha]_D^{25}$=+5.50 (c=0.20, $CH_3OH$).

(R*)-4-bromo-5-methoxy-5,6,7,8-tetrahydro-1H-benzo[f]indazole (I-24h-ii) (400 mg, 50%, Rt: 1.731 min, Peak 2) as a white solid. $^1$H NMR (400 MHz, MeOD) δ 7.99 (s, 1H), 7.27 (s, 1H), 4.73 (s, 1H), 3.48 (s, 3H), 3.04 (d, J=16.5 Hz, 1H), 2.91-2.80 (m, 1H), 2.46-2.37 (m, 1H), 2.02-1.88 (m, 1H), 1.79-1.71 (m, 1H), 1.69-1.58 (m, 1H). LCMS (ESI) m/z: 281 [M+H]$^+$, $[\alpha]_D^{25}$=−5.50 (c=0.20, $CH_3OH$).

Step 9: Synthesis of (R*)-4-bromo-5-methoxy-1-((2-(trimethylsilyl)ethoxy)methyl)-5,6,7,8-tetrahydro-1H-benzo[f]indazole (I-24i and I-24ii)

To a solution of (R*)-4-bromo-5-methoxy-5,6,7,8-tetrahydro-1H-benzo[f]indazole (80 mg, 0.28 mmol) in DMF (3 mL) was added NaH (22.8 mg, 0.569 mmol) at 0° C. under $N_2$. The mixture was stirred at 0° C. for 1 h. Then a solution of SEMCl (94.9 mg, 0.569 mmol) in DMF (1 mL) was added to above solution at 0° C. The resulting mixture was stirred at 20° C. for 1 h. LCMS showed that the starting material was consumed and the desired product was detected. The mixture was quenched with aq. $NH_4Cl$ (0.5 mL) and concentrated under reduced pressure. The residue was purified by flash column chromatography (5 g silica gel, 0-20% of EtOAc in petroleum ether) to give (R*)-4-bromo-5-methoxy-1-((2-(trimethylsilyl)ethoxy)methyl)-5,6,7,8-tetrahydro-1H-benzo[f]indazole (100 mg, 85%) as an oil. $^1$H NMR (400 MHz, CDCl$_3$) δ 8.06 (s, 1H), 7.33 (s, 1H), 5.74 (s, 2H), 4.77 (t, J=2.8 Hz, 1H), 3.61-3.50 (m, 5H), 3.16-3.07 (m, 1H), 2.95-2.84 (m, 1H), 2.47-2.39 (m, 1H), 2.06 (ddd, J=8.9, 8.2, 2.7 Hz, 1H), 1.90-1.76 (m, 1H), 1.72-1.63 (m, 1H), 0.97-0.89 (m, 2H), 0.01-−0.02 (m, 9H). LCMS (ESI) m/z 411 [M+H]$^+$.

Synthesis of Intermediate 25 (I-25): ((7aS,Z)-2-(2-((tert-butyldimethylsilyl)oxy)propylidene)tetrahydro-1H-pyrrolizin-7a(5H)-yl)methanol

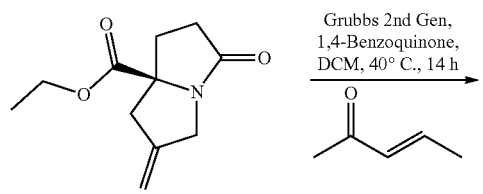

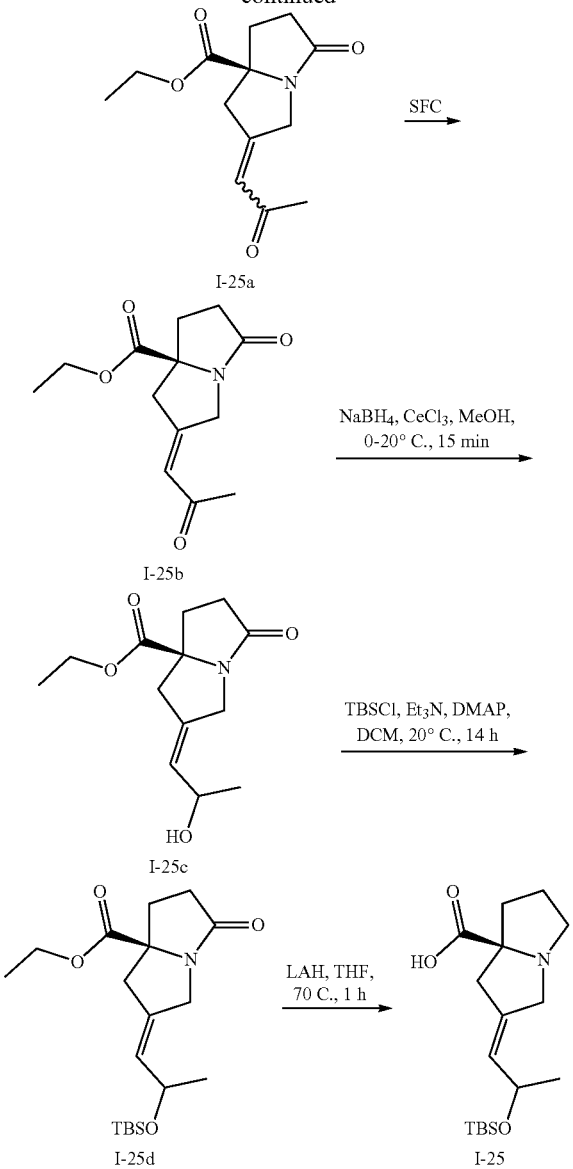

Step 1: Synthesis of (S)-5-oxo-2-(2-oxopropylidene)tetrahydro-1H-pyrrolizine-7a(5H)-carboxylate (I-25a)

To a solution of ethyl (S)-2-methylene-5-oxotetrahydro-1H-pyrrolizine-7a(5H)-carboxylate (1 g, 4.779 mmol) and (E)-pent-3-en-2-one (2010 mg, 23.9 mmol) in DMC (20 mL) was added 1,4-Benzoquinone (52 mg, 0.478 mmol) and Grubbs-2nd-catalyst (406 mg, 0.478 mmol). Then the mixture was stirred at 40° C. for 14 h. LCMS showed the starting material was consumed and the desired product was formed. The reaction mixture was filtrate was concentrated under reduced pressure. The residue was purified by flash column chromatography (silica gel, 0-100% of EtOAc in petroleum ether) to afford ethyl (S)-5-oxo-2-(2-oxopropylidene)tetrahydro-1H-pyrrolizine-7a(5H)-carboxylate (250 mg, 21%) as a brown oil. $^1$H NMR (400 MHz, CDCl$_3$) δ 6.33-6.26 (m, 1H), 4.80 (d, J=19.9 Hz, 1H), 4.20 (dd, J=8.9, 5.4 Hz, 2H), 4.13 (d, J=20.1 Hz, 1H), 3.21 (d, J=17.3 Hz, 1H), 2.88-2.79 (m, 1H), 2.71-2.60 (m, 2H), 2.54-2.46 (m, 1H), 2.23 (s, 3H), 2.13 (dd, J=10.1, 2.9 Hz, 1H), 1.26 (t, J=7.1 Hz, 3H). LCMS (ESI) m/z: 252.1 [M+H]+.

Step 2: Synthesis of ethyl (S,Z)-5-oxo-2-(2-oxopropylidene)tetrahydro-1H-pyrrolizine-7a(5H)-carboxylate (I-25b)

Ethyl (S)-5-oxo-2-(2-oxopropylidene)tetrahydro-1H-pyrrolizine-7a(5H)-carboxylate (250 mg, 0.995 mmol) was purified by SFC eluting with CO₂/MeOH [0.2% NH₃ (7M Solution in MeOH)]=70/30 at 35° C. (Instrument: SFC80; Column: CHIRALPAK IE-3 3 mm*150 mm, 3 um; Flow Rate: 80 g/min) to afford ethyl (S,Z)-5-oxo-2-(2-oxopropylidene)tetrahydro-1H-pyrrolizine-7a(5H)-carboxylate (75 mg, 30%) as a yellow oil. ¹H NMR (400 MHz, CDCl₃) δ 6.29 (s, 1H), 4.81 (d, J=19.9 Hz, 1H), 4.23-4.17 (m, 2H), 4.11 (s, 1H), 3.21 (d, J=16.7 Hz, 1H), 2.93-2.78 (m, 1H), 2.73-2.57 (m, 2H), 2.56-2.44 (m, 1H), 2.22 (s, 3H), 2.18-2.09 (m, 1H), 1.26 (t, J=7.1 Hz, 3H). LCMS (ESI) m/z: 252.2 [M+H]+.

Step 3: Synthesis of ethyl (7aS,Z)-2-(2-hydroxypropylidene)-5-oxotetrahydro-1H-pyrrolizine-7a(5H)-carboxylate (I-25c)

To a solution of ethyl (S,Z)-5-oxo-2-(2-oxopropylidene) tetrahydro-1H-pyrrolizine-7a(5H)-carboxylate (65 mg, 0.26 mmol) in methanol (3 mL) at 0° C. was added cerium(III) chloride (77 mg, 0.31 mmol) followed by NaBH₄ (11 mg, 0.285 mmol). The reaction mixture was allowed to warm up to 20° C., stirred at 20° C. for 15 minutes. The reaction mixture was quenched with H₂O (10 mL) and then extracted with DCM (20 mL×5). The combined organic phase was washed with brine (20 mL), dried over sodium sulfate and filtered. The filtrate was concentrated under reduced pressure to afford crude ethyl (7aS,Z)-2-(2-hydroxypropylidene)-5-oxotetrahydro-1H-pyrrolizine-7a(5H)-carboxylate (60 mg, 92%) as a colorless oil. LCMS (ESI) m/z: 254.2 [M+H]+

Step 4: Synthesis of ethyl (7aS,Z)-2-(2-((tert-butyldimethylsilyl)oxy)propylidene)-5-oxotetrahydro-1H-pyrrolizine-7a(5H)-carboxylate (I-25d)

To a solution of ethyl (7aS,Z)-2-(2-hydroxypropylidene)-5-oxotetrahydro-1H-pyrrolizine-7a(5H)-carboxylate (55 mg, 0.22 mmol) in DCM (3 mL) were added TBSCl (43 mg, 0.282 mmol), TEA (66 mg, 0.651 mmol) and DMAP (13 mg, 0.109 mmol). The reaction mixture was stirred at 20° C. for 14 h under N₂. LCMS showed the DP was formed. The reaction mixture was filtered and concentrated under reduced pressure. The residue was purified by flash column chromatography (silica gel, 0-30% of EtOAc in petroleum ether) to give ethyl (7aS,Z)-2-(2-((tert-butyldimethylsilyl)oxy)propylidene)-5-oxotetrahydro-1H-pyrrolizine-7a(5H)-carboxylate (45 mg, 56%) as yellow oil. ¹H NMR (400 MHz, CDCl3) δ 5.52-5.31 (m, 1H), 4.27 (d, J=14.6 Hz, 1H), 4.19-4.13 (m, 3H), 3.78-3.66 (m, 1H), 2.95 (dd, J=22.8, 15.5 Hz, 1H), 2.79-2.69 (m, 1H), 2.63-2.53 (m, 1H), 2.49-2.38 (m, 2H), 2.09 (ddd, J=9.6, 8.3, 2.9 Hz, 1H), 1.24-1.23 (m, 3H), 1.15 (dd, J=6.2, 4.3 Hz, 3H), 0.84 (d, J=2.3 Hz, 9H), 0.02--0.02 (m, 6H). LCMS (ESI) m/z: 390.13 [M+Na]+.

Step 5: Synthesis of ((7aS,Z)-2-(2-((tert-butyldimethylsilyl)oxy)propylidene)tetrahydro-1H-pyrrolizin-7a(5H)-yl)methanol (I-25)

To a solution of ethyl (7aS,Z)-2-(2-((tert-butyldimethylsilyl)oxy)propylidene)-5-oxotetrahydro-1H-pyrrolizine-7a (5H)-carboxylate (40 mg, 0.11 mmol) in THF (2 mL) was added 1 M LiAlH₄ (0.22 mL, 0.218 mmol). The reaction mixture was stirred at 70° C. for 1 h under N₂. LCMS showed the starting material was consumed and the desired product was formed. Sodium sulfate decahydrate added to the mixture and filtered. The filtrate was concentrated under reduced pressure to afford crude ((7aS,Z)-2-(2-((tert-butyldimethylsilyl)oxy)propylidene)tetrahydro-1H-pyrrolizin-7a(5H)-yl)methanol (35 mg) as a yellow oil. LCMS (ESI) m/z: 312.2 [M+H]+.

Synthesis of Intermediate 26i and 26ii (I-26i and I-26ii): [(2Z,7aS)-2-ethylidenetetrahydro-1H-pyrrolizin-7a(5H)-yl]methanol and [(2E,7aS)-2-ethylidenetetrahydro-1H-pyrrolizin-7a(5H)-yl]methanol

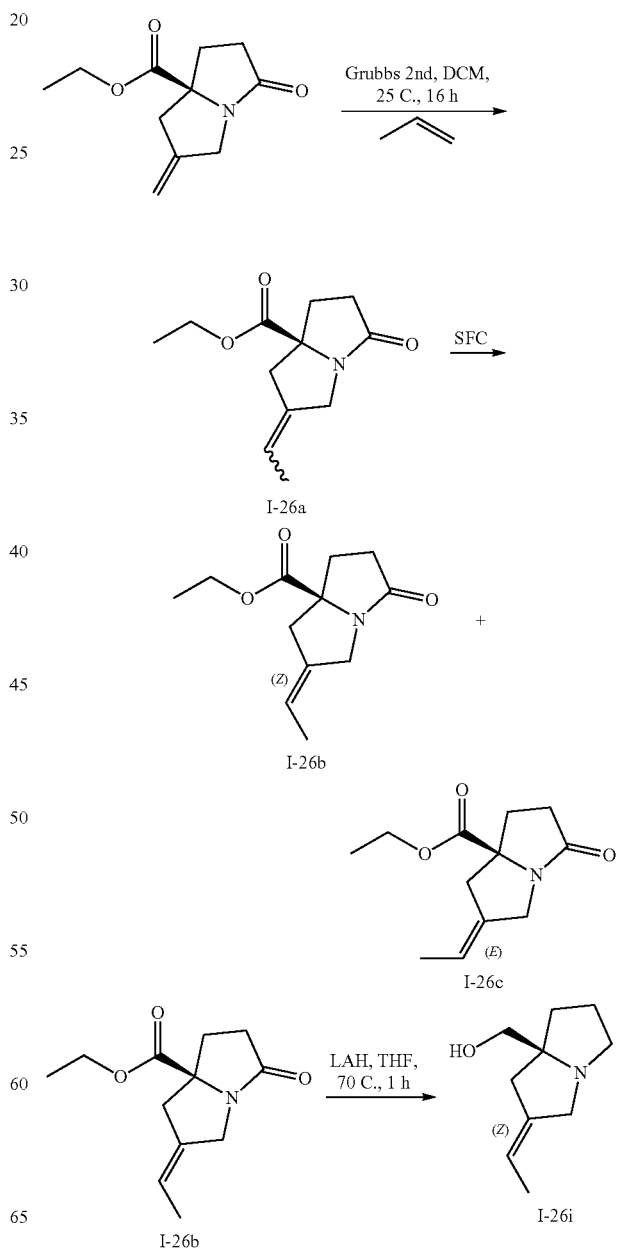

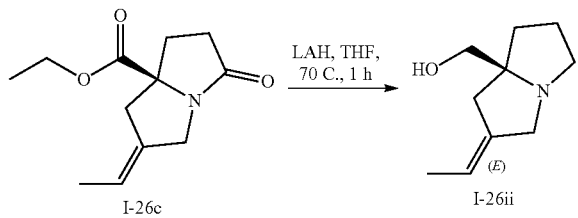

Step 1: Synthesis of ethyl (7aS)-2-ethylidene-5-oxotetrahydro-1H-pyrrolizine-7a(5H)-carboxylate (Intermediate I-26a)

To a solution of ethyl (S)-2-methylene-5-oxotetrahydro-1H-pyrrolizine-7a(5H)-carboxylate (CAS #2820536-98-7, 627 mg, 3.00 mmol) and Grubbs second generation catalyst (254 mg, 0.300 mmol) in DCM (5 mL) was added propylene (15 mL, 15.0 mmol). Then the mixture was stirred at 0° C. for 20 h. The solution was concentrated under reduced pressure. The residue was purified by Prep-HPLC to give ethyl (7aS)-2-ethylidene-5-oxotetrahydro-1H-pyrrolizine-7a(5H)-carboxylate (Intermediate I-26a, 230 mg, 34%) as a brown oil. $^1$H NMR (400 MHz, DMSO) δ 5.43-539 (m, 1H), 4.16-3.98 (m, 3H), 3.66-3.48 (m, 1H), 3.06-2.81 (m, 1H), 2.60-2.56 (m, 1H), 2.45-2.14 (m, 4H), 1.61-1.49 (m, 3H), 1.23-1.14 (m, 3H). LCMS (ESI) m/z: 224.1

Step 2: Synthesis of ethyl (2Z,7aS)-2-ethylidene-5-oxotetrahydro-1H-pyrrolizine-7a(5H)-carboxylate (Intermediate I-26b) and ethyl (2E,7aS)-2-ethylidene-5-oxotetrahydro-1H-pyrrolizine-7a(5H)-carboxylate (Intermediate I-26c)

Ethyl (7aS)-2-ethylidene-5-oxotetrahydro-1H-pyrrolizine-7a(5H)-carboxylate (intermediate I-26a, 450 mg) was purified by chiral separation (Apparatus: SFC 150; Column: Daicel CHIRALCEL® AS, 250 mm×30 mm I.D., 10 μm; Mobile phase: CO2/MeOH[0.2% NH3 (7M Solution in MeOH)]=90/10; Flow rate: 80 g/min; wavelength: UV 214 nm; Temperature: 35° C.) to give: (2Z,7aS)-2-ethylidene-5-oxotetrahydro-1H-pyrrolizine-7a(5H)-carboxylate (intermediate I-26b, 180 mg, peak 1 of 2, Rt: 1.902 min, yield: 40%). $^1$H NMR (400 MHz, CDCl$_3$) δ 5.48-5.42 (m, 1H), 4.30-4.11 (m, 3H), 3.72 (d, J=15.6 Hz, 1H), 3.00 (d, J=15.3 Hz, 1H), 2.86-2.71 (m, 1H), 2.63-2.53 (m, 1H), 2.51-2.40 (m, 2H), 2.11 (ddd, J=13.2, 10.8, 9.6 Hz, 1H), 1.63-1.55 (m, 3H), 1.31-1.23 (m, 3H) and ethyl (2E,7aS)-2-ethylidene-5-oxotetrahydro-1H-pyrrolizine-7a(5H)-carboxylate (intermediate I-26c, 230 mg, peak 2 of 2, Rt: 2.415 min, yield: 51%). $^1$H NMR (400 MHz, CDCl$_3$) δ 5.49-5.39 (m, 1H), 4.32-4.15 (m, 3H), 3.69 (d, J=15.0 Hz, 1H), 3.18-3.08 (m, 1H), 2.77 (dt, J=16.5, 10.0 Hz, 1H), 2.62 (ddd, J=13.0, 9.1, 1.4 Hz, 1H), 2.49-2.38 (m, 1H), 2.35-2.24 (m, 1H), 2.18-2.12 (m, 1H), 1.67-1.58 (m, 3H), 1.27 (t, J=7.1 Hz, 3H).

Step 3: Synthesis of [(2Z,7aS)-2-ethylidenetetrahydro-1H-pyrrolizin-7a(5H)-yl]methanol (Intermediate I-26i)

To a solution of ethyl (2Z,7aS)-2-ethylidene-5-oxotetrahydro-1H-pyrrolizine-7a(SH)-carboxylate (Intermediate I-26b, 150 mg, 0.672 mmol) in THF (20 mL) was added LiAlH$_4$ (1.3 mL, 1.3 mmol, 1 M in THF) at 20° C. under nitrogen atmosphere. The resulting mixture was allowed to warm up to 70° C. and stirred for 1 h. The mixture was quenched with Na$_2$SO$_4$·10 H$_2$O (2 g), filtered and concentrated under reduced pressure to obtain [(2Z,7aS)-2-ethylidenetetrahydro-1H-pyrrolizin-7a(SH)-yl]methanol (Intermediate I-261, 120 mg, 89%) as a colorless oil. $^1$H NMR (400 MHz, CDCl$_3$) δ 4.93-4.83 (m, 2H), 4.80 (d, J=3.8 Hz, 1H), 4.21 (d, J=3.2 Hz, 1H), 3.51 (d, J=13.9 Hz, 1H), 3.34 (d, J=13.9 Hz, 2H), 3.07 (dd, J=9.8, 5.3 Hz, 1H), 3.02 (s, 2H), 2.46 (dd, J=9.7, 8.4 Hz, 2H), 2.10 (dd, J=12.8, 6.6 Hz, 1H), 1.52 (dd, J=12.8, 6.3 Hz, 1H). LCMS (ESI) m/z: 168.3 [M+H]$^+$.

Step 3': Synthesis of [(2E,7aS)-2-ethylidenetetrahydro-1H-pyrrolizin-7a(5H)-yl]methanol (Intermediate I-26ii)

To a solution of ethyl (2E,7aS)-2-ethylidene-5-oxotetrahydro-1H-pyrrolizine-7a(5H)-carboxylate (intermediate I-26c, 180 mg, 0.806 mmol) in THF (20 mL) was added LiAlH4 (1.6 mL, 1.6 mmol, 1 M in THF) at 20° C. under nitrogen atmosphere. The resulting mixture was allowed to warm up to 70° C. and stirred for 1 h. The mixture was quenched with Na$_2$SO$_4$·10 H$_2$O (2 g), filtered and concentrated under reduced pressure. The crude mixture was purified by flash column chromatography (12 g silica gel, 0-20% MeOH (5% NH$_4$OH in MeOH) in DCM) to give [(2Z,7aS)-2-ethylidenetetrahydro-1H-pyrrolizin-7a(5H)-yl]methanol (Intermediate I-26ii, 70 mg, 41%) as a colorless oil. LCMS (ESI) m/z: 168.3 [M+H]$^+$.

EXAMPLES AND GENERAL METHODS

Key preparations and procedures are illustrated to exemplify the methodology for synthesis of examples.

Example 1 (General Method A): (8aS)-46-chloro-5-cyclopropyl-1H-indazol-4-yl)-4-fluoro-2-{[(2R,7aS)-2-fluorotetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene

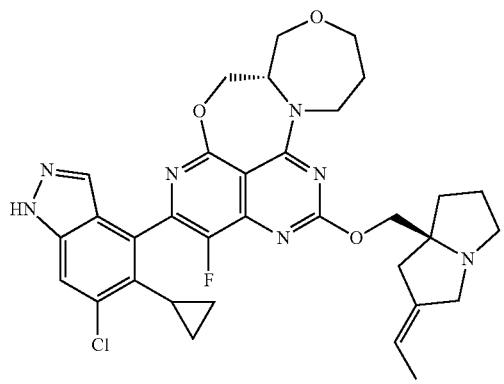 [SMILES: C/C=C1\CN2CCC[C@@]2(COc2nc3c4c(nc(-c5c(C6CC6)c(Cl)cc6[nH]ncc56)c(F)c4n2)OC[C@@H]2COCCCN32)C1]

Example 1

Preparation of Example 1

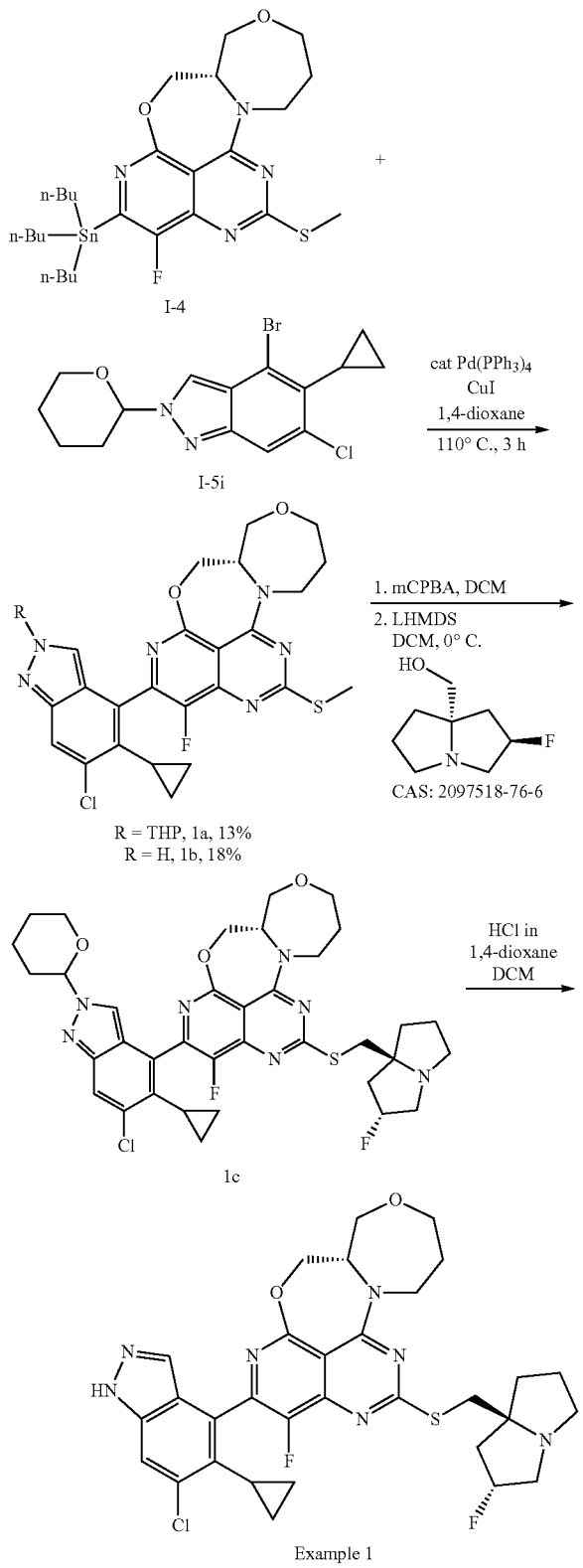

Step 1: Preparation of (8aS)-5-[6-chloro-5-cyclopropyl-2-(oxan-2-yl)-2H-indazol-4-yl]-4-fluoro-2-(methylsulfanyl)-8a,9,12,13-tetrahydro-8H,11H-7,10-dioxa-1,3,6,13a-tetraazanaphtho[1,8-ab]heptalene (1a)

To a solution of (S)-4-fluoro-2-(methylthio)-5-(tributylstannyl)-8a,9,12,13-tetrahydro-8H,11H-7,10-dioxa-1,3,6,13a-tetraazanaphtho[1,8-ab]heptalene (I-4, 295 mg, 0.482 mmol) and 4-bromo-6-chloro-5-cyclopropyl-2-(oxan-2-yl)-2H-indazole (I-51, 172 mg, 0.482 mmol) in 1,4-dioxane (3 mL) was added CuI (91.9 mg, 0.482 mmol) and Pd(PPh$_3$)$_4$ (55.8 mg, 0.0482 mmol). The reaction was stirred under N$_2$ at 110° C. for 3 h, concentrated and the residue was purified by silica gel chromatography using a gradient of 0-100% EtOAc in petroleum ether which separated 1a from 1b. (8aS)-5-[6-chloro-5-cyclopropyl-2-(oxan-2-yl)-2H-indazol-4-yl]-4-fluoro-2-(methylsulfanyl)-8a,9,12,13-tetrahydro-8H,11H-7,10-dioxa-1,3,6,13a-tetraazanaphtho[1,8-ab]heptalene (1a, 38 mg, 13%) was obtained as a yellow solid. 1H NMR (400 MHz, CDCl3) δ 7.86 (dd, J=28.4, 5.9 Hz, 1H), 7.77 (d, J=17.1 Hz, 1H), 5.69 (dd, J=18.8, 7.1 Hz, 1H), 5.29-5.17 (m, 1H), 4.60 (dd, J=36.6, 20.6 Hz, 2H), 4.22 (d, J=11.4 Hz, 2H), 4.03 (s, 2H), 3.91-3.67 (m, 2H), 3.49 (dd, J=22.9, 9.5 Hz, 2H), 2.62 (d, J=5.4 Hz, 2H), 2.24 (s, 1H), 2.05 (s, 3H), 1.83-1.61 (m, 3H), 0.89 (ddd, J=17.5, 11.4, 6.3 Hz, 1H), 0.69 (s, 1H), 0.33-0.08 (m, 2H), MS: 597 [M+H]+. Also recovered but not taken on to the next step was (8aS)-5-(6-chloro-5-cyclopropyl-2H-indazol-4-yl)-4-fluoro-2-(methylsulfanyl)-8a,9,12,13-tetrahydro-8H,11H-7,10-dioxa-1,3,6,13a-tetraazanaphtho[1,8-ab]heptalene (1b, 45 mg, 18%) as a yellow solid.

Step 2: Preparation of (8aS)-5-[6-chloro-5-cyclopropyl-2-(oxan-2-yl)-2H-indazol-4-yl]-4-fluoro-2-{[(2R,7aS)-2-fluorotetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene (1c)

To a solution of (8aS)-5-[6-chloro-5-cyclopropyl-2-(oxan-2-yl)-2H-indazol-4-yl]-4-fluoro-2-(methylsulfanyl)-8a,9,12,13-tetrahydro-8H,11H-7,10-dioxa-1,3,6,13a-tetraazanaphtho[1,8-ab]heptalene (1a, 38 mg, 0.046 mmol) in DCM (2 mL) was added mCPBA (12 mg, 0.069 mmol). The reaction was stirred at RT for 2 h. LCMS analysis showed that starting material was consumed and the sulfoxide was detected. The mixture was quenched with aq. Na$_2$SO$_3$ (10 mL) and diluted with DCM (20 mL). The organic layer was washed with aq. NaHCO$_3$ (20 mL) followed by satd. aq. NaCl (20 mL). After drying over NaSO$_4$ and concentrating, 32 mg of the sulfoxide was obtained as yellow solid, MS 613 [M+H]$^+$. A solution of the sulfoxide (32 mg, 0.052 mmol) and ((2S,7aR)-2-fluorotetrahydro-1H-pyrrolizin-7a(5H)-yl) methanol, CAS 2097518-76-6 (16.6 mg, 0.104 mmol) in DCM (2 mL) was cooled to 0° C. LIHMDS (0.0626 mL of 1 M in THF, 0.0626 mmol) was added and the mixture was stirred at 25° C. for 1 h. LCMS analysis showed the formation of product. The reaction mixture was extracted with EA (2×20 mL) and the combined organic extract was washed with water (10 mL). After concentrating, the residue was purified by prep-TLC using DCM/MeOH 10/1 to give (8aS)-5-[6-chloro-5-cyclopropyl-2-(oxan-2-yl)-2H-indazol-4-yl]-4-fluoro-2-{[(2R,7aS)-2-fluorotetrahydro-1H-pyrrolizin-7a(5H)-yl]methoxy)-8a,9,12,13-tetrahydro-8H,11H-

7,10-dioxa-1,3,6,13a-tetraazanaphtho[1,8-ab]heptalene (1c, 20 mg) as a yellow solid, MS: 708 [M+H]⁺.

Step 3: Synthesis of (8aS)-5-(6-chloro-5-cyclopropyl-1H-indazol-4-yl)-4-fluoro-2-{[(2R,7aS)-2-fluorotetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene, Example 1

A solution of (8aS)-5-[6-chloro-5-cyclopropyl-2-(oxan-2-yl)-2H-indazol-4-yl]-4-fluoro-2-{[(2R,7aS)-2-fluorotetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene (1c, 15 mg, 0.021 mmol) in DCM (1 mL) was treated with HCl in 1,4-dioxane (0.5 mL of 4 M, 2.0 mmol) and the mixture was stirred at RT for 1 h. The mixture was concentrated the residue was purified by preparative HPLC to afford Example 1 as a white solid (5.5 mg). ¹H NMR (400 MHz, MeOD) δ 8.53 (s, 1H), 7.87 and 7.81 (2 s, major and minor rotamer respectively, 1H), 7.75 (s, 1H), 5.38 (d, J=53.6 Hz, 1H), 5.24 (dtd, J=9.4, 6.8, 2.8 Hz, 1H), 4.76 (ddd, J=13.4, 4.1, 2.1 Hz, 1H), 4.61 (t, J=13.0 Hz, 1H), 4.50-4.28 (m, 3H), 4.26-4.15 (m, 1H), 4.00 (dt, J=10.9, 5.1 Hz, 1H), 3.83 (ddd, J=34.2, 12.3, 10.0 Hz, 1H), 3.64-3.55 (m, 1H), 3.50-3.37 (m, 4H), 3.19-3.08 (m, 1H), 2.51-2.28 (m, 2H), 2.28-2.15 (m, 2H), 2.14-1.89 (m, 5H), 0.99-0.81 (m, 1H), 0.74-0.62 (m, 1H), 0.34-0.10 (m, 2H), MS 624 [M+H]⁺.

Example 24 (General Method B): (8aS)-5-[6-chloro-5-(propan-2-yl)-1H-indazol-4-yl]-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene

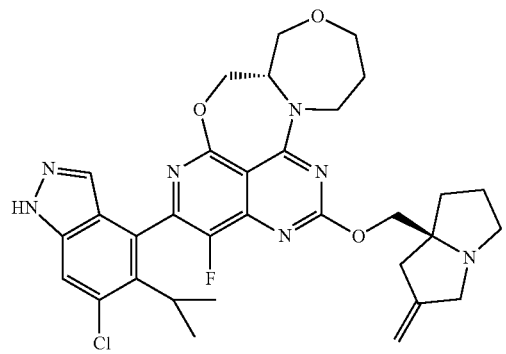 [SMILES: C=C1CN2CCC[C@@]2(COc2nc3c4c(nc(-c5c(C(C)C)c(Cl)cc6[nH]ncc56)c(F)c4n2)OC[C@@H]2COCCCN32)C1]

Example 24 was prepared similarly to Example 1, however using one-pot Suzuki coupling methodology without stannane chemistry. The one-pot procedure is exemplified in General Scheme 2 (Method B).

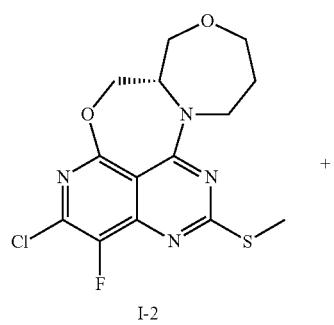

I-2

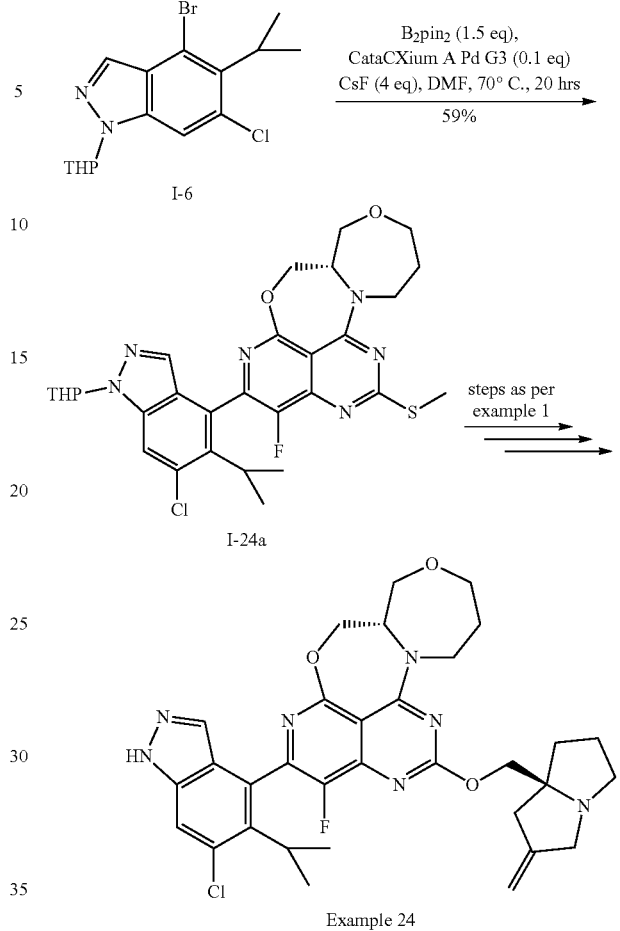

Synthesis of (8aS)-5-(6-chloro-5-Isopropyl-1-(tetrahydro-2H-pyran-2-yl)-1H-indazol-4-yl)-4-fluoro-2-(methylthio)-8a,9,12,13-tetrahydro-8H,11H-7,10-dioxa-1,3,6,13a-tetraazanaphtho[1,8-ab]heptalene (I-24a)

To a solution of 4-bromo-6-chloro-5-isopropyl-1-(tetrahydro-2H-pyran-2-yl)-1H-indazole (I-6, 45.3 mg, 0.127 mmol) in DMF (3.2 mL) was added (S)-5-chloro-4-fluoro-2-(methylthio)-8a,9,12,13-tetrahydro-8H,11H-7,10-dioxa-1,3,6,13a-tetraazanaphtho[1,8-ab]heptalene (I-2, 40 mg, 0.11 mmol), bis(pinacolato)diboron (41.9 mg, 0.165 mmol), CsF (66.8 mg, 0.44 mmol) and cataCXium A Pd G3 (8.16 mg, 0.0112 mmol) at 25° C. under nitrogen. The resulting mixture was stirred at 70° C. for 20 h. LCMS showed the desired product was detected and the raw material was consumed.

The mixture was concentrated in vacuo. The residue was purified by flash column chromatography (Combi-flash, 12 g silica gel, 0-100% EtOAc in Petroleum ether) to give the title intermediate (45 mg, 59%) as a yellow solid. ¹H NMR (400 MHz, CDCl₃) δ 7.76 and 7.72 (2 s, 1H, major and minor rotamer respectively), 7.59-7.46 (m, 1H), 5.73-5.62 (m, 1H), 5.31-5.19 (m, 1H), 4.74-4.47 (m, 2H), 4.31-4.13 (m, 2H), 4.07-3.96 (m, 2H), 3.85-3.70 (m, 2H), 3.56-3.14 (m, 3H), 2.63 (s, 3H), 2.52-2.43 (m, 1H), 2.31-2.11 (m, 3H), 1.78-1.65 (m, 4H), 1.47-1.39 (m, 3H), 1.37-1.29 (m, 3H). ¹⁹F NMR (376 MHz, CDCl₃) δ −140.59. MS: 599.2 [M+H]⁺.

Compound I-24a was converted to example 24 as per the methodology outlined and exemplified in General method A, example 1 with non-critical changes and/or substitutions. See table 1 for example characterization.

Example 40 (General Method C): (8aS)-5-(6-chloro-5-cyclopropyl-1H-indazol-4-yl)-2-{[(7aS)-2-cyclopropylidenetetrahydro-1H-pyrrolizin-7a(5H)-yl]methoxy}-4-fluoro-8a,9,12,13-tetrahydro-8H,11H-7,10-dioxa-1,3,6,13a-tetraazanaphtho[1,8-ab]heptalene

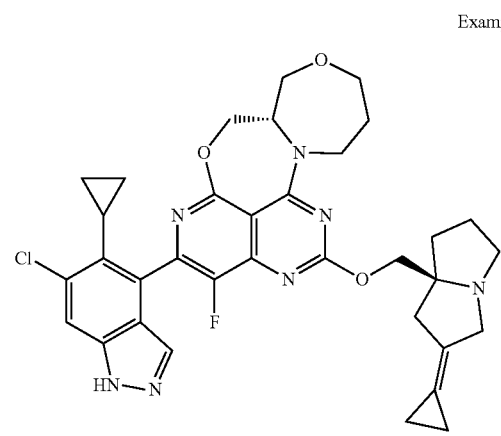

Example 40

Example 40 was prepared similarly to Example 1, however using Suzuki coupling methodology with an indazole boronate derivative. The procedure is exemplified in General Scheme 3 (Method c).

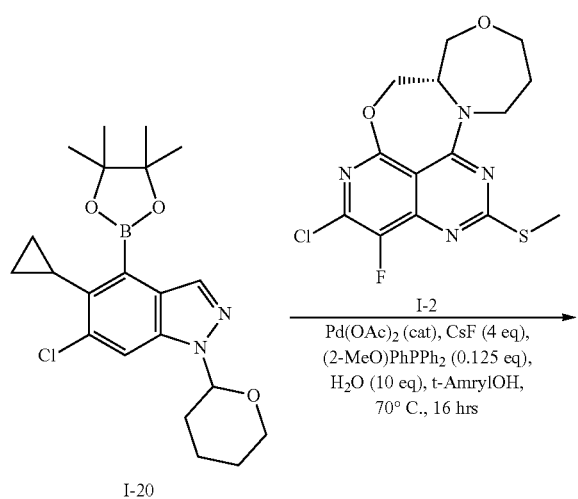

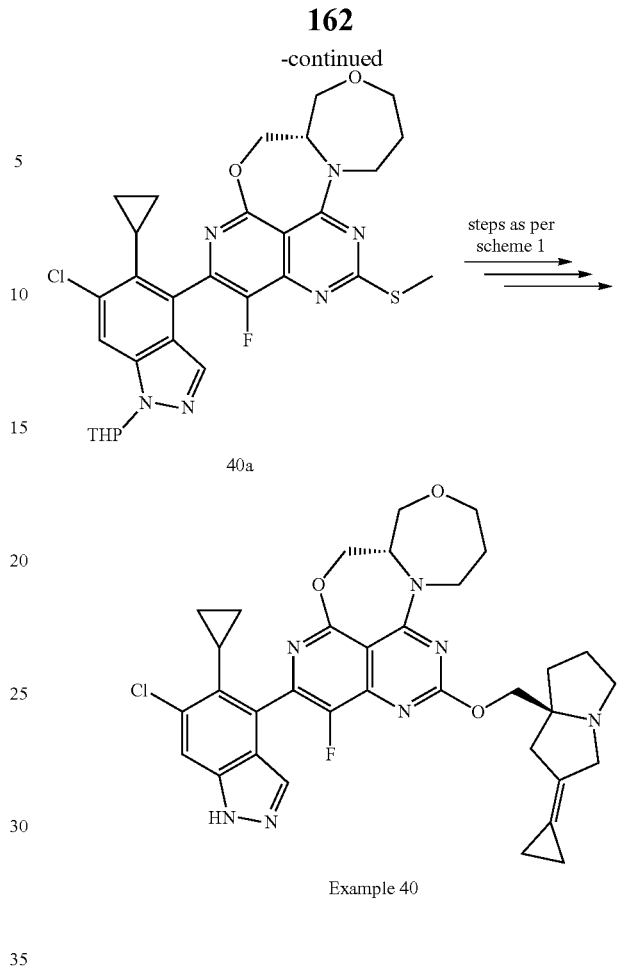

Synthesis of (8aS)-5-(6-chloro-5-cyclopropyl-1-(tetrahydro-2H-pyran-2-yl)-1H-indazol-4-yl)-4-fluoro-2-(methylthio)-8a,9,12,13-tetrahydro-8H,11H-7,10-dioxa-1,3,6,13a-tetraazanaphtho[1,8-ab]heptalene A 100 mL vial was charged with 6-chloro-5-cyclopropyl-1-(tetrahydro-2H-pyran-2-yl)-4-(4,4,5,5-tetramethyl-1,3,2-dioxaborolan-2-yl)-1H-indazole (I-20, 4.38 g, 9.8 mmol, 1 eq), (S)-5-chloro-4-fluoro-2-(methylthio)-8a,9,12,13-tetrahydro-8H,11H-7,10-dioxa-1,3,6,13a-tetraazanaphtho[1,8-ab]heptalene (3.84 g, 10.8 mmol, 1.1 eq), Pd(OAc)2 (137 mg, 0.6 mmol, 0.0625 eq), CsF (5.95 g, 39.2 mmol, 4 eq), Ph₂P(2-MeO)Ph (358 mg, 1.22 mmol, 0.125 eq), water (1760 mg, 97.9 mmol, 10 eq) and t-AmylOH (50 mL). The reaction was purged with nitrogen for three times and heated to 70° C. for 16 h under nitrogen. LCMS showed most starting material was consumed and a major peak with desired MS was detected. The reaction mixture was filtered. The filtrate was diluted with water (200 mL) and extracted with CH₂Cl₂ (3×100 mL). The combined organic layers were dried over Na₂SO₄, filtered and concentrated to dryness. The residue was purified by flash column chromatography (120 silica gel, 0 to 25% of EtOAc in DCM) to give (8aS)-5-(6-chloro-5-cyclopropyl-1-(tetrahydro-2H-pyran-2-yl)-1H-indazol-4-yl)-4-fluoro-2-(methylthio)-8a,9,12,13-tetrahydro-8H,11H-7,10-dioxa-1,3,6,13a-tetraazanaphtho[1,8-ab]heptalene (40a, 1.8 g, 31%) as a gray solid. 1H NMR (400 MHz, MeOD) δ 7.94-7.89 (m, 1H), 7.85 and 7.80 (2 s, 1H, major and minor rotamer respectively), 5.90-5.74 (m, 1H), 5.32-5.20 (m, 1H), 4.78-4.69 (m, 1H), 4.67-4.55 (m, 1H), 4.38-4.26 (m, 1H), 4.21 and 4.19 (2 dd, J=12.6, 4.2 Hz, 1H, major and minor rotamer respectively), 3.99 (dt, J=12.5, 5.1 Hz, 2H), 3.92-3.73 (m, 2H), 3.62-3.53 (m, 1H), 3.51-3.38 (m, 1H), 2.62 (s, 3H), 2.51-2.38 (m, 1H), 2.28-1.95 (m, 5H), 1.90-1.61 (m, 3H), 0.97-0.83 (m, 1H), 0.78-0.65 (m, 1H), 0.34-0.09 (m, 2H). LCMS (ESI) m/z: 597.3 (M+H)+.

Compound 40a was converted to example 40 as per the methodology outlined and exemplified in General method A, example 1 with non-critical changes and/or substitutions. See table 1 for example characterization.

Example 46 (General Method D): (8aS)-5-(3,6-dichloro-5-cyclopropyl-1H-indazol-4-yl)-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene

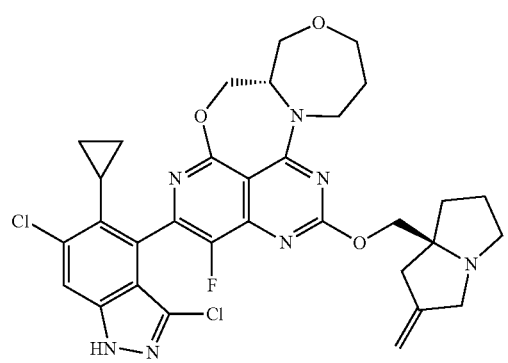

Example 46

Example 46 was prepared similarly to Example 1, however chlorination and oxidation was achieved through treatment of the indazole precursor with N-chloro succinimide. The procedure is exemplified in General Scheme 4 (Method D).

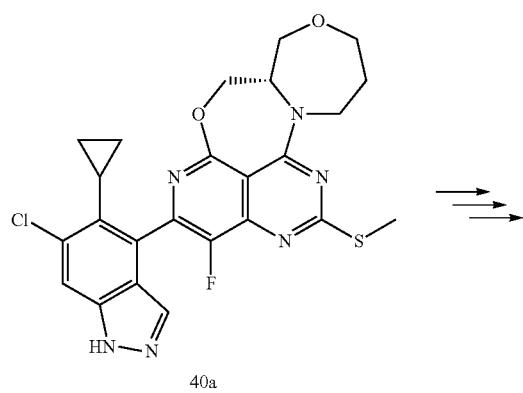

40a

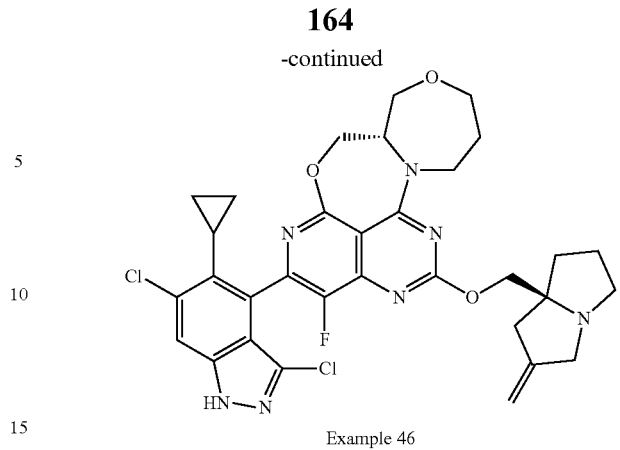

Example 46

(8aS)-5-(6-chloro-5-cyclopropyl-1-(tetrahydro-2H-pyran-2-yl)-1H-indazol-4-yl)-4-fluoro-2-(methylthio)-8a,9,12,13-tetrahydro-8H,11H-7,10-dioxa-1,3,6,13a-tetraazanaphtho[1,8-ab]heptalene Intermediate (40a, 300 mg, 0.50 mmol) was dissolved in DMF (2.5 mL). N-Chloro succinamide (168 mg, 1.26 mmol) was added and the reaction was stirred at room temperature for 3 h. A mixture of products was obtained by LCMS. The reaction was diluted with EtOAc (30 mL) and water (5 mL). After separation of the layers, the organic extract was washed with water (3×10 mL) to remove all the DMF. After drying over $Na_2SO_4$, the extract was concentrated and the crude material taken on to the next step without purification. The crude material from the chlorination step and (S)-(2-methylenetetrahydro-1H-pyrrolizin-7a(5H)-yl)methanol (97.0 mg, 0.63 mmol) was dissolved in $CH_3CN$ (4.52 mL). The solution was cooled to 0° C. and LiOtBu (0.31 mL of 2.2 M, 0.68 mmol) was added quickly over 30 seconds giving a suspension. After stirring for 15 min, the reaction was removed from the ice bath and stirred at room temperature for 20 min. LCMS analysis showed that THP protected Example 46 had formed and 1 drop of HOAc was added. After stirring for 5 min, TFA (2 mL) was added to the mixture and the reaction was allowed to stir at room temperature for 16 h. Partial deprotection had occurred and the mixture was heated to 50° C. for 4 h until deprotection of the THP group was complete. The mixture was concentrated and pre-purified via flash chromatography eluting with a gradient of 0-10% MeOH in DCM. The pure fractions were collected and concentrated to afford a white foam which was purified further using HPLC (PHENEMONEX® GEMINI® NX C18, 150×21.2 mm, 5 um, AXIA Pack Mobile phase A: water+10 mM ammonium acetate, Mobile phase B: Acetonitrile 20-70% B in 8.0 minutes, 40 mL/min). On a chiral column, evidence of atropisomers was observed and attempted separation of the atropisomers resulted in equilibration back to the mixture at room temperature. (8aS)-5-(3,6-dichloro-5-cyclopropyl-1H-indazol-4-yl)-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene (example 46) was submitted as a single compound (19 mg, 5.8%). $^1$H NMR (400 MHz, DMSO-d6) δ 7.82 (s, 1H), 7.33 (d, J=4.3 Hz, 1H), 5.09-4.95 (m, 1H), 4.92 (d, J=3.7 Hz, 2H), 4.66 (dd, J=13.1, 4.5 Hz, 1H), 4.55 (dd, J=13.2, 7.0 Hz, 1H), 4.33 (dt, J=9.8, 5.1 Hz, 1H), 4.09 (ddd, J=16.6, 8.4, 4.7 Hz, 4H), 3.95-3.83 (m, 1H), 3.66-3.55 (m, 3H), 3.03 (dt, J=10.7, 5.2 Hz, 2H), 2.69-2.53 (m, 2H), 2.42-2.28 (m, 2H), 2.10-1.94 (m, 3H), 1.84-1.63 (m, 3H), 0.88-0.57 (m, 2H), 0.37-0.12 (m, 2H); LCMS m/z: 652.2 [M+H]$^+$.

Example 3 (General Method E): (8aS)-4-fluoro-2-{[(2R,7aS)-2-fluorotetrahydro-1H-pyrrolizin-7a(5H)-yl]methoxy}-1H-indazol-4-yl)-8a,9,12,13-tetrahydro-8H,11H-7,10-dioxa-1,3,6,13a-tetraazanaphtho[1,8-ab]heptalene

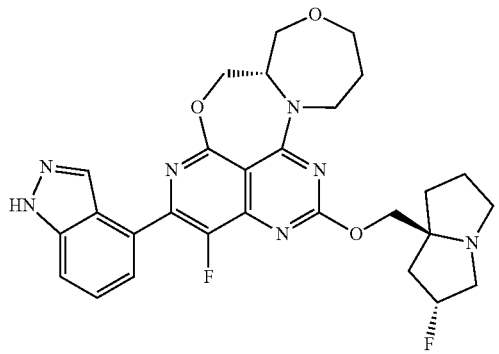

Example 3

Example 3 was prepared via General Scheme 5 (Method E).

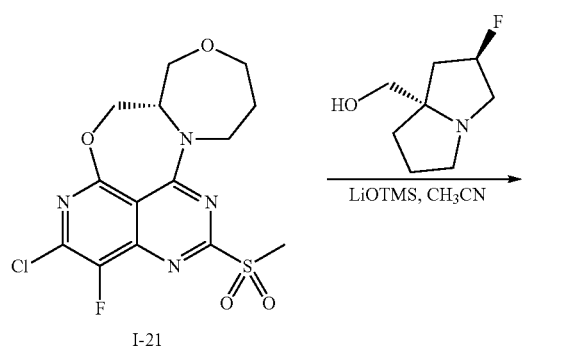

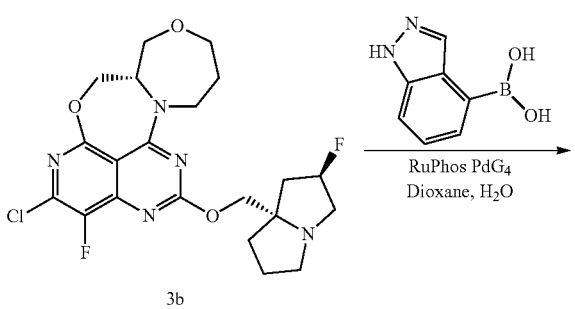

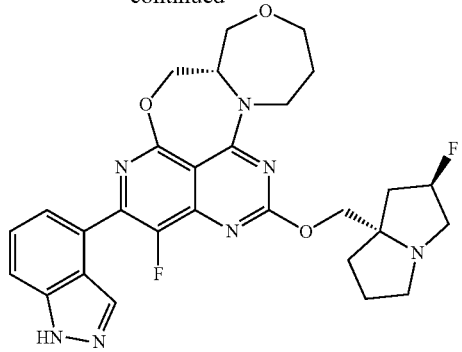

Example 3

Step 1: synthesis of (8aS)-5-chloro-4-fluoro-2-{[(2R,7aS)-2-fluorotetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene (3b)

To a solution of crude (8aS)-5-chloro-4-fluoro-2-(methanesulfonyl)-8a,9,12,13-tetrahydro-8H,11H-7,10-dioxa-1,3,6,13a-tetraazanaphtho[1,8-ab]heptalene (3.2 g, 8.97 mmol, 1 equiv) in acetonitrile (29.9 mL, 0.3M) was added ((2R,7aS)-2-fluorotetrahydro-1H-pyrrolizin-7a(5H)-yl)methanol, CAS #2097518-76-6 (1.71 g, 10.7 mmol), followed by lithium trimethylsilanolate (2.5 g, 26.8 mmol). The mixture was warmed to 60° C. until full conversion was achieved, then cooled to 0° C. in an ice bath and quenched with water (100 mL). The aqueous mixture was extracted with EtOAc (3×100 mL), the combined organic layers washed with brine, dried with sodium sulfate, filtered, and concentrated to afford the desired product (3.88 g, 92% over two steps) as a solid which was used crude with no purification.

Step 2: Synthesis of (8aS)-4-fluoro-2-{[(2R,7aS)-2-fluorotetrahydro-1H-pyrrolizin-7a(5H)-yl]methoxy}-5-(1H-indazol-4-yl)-8a,9,12,13-tetrahydro-8H,11H-7,10-dioxa-1,3,6,13a-tetraazanaphtho[1,8-ab]heptalene (Example 3)

A mixture of (8aS)-5-chloro-4-fluoro-2-{[(2R,7aS)-2-fluorotetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene (70 mg, 0.15 mmol, 1.0 equiv), 1H-indazole-4-boronic acid (31.5 mg, 0.194 mmol, 1.3 equiv), RuPhos PdG4 (25.4 mg, 0.03 mmol 0.2 equiv), K2CO3 (62.0 mg, 0.45 mmol, 3.0 equiv) was dissolved in dioxane (0.748 mL) and H2O (0.0748 mL), then degassed by bubbling nitrogen through the stirred mixture for 5 min. The reaction was capped and heated to 90° C. until the reaction was complete. The resulting slurry was cooled to room temperature, at which point H2O (2 mL) was added dropwise. The slurry was filtered, rinsed with H2O, and the solids purified by chromatography to afford the title product (24.5 mg) as a solid. $^1$H NMR (400 MHz, DMSO) δ 13.16 (s, 1H), 8.26 (d, J=1.5 Hz, 1H), 7.61 (d, J=8.1 Hz, 1H), 7.59-7.54 (m, 1H), 7.43 (dd, J=8.3, 7.2 Hz, 1H), 5.34-5.12 (m, 1H), 4.93 (ddd, J=13.7, 6.4, 3.3 Hz, 1H), 4.64 (dd, J=13.4, 4.4 Hz, 1H), 4.47 (d, J=13.2 Hz, 1H), 4.24 (dt, J=9.1, 4.2 Hz, 1H), 4.11 (d, J=10.3 Hz, 1H), 4.06 (dd, J=12.3, 4.0 Hz, 1H), 4.03-3.98 (m, 1H), 3.82 (dt, J=12.6, 5.0 Hz, 1H), 3.59 (dd, J=12.3, 9.8 Hz, 1H), 3.34 (dddd, J=28.2, 13.9, 9.1, 4.7 Hz, 2H), 3.10 (d, J=5.3 Hz, 1H), 3.06-3.00 (m, 2H), 2.96 (d, J=2.2 Hz, 1H), 2.77 (q, J=8.1 Hz, 1H), 2.10-1.89 (m, 4H), 1.88-1.66 (m, 4H). 19F NMR (377 MHz, DMSO) δ −145.28, −171.96, −171.99, −172.05, −172.10, −172.12, −172.15, −172.20, −172.22, −172.26, −172.29.

Examples 56 and 57 were prepared via General Scheme A, however an additional deprotection step was needed to afford the product (Scheme A+):

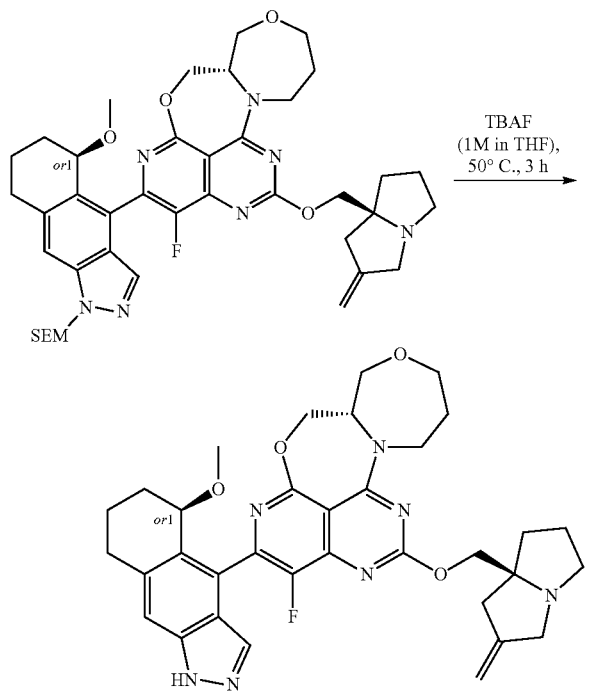

Example 56: Synthesis of (8aS)-4-fluoro-5-((R*)-5-methoxy-5,6,7,8-tetrahydro-1H-benzo[f]indazol-4-yl)-2-(((S)-2-methylenetetrahydro-1H-pyrrolizin-7a(5H)-yl)methoxy)-8a,9,12,13-tetrahydro-8H,11H-7,10-dioxa-1,3,6,13a-tetraazanaphtho[1,8-ab]heptalene A solution of (8aS)-4-fluoro-5-((R*)-5-methoxy-1-((2-(trimethylsilyl)ethoxy)methyl)-5,6,7,8-tetrahydro-1H-benzo[f]indazol-4-yl)-2-(((S)-2-methylenetetrahydro-1H-pyrrolizin-7a(5H)-yl)methoxy)-8a,9,12,13-tetrahydro-8H,11H-7,10-dioxa-1,3,6,13a-tetraazanaphtho[1,8-ab]heptalene (obtained from coupling Intermediates I-24i or I-24ii with Intermediate I-4 as per scheme A, example 1 (50 mg, 0.066 mmol)) in TBAF (0.858 mL, 0.858 mmol) was stirred at 50° C. for 3 h. LCMS showed that the starting material was consumed and the desired product was detected, the reaction mixture was purified by Prep-HPLC (Column: WELCH Xtimate C18 21.2*250 mm 10 um; mobile phase: CH3CN—H2O (0.1% NH4HCO3); gradient: 30% CH3CN to 100% CH3CN; flow rate: 30 mL/min) to give the product (8aS)-4-fluoro-5-((R*)-5-methoxy-5,6,7,8-tetrahydro-1H-benzo[f]indazol-4-yl)-2-(((S)-2-methylenetetrahydro-1H-pyrrolizin-7a(5H)-yl)methoxy)-8a,9,12,13-tetrahydro-8H,11H-7,10-dioxa-1,3,6,13a-tetraazanaphtho[1,8-ab]heptalene (9.04 mg, Y: 22%) as white solid. 1H NMR (400 MHz, MeOD) δ 7.78 and 7.68 (2 s, 1H, minor and major rotamer respectively), 7.42 (s, 1H), 5.29-5.18 (m, 1H), 5.00 (s, 2H), 4.86-4.71 (m, 2H), 4.63 and 4.59 (2 d, J=13.1 Hz, 1H, minor and major rotamer respectively), 4.59 (d, J=13.1 Hz, 1H), 4.40-4.29 (m, 3H), 4.18 (dd, J=12.4, 4.0 Hz, 1H), 4.04-3.95 (m, 1H), 3.85-3.71 (m, 2H), 3.61-3.52 (m, 1H), 3.51-3.40 (m, 1H), 3.39-3.35 (m, 1H), 3.21-3.07 (m, 2H), 2.98-2.85 (m, 4H), 2.81 (d, J=16.3 Hz, 1H), 2.77-2.70 (m, 1H), 2.50 (d, J=15.8 Hz, 1H), 2.24-2.13 (m, 3H), 2.05-1.83 (m, 6H), 1.80-1.67 (m, 1H).LCMS (ESI) m/z 628 [M+1]+.

Example 62: (8aS)-5-[(5R)-3-chloro-5-methyl-5,6,7,8-tetrahydro-1H-benzo[f]indazol-4-yl]-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene

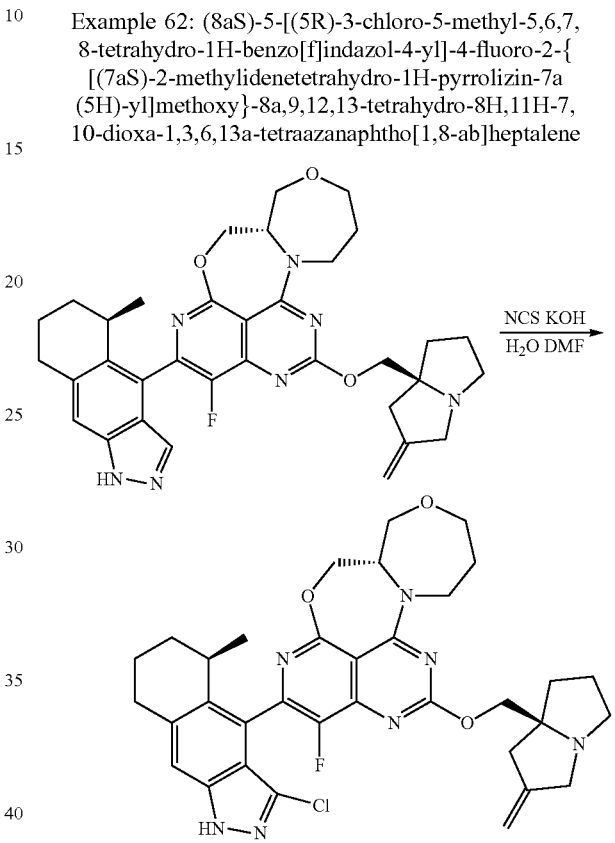

To a solution of (8aS)-4-fluoro-2-{[(7aS)-2-methylidenetetrahydro-1H-pyrrolizin-7a(5H)-yl]methoxy}-5-[(5R)-5-methyl-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene (example 29, 50 mg, 0.049 mmol) and N-Chlorosuccinimide (13 mg, 0.098 mmol) in DMF (1.5 mL) was added 3 M potassium hydroxide solution in water (0.065 mL, 0.2 mmol). The mixture was stirred for 14 h. LCMS showed the starting material was consumed and the desired product was formed as a mixture of two atropisomers. The reaction mixture was diluted with ethyl acetate (6 mL). Washed with water (5 mL) and brine (5 mL) then dried over sodium sulfate and concentrated under reduced pressure. The residue was purified by prep. HPLC (Waters XSELECT CSH Prep C18 OBD, 100×30 mm, 5 um. Mobile phase A: Water+10 mM ammonium acetate. Mobile phase B: Acetonitrile. Gradient 35% B to 100% B over 8.5 minutes) to afford (8aS)-5-[(5R)-3-chloro-5-methyl-5,6,7,8-tetrahydro-1H-benzo[f]indazol-4-yl]-4-fluoro-2-[(7aS)-2-methylidenetetrahydro-1H-pyrrolizin-7a(5H)-yl]methoxy)-8a,9,12,13-tetrahydro-8H,11H-7,10-dioxa-1,3,6,13a-tetraazanaphtho[1,8-ab]heptalene as a mixture of two atropisomers (18 mg, 57%) as a cream solid. 1H NMR (600 MHz, DMSO 120° C.) δ ppm 8.51 (br s, 1H), 7.35 (s, 1H), 4.98-5.12 (m, 1H), 4.92 (d, J=1.00 Hz, 2H), 4.63-4.71 (m, 1H), 4.50-4.63 (m, 1H), 4.25-4.38 (m, 1H), 4.09-4.24 (m, 3H), 3.89-3.99 (m, 1H), 3.68-3.78 (m, 1H), 3.52-3.65 (m, 2H), 3.41-3.52 (m, 1H), 3.26-3.36 (m, 1H), 3.22 (d, J=1.00 Hz, 1H), 3.04-3.12 (m, 2H), 2.89-3.02 (m, 2H), 2.56-2.73 (m, 2H), 2.36-2.45 (m, 1H), 1.94 (br dd, J=5.18, 1.73 Hz, 4H), 1.66-1.86 (m, 5H), 1.06 (dd, J=1.00 Hz, 3H). LCMS (ESI) m/z: 646.2 [M+H]+.

The following examples were made under similar conditions to preceding examples prepared via schemes A through E as indicated with non-critical changes or substitutions that one skilled in the art would be able to appreciate. For analytical data, see table 1:

Example 2: (8aS)-5-(6-chloro-5-cyclopropyl-1H-indazol-4-yl)-4-fluoro-2-{[(7aS)-2-methylidenetetrahydro-1H-pyrrolizin-7a(5H)-yl]methoxy}8a,9,12,13-tetrahydro-8H,11H-7,10-dioxa-1,3,6,13a-tetraazanaphtho[1,8-ab]heptalene

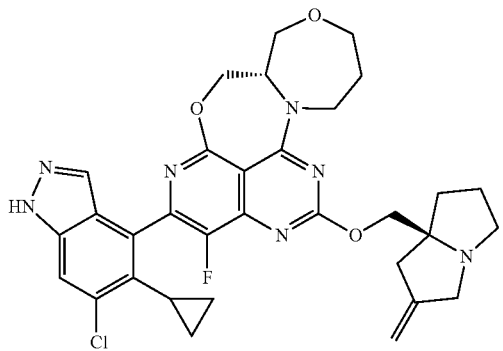 [SMILES: C=C1CN2CCC[C@@]2(COc2nc3c4c(nc(-c5c(C6CC6)c(Cl)cc6[nH]ncc56)c(F)c4n2)OC[C@@H]2COCCCN32)C1]

Example 2 was prepared according to scheme A (as fully exemplified with Example 1) however substituting in the alkene amine [(7aS)-2-methylidenetetrahydro-1H-pyrrolizin-7a(5H)-yl]methanol (CAS #2820536-99-8) in place of the fluoro amine ((2S,7aR)-2-fluorotetrahydro-1H-pyrrolizin-7a(5H)-yl)methanol (CAS #2097518-76-6) to furnish the title compound, (8aS)-5-(6-chloro-5-cyclopropyl-1H-indazol-4-yl)-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene.

Example 26: (8aS)-5-(6-chloro-5-cyclopropyl-1H-indazol-4-yl)-2-{[(2Z,7aS)-2-ethylidenetetrahydro-1H-pyrrolizin-7a(5H)-yl]methoxy}-4-fluoro-8a,9,12,13-tetrahydro-8H,11H-7,10-dioxa-1,3,6,13a-tetraazanaphtho[1,8-ab]heptalene

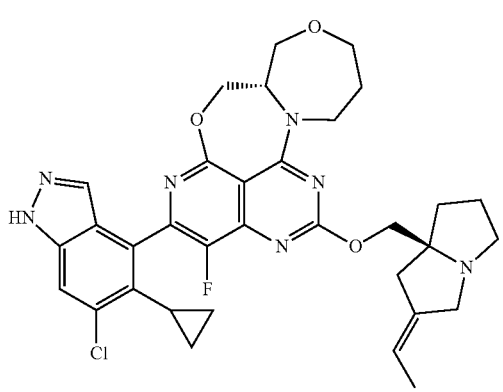 [SMILES: C/C=C1\CN2CCC[C@@]2(COc2nc3c4c(nc(-c5c(C6CC6)c(Cl)cc6[nH]ncc56)c(F)c4n2)OC[C@@H]2COCCCN32)C1]

Example 26 was prepared according to scheme A (as fully exemplified with Example 1) however substituting in the alkene amine [(2Z,7aS)-2-ethylidenetetrahydro-1H-pyrrolizin-7a(5H)-yl]methanol (Intermediate I-261) in place of the fluoro-amine ((2S,7aR)-2-fluorotetrahydro-1H-pyrrolizin-7a(5H)-yl)methanol (CAS #2097518-76-6) to furnish the title compound, (8aS)-5-(6-chloro-5-cyclopropyl-1H-indazol-4-yl)-2-{[(2Z,7aS)-2-ethylidenetetrahydro-1H-pyrrolizin-7a(5H)-yl]methoxy}-4-fluoro-8a,9,12,13-tetrahydro-8H,11H-7,10-dioxa-1,3,6,13a-tetraazanaphtho[1,8-ab]heptalene.

Example 28: (8aS)-5-(6-chloro-5-cyclopropyl-1H-indazol-4-yl)-4-fluoro-2-{[(2Z,7aS)-2-(2-methoxyethylidene)tetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene

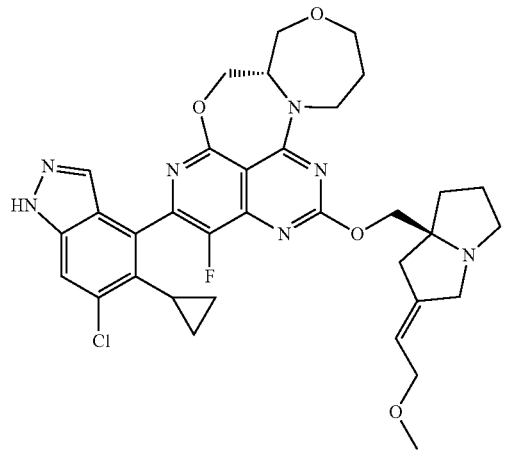 [SMILES: COC/C=C1\CN2CCC[C@@]2(COc2nc3c4c(nc(-c5c(C6CC6)c(Cl)cc6[nH]ncc56)c(F)c4n2)OC[C@@H]2COCCCN32)C1]

Example 28 was prepared according to scheme A (as fully exemplified with example 1) however substituting in the alkene amine [(2Z,7aS)-2-(2-methoxyethylidene)tetrahydro-1H-pyrrolizin-7a(5H)-yl]methanol (Intermediate 8) in place of the fluoro amine ((2S,7aR)-2-fluorotetrahydro-1H-pyrrolizin-7a(5H)-yl)methanol (CAS #2097518-76-6) to furnish the title compound, (8aS)-5-(6-chloro-5-cyclopropyl-1H-indazol-4-yl)-4-fluoro-2-{[(2Z,7aS)-2-(2-methoxyethylidene)tetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene.

Example 29: (8aS)-4-fluoro-2-{[(7aS)-2-methylidenetetrahydro-1H-pyrrolizin-7a(5H)-yl]methoxy}-5-[(5R)-5-methyl-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene

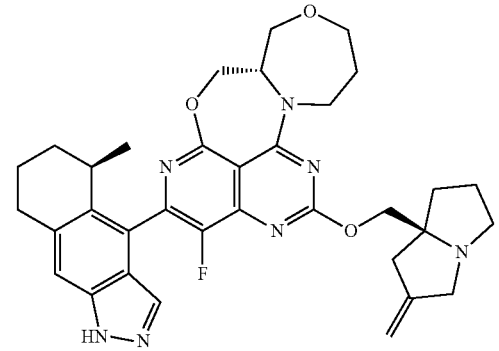 [SMILES: C=C1CN2CCC[C@@]2(COc2nc3c4c(nc(-c5c6c(cc7[nH]ncc57)CCC[C@H]6C)c(F)c4n2)OC[C@@H]2COCCCN32)C1]

Example 29 was prepared according to scheme A (as fully exemplified with example 1) however substituting in (5R)-4-bromo-5-methyl-1-(tetrahydro-2H-pyran-2-yl)-5,6,7,8-tetrahydro-1H-benzo[f]indazole (Intermediate I-91) in place of 4-bromo-8-chloro-5-cyclopropyl-2-(oxan-2-yl)-2H-indazole (Intermediate I-51) and additionally substituting the alkene amine [(7aS)-2-methylidenetetrahydro-1H-pyrrolizin-7a(5H)-yl]methanol (CAS #2820536-99-8) in place of the fluoro amine ((2S,7aR)-2-fluorotetrahydro-1H-pyrrolizin-7a(5H)-yl)methanol (CAS #2097518-76-6) to furnish the title compound, (8aS)-5-(6-chloro-5-cyclopropyl-1H-indazol-4-yl)-4-fluoro-2-{[(2Z,7aS)-2-(2-methoxyethylidene)tetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene.

Example 36: (8aS)-4-fluoro-2-{[(2R,7aS)-2-fluorotetrahydro-1H-pyrrolizin-7a(5H)-yl]methoxy}-5-[(5R)-5-methyl-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene

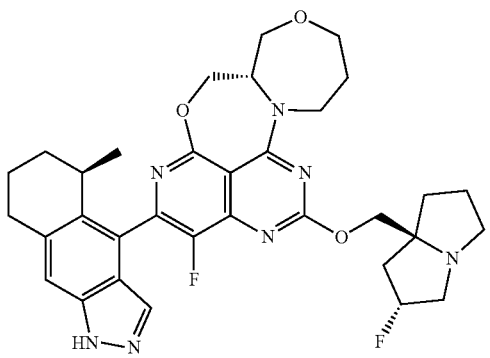 [SMILES: C[C@@H]1CCCc2cc3[nH]ncc3c(-c3nc4c5c(nc(OC[C@@]67CCCN6C[C@H](F)C7)nc5c3F)N3CCCOC[C@H]3CO4)c21]

Example 36 was prepared according to scheme A (as fully exemplified with example 1) however substituting in (5R)-4-bromo-5-methyl-1-(tetrahydro-2H-pyran-2-yl)-5,6,7,8-tetrahydro-1H-benzo[f]indazole (Intermediate I-91) in place of 4-bromo-8-chloro-5-cyclopropyl-2-(oxan-2-yl)-2H-indazole (Intermediate I-51) to furnish the title compound, (8aS)-4-fluoro-2-{[(2R,7aS)-2-fluorotetrahydro-1H-pyrrolizin-7a(5H)-yl]methoxy}-5-[(5R)-5-methyl-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene.

Example 37: (8aS)-4-fluoro-2-{[(2Z,7aS)-2-(2-methoxyethylidene)tetrahydro-1H-pyrrolizin-7a(5H)-yl]methoxy}-5-[(5R)-5-methyl-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene

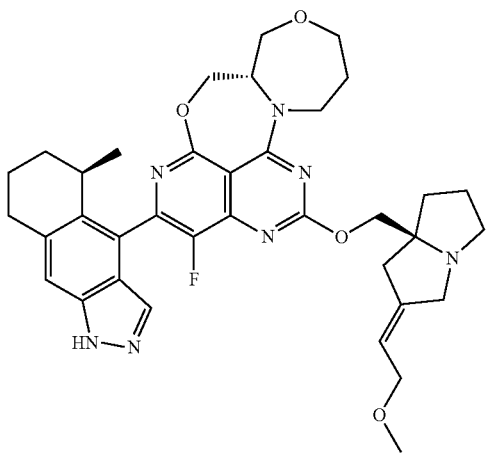 [SMILES: COC/C=C1\CN2CCC[C@@]2(COc2nc3c4c(nc(-c5c6c(cc7[nH]ncc57)CCC[C@H]6C)c(F)c4n2)OC[C@@H]2COCCCN32)C1]

Example 37 was prepared according to scheme A (as fully exemplified with example 1) however substituting in (5R)-4-bromo-5-methyl-1-(tetrahydro-2H-pyran-2-yl)-5,6,7,8-tetrahydro-1H-benzo[f]indazole (Intermediate I-91) in place of 4-bromo-6-chloro-5-cyclopropyl-2-(oxan-2-yl)-2H-indazole (Intermediate I-51) and additionally substituting the alkene amine [(2Z,7aS)-2-(2-methoxyethylidene)tetrahydro-1H-pyrrolizin-7a(5H)-yl]methanol (Intermediate 8) in place of the fluoro amine ((2S,7aR)-2-fluorotetrahydro-1H-pyrrolizin-7a(5H)-yl)methanol (CAS #2097518-76-6) to furnish the title compound, (8aS)-4-fluoro-2-{[(2Z,7aS)-2-(2-methoxyethylidene)tetrahydro-1H-pyrrolizin-7a(5H)-yl]methoxy}-5-[(5R)-5-methyl-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene.

Example 39: (8aS)-5-[6-chloro-5-(1-methylcyclopropyl)-1H-indazol-4-yl-4-fluoro-2-{(7aS)-2-methylidenetetrahydro-1H-pyrrolizin-7a(5H)-yl]methoxy}8a,9,12,13-tetrahydro-8H,11H-7,10-dioxa-1,3,6,13a-tetraazanaphtho[1,8-ab]heptalene

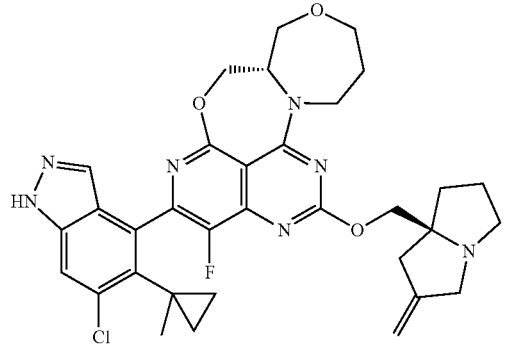 [SMILES: C=C1CN2CCC[C@@]2(COc2nc3c4c(nc(-c5c(C6(C)CC6)c(Cl)cc6[nH]ncc56)c(F)c4n2)OC[C@@H]2COCCCN32)C1]

Example 39 was prepared according to scheme A (as fully exemplified with example 1) however substituting in however substituting in 4-bromo-6-chloro-5-(1-methylcyclopropyl)-1-(tetrahydro-2H-pyran-2-yl)-1H-indazole (Intermediate I-13) in place of 4-bromo-8-chloro-5-cyclopropyl-2-(oxan-2-yl)-2H-indazole (Intermediate I-51) and additionally substituting in the alkene amine [(7aS)-2-methylidenetetrahydro-1H-pyrrolizin-7a(5H)-yl]methanol (CAS #2820536-99-8) in place of the fluoro amine ((2S,7aR)-2-fluorotetrahydro-1H-pyrrolizin-7a(5H)-yl)methanol (CAS #2097518-76-6) to furnish the title compound, (8aS)-5-[6-chloro-5-(1-methylcyclopropyl)-1H-indazol-4-yl]-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene.

Example 41: (8aS)-5-(6-chloro-5-cyclopropyl-1H-indazol-4-yl)-4-fluoro-2-{[(7aS)-2-(oxetan-3-ylidene)tetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene

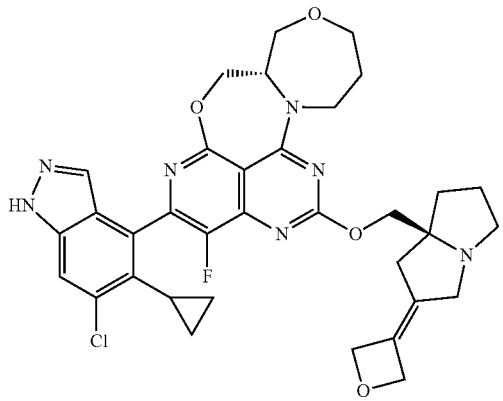 [SMILES: Fc1c(-c2c(C3CC3)c(Cl)cc3[nH]ncc23)nc2c3c(nc(OC[C@@]45CCCN4CC(=C4COC4)C5)nc13)N1CCCOC[C@H]1CO2]

Example 41 was prepared according to scheme C (as fully exemplified with example 40) from (8aS)-5-(6-chloro-5-cyclopropyl-1-(tetrahydro-2H-pyran-2-yl)-1H-indazol-4-yl)-4-fluoro-2-(methylthio)-8a,9,12,13-tetrahydro-8H,11H-7,10-dioxa-1,3,6,13a-tetraazanaphtho[1,8-ab]heptalene (Intermediate 40a), however the subsequent alcohol displacement of the sulphone as detailed in Scheme A with Example 1 was performed with (S)-(2-(oxetan-3-ylidene)tetrahydro-1H-pyrrolizin-7a(5H)-yl)methanol (Intermediate I-15) in place of the fluoro amine ((2S,7aR)-2-fluorotetrahydro-1H-pyrrolizin-7a(5H)-yl)methanol (CAS #2097518-76-6) to afford the title product, (8aS)-5-(6-chloro-5-cyclopropyl-1H-indazol-4-yl)-4-fluoro-2-{[(7aS)-2-(oxetan-3-ylidene)tetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene.

Example 47: (8aS)-4-fluoro-5-[(5R)-5-methyl-5,6,7,8-tetrahydro-1H-benzo[f]indazol-4-yl]-2-{[(7aS)-2-(oxetan-3-ylidene)tetrahydro-1H-pyrrolizin-7a(5H)-yl]methoxy}-a,9,12,13-tetrahydro-8H,11H-7,10-dioxa-1,3,6,13a-tetraazanaphtho[1,8-ab]heptalene

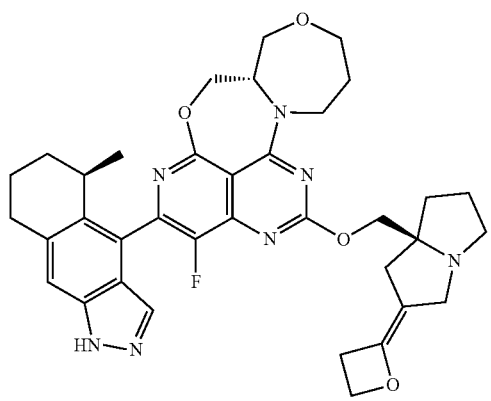 [SMILES: C[C@@H]1CCCc2cc3[nH]ncc3c(-c3nc4c5c(nc(OC[C@@]67CCCN6C/C(=C6/CCO6)C7)nc5c3F)N3CCCOC[C@H]3CO4)c21]

Example 47 was prepared according to scheme A (as fully exemplified with example 1) however substituting in (5R)-4-bromo-5-methyl-1-(tetrahydro-2H-pyran-2-yl)-5,6,7,8-tetrahydro-1H-benzo[f]indazole (Intermediate I-91) in place of 4-bromo-6-chloro-5-cyclopropyl-2-(oxan-2-yl)-2H-indazole (Intermediate I-51) and sulphone displacement was performed with (S)-(2-(oxetan-3-ylidene)tetrahydro-1H-pyrrolizin-7a(5H)-yl)methanol (Intermediate I-15) in place of fluoro amine ((2S,7aR)-2-fluorotetrahydro-1H-pyrrolizin-7a(5H)-yl)methanol (CAS #2097518-76-6) to afford the title product, (8aS)-4-fluoro-5-[(5R)-5-methyl-5,6,7,8-tetrahydro-1H-benzo[f]indazol-4-yl]-2-{[(7aS)-2-(oxetan-3-ylidene)tetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene.

Example 53: (8aS)-2-{[(2Z,7aS)-2-ethylidenetetrahydro-1H-pyrrolizin-7a(5H)-yl]methoxy}-4-fluoro-5-[(5R)-5-methyl-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene

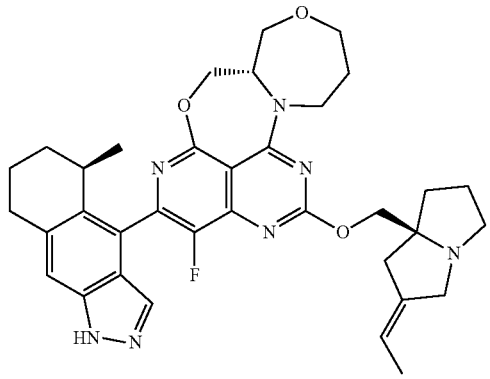 [SMILES: C/C=C1\CN2CCC[C@@]2(COc2nc3c4c(nc(-c5c6c(cc7[nH]ncc57)CCC[C@H]6C)c(F)c4n2)OC[C@@H]2COCCCN32)C1]

Example 53 was prepared according to scheme A (as fully exemplified with example 1) however substituting in (5R)-4-bromo-5-methyl-1-(tetrahydro-2H-pyran-2-yl)-5,6,7,8-tetrahydro-1H-benzo[f]indazole (Intermediate I-9i) in place of 4-bromo-8-chloro-5-cyclopropyl-2-(oxan-2-yl)-2H-indazole (Intermediate I-5i) and sulphone displacement was performed with [(2Z,7aS)-2-ethylidenetetrahydro-1H-pyrrolizin-7a(5H)-yl]methanol (Intermediate I-26i) in place of fluoro amine ((2S,7aR)-2-fluorotetrahydro-1H-pyrrolizin-7a(5H)-yl)methanol (CAS #2097518-76-6) to afford the title product, (8aS)-2-{[(2Z,7aS)-2-ethylidenetetrahydro-1H-pyrrolizin-7a(5H)-yl]methoxy}-4-fluoro-5-[(5R)-5-methyl-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene.

Example 54: (8aS)-4-fluoro-2-([(2Z,7aS)-2-(fluoromethylidene)tetrahydro-1H-pyrrolizin-7a(5H)-yl]methoxy)-5-[(5R)-5-methyl-5,6,7,8-tetrahydro-1H-benzo[f]indazol-4-yl]-8a,9,12,13-tetrahydro-8H, 11H-7,10-dioxa-1,3,6,13a-tetraazanaphtho[1,8-ab]heptalene

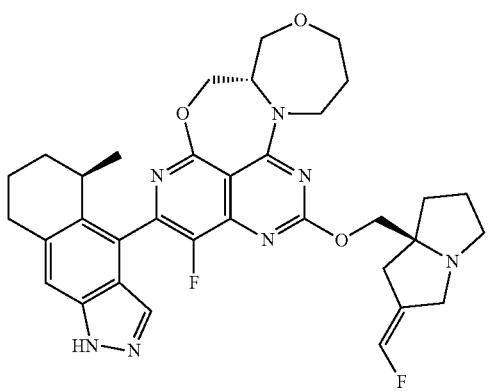 [SMILES: C[C@@H]1CCCc2cc3[nH]ncc3c(-c3nc4c5c(nc(OC[C@@]67CCCN6C/C(=C\F)C7)nc5c3F)N3CCCOC[C@H]3CO4)c21]

Example 54 was prepared according to scheme A (as fully exemplified with example 1) however substituting in (5R)-4-bromo-5-methyl-1-(tetrahydro-2H-pyran-2-yl)-5,6,7,8-tetrahydro-1H-benzo[f]indazole (Intermediate I-91) in place of 4-bromo-8-chloro-5-cyclopropyl-2-(oxan-2-yl)-2H-indazole (Intermediate I-51) and sulphone displacement was performed with [(2Z,7aS)-2-(fluoromethylidene)tetrahydro-1H-pyrrolizin-7a(5H)-yl]methanol (CAS #2820537-73-1) in place of fluoro amine ((2S,7aR)-2-fluorotetrahydro-1H-pyrrolizin-7a(5H)-yl)methanol (CAS #2097518-76-6) to afford the title product, (8aS)-4-fluoro-2-([(2Z,7aS)-2-(fluoromethylidene)tetrahydro-1H-pyrrolizin-7a(5H)-yl]methoxy)-5-[(5R)-5-methyl-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene.

Additional Examples reported in Table 1 were prepared according to General Method A, B, C, D or E with non-critical modifications that one skilled in the art would appreciate. In examples where intermediated contain additional protecting groups, a single last-step global deprotection was employed unless otherwise indicated.

Additional compounds of the invention were prepared by modifications of the methods exemplified herein. Except where otherwise indicated, all compounds having chiral centers were prepared and/or isolated as a single enantiomer having a known relative configuration. Compounds marked "absolute stereochemistry unknown" were typically prepared from racemic intermediates and resolved into single enantiomers by an appropriate chiral preparative SFC method before characterization and testing.

Examples and their corresponding characterization data are all presented in Table 1 below.

Table 1: Examples

| Example Num (Gen. Method) | Structure IUPAC name | Low Res Mass Spec | $^1$H NMR (ppm); $^{19}$F NMR (ppm); optical rotation; |
|---|---|---|---|
| 2 (A) | (8aS)-5-(6-chloro-5-cyclopropyl-1H-indazol-4-yl)-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 618 [M + H]$^+$ | $^1$H NMR (400 MHz, MeOD) δ 7.87 and 7.81 (2s, major and minor rotamer respectively, 1H), 7.75 (s, 1H), 5.28-5.18 (m, 1H), 5.12 (s, 2H), 4.76 (ddd, J = 13.5, 4.3, 2.2 Hz, 1H), 4.66-4.56 (m, 1H), 4.52-4.42 (m, 2H), 4.41-4.30 (m, 1H), 4.21 (td, J = 12.1, 4.2 Hz, 1H), 4.06 - 3.94 (m, 2H), 3.83 (ddd, J = 34.4, 12.4, 9.9 Hz, 1H), 3.64-3.54 (m, 2H), 3.52-3.39 (m, 2H), 3.02-2.87 (m, 2H), 2.62 (d, J = 16.0 Hz, 1H), 2.30-1.93 (m, 7H), 0.98-0.82 (m, 1H), 0.77-0.59 (m, 1H), 0.37-0.08 (m, 2H). |

| Example Num (Gen. Method) | Structure IUPAC name | Low Res Mass Spec | $^1$H NMR (ppm); $^{19}$F NMR (ppm); optical rotation; |
|---|---|---|---|
| 3 (E) | 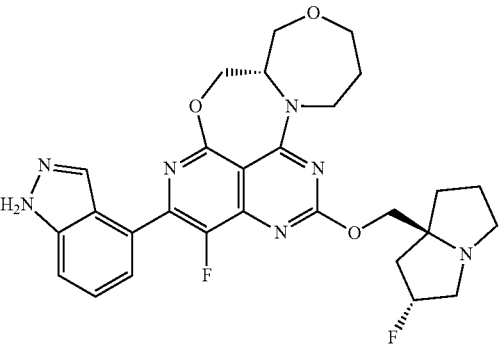<br>(8aS)-4-fluoro-2-{[(2R,7aS)-2-fluorotetrahydro-1H-pyrrolizin-7a(5H)-yl]methoxy}-5-(1H-indazol-4-yl)-8a,9,12,13-tetrahydro-8H,11H-7,10-dioxa-1,3,6,13a-tetraazanaphtho[1,8-ab]heptalene | 550 [M + H]$^+$ | $^1$H NMR (400 MHz, DMSO) δ 13.16 (s, 1H), 8.26 (d, J = 1.5 Hz, 1H), 7.61 (d, J = 8.1 Hz, 1H), 7.59-7.54 (m, 1H), 7.43 (dd, J = 8.3, 7.2 Hz, 1H), 5.34-5.12 (m, 1H), 4.93 (ddd, J = 13.7, 6.4, 3.3 Hz, 1H), 4.64 (dd, J = 13.4, 4.4 Hz, 1H), 4.47 (d, J = 13.2 Hz, 1H), 4.24 (dt, J = 9.1, 4.2 Hz, 1H), 4.11 (d, J = 10.3 Hz, 1H), 4.06 (dd, J = 12.3, 4.0 Hz, 1H), 4.03-3.98 (m, 1H), 3.82 (dt, J = 12.6, 5.0 Hz, 1H), 3.59 (dd, J = 12.3, 9.8 Hz, 1H), 3.34 (dddd, J = 28.2, 13.9, 9.1, 4.7 Hz, 2H), 3.10 (d, J = 5.3 Hz, 1H), 3.06-3.00 (m, 2H), 2.96 (d, J = 2.2 Hz, 1H), 2.77 (q, J = 8.1 Hz, 1H), 2.10-1.89 (m, 4H), 1.88-1.66 (m, 4H).<br>$^{19}$F NMR (377 MHz, DMSO) δ −145.28, −171.96, −171.99, −172.05, −172.10, −172.12, −172.15, −172.20, −172.22, −172.26, −172.29. |
| 4 (C) | 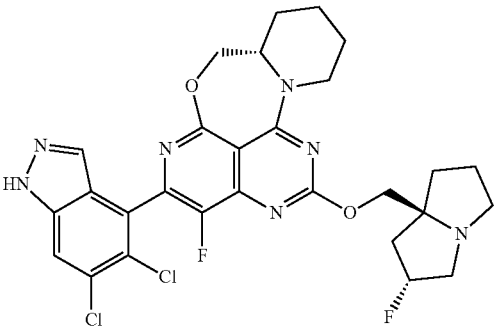 [SMILES: Fc1c(-c2c(Cl)c(Cl)cc3[nH]ncc23)nc2c3c(nc(OC[C@@]45CCCN4C[C@H](F)C5)nc13)N1CCCC[C@H]1CO2]<br>(8aS)-5-(5,6-dichloro-1H-indazol-4-yl)-4-fluoro-2-{[(2R,7aS)-2-fluorotetrahydro-1H-pyrrolizin-7a(5H)-yl]methoxy}-8,8a,9,10,11,12-hexahydro-7-oxa-1,3,6,12a-tetraazabenzo[4,5]cyclohepta[1,2,3-de]naphthalene | 602 [M + H]$^+$ | $^1$H NMR (400 MHz, MeOD) δ 7.93 and 7.92 (2s, 1H, major and minor rotamer respectively), 7.84 and 7.79 (2s, 1H, major and minor rotamer respectively), 5.49-5.29 (m, 2H), 4.59-4.54 (m, 2H), 4.44 (d, J = 10.8 Hz, 1H), 4.35 (d, J = 11.0 Hz, 1H), 4.06-3.92 (m, 1H), 3.58-3.41 (m, 3H), 3.17-3.05 (m, 2H), 2.52-2.20 (m, 3H), 2.15-1.94 (m, 5H), 1.91-1.81 (m, 3H), 1.72-1.55 (m, 1H).<br>$^{19}$F NMR (376.5 MHz, MeOD) δ −144.04, −173.82. |
| 5 (C) | 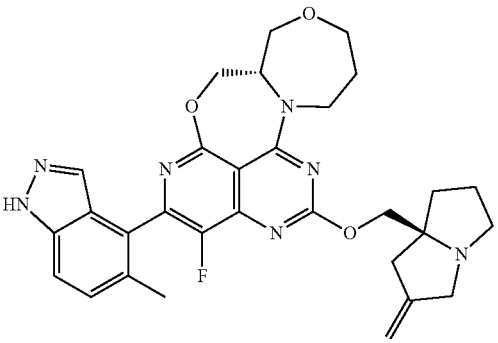 [SMILES: C=C1CN2CCC[C@@]2(COc2nc3c4c(nc(-c5c(C)ccc6[nH]ncc56)c(F)c4n2)OC[C@@H]2COCCCN32)C1]<br>(8aS)-4-fluoro-2-{[(7aS)-2-methylidenetetrahydro-1H-pyrrolizin-7a(5H)-yl]methoxy}-5-(5-methyl-1H-indazol-4-yl)-8a,9,12,13-tetrahydro-8H,11H-7,10-dioxa-1,3,6,13a-tetraazanaphtho[1,8-ab]heptalene | 558 [M + H]$^+$ | $^1$H NMR (400 MHz, MeOD) δ 7.77 (s, 1H), 7.60 (d, J = 8.6 Hz, 1H), 7.42 (d, J = 8.6 Hz, 1H), 5.25 (ddd, J = 13.7, 6.4, 2.7 Hz, 1H), 5.14 (s, 2H), 4.77 (dd, J = 13.5, 4.4 Hz, 1H), 4.61 (d, J = 13.3 Hz, 1H), 4.48 (s, 2H), 4.40-4.34 (m, 1H), 4.22 (dd, J = 12.5, 4.2 Hz, 1H), 4.02 (dt, J = 12.6, 5.0 Hz, 2H), 3.85 (t, J = 3.9 Hz, 1H), 3.61 (ddd, J = 12.9, 8.5, 4.2 Hz, 2H), 3.53-3.39 (m, 2H), 3.01-2.88 (m, 2H), 2.64 (d, J = 15.3 Hz, 1H), 2.38 (s, 3H), 2.30-2.16 (m, 2H), 2.14-1.96 (m, 4H).<br>$^{19}$F NMR (376.5 MHz, MeOD) δ −145.44. |

| Example Num (Gen. Method) | Structure IUPAC name | Low Res Mass Spec | ¹H NMR (ppm); ¹⁹F NMR (ppm); optical rotation; |
|---|---|---|---|
| 6 (C) | 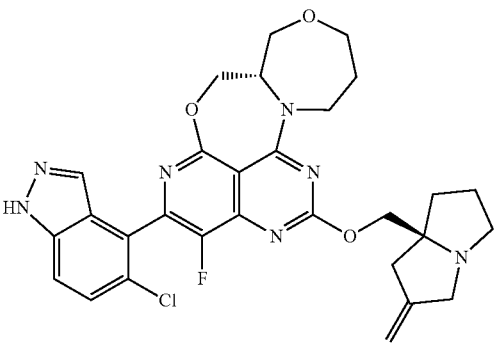<br>(8aS)-5-(5-chloro-1H-indazol-4-yl)-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 578 [M + H]⁺ | ¹H NMR (400 MHz, MeOD) δ 7.83 (s, 1H), 7.68 (d, J = 8.8 Hz, 1H), 7.54 (d, J = 8.9 Hz, 1H), 5.23 (m, 3H), 4.76 (dd, J = 13.5, 4.4 Hz, 1H), 4.60 (m, 3H), 4.36 (m, 1H), 4.20 (m, 2H), 4.00 (dt, J = 12.7, 5.2 Hz, 1H), 3.83 (br s, 1H), 3.73 (d, J = 14.0 Hz, 1H), 3.58 (m, 2H), 3.50 (m, 1H), 3.11 (m, 1H), 2.98 (d, J = 16.2 Hz, 1H), 2.70 (d, J = 16.1 Hz, 1H), 2.31 (m, 1H), 2.17 (m, 2H), 2.06 (m, 3H). ¹⁹F NMR (376.5 MHz, MeOD) δ −144.30. |
| 7 (C) | 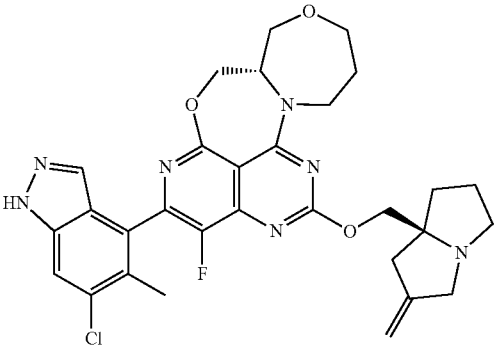 [SMILES: C=C1CN2CCC[C@@]2(COc2nc3c4c(nc(-c5c(C)c(Cl)cc6[nH]ncc56)c(F)c4n2)OC[C@@H]2COCCCN32)C1]<br>(8aS)-5-(6-chloro-5-methyl-1H-indazol-4-yl)-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 592 [M + H]⁺ | ¹H NMR (400 MHz, MeOD) δ 7.75 (m, 2H), 5.22 (m, 3H), 4.76 (dd, J = 13.2, 3.9 Hz, 1H), 4.59 (m, 3H), 4.36 (m, 1H), 4.18 (m, 2H), 4.00 (m, 1H), 3.83 (m, 1H), 3.72 (d, J = 14.4 Hz, 1H), 3.57 (m, 2H), 3.48 (m, 1H), 3.09 (m, 1H), 2.98 (d, J = 15.9 Hz, 1H), 2.70 (d, J = 15.9 Hz, 1H), 2.32 (m, 4H), 2.10 (m, 5H). ¹⁹F NMR (376.5 MHz, MeOD) δ −145.54. |
| 8 (A) | 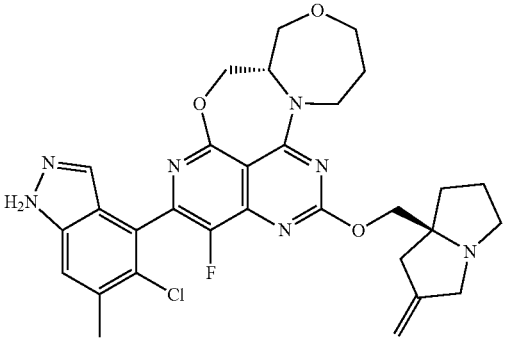<br>(8aS)-5-(5-chloro-6-methyl-1H-indazol-4-yl)-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 592 [M + H]⁺ | ¹H NMR (400 MHz, MeOD) δ 7.80 and 7.75 (2s, 1H, major and minor rotamer respectively), 7.66 (s, 1H), 5.30-5.14 (m, 3H), 4.78 (d, J = 13.3 Hz, 1H), 4.66-4.50 (m, 3H), 4.43-4.32 (m, 1H), 4.27-4.10 (m, 2H), 4.02 (dt, J = 10.4, 5.0 Hz, 1H), 3.96-3.77 (m, 1H), 3.72 (d, J = 14.3 Hz, 1H), 3.68-3.43 (m, 3H), 3.12-3.02 (m, 1H), 2.99 (d, J = 15.7 Hz, 1H), 2.71 (d, J = 16.0 Hz, 1H), 2.60 (s, 3H), 2.39-2.28 (m, 1H), 2.26-1.98 (m, 5H). ¹⁹F NMR (376.5 MHz, MeOD) δ −144.43. |

-continued

| Example Num (Gen. Method) | Structure IUPAC name | Low Res Mass Spec | ¹H NMR (ppm); ¹⁹F NMR (ppm); optical rotation; |
|---|---|---|---|
| 9 (A) | (8aS)-5-(5-chloro-6-fluoro-1H-indazol-4-yl)-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 596 [M + H]⁺ | ¹H NMR (400 MHz, MeOD) δ 7.85 (s, 1H), 7.58 and 7.55 (2s, 1H, major and minor rotamer respectively), 5.26-5.11 (m, 3H), 4.74 (dd, J = 13.5, 4.3 Hz, 1H), 4.63-4.50 (m, 3H), 4.39-4.28 (m, 1H), 4.22-4.08 (m, 2H), 3.97 (dt, J = 12.5, 5.0 Hz, 1H), 3.80 (br s, 1H), 3.69 (d, J = 14.3 Hz, 1H), 3.61-3.51 (m, 2H), 3.50-3.39 (m, 1H), 3.09-2.99 (m, 1H), 2.95 (d, J = 15.9 Hz, 1H), 2.67 (d, J = 15.9 Hz, 1H), 2.34-2.24 (m, 1H), 2.22-1.90 (m, 5H). ¹⁹F NMR (376.5 MHz, MeOD) δ −116.10, 144.06. |
| 10 (C) | (8aS)-5-[5-(difluoromethyl)-1H-indazol-4-yl]-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 594 [M + H]⁺ | ¹H NMR (400 MHz, MeOD) δ 7.92 (s, 1H), 7.85-7.78 (m, 2H), 6.91 (t, J = 54.9 Hz, 1H), 5.28-5.18 (m, 3H), 4.76 (dd, J = 13.5, 4.4 Hz, 1H), 4.67-4.57 (m, 3H), 4.41-4.33 (m, 1H), 4.30-4.17 (m, 2H), 4.00 (dt, J = 10.4, 5.0 Hz, 1H), 3.89-3.76 (m, 2H), 3.70-3.55 (m, 2H), 3.54-3.43 (m, 1H), 3.21-3.10 (m, 1H), 3.01 (d, J = 15.9 Hz, 1H), 2.74 (d, J = 15.9 Hz, 1H), 2.41-2.30 (m, 1H), 2.25-2.05 (m, 4H), 2.04-1.94 (m, 1H) ¹⁹F NMR (376.5 MHz, MeOD) δ −107.94, 145.53. |
| 11 (A) | (8aS)-5-(5,6-dichloro-1H-indazol-4-yl)-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 612 [M + H]⁺ | ¹H NMR (400 MHz, MeOD) δ 7.93 and 7.93 (2s, 1H, major and minor rotamer respectively), 7.86 and 7.81 (2 s, 1H, major and minor rotamer respectively), 5.28-5.15 (m, 3H), 4.76 (d, J = 13.6 Hz, 1H), 4.64-4.51 (m, 3H), 4.41-4.32 (m, 1H), 4.20 (dd, J = 12.4, 3.9 Hz, 1H), 4.13 (d, J = 14.2 Hz, 1H), 4.00 (dt, J = 12.7, 5.1 Hz, 1H), 3.93-3.75 (m, 1H), 3.69 (d, J = 14.3 Hz, 1H), 3.63-3.43 (m, 3H), 3.10-3.01 (m, 1H), 2.96 (d, J = 16.0 Hz, 1H), 2.68 (d, J = 15.8 Hz, 1H), 2.35-2.25 (m, 1H), 2.23-1.93 (m, 5H). ¹⁹F NMR (376.5 MHz, MeOD) δ −144.30. |

-continued

| Example Num (Gen. Method) | Structure IUPAC name | Low Res Mass Spec | ¹H NMR (ppm); ¹⁹F NMR (ppm); optical rotation; |
|---|---|---|---|
| 12 (A) | (8aS)-4-fluoro-2-{[(7aS)-2-methylidenetetrahydro-1H-pyrrolizin-7a(5H)-yl]methoxy}-5-[5-(trifluoromethyl)-1H-indazol-4-yl]-8a,9,12,13-tetrahydro-8H,11H-7,10-dioxa-1,3,6,13a-tetraazanaphtho[1,8-ab]heptalene | 612 [M + H]⁺ | ¹H NMR (400 MHz, MeOD) δ 7.95-7.80 (m, 3H), 5.30-5.17 (m, 3H), 4.78 (dd, J = 13.4, 4.2 Hz, 1H), 4.63 (dd, J = 13.5, 4.1 Hz, 1H), 4.58 (s, 2H), 4.45-4.34 (m, 1H), 4.23 (dd, J = 12.5, 3.7 Hz, 1H), 4.19-4.10 (m, 1H), 4.08-3.98 (m, 1H), 3.85 (ddd, J = 32.5, 12.2, 10.0 Hz, 1H), 3.72 (d, J = 13.5 Hz, 1H), 3.65-3.45 (m, 3H), 3.18-3.04 (m, 1H), 2.99 (d, J = 16.2 Hz, 1H), 2.71 (d, J = 16.1 Hz, 1H), 2.36-1.96 (m, 6H). ¹⁹F NMR (376.5 MHz, MeOD) δ −58.10, 145.71. |
| 13 (A) | (8aS)-5-[6-chloro-5-(trifluoromethyl)-1H-indazol-4-yl]-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 646 [M + H]⁺ | ¹H NMR (400 MHz, MeOD) δ 8.00 (s, 1H), 7.89 and 7.83 (2s, 1H, major and minor rotamer respectively), 5.32 (d, J = 1.7 Hz, 2H), 5.29-5.22 (m, 1H), 4.84-4.82 (m, 1H), 4.82-4.79 (m, 2H), 4.67 (dd, J = 13.5, 6.4 Hz, 1H), 4.48 (ddd, J = 13.5, 9.0, 4.2 Hz, 1H), 4.40 (d, J = 14.4 Hz, 1H), 4.23 (dd, J = 12.5, 4.3 Hz, 1H), 4.07-3.97 (m, 1H), 3.96-3.90 (m, 1H), 3.90-3.77 (m, 2H), 3.70-3.55 (m, 2H), 3.28-3.22 (m, 1H), 3.14-3.05 (m, 1H), 2.83 (d, J = 15.9 Hz, 1H), 2.49-2.38 (m, 1H), 2.29-2.13 (m, 4H), 2.07-1.97 (m, 1H). ¹⁹F NMR (376.5 MHz, MeOD) δ −56.69, −147.60. |
| 14 (A) | (8aS)-5-(6-chloro-5-cyclopropyl-1H-indazol-4-yl)-4-fluoro-2-{[(2R,7aR)-2-fluoro-6-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 636 [M + H]⁺ | ¹H NMR (400 MHz, MeOD) δ 7.90 and 7.84 (2s, 1H, major and minor rotamer respectively), 7.77 (s, 1H), 5.45-5.21 (m, 2H), 5.03 (s, 2H), 4.81-4.74 (m, 1H), 4.63 (t, J = 12.9 Hz, 1H), 4.47-4.31 (m, 3H), 4.28-4.18 (m, 1H), 4.07-3.97 (m, 1H), 3.93-3.74 (m, 2H), 3.60 (ddd, J = 12.4, 8.2, 4.2 Hz, 1H), 3.53-3.37 (m, 2H), 3.31-3.27 (m, 1H), 3.03-2.85 (m, 2H), 2.60-2.44 (m, 2H), 2.27-1.96 (m, 4H), 1.02-0.85 (m, 1H), 0.81-0.61 (m, 1H), 0.41-0.12 (m, 2H). ¹⁹F NMR (376.5 MHz, MeOD) δ −143.86, −173.93. |

| Example Num (Gen. Method) | Structure IUPAC name | Low Res Mass Spec | ¹H NMR (ppm); ¹⁹F NMR (ppm); optical rotation; |
|---|---|---|---|
| 15 (A) | 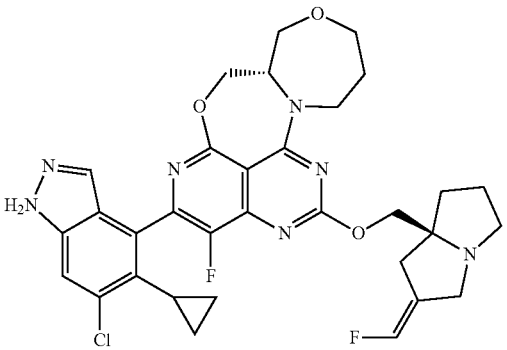<br>(8aS)-5-(6-chloro-5-cyclopropyl-1H-indazol-4-yl)-4-fluoro-2-{[(2E,7aS)-2-(fluoromethylidene)tetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 636 [M + H]⁺ | ¹H NMR (400 MHz, MeOD) δ 7.87 and 7.81 (2s, 1H, major and minor rotamer respectively), 7.75 (s, 1H), 6.85 (d, J = 82.5 Hz, 1H), 5.24 (dtd, J = 9.2, 6.4, 3.0 Hz, 1H), 4.76 (ddd, J = 13.4, 4.2, 2.0 Hz, 1H), 4.66-4.57 (m, 1H), 4.57-4.49 (m, 2H), 4.37 (ddd, J = 13.9, 9.1, 4.2 Hz, 1H), 4.21 (td, J = 12.1, 4.3 Hz, 1H), 4.08 (d, J = 13.9 Hz, 1H), 4.04-3.97 (m, 1H), 3.83 (ddd, J = 34.1, 12.3, 10.0 Hz, 1H), 3.67 (d, J = 13.9 Hz, 1H), 3.63-3.55 (m, 1H), 3.53-3.42 (m, 2H), 3.04-2.92 (m, 2H), 2.77 (d, J = 16.2 Hz, 1H), 2.34-2.25 (m, 1H), 2.24-2.09 (m, 2H), 2.09-1.93 (m, 4H), 0.97-0.83 (m, 1H), 0.74-0.62 (m, 1H), 0.34-0.09 (m, 2H).<br>¹⁹F NMR (376.5 MHz, MeOD) δ −130.75, −144.21. |
| 16 (A) | 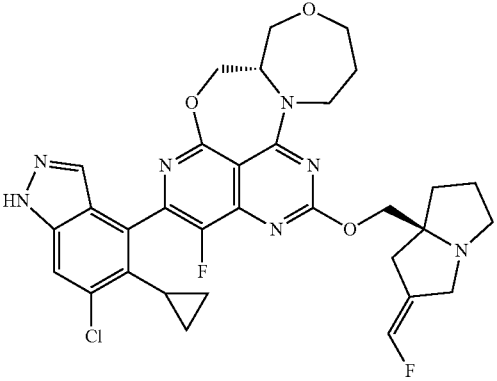 [SMILES: F/C=C1\CN2CCC[C@@]2(COc2nc3c4c(nc(-c5c(C6CC6)c(Cl)cc6[nH]ncc56)c(F)c4n2)OC[C@@H]2COCCCN32)C1]<br>(8aS)-5-(6-chloro-5-cyclopropyl-1H-indazol-4-yl)-4-fluoro-2-{[(2Z,7aS)-2-(fluoromethylidene)tetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 636 [M + H]⁺ | ¹H NMR (400 MHz, MeOD) δ 7.87 and 7.81(2 s, 1H, major and minor rotamer respectively), 7.76 (s, 1H), 6.76 (d, J = 83.3 Hz, 1H), 5.24 (dtd, J = 9.3, 6.2, 2.8 Hz, 1H), 4.77 (ddd, J = 13.4, 4.3, 2.3 Hz, 1H), 4.66-4.57 (m, 1H), 4.54-4.45 (m, 2H), 4.37 (ddd, J = 14.1, 9.3, 4.1 Hz, 1H), 4.21 (ddd, J = 12.2, 11.2, 4.3 Hz, 1H), 4.12 (d, J = 15.0 Hz, 1H), 4.00 (dt, J = 10.6, 5.1 Hz, 1H), 3.94-3.72 (m, 2H), 3.65-3.56 (m, 1H), 3.53-3.39 (m, 2H), 3.03-2.94 (m, 1H), 2.87 (d, J = 15.5 Hz, 1H), 2.61 (d, J = 15.6 Hz, 1H), 2.31-1.93 (m, 7H), 0.99-0.82 (m, 1H), 0.76-0.61 (m, 1H), 0.36-0.08 (m, 2H).<br>¹⁹F NMR (376.5 MHz, MeOD) δ −130.02, −144.18. |
| 17 (A) | 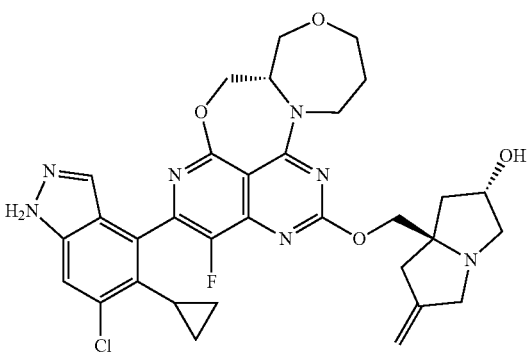<br>(2S,7aR)-7a-({[(8aS)-5-(6-chloro-5-cyclopropyl-1H-indazol-4-yl)-4-fluoro-8a,9,12,13-tetrahydro-8H,11H-7,10-dioxa-1,3,6,13a-tetraazanaphtho[1,8-ab]heptalen-2-yl]oxy}methyl)-6-methylidenehexahydro-1H-pyrrolizin-2-ol | 634 [M + H]⁺ | ¹H NMR (400 MHz, MeOD) δ 7.89 and 7.83 (2s, 1H, major and minor rotamer respectively), 7.78 (s, 1H), 5.31-5.21 (m, 1H), 5.18 (s, 2H), 4.79 (ddd, J = 13.5, 4.4, 2.0 Hz, 1H), 4.72-4.55 (m, 3H), 4.48 (dd, J = 11.7, 9.1 Hz, 1H), 4.44-4.33 (m, 1H), 4.23 (td, J = 12.2, 4.4 Hz, 1H), 4.16 (d, J = 13.9 Hz, 1H), 4.08 - 3.98 (m, 2H), 3.86 (ddd, J = 33.7, 12.3, 9.7 Hz, 1H), 3.73-3.57 (m, 2H), 3.56-3.45 (m, 1H), 3.26-3.16 (m, 1H), 3.06 (d, J = 15.7 Hz, 1H), 2.94 (d, J = 15.5 Hz, 1H), 2.54 (ddd, J = 13.7, 5.6, 3.6 Hz, 1H), 2.28 - 2.11 (m, 2H), 2.09-1.89 (m, 2H), 1.00-0.86 (m, 1H), 0.76-0.63 (m, 1H), 0.40-0.13 (m, 2H).<br>¹⁹F NMR (376.5 MHz, MeOD) δ −144.40. |

| Example Num (Gen. Method) | Structure IUPAC name | Low Res Mass Spec | $^1$H NMR (ppm); $^{19}$F NMR (ppm); optical rotation; |
|---|---|---|---|
| 18 (A) | (8aS)-2-{[(7'aS)-dihydro-1'H,3'H-spiro[cyclopropane-1,2'-pyrrolizin]-7'a(5'H)-yl]methoxy}-5-(6-chloro-5-cyclopropyl-1H-indazol-4-yl)-4-fluoro-8a,9,12,13-tetrahydro-8H,11H-7,10-dioxa-1,3,6,13a-tetraazanaphtho[1,8-ab]heptalene | 632 [M + H]$^+$ | $^1$H NMR (400 MHz, MeOD) δ 7.90 and 7.84 (2s, 1H, major and minor rotamer respectively), 7.78 (s, 1H), 5.32-5.22 (m, 1H), 4.83-4.75 (m, 1H), 4.72-4.59 (m, 3H), 4.47-4.35 (m, 1H), 4.24 (td, J = 12.2, 4.2 Hz, 1H), 4.08-3.99 (m, 1H), 3.87 (ddd, J = 33.4, 12.3, 9.9 Hz, 1H), 3.69-3.42 (m, 4H), 3.29-3.21 (m, 1H), 3.18-3.12 (m, 1H), 2.33-1.99 (m, 9H), 0.99-0.88 (m, 1H), 0.86-0.80 (m, 2H), 0.77-0.67 (m, 3H), 0.37-0.13 (m, 2H). $^{19}$F NMR (376.5 MHz, MeOD) δ −144.42. [α] 25D = −56.67 (c 0.06, MeOH). |
| 19 (A) | (8aS)-2-{[(7'aR)-dihydro-1'H,3'H-spiro[cyclopropane-1,2'-pyrrolizin]-7'a(5'H)-yl]methoxy}-5-(6-chloro-5-cyclopropyl-1H-indazol-4-yl)-4-fluoro-8a,9,12,13-tetrahydro-8H,11H-7,10-dioxa-1,3,6,13a-tetraazanaphtho[1,8-ab]heptalene | 632 [M + H]$^+$ | $^1$H NMR (400 MHz, MeOD) δ 7.90 and 7.84 (2s, 1H, major and minor rotamer respectively), 7.78 (s, 1H), 5.32-5.22 (m, 1H), 4.83-4.58 (m, 4H), 4.47-4.35 (m, 1H), 4.24 (td, J = 12.1, 4.4 Hz, 1H), 4.07-3.98 (m, 1H), 3.87 (ddd, J = 33.2, 12.3, 9.9 Hz, 1H), 3.70-3.59 (m, 2H), 3.56-3.46 (m, 2H), 3.32-3.14 (m, 2H), 2.40-1.99 (m, 9H), 1.01-0.81 (m, 3H), 0.79-0.64 (m, 3H), 0.36-0.13 (m, 2H). $^{19}$F NMR (376.5 MHz, MeOD) δ −144.50. [α] 25D = −15.00 (c 0.06, MeOH). |
| 20 (A) | (8aS)-5-(5-cyclopropyl-1H-indazol-4-yl)-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 584 [M + H]$^+$ | $^1$H NMR (400 MHz, MeOD) δ 7.79 and 7.74 (2s, 1H, major and minor rotamer respectively), 7.60 (d, J = 8.8 Hz, 1H), 7.18 (d, J = 8.9 Hz, 1H), 5.30-5.22 (m, 1H), 5.17 (s, 2H), 4.77 (dd, J = 13.5, 4.4 Hz, 1H), 4.67-4.48 (m, 3H), 4.37 (s, 1H), 4.22 (d, J = 12.5 Hz, 1H), 4.12-3.97 (m, 2H), 3.95-3.76 (m, 1H), 3.70-3.56 (m, 2H), 3.54-3.43 (m, 2H), 3.06-2.90 (m, 2H), 2.67 (d, J = 15.8 Hz, 1H), 2.36-1.93 (m, 7H), 0.93-0.76 (m, 2H), 0.67 (s, 2H). $^{19}$F NMR (376.5 MHz, MeOD) δ −144.78. |

-continued

| Example Num (Gen. Method) | Structure IUPAC name | Low Res Mass Spec | ¹H NMR (ppm); ¹⁹F NMR (ppm); optical rotation; |
|---|---|---|---|
| 21 (B) | 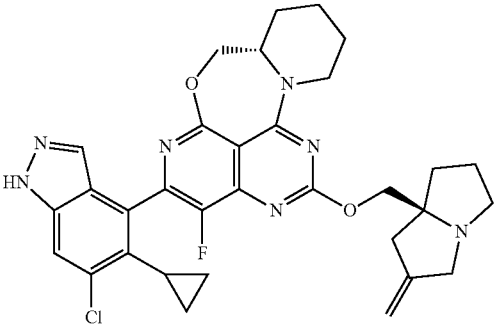 [SMILES: C=C1CN2CCC[C@@]2(COc2nc3c4c(nc(-c5c(C6CC6)c(Cl)cc6[nH]ncc56)c(F)c4n2)OC[C@@H]2CCCCN32)C1]<br>(8aS)-5-(6-chloro-5-cyclopropyl-1H-indazol-4-yl)-4-fluoro-2-{[(7aS)-2-methylidenetetrahydro-1H-pyrrolizin-7a(5H)-yl]methoxy}-8,8a,9,10,11,12-hexahydro-7-oxa-1,3,6,12a-tetraaza-benzo[4,5]cyclohepta[1,2,3-de]naphthalene | 602 [M + H]⁺ | ¹H NMR (400 MHz, MeOD) δ 7.84 and 7.79 (2s, 1H, major and minor rotamer respectively), 7.74 (s, 1H), 5.43-5.32 (m, 1H), 5.11 (s, 2H), 4.61-4.52 (m, 2H), 4.50-4.36 (m, 2H), 3.99 (d, J = 12.4 Hz, 2H), 3.56 (d, J = 14.1 Hz, 1H), 3.44-3.36 (m, 1H), 3.12 (td, J = 12.7, 1.3 Hz, 1H), 2.98-2.85 (m, 2H), 2.60 (d, J = 15.9 Hz, 1H), 2.29-2.17 (m, 1H), 2.09-1.93 (m, 6H), 1.90-1.80 (m, 3H), 1.71-1.57 (m, 1H), 0.96-0.82 (m, 1H), 0.72-0.60 (m, 1H), 0.32-0.09 (m, 2H).<br>¹⁹F NMR (376.5 MHz, MeOD) δ -143.90. |
| 22 (B) | 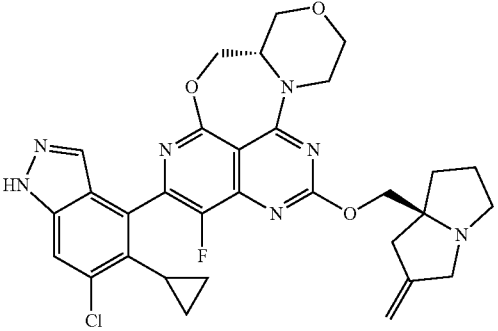 [SMILES: C=C1CN2CCC[C@@]2(COc2nc3c4c(nc(-c5c(C6CC6)c(Cl)cc6[nH]ncc56)c(F)c4n2)OC[C@@H]2COCCN32)C1]<br>(8aS)-5-(6-chloro-5-cyclopropyl-1H-indazol-4-yl)-4-fluoro-2-{[(7aS)-2-methylidenetetrahydro-1H-pyrrolizin-7a(5H)-yl]methoxy}-8a,9,11,12-tetrahydro-8H-7,10-dioxa-1,3,6,12a-tetraaza-benzo[4,5]cyclohepta[1,2,3-de]naphthalene | 604 [M + H]⁺ | ¹H NMR (400 MHz, MeOD) δ 7.82 (s, 1H), 7.76 (s, 1H), 5.24-5.14 (m, 3H), 4.62-4.51 (m, 4H), 4.28-4.18 (m, 1H), 4.18-4.01 (m, 3H), 3.74-3.64 (m, 3H), 3.59-3.50 (m, 1H), 3.44-3.34 (m, 1H), 3.13-3.00 (m, 1H), 2.96 (d, J = 15.8 Hz, 1H), 2.69 (d, J = 16.0 Hz, 1H), 2.37-2.25 (m, 1H), 2.22-1.98 (m, 4H), 0.98-0.86 (m, 1H), 0.73-0.59 (m, 1H), 0.32-0.23 (m, 1H), 0.21-0.12 (m, 1H).<br>¹⁹F NMR (376.5 MHz, MeOD) δ -143.60. |
| 23 (B) | 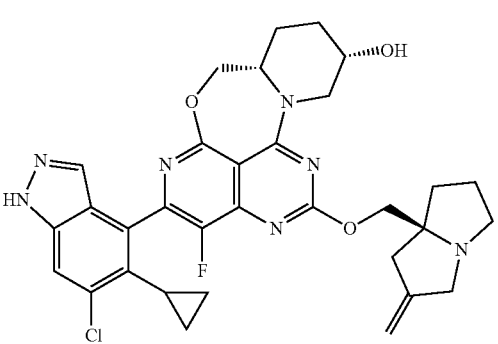 [SMILES: C=C1CN2CCC[C@@]2(COc2nc3c4c(nc(-c5c(C6CC6)c(Cl)cc6[nH]ncc56)c(F)c4n2)OC[C@@H]2CC[C@H](O)CN32)C1]<br>(8aS,11S)-5-(6-chloro-5-cyclopropyl-1H-indazol-4-yl)-4-fluoro-2-{[(7aS)-2-methylidenetetrahydro-1H-pyrrolizin-7a(5H)-yl]methoxy}-8,8a,9,10,11,12-hexahydro-7-oxa-1,3,6,12a-tetraazabenzo[4,5]cyclohepta[1,2,3-de]naphthalen-11-ol | 618 [M + H]⁺ | ¹H NMR (400 MHz, MeOD) δ 7.72 and 7.63 (2s, 1H, major and minor rotamer respectively), 7.60 (s, 1H), 5.34 (m, 1H), 5.04 (s, 2H), 4.46 (m, 3H), 4.37 (dd, J = 11.7, 7.5 Hz, 1H), 4.02 (m, 2H), 3.84 (d, J = 11.6 Hz, 1H), 3.57 (dd, J = 13.9, 4.1 Hz, 1H), 3.42 (m, 1H), 3.19 (m, 1H), 2.94 (m, 1H), 2.83 (d, J = 16.0 Hz, 1H), 2.54 (d, J = 15.9 Hz, 1H), 2.17 (m, 2H), 2.00 (m, 2H), 1.87 (m, 4H), 1.65 (m, 1H), 0.76 (m, 1H), 0.52 (m, 1H), 0.07 (m, 2H).<br>¹⁹F NMR (376.5 MHz, MeOD) δ -144.20. |

-continued

| Example Num (Gen. Method) | Structure IUPAC name | Low Res Mass Spec | ¹H NMR (ppm); ¹⁹F NMR (ppm); optical rotation; |
|---|---|---|---|
| 24 (B) | 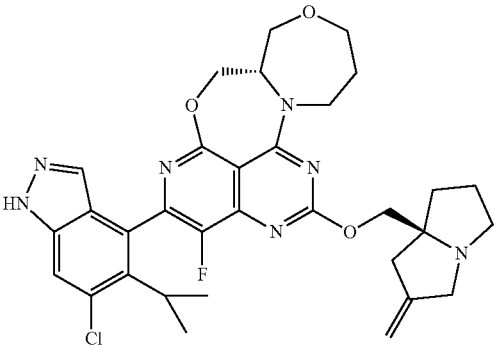 [SMILES: C=C1CN2CCC[C@@]2(COc2nc3c4c(nc(-c5c(C(C)C)c(Cl)cc6[nH]ncc56)c(F)c4n2)OC[C@@H]2COCCCN32)C1]<br>(8aS)-5-[6-chloro-5-(propan-2-yl)-1H-indazol-4-yl]-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 620 [M + H]⁺ | ¹H NMR (400 MHz, MeOD) δ 7.73 (s, 1H), 7.63 and 7.58 (2s, 1H, major and minor rotamer respectively), 5.28-5.21 (m, 1H), 5.16 (s, 2H), 4.75 (dd, J = 13.5, 4.3 Hz, 1H), 4.60 (dd, J = 13.4, 2.1 Hz, 1H), 4.52 (s, 2H), 4.39-4.30 (m, 1H), 4.20 (dd, J = 12.4, 4.3 Hz, 1H), 4.08 (d, J = 14.4 Hz, 1H), 4.00 (dt, J = 12.7, 5.1 Hz, 1H), 3.83 (ddd, J = 22.5, 12.4, 9.8 Hz, 1H), 3.70-3.57 (m, 2H), 3.52-3.43 (m, 2H), 3.29-3.14 (m, 1H), 3.07-2.97 (m, 1H), 2.94 (d, J = 15.7 Hz, 1H), 2.66 (d, J = 16.0 Hz, 1H), 2.31-1.94 (m, 6H), 1.49-1.24 (m, 6H). <br>¹⁹F NMR (376.5 MHz, MeOD) δ −145.28. |
| 25 (A) | 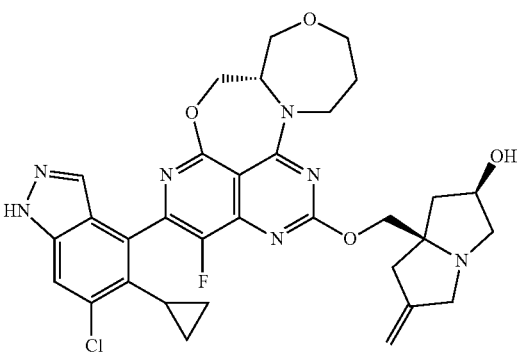 [SMILES: C=C1CN2C[C@H](O)C[C@@]2(COc2nc3c4c(nc(-c5c(C6CC6)c(Cl)cc6[nH]ncc56)c(F)c4n2)OC[C@@H]2COCCCN32)C1]<br>(2R,7aR)-7a-({[(8aS)-5-(6-chloro-5-cyclopropyl-1H-indazol-4-yl)-4-fluoro-8a,9,12,13-tetrahydro-8H,11H-7,10-dioxa-1,3,6,13a-tetraazanaphtho[1,8-ab]heptalen-2-yl]oxy}methyl)-6-methylidenehexahydro-1H-pyrrolizin-2-ol | 634 [M + H]⁺ | ¹H NMR (400 MHz, MeOD) δ 7.88 and 7.82 (2s, 1H, major and minor rotamer respectively), 7.76 (s, 1H), 5.28-5.21 (m, 3H), 4.81-4.78 (m, 1H), 4.77-4.75 (m, 1H), 4.72-4.61 (m, 2H), 4.59-4.55 (m, 1H), 4.44 - 4.33 (m, 1H), 4.22 (td, J = 12.2, 4.2 Hz, 2H), 4.01 (dt, J = 12.0, 5.0 Hz, 1H), 3.84 (ddd, J = 34.1, 12.3, 9.9 Hz, 1H), 3.70 (d, J = 14.0 Hz, 1H), 3.65-3.56 (m, 1H), 3.54-3.44 (m, 2H), 3.15-3.07 (m, 2H), 2.65 (d, J = 15.8 Hz, 1H), 2.32 (d, J = 14.3 Hz, 1H), 2.27-2.16 (m, 2H), 2.08-1.95 (m, 2H), 0.99-0.84 (m, 1H), 0.76 - 0.61 (m, 1H), 0.34-0.10 (m, 2H). <br>¹⁹F NMR (376.5 MHz, MeOD) δ −144.30. |
| 26 (A) | 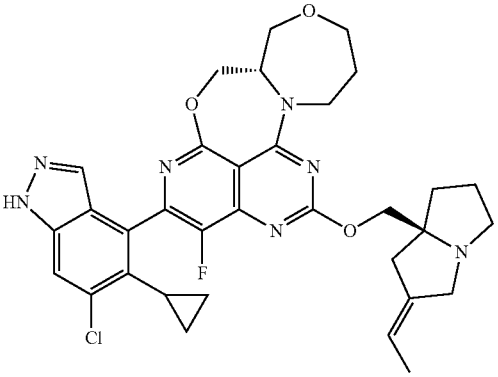 [SMILES: C/C=C1\CN2CCC[C@@]2(COc2nc3c4c(nc(-c5c(C6CC6)c(Cl)cc6[nH]ncc56)c(F)c4n2)OC[C@@H]2COCCCN32)C1]<br>(8aS)-5-(6-chloro-5-cyclopropyl-1H-indazol-4-yl)-2-{[(2Z,7aS)-2-ethylidenetetrahydro-1H-pyrrolizin-7a(5H)-yl]methoxy}-4-fluoro-8a,9,12,13-tetrahydro-8H,11H-7,10-dioxa-1,3,6,13a-tetraaza-naphtho[1,8-ab]heptalene | 632 [M + H]⁺ | ¹H NMR (400 MHz, MeOD) δ 7.87 and 7.80 (2s, 1H, major and minor rotamer respectively), 7.76 (s, 1H), 5.71 (q, J = 6.5 Hz, 1H), 5.23 (dtd, J = 9.3, 6.5, 2.9 Hz, 1H), 4.81-4.73 (m, 1H), 4.71-4.55 (m, 3H), 4.45-4.36 (m, 1H), 4.32 (d, J = 14.6 Hz, 1H), 4.21 (td, J = 12.1, 4.4 Hz, 1H), 4.04-3.96 (m, 2H), 3.92-3.74 (m, 2H), 3.62 (ddt, J = 12.3, 8.0, 4.0 Hz, 1H), 3.55-3.43 (m, 1H), 3.29-3.21 (m, 1H), 3.00 (d, J = 15.4 Hz, 1H), 2.76 (d, J = 14.7 Hz, 1H), 2.42-2.33 (m, 1H), 2.30-2.09 (m, 4H), 2.07-1.93 (m, 2H), 1.70 (d, J = 6.8 Hz, 3H), 0.98-0.84 (m, 1H), 0.74-0.62 (m, 1H), 0.34-0.11 (m, 2H). <br>¹⁹F NMR (376.5 MHz, MeOD) δ −144.59. |

| Example Num (Gen. Method) | Structure IUPAC name | Low Res Mass Spec | $^1$H NMR (ppm); $^{19}$F NMR (ppm); optical rotation; |
|---|---|---|---|
| 27 (A) | 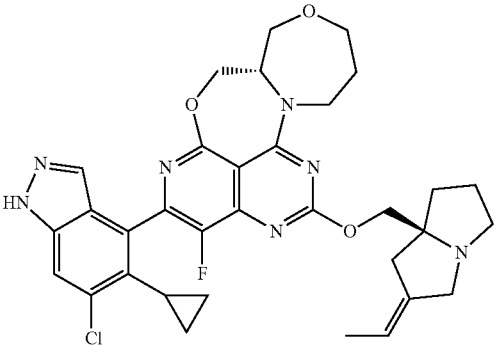 [SMILES: C/C=C1/CN2CCC[C@@]2(COc2nc3c4c(nc(-c5c(C6CC6)c(Cl)cc6[nH]ncc56)c(F)c4n2)OC[C@@H]2COCCCN32)C1]<br>(8aS)-5-(6-chloro-5-cyclopropyl-1H-indazol-4-yl)-2-{[(2E,7aS)-2-ethylidenetetrahydro-1H-pyrrolizin-7a(5H)-yl]methoxy}-4-fluoro-8a,9,12,13-tetrahydro-8H,11H-7,10-dioxa-1,3,6,13a-tetraaza-naphtho[1,8-ab]heptalene | 632 [M + H]$^+$ | $^1$H NMR (400 MHz, MeOD) δ 7.87 and 7.81 (2s, 1H, major and minor rotamer respectively), 7.75 (s, 1H), 5.61 (q, J = 7.1 Hz, 1H), 5.23 (dtd, J = 9.2, 6.3, 2.9 Hz, 1H), 4.77 (ddd, J = 13.4, 4.1, 2.1 Hz, 1H), 4.67-4.49 (m, 3H), 4.44-4.32 (m, 1H), 4.21 (td, J = 12.0, 4.3 Hz, 1H), 4.10-3.96 (m, 2H), 3.84 (ddd, J = 34.1, 12.3, 9.9 Hz, 1H), 3.68-3.56 (m, 2H), 3.54-3.42 (m, 2H), 3.06-2.96 (m, 1H), 2.87 (d, J = 16.4 Hz, 1H), 2.64 (d, J = 16.3 Hz, 1H), 2.35-2.26 (m, 1H), 2.24-1.95 (m, 6H), 1.69 (d, J = 6.7 Hz, 3H), 0.98-0.83 (m, 1H), 0.74-0.62 (m, 1H), 0.34-0.10 (m, 2H).<br>19F NMR (376.5 MHz, MeOD) δ −144.26. |
| 28 (A) | 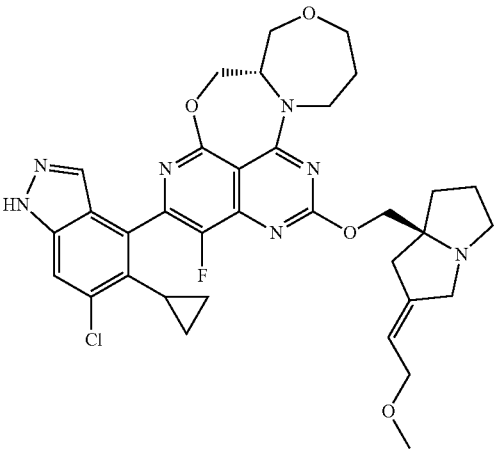 [SMILES: COC/C=C1\CN2CCC[C@@]2(COc2nc3c4c(nc(-c5c(C6CC6)c(Cl)cc6[nH]ncc56)c(F)c4n2)OC[C@@H]2COCCCN32)C1]<br>(8aS)-5-(6-chloro-5-cyclopropyl-1H-indazol-4-yl)-4-fluoro-2-{[(2Z,7aS)-2-(2-methoxyethylidene)tetra-hydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 662 [M + H]$^+$ | $^1$H NMR (400 MHz, MeOD) δ 7.87 and 7.81 (2s, 1H, major and minor rotamer respectively), 7.76 (s, 1H), 5.68-5.59 (m, 1H), 5.23 (dtd, J = 9.5, 6.4, 2.9 Hz, 1H), 4.77 (ddd, J = 13.5, 4.3, 2.2 Hz, 1H), 4.65-4.57 (m, 1H), 4.53-4.45 (m, 2H), 4.43-4.32 (m, 1H), 4.21 (td, J = 12.0, 4.3 Hz, 1H), 4.08 (d, J = 14.7 Hz, 1H), 4.04-3.96 (m, 1H), 3.96-3.91 (m, 2H), 3.88 and 3.80 (2dd, J = 12.4, 9.9 Hz, 1H, major and minor rotamer respectively), 3.70 (d, J = 14.5 Hz, 1H), 3.65-3.57 (m, 1H), 3.51-3.40 (m, 2H), 3.32 (s, 3H), 3.03-2.89 (m, 2H), 2.68 (d, J = 16.1 Hz, 1H), 2.32-2.16 (m, 2H), 2.13-1.93 (m, 5H), 0.99-0.83 (m, 1H), 0.73-0.61 (m, 1H), 0.36-0.08 (m, 2H). |
| 29 (A) | 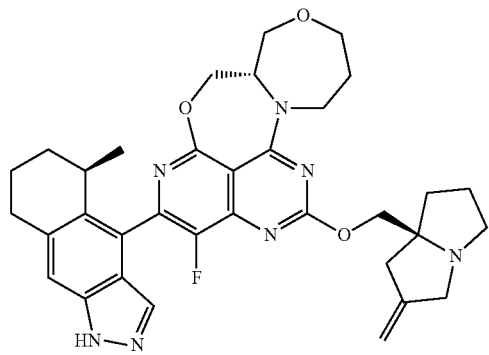 [SMILES: C=C1CN2CCC[C@@]2(COc2nc3c4c(nc(-c5c6c(cc7[nH]ncc57)CCC[C@H]6C)c(F)c4n2)OC[C@@H]2COCCCN32)C1]<br>(8aS)-4-fluoro-2-{[(7aS)-2-methylidenetetrahydro-1H-pyrrolizin-7a(5H)-yl]methoxy}-5-[(5R)-5-methyl-5,6,7,8-tetrahydro-1H-benzo[f]indazol-4-yl]-8a,9,12,13-tetrahydro-8H,11H-7,10-dioxa-1,3,6,13a-tetraaza-naphtho[1,8-ab]heptalene<br>(stereochemistry of tricyclicindazole confirmed by protein co-crystalography) | 612 [M + H]$^+$ | $^1$H NMR (400 MHz, MeOD) δ 7.65 and 7.55 (2s, 1H, major and minor rotamer respectively), 7.38 (s, 1H), 5.24 (dtd, J = 8.9, 6.0, 2.9 Hz, 1H), 5.16 (s, 2H), 4.75 (dt, J = 13.4, 4.0 Hz, 1H), 4.62 (dd, J = 13.3, 5.3 Hz, 1H), 4.57-4.46 (m, 2H), 4.42-4.30 (m, 1H), 4.18 (ddd, J = 12.4, 4.1, 2.6 Hz, 1H), 4.08 (d, J = 14.5 Hz, 1H), 3.99 (dt, J = 12.6, 5.1 Hz, 1H), 3.81 and 3.77 (2dd, J = 12.4, 9.9 Hz, 1H, major and minor rotamer respectively), 3.68-3.55 (m, 2H), 3.54-3.42 (m, 2H), 3.23-2.85 (m, 5H), 2.65 (d, J = 15.7 Hz, 1H), 2.34-1.89 (m, 8H), 1.88-1.64 (m, 2H), 0.99 and 0.98 (2d, J = 6.9 Hz, 3H, major and minor rotamer respectively). Stereochemistry of chiral methyl unknown at time of filing. Derived from intermediate I9 |

-continued

| Example Num (Gen. Method) | Structure IUPAC name | Low Res Mass Spec | $^1$H NMR (ppm); $^{19}$F NMR (ppm); optical rotation; |
|---|---|---|---|
| 30 (A) | 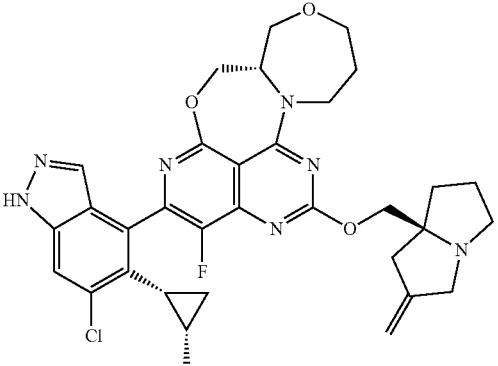<br>(8aS)-5-{6-chloro-5-[(1R*,2S*)-2-methylcyclopropyl]-1H-indazol-4-yl}-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene (*Unknown absolutestereochemistry. Cis stereochemistry. Isomer A) | 632 [M + H]$^+$ | $^1$H NMR (400 MHz, MeOD) δ 7.86 and 7.79 (2s, 1H, major and minor rotamer respectively), 7.78 (s, 1H), 5.29-5.19 (m, 1H), 5.15 (s, 2H), 4.82-4.70 (m, 1H), 4.60 and 4.59 (2d, J = 13.4 Hz, 1H, major and minor rotamer respectively), 4.56-4.47 (m, 2H), 4.41-4.31 (m, 1H), 4.29-4.12 (m, 1H), 4.13-3.96 (m, 2H), 3.91 and 3.77 (2dd, J = 12.4, 9.8 Hz, J = 12.2, 10.1 Hz, 1H, major and minor rotamer respectively), 3.69-3.54 (m, 2H), 3.54-3.40 (m, 2H), 3.07-2.98 (m, 1H), 2.94 (d, J = 16.0 Hz, 1H), 2.66 (d, J = 15.9 Hz, 1H), 2.34-1.91 (m, 7H), 1.36-1.18 (m, 1H), 0.77 (td, J = 8.2, 5.1 Hz, 1H), 0.70 and 0.65 (2d, J = 6.2 Hz, J = 5.2 Hz, 3H, major and minor rotamer respectively), −0.18−−0.41 (m, 1H). [α]$_{D25}$ = +108.7 (c 0.15, MeOH). |
| 31 (A) | 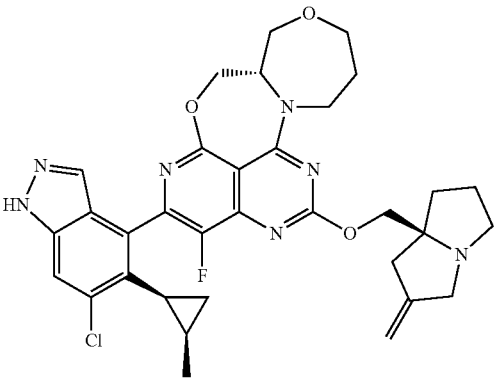 [SMILES: C=C1CN2CCC[C@@]2(COc2nc3c4c(nc(-c5c([C@H]6C[C@H]6C)c(Cl)cc6[nH]ncc56)c(F)c4n2)OC[C@@H]2COCCCN32)C1]<br>(8aS)-5-{6-chloro-5-[(1S*,2R*)-2-methylcyclopropyl]-1H-indazol-4-yl}-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene (*Unknown absolutestereochemistry. Cis stereochemistry. Isomer B) | 632 [M + H]$^+$ | $^1$H NMR (400 MHz, MeOD) δ 7.91 and 7.71 (2s, 1H, major and minor rotamer respectively), 7.77 (s, 1H), 5.31-5.16 (m, 1H), 5.11 (s, 2H), 4.81-4.70 (m, 1H), 4.64 and 4.58 (2d, J = 13.4 Hz, 1H, major and minor rotamer respectively), 4.52-4.41 (m, 2H), 4.41-4.29 (m, 1H), 4.22-4.14 (m, 1H), 4.03-3.93 (m, 2H), 3.79 (dd, J = 12.3, 10.0 Hz, 1H), 3.65-3.53 (m, 2H), 3.51-3.35 (m, 2H), 2.98-2.86 (m, 2H), 2.61 (d, J = 15.9 Hz, 1H), 2.31-1.90 (m, 7H), 1.32-1.18 (m, 1H), 0.91-0.70 (m, 1H), 0.67 (d, J = 6.1 Hz, 3H), −0.13−−0.44 (m, 1H). [α]$_{D25}$ = −169.3 (c 0.15, MeOH). |
| 32 (A) | 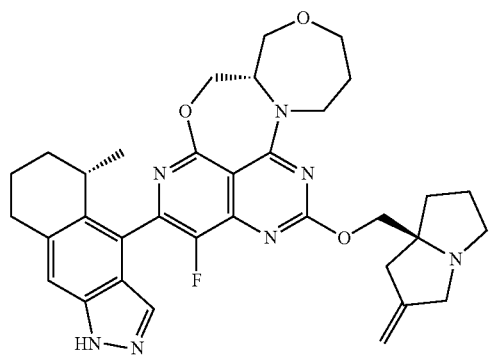 [SMILES: C=C1CN2CCC[C@@]2(COc2nc3c4c(nc(-c5c6c(cc7[nH]ncc57)CCC[C@@H]6C)c(F)c4n2)OC[C@@H]2COCCCN32)C1]<br>(8aS)-4-fluoro-2-{[(7aS)-2-methylidenetetrahydro-1H-pyrrolizin-7a(5H)-yl]methoxy}-5-[(5S)-5-methyl-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene (singleenantiomer,stereochemistry inferred by eutomer co-crystal) | 612 [M + H]$^+$ | $^1$H NMR (400 MHz, MeOD) δ 7.61 (s, 1H), 7.40 (s, 1H), 5.29-5.16 (m, 3H), 4.80-4.72 (m, 1H), 4.63-4.53 (m, 3H), 4.41-4.33 (m, 1H), 4.23 (dt, J = 12.3, 4.5 Hz, 1H), 4.13 (d, J = 14.2 Hz, 1H), 4.02 (dt, J = 10.5, 5.0 Hz, 1H), 3.91 and 3.85 (2dd, J = 12.4, 9.8 Hz, 1H, minor and major rotamer respectively), 3.73-3.60 (m, 2H), 3.58-3.43 (m, 2H), 3.29-2.93 (m, 5H), 2.69 (d, J = 15.8 Hz, 1H), 2.37-1.96 (m, 8H), 1.87-1.70 (m, 2H), 1.06 and 0.96 (2d, J = 7.1 Hz, 3H, minor and major rotamer respectively). |

| Example Num (Gen. Method) | Structure IUPAC name | Low Res Mass Spec | $^1$H NMR (ppm); $^{19}$F NMR (ppm); optical rotation; |
|---|---|---|---|
| 33 (B) | 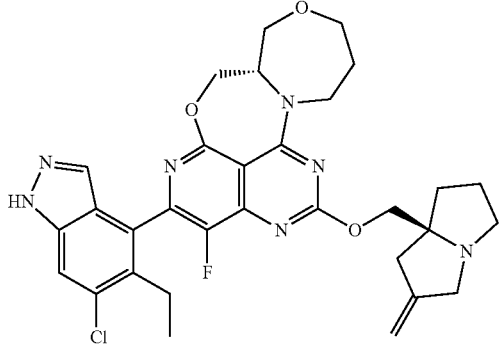 [SMILES: C=C1CN2CCC[C@@]2(COc2nc3c4c(nc(-c5c(CC)c(Cl)cc6[nH]ncc56)c(F)c4n2)OC[C@@H]2COCCCN32)C1] (8aS)-5-(6-chloro-5-ethyl-1H-indazol-4-yl)-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 606 [M + H]$^+$ | $^1$H NMR (400 MHz, MeOD) δ 7.77 and 7.77 (2s, 1H, major and minor rotamer respectively), 7.69 and 7.65 (2 s, 1H, major and minor rotamer respectively), 5.29-5.14 (m, 3H), 4.75 (dd, J = 13.5, 4.4 Hz, 1H), 4.64-4.51 (m, 3H), 4.40-4.32 (m, 1H), 4.20 (dd, J = 12.4, 4.3 Hz, 1H), 4.14 (d, J = 14.0 Hz, 1H), 4.00 (ddd, J = 12.7, 5.7, 4.8 Hz, 1H), 3.83 (td, J = 13.0, 10.1 Hz, 1H), 3.70 (d, J = 14.1 Hz, 1H), 3.65-3.42 (m, 3H), 3.11 - 3.01 (m, 1H), 2.97 (d, J = 16.0 Hz, 1H), 2.92-2.65 (m, 3H), 2.36-2.26 (m, 1H), 2.24-1.94 (m, 5H), 1.13 and 1.11 (2 t, J = 7.5 Hz, 3H, major and minor rotamer respectively). |
| 34 (C) | 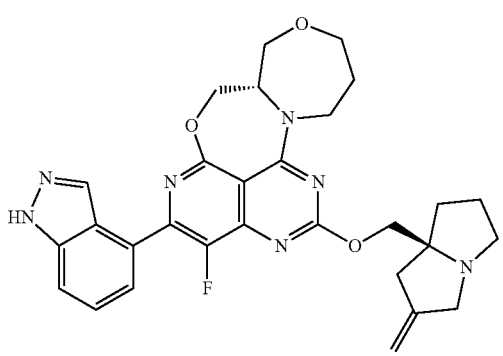 [SMILES: C=C1CN2CCC[C@@]2(COc2nc3c4c(nc(-c5cccc6[nH]ncc56)c(F)c4n2)OC[C@@H]2COCCCN32)C1] (8aS)-4-fluoro-5-(1H-indazol-4-yl)-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 544 [M + H]$^+$ | $^1$H NMR (400 MHz, MeOD) δ 8.40 (s, 1H), 7.72 (d, J = 7.9 Hz, 2H), 7.60-7.54 (m, 1H), 5.32-5.27 (m, 2H), 5.22 (ddd, J = 13.7, 6.2, 2.8 Hz, 1H), 4.80 (dd, J = 13.6, 4.4 Hz, 1H), 4.65 (m , 3H), 4.42-4.31 (m, 2H), 4.24 (dd, J = 12.4, 4.2 Hz, 1H), 4.01 (dt, J = 10.4, 4.9 Hz, 1H), 3.91-3.80 (m, 2H), 3.79-3.71 (m, 1H), 3.58 (ddd, J = 12.5, 8.1, 4.2 Hz, 1H), 3.52-3.43 (m, 1H), 3.28-3.19 (m, 1H), 3.07 (d, J = 15.9 Hz, 1H), 2.79 (d, J = 15.9 Hz, 1H), 2.45-2.35 (m, 1H), 2.31-2.09 (m, 4H), 2.05-1.93 (m, 1H). $^{19}$F NMR (376.5 MHz, MeOD) δ −146.69. |
| 35 (A) | 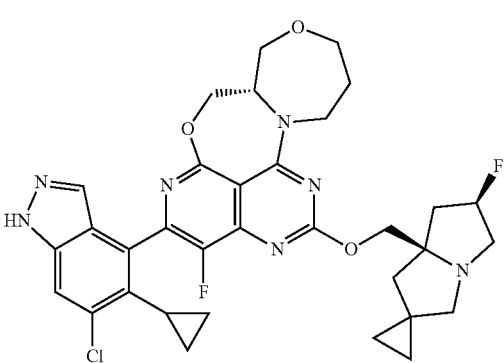 [SMILES: Fc1c(-c2c(C3CC3)c(Cl)cc3[nH]ncc23)nc2c3c(nc(OC[C@@]45C[C@@H](F)CN4CC4(CC4)C5)nc13)N1CCCOC[C@H]1CO2] (8aS)-2-{[(6'R,7'aR)-6'-fluorodihydro-1'H,3'H-spiro[cyclopropane-1,2'-pyrrolizin]-7'a(5'H)-yl]methoxy}-5-(6-chloro-5-cyclopropyl-1H-indazol-4-yl)-4-fluoro-8a,9,12,13-tetrahydro-8H,11H-7,10-dioxa-1,3,6,13a-tetraazanaphtho[1,8-ab]heptalene | 650 [M + H]$^+$ | $^1$H NMR (400 MHz, MeOD) δ 7.87 and 7.82 (2s, 1H, major and minor rotamer respectively), 7.75 (s, 1H), 5.48 (d, J = 52.1 Hz, 1H), 5.25 (tdd, J = 9.0, 6.0, 2.8 Hz, 1H), 4.77 (ddd, J = 13.4, 4.3, 2.1 Hz, 1H), 4.65-4.57 (m, 3H), 4.42-4.33 (m, 1H), 4.21 (td, J = 12.1, 4.3 Hz, 1H), 4.03-3.97 (m, 1H), 3.90-3.70 (m, 2H), 3.63-3.56 (m, 1H), 3.56-3.34 (m, 3H), 2.89 (d, J = 11.1 Hz, 1H), 2.72-2.60 (m, 1H), 2.48-2.27 (m, 2H), 2.25-2.12 (m, 1H), 2.10-1.94 (m, 2H), 1.86 (d, J = 13.2 Hz, 1H), 0.99-0.86 (m, 1H), 0.82-0.74 (m, 2H), 0.73-0.61 (m, 3H), 0.32-0.12 (m, 2H). $^{19}$F NMR (376.5 MHz, MeOD) δ −144.19, −176.83. |

| Example Num (Gen. Method) | Structure IUPAC name | Low Res Mass Spec | $^1$H NMR (ppm); $^{19}$F NMR (ppm); optical rotation; |
|---|---|---|---|
| 36 (A) | 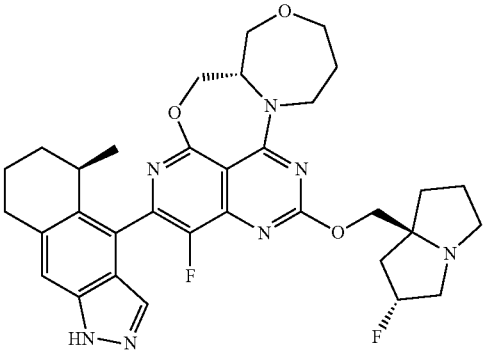 [SMILES: C[C@@H]1CCCc2cc3[nH]ncc3c(-c3nc4c5c(nc(OC[C@@]67CCCN6C[C@H](F)C7)nc5c3F)N3CCCOC[C@H]3CO4)c21]<br>(8aS)-4-fluoro-2-{[(2R,7aS)-2-fluorotetrahydro-1H-pyrrolizin-7a(5H)-yl]methoxy}-5-[(5R)-5-methyl-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene | 618 [M + H]$^+$ | $^1$H NMR (400 MHz, MeOD) δ 7.65 and 7.54 (2s, 1H, major and minor rotamer respectively), 7.38 (s, 1H), 5.46 (d, J = 52.9 Hz, 1H), 5.28-5.20 (m, 1H), 4.76 and 4.75 (2dd, J = 13.4, 4.1 Hz, 1H, major and minor rotamer respectively), 4.62 and 4.61 (2d, J = 13.4 Hz, 1H, major and minor rotamer respectively), 4.58-4.45 (m, 2H), 4.42-4.32 (m, 1H), 4.22-4.14 (m, 1H), 3.99 (dt, J = 12.8, 5.1 Hz, 1H), 3.85-3.42 (m, 7H), 3.27-2.94 (m, 3H), 2.62-2.37 (m, 2H), 2.34-2.14 (m, 4H), 2.10-1.89 (m, 4H), 1.85-1.69 (m, 2H), 0.99 and 0.98 (2d, J = 7.0 Hz, 3H, major and minor rotamer respectively).<br>$^{19}$F NMR (376.5 MHz, MeOD) δ −145.48, −173.90. |
| 37 (A) | 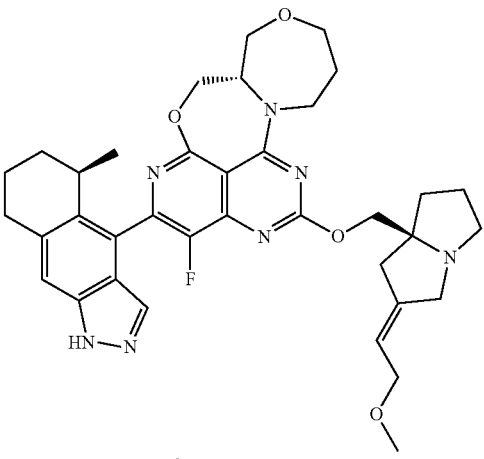 [SMILES: COC/C=C1\CN2CCC[C@@]2(COc2nc3c4c(nc(-c5c6c(cc7[nH]ncc57)CCC[C@H]6C)c(F)c4n2)OC[C@@H]2COCCCN32)C1]<br>(8aS)-4-fluoro-2-{[(2Z,7aS)-2-(2-methoxyethylidene)tetrahydro-1H-pyrrolizin-7a(5H)-yl]methoxy}-5-[(5R)-5-methyl-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene | 656 [M + H]$^+$ | $^1$H NMR (400 MHz, MeOD) δ 7.64 and 7.54 (2s, 1H, major and minor rotamer respectively), 7.39 (s, 1H), 5.79-5.72 (m, 1H), 5.27-5.18 (m, 1H), 4.76 and 4.75 (2dd, J = 13.4, 4.3 Hz, 1H, major and minor rotamer respectively), 4.71-4.58 (m, 3H), 4.44-4.32 (m, 2H), 4.22-4.14 (m, 1H), 4.07-3.93 (m, 4H), 3.84-3.70 (m, 2H), 3.65-3.41 (m, 3H), 3.31 (s, 3H), 3.25-2.97 (m, 4H), 2.82 (d, J = 16.1 Hz, 1H), 2.39-2.08 (m, 5H), 2.07-1.89 (m, 3H), 1.85-1.69 (m, 2H), 0.99 and 0.97 (2d, J = 7.3 Hz, 3H, major and minor rotamer respectively).<br>$^{19}$F NMR (376.5 MHz, MeOD) δ −145.72. |
| 38 (C) | 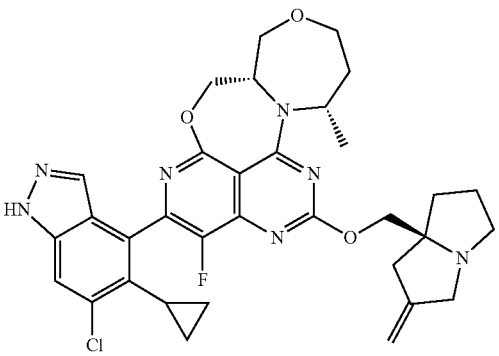 [SMILES: C=C1CN2CCC[C@@]2(COc2nc3c4c(nc(-c5c(C6CC6)c(Cl)cc6[nH]ncc56)c(F)c4n2)OC[C@@H]2COCC[C@H](C)N32)C1]<br>(8aS,13S)-5-(6-chloro-5-cyclopropyl-1H-indazol-4-yl)-4-fluoro-13-methyl-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 632 [M + H]$^+$ | $^1$H NMR (400 MHz, MeOD) δ 7.86 and 7.82 (2s, 1H, minor and major rotamer respectively), 7.77 (s, 1H), 5.27 (s, 2H), 4.79-4.65 (m, 3H), 4.65-4.52 (m, 2H), 4.43-4.23 (m, 3H), 4.07 (ddd, J = 12.7, 6.1, 2.2 Hz, 1H), 3.95-3.69 (m, 3H), 3.53-3.40 (m, 1H), 3.27-3.20 (m, 1H), 3.04 (d, J = 16.0 Hz, 1H), 2.80 (d, J = 16.2 Hz, 1H), 2.56-2.45 (m, 1H), 2.43-2.32 (m, 1H), 2.29-1.98 (m, 5H), 1.85 (d, J = 6.8 Hz, 3H), 1.00-0.80 (m, 1H), 0.74-0.63 (m, 1H), 0.35-0.09 (m, 2H).<br>$^{19}$F NMR (376.5 MHz, MeOD) δ −144.31. |

-continued

| Example Num (Gen. Method) | Structure IUPAC name | Low Res Mass Spec | ¹H NMR (ppm); ¹⁹F NMR (ppm); optical rotation; |
|---|---|---|---|
| 39 (A) | (8aS)-5-[6-chloro-5-(1-methylcyclopropyl)-1H-indazol-4-yl]-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 632 [M + H]⁺ | ¹H NMR (400 MHz, MeOD) δ 7.75 (s, 1H), 7.73-7.60 (m, 1H), 5.30-5.17 (m, 3H), 4.75 (dd, J = 13.5, 4.4 Hz, 1H), 4.69-4.53 (m, 3H), 4.46-4.32 (m, 1H), 4.27-4.14 (m, 2H), 4.06-3.95 (m, 1H), 3.86-3.70 (m, 2H), 3.69-3.56 (m, 2H), 3.54-3.41 (m, 1H), 3.16-3.06 (m, 1H), 3.00 (d, J = 15.9 Hz, 1H), 2.71 (d, J = 16.1 Hz, 1H), 2.40-2.28 (m, 1H), 2.25-2.13 (m, 2H), 2.12-1.93 (m, 3H), 1.58-1.39 (m, 3H), 0.88-0.77 (m, 1H), 0.76-0.39 (m, 2H), 0.37-0.14 (m, 1H). ¹⁹F NMR (376.5 MHz, MeOD) δ −148.62. |
| 40 (C) | (8aS)-5-(6-chloro-5-cyclopropyl-1H-indazol-4-yl)-2-{[(7aS)-2-cyclopropylidenetetrahydro-1H-pyrrolizin-7a(5H)-yl]methoxy}-4-fluoro-8a,9,12,13-tetrahydro-8H,11H-7,10-dioxa-1,3,6,13a-tetraazanaphtho[1,8-ab]heptalene | 644 [M + H]⁺ | ¹H NMR (400 MHz, MeOD) δ 7.87 and 7.81 (2s, 1H, major and minor rotamer respectively), 7.76 (s, 1H), 5.29-5.17 (m, 1H), 4.80-4.73 (m, 1H), 4.68-4.55 (m, 3H), 4.44-4.33 (m, 1H), 4.30-4.16 (m, 2H), 4.00 (dt, J = 10.7, 5.1 Hz, 1H), 3.92-3.75 (m, 2H), 3.67-3.55 (m, 2H), 3.54-3.42 (m, 1H), 3.16-3.01 (m, 2H), 2.79 (d, J = 15.5 Hz, 1H), 2.38-2.28 (m, 1H), 2.23-1.94 (m, 6H), 1.24-1.06 (m, 4H), 0.99-0.83 (m, 1H), 0.76-0.63 (m, 1H), 0.35-0.10 (m, 2H). ¹⁹F NMR (376.5 MHz, MeOD) δ −144.40. |
| 41 (C) | (8aS)-5-(6-chloro-5-cyclopropyl-1H-indazol-4-yl)-4-fluoro-2-{[(7aS)-2-(oxetan-3-ylidene)tetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 660 [M + H]⁺ | ¹H NMR (400 MHz, MeOD) δ 7.87 and 7.81 (2s, 1H, major and minor rotamer respectively), 7.76 (s, 1H), 5.32-5.08 (m, 5H), 4.82-4.68 (m, 3H), 4.63 and 4.61 (2d, J = 13.4 Hz, 1H, major and minor rotamer respectively), 4.45-4.35 (m, 1H), 4.30-4.15 (m, 2H), 4.05-3.95 (m, 1H), 3.92-3.73 (m, 3H), 3.67-3.56 (m, 1H), 3.55-3.43 (m, 1H), 3.30-3.25 (m, 1H), 2.90 (d, J = 16.0 Hz, 1H), 2.66 (d, J = 15.4 Hz, 1H), 2.39-2.14 (m, 5H), 2.10-1.94 (m, 2H), 0.97-0.85 (m, 1H), 0.74-0.61 (m, 1H), 0.37-0.10 (m, 2H). ¹⁹F NMR (376.5 MHz, MeOD) δ −144.66. |

| Example Num (Gen. Method) | Structure IUPAC name | Low Res Mass Spec | $^1$H NMR (ppm); $^{19}$F NMR (ppm); optical rotation; |
|---|---|---|---|
| 42 (C) | 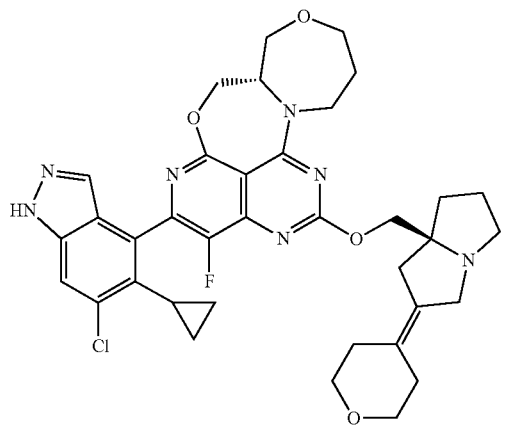 [SMILES: Fc1c(-c2c(C3CC3)c(Cl)cc3[nH]ncc23)nc2c3c(nc(OC[C@@]45CCCN4CC(=C4CCOCC4)C5)nc13)N1CCCOC[C@H]1CO2]<br>(8aS)-5-(6-chloro-5-cyclopropyl-1H-indazol-4-yl)-4-fluoro-2-{[(7aS)-2-(oxan-4-ylidene)tetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 688 [M + H]$^+$ | $^1$H NMR (400 MHz, MeOD) δ 7.86 and 7.80 (2s, 1H, major and minor rotamer respectively), 7.76 (s, 1H), 5.28-5.18 (m, 1H), 4.77 and 4.76 (2dd, J = 13.4, 4.2 Hz, 1H, major and minor rotamer respectively), 4.67-4.54 (m, 3H), 4.44-4.33 (m, 1H), 4.25-4.14 (m, 2H), 4.04-3.95 (m, 1H), 3.91-3.75 (m, 2H), 3.69-3.54 (m, 6H), 3.53-3.42 (m, 1H), 3.15-3.05 (m, 1H), 2.95 (d, J = 16.5 Hz, 1H), 2.71 (d, J = 15.9 Hz, 1H), 2.31-2.15 (m, 7H), 2.13-1.97 (m, 4H), 0.98-0.83 (m, 1H), 0.74-0.63 (m, 1H), 0.35-0.10 (m, 2H). $^{19}$F NMR (376.5 MHz, MeOD) δ −144.37. |
| 43 (C) | 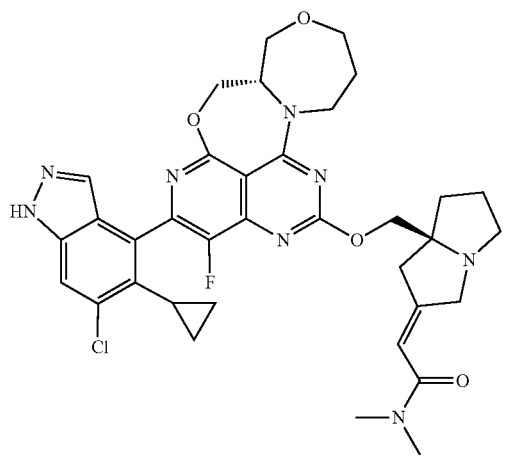 [SMILES: CN(C)C(=O)/C=C1\CN2CCC[C@@]2(COc2nc3c4c(nc(-c5c(C6CC6)c(Cl)cc6[nH]ncc56)c(F)c4n2)OC[C@@H]2COCCCN32)C1]<br>(2Z)-2-[(7aS)-7a-({[(8aS)-5-(6-chloro-5-cyclopropyl-1H-indazol-4-yl)-4-fluoro-8a,9,12,13-tetrahydro-8H,11H-7,10-dioxa-1,3,6,13a-tetraazanaphtho[1,8-ab]heptalen-2-yl]oxy}methyl)tetrahydro-1H-pyrrolizin-2(3H)-ylidene]-N,N-dimethylacetamide | 689 [M + H]$^+$ | $^1$H NMR (400 MHz, MeOD) δ 7.87 and 7.81 (2s, 1H, major and minor rotamer respectively), 7.75 (s, 1H), 5.62 (s, 1H), 5.26-5.17 (m, 1H), 4.76 and 4.76 (2dd, J = 13.5, 4.3 Hz, 1H, major and minor rotamer respectively), 4.60 ( m, 2H), 4.50-4.41 (m, 1H), 4.40-4.29 (m, 1H), 4.26-4.10 (m, 2H), 4.06-3.94 (m, 1H), 3.88 and 3.79 (2dd, J = 12.4, 9.9 Hz, 1H, major and minor rotamer respectively), 3.69-3.53 (m, 2H), 3.52-3.32 (m, 3H), 3.29-3.23 (m, 1H), 3.05 and 3.04 (2s, 3H, major and minor rotamer respectively), 3.00-2.93 (m, 1H), 2.92 and 2.92 (2s, 3H, major and minor rotamer respectively), 2.28-1.86 (m, 7H), 1.00-0.82 (m, 1H), 0.76-0.59 (m, 1H), 0.35-0.08 (m, 2H). $^{19}$F NMR (376.5 MHz, MeOD) δ −144.25. |

| Example Num (Gen. Method) | Structure IUPAC name | Low Res Mass Spec | ¹H NMR (ppm); ¹⁹F NMR (ppm); optical rotation; |
|---|---|---|---|
| 44 (A) | (2Z)-2-[(7aS)-7a-({[(8aS)-5-(6-chloro-5-cyclopropyl-1H-indazol-4-yl)-4-fluoro-8a,9,12,13-tetrahydro-8H,11H-7,10-dioxa-1,3,6,13a-tetraazanaphtho[1,8-ab]heptalen-2-yl]oxy}methyl)tetrahydro-1H-pyrrolizin-2(3H)-ylidene]ethan-1-ol | 648 [M + H]⁺ | ¹H NMR (400 MHz, MeOD) δ 7.87 and 7.81 (2s, 1H, major and minor rotamer respectively), 7.75 (s, 1H), 5.67-5.59 (m, 1H), 5.28-5.18 (m, 1H), 4.76 and 4.76 (2dd, J = 13.3, 4.3 Hz, 1H, major and minor rotamer respectively), 4.65-4.56 (m, 1H), 4.48-4.31 (m, 3H), 4.22 and 4.19 (2dd, J = 12.0, 4.2 Hz, 1H, major and minor rotamer respectively), 4.06 (d, J = 6.3 Hz, 2H), 4.04-3.95 (m, 2H), 3.88 and 3.79 (2dd, J = 12.4, 9.8 Hz, 1H, major and minor rotamer respectively), 3.67-3.55 (m, 2H), 3.53-3.34 (m, 2H), 3.01-2.81 (m, 2H), 2.63 (d, J = 16.0 Hz, 1H), 2.27-2.14 (m, 2H), 2.12-1.90 (m, 5H), 0.98-0.83 (m, 1H), 0.74-0.63 (m, 1H), 0.34-0.10 (m, 2H). ¹⁹F NMR (376.5 MHz, MeOD) δ −144.10. |
| 45 (A) | (1R,7aS*)-7a-({[(8aS)-5-(6-chloro-5-cyclopropyl-1H-indazol-4-yl)-4-fluoro-8a,9,12,13-tetrahydro-8H,11H-7,10-dioxa-1,3,6,13a-tetraazanaphtho[1,8-ab]heptalen-2-yl]oxy}methyl)-6-methylidenehexahydro-1H-pyrrolizin-1-ol | 634 [M + H]⁺ | ¹H NMR (400 MHz, MeOD) δ 7.87 and 7.82 (2s, 1H, major and minor rotamer respectively), 7.75 (s, 1H), 5.31-5.19 (m, 1H), 5.02 (s, 2H), 4.76 and 4.76 (2dd, J = 13.3, 4.3 Hz, 1H, major and minor rotamer respectively), 4.70-4.57 (m, 2H), 4.43-4.31 (m, 2H), 4.27 (t, J = 5.0 Hz, 1H), 4.23 and 4.20 (2dd, J = 12.3, 4.2 Hz, 1H, major and minor rotamer respectively), 4.06-3.94 (m, 1H), 3.91-3.74 (m, 2H), 3.58 (ddd, J = 11.8, 7.8, 4.0 Hz, 1H), 3.53-3.43 (m, 1H), 3.42-3.34 (m, 2H), 2.88 (d, J = 15.9 Hz, 1H), 2.78-2.66 (m, 1H), 2.38 (d, J = 16.1 Hz, 1H), 2.33-2.14 (m, 2H), 2.10-1.85 (m, 3H), 0.99-0.82 (m, 1H), 0.76-0.63 (m, 1H), 0.36-0.09 (m, 2H). ¹⁹F NMR (376.5 MHz, MeOD) δ −144.10. |
| 46 (D) | (8aS)-5-(3,6-dichloro-5-cyclopropyl-1H-indazol-4-yl)-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 652 [M + H]⁺ | ¹H NMR (400 MHz, DMSO-d6) δ 7.82 (s, 1H), 7.33 (d, J = 4.3 Hz, 1H), 5.09-4.95 (m, 1H), 4.92 (d, J = 3.7 Hz, 2H), 4.66 (dd, J = 13.1, 4.5 Hz, 1H), 4.55 (dd, J = 13.2, 7.0 Hz, 1H), 4.33 (dt, J = 9.8, 5.1 Hz, 1H), 4.09 (ddd, J = 16.6, 8.4, 4.7 Hz, 4H), 3.95-3.83 (m, 1H), 3.66-3.55 (m, 3H), 3.03 (dt, J = 10.7, 5.2 Hz, 2H), 2.69-2.53 (m, 2H), 2.42-2.28 (m, 2H), 2.10-1.94 (m, 3H), 1.84-1.63 (m, 3H), 0.88-0.57 (m, 2H), 0.37-0.12 (m, 2H); LCMS m/z: 652.2 [M + H]⁺. |

| Example Num (Gen. Method) | Structure IUPAC name | Low Res Mass Spec | ¹H NMR (ppm); ¹⁹F NMR (ppm); optical rotation; |
|---|---|---|---|
| 47 (A) | 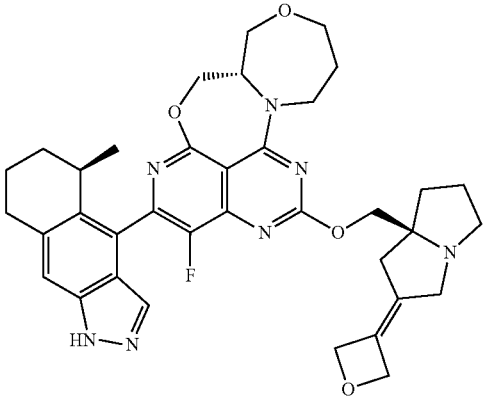 [SMILES: C[C@@H]1CCCc2cc3[nH]ncc3c(-c3nc4c5c(nc(OC[C@@]67CCCN6CC(=C6COC6)C7)nc5c3F)N3CCCOC[C@H]3CO4)c21]<br>(8aS)-4-fluoro-5-[(5R)-5-methyl-5,6,7,8-tetrahydro-1H-benzo[f]indazol-4-yl]-2-{[(7aS)-2-(oxetan-3-ylidene)tetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 655 [M + H]⁺ | ¹H NMR (400 MHz, MeOD) δ 7.65 and 7.56 (2s, 1H, major and minor rotamer respectively), 7.39 (s, 1H), 5.30-5.08 (m, 5H), 4.84-4.60 (m, 4H), 4.45-4.35 (m, 1H), 4.27 (d, J = 14.9 Hz, 1H), 4.19 and 4.18 (2dd, J = 12.2, 4.1 Hz, 1H, major and minor rotamer respectively), 4.03-3.95 (m, 1H), 3.88-3.73 (m, 3H), 3.66-3.43 (m, 3H), 3.20-3.06 (m, 2H), 3.05-2.95 (m, 1H), 2.89 (d, J = 15.2 Hz, 1H), 2.67 (d, J = 16.7 Hz, 1H), 2.42-2.14 (m, 5H), 2.07-1.92 (m, 3H), 1.85-1.71 (m, 2H), 0.99 and 0.97 (2d, J = 7.7 Hz, 3H, major and minor rotamer respectively). |
| 48 (C) | 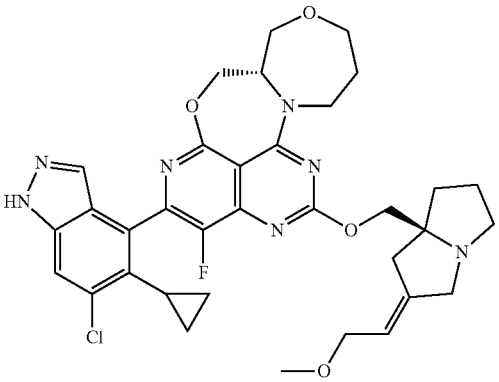 [SMILES: COC/C=C1/CN2CCC[C@@]2(COc2nc3c4c(nc(-c5c(C6CC6)c(Cl)cc6[nH]ncc56)c(F)c4n2)OC[C@@H]2COCCCN32)C1]<br>(8aS)-5-(6-chloro-5-cyclopropyl-1H-indazol-4-yl)-4-fluoro-2-{[(2E,7aS*)-2-(2-methoxyethylidene)tetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 662 [M + H]⁺ | ¹H NMR (400 MHz, DMSO-d6) δ ppm 7.80 (br d, J = 16.38 Hz, 1H) 7.76 (s, 1H) 5.36-5.43 (m, 1H) 4.95-5.03 (m, 1H) 4.64-4.72 (m, 1H) 4.57 (br d, J = 8.00 Hz, 1H) 4.27-4.38 (m, 1H) 4.03-4.18 (m, 3H) 3.87-3.93 (m, 1H) 3.83 (d, J = 6.50 Hz, 2H) 3.55-3.79 (m, 2H) 3.35 - 3.52 (m, 3H) 3.21-3.27 (m, 1H) 3.15 (d, J = 1.38 Hz, 3H) 3.00 (br s, 1H) 2.61-2.69 (m, 1H) 2.30-2.37 (m, 1H) 1.63-2.11 (m, 8H) 0.87 (br d, J = 4.13 Hz, 1H) 0.59-0.68 (m, 1H) 0.03-0.24 (m, 2H) |
| 49 (C) | 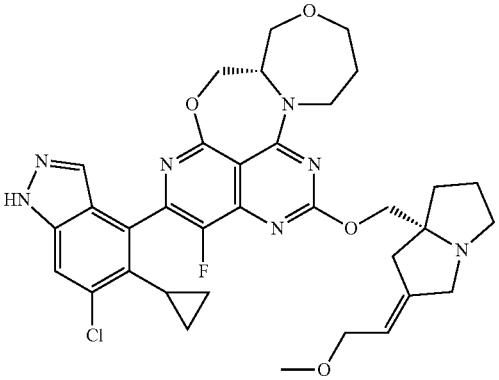 [SMILES: COC/C=C1/CN2CCC[C@]2(COc2nc3c4c(nc(-c5c(C6CC6)c(Cl)cc6[nH]ncc56)c(F)c4n2)OC[C@@H]2COCCCN32)C1]<br>(8aS)-5-(6-chloro-5-cyclopropyl-1H-indazol-4-yl)-4-fluoro-2-{[(2E,7aR*)-2-(2-methoxyethylidene)tetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 662 [M + H]⁺ | ¹H NMR (400 MHz, DMSO-d6) δ ppm 7.80 (br d, J = 16.38 Hz, 1H) 7.76 (s, 1H) 5.36-5.43 (m, 1H) 4.95-5.03 (m, 1H) 4.64-4.72 (m, 1H) 4.57 (br d, J = 8.00 Hz, 1H) 4.27-4.38 (m, 1H) 4.03-4.18 (m, 3H) 3.87-3.93 (m, 1H) 3.83 (d, J = 6.50 Hz, 2H) 3.55-3.79 (m, 2H) 3.35-3.52 (m, 3H) 3.21-3.27 (m, 1H) 3.15 (d, J = 1.38 Hz, 3H) 3.00 (br s, 1H) 2.61-2.69 (m, 1H) 2.30-2.37 (m, 1H) 1.63-2.11 (m, 8H) 0.87 (br d, J = 4.13 Hz, 1H) 0.59-0.68 (m, 1H) 0.03-0.24 (m, 2H) |

| Example Num (Gen. Method) | Structure IUPAC name | Low Res Mass Spec | ¹H NMR (ppm); ¹⁹F NMR (ppm); optical rotation; |
|---|---|---|---|
| 50 (A) | 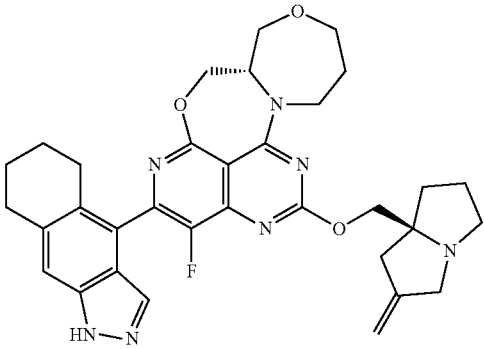 [SMILES: C=C1CN2CCC[C@@]2(COc2nc3c4c(nc(-c5c6c(cc7[nH]ncc57)CCCC6)c(F)c4n2)OC[C@@H]2COCCCN32)C1]<br>(8aS)-4-fluoro-2-{[(7aS)-2-methylidenetetrahydro-1H-pyrrolizin-7a(5H)-yl]methoxy}-5-(5,6,7,8-tetrahydro-1H-benzo[f]indazol-4-yl)-8a,9,12,13-tetrahydro-8H,11H-7,10-dioxa-1,3,6,13a-tetraazanaphtho[1,8-ab]heptalene | 598 [M + H]⁺ | ¹H NMR (400 MHz, MeOD) δ 7.68 and 7.63 (2s, 1H, minor and major rotamer respectively), 7.41 (s, 1H), 5.29-5.18 (m, 3H), 4.75 (dd, J = 13.5, 4.3 Hz, 1H), 4.71-4.55 (m, 3H), 4.41-4.33 (m, 1H), 4.32-4.24 (m, 1H), 4.23-4.17 (m, 1H), 4.04-3.96 (m, 1H), 3.89-3.77 (m, 2H), 3.75-3.65 (m, 1H), 3.63-3.56 (m, 1H), 3.53-3.44 (m, 1H), 3.26-3.11 (m, 1H), 3.07-2.96 (m, 3H), 2.91-2.53 (m, 3H), 2.40-2.32 (m, 1H), 2.27-2.06 (m, 4H), 2.05-1.95 (m, 1H), 1.93-1.74 (m, 4H).<br>¹⁹F NMR (376.5 MHz, MeOD) δ −145.82 |
| 51 (A)<br>*(Note: trans configuration of cyclopropyl group although absolute configuration unknown) | 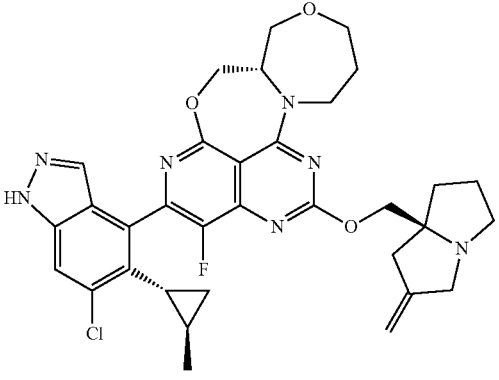 [SMILES: C=C1CN2CCC[C@@]2(COc2nc3c4c(nc(-c5c([C@@H]6C[C@H]6C)c(Cl)cc6[nH]ncc56)c(F)c4n2)OC[C@@H]2COCCCN32)C1]<br>(8aS)-5-{6-chloro-5-[(1R*,2R*)-2-methylcyclopropyl]-1H-indazol-4-yl}-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 632 [M + H]⁺ | ¹H NMR (400 MHz, MeOD) δ 7.86 and 7.80 (2s, 1H, major and minor rotamer respectively), 7.78-7.73 (m, 1H), 5.29-5.15 (m, 3H), 4.78 and 4.77 (2dd, J = 13.4, 4.3 Hz, 1H, major and minor rotamer respectively), 4.66-4.52 (m, 3H), 4.43-4.32 (m, 1H), 4.27-4.12 (m, 2H), 4.05-3.96 (m, 1H), 3.88 and 3.77 (2dd, J = 12.4, 9.9 Hz, 1H, major and minor rotamer respectively), 3.71 (d, J = 14.3 Hz, 1H), 3.65-3.42 (m, 3H), 3.12-3.02 (m, 1H), 2.98 (d, J = 15.9 Hz, 1H), 2.69 (d, J = 15.9 Hz, 1H), 2.37 - 2.27 (m, 1H), 2.25-1.93 (m, 5H), 1.79-1.66 (m, 1H), 1.02 and 0.88 (2d, J = 5.9 Hz, 3H, major and minor rotamer respectively), 0.71-0.29 (m, 3H).<br>¹⁹F NMR (376.5 MHz, MeOD) δ −144.4. |
| 52 (A)<br>*(Note: trans configuration of cyclopropyl group although absolute config-uration unknown) | 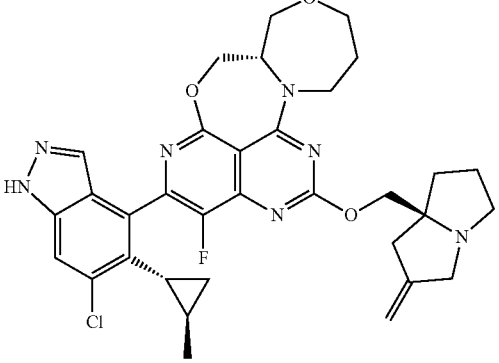<br>(8aS)-5-{6-chloro-5-[(1R*,2R*)-2-methylcyclopropyl]-1H-indazol-4-yl}-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 632 [M + H]⁺ | ¹H NMR (400 MHz, MeOD) δ 7.86 and 7.81 (2s, 1H, major and minor rotamer respectively), 7.78-7.73 (m, 1H), 5.30-5.17 (m, 3H), 4.78 and 4.77 (2dd, J = 13.5, 4.2 Hz, 1H, major and minor rotamer respectively), 4.68-4.54 (m, 3H), 4.44-4.31 (m, 1H), 4.29-4.16 (m, 2H), 4.00 (dt, J = 12.7, 5.2 Hz, 1H), 3.91-3.74 (m, 2H), 3.69-3.43 (m, 3H), 3.19-3.09 (m, 1H), 3.01 (d, J = 15.5 Hz, 1H), 2.73 (d, J = 16.0 Hz, 1H), 2.40-2.29 (m, 1H), 2.25-1.93 (m, 5H), 1.76-1.66 (m, 1H), 1.09 and 0.82 (2d, J = 5.9 Hz, 3H, major and minor rotamer respectively), 0.70-0.35 (m, 3H).<br>¹⁹F NMR (376.5 MHz, MeOD) δ −144.5. |

| Example Num (Gen. Method) | Structure IUPAC name | Low Res Mass Spec | ¹H NMR (ppm); ¹⁹F NMR (ppm); optical rotation; |
|---|---|---|---|
| 53 (A) | 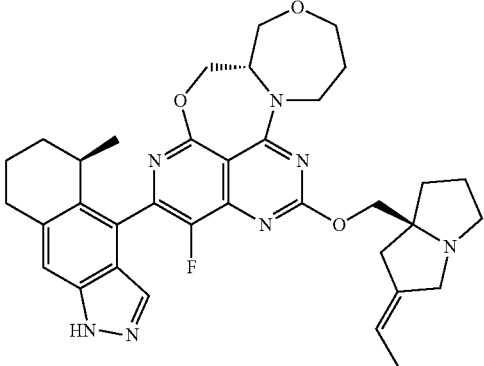 [SMILES: C/C=C1\CN2CCC[C@@]2(COc2nc3c4c(nc(-c5c6c(cc7[nH]ncc57)CCC[C@H]6C)c(F)c4n2)OC[C@@H]2COCCCN32)C1]<br>(8aS)-2-{[(2Z,7aS)-2-ethylidenetetrahydro-1H-pyrrolizin-7a(5H)-yl]methoxy}-4-fluoro-5-[(5R)-5-methyl-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene | 626 [M + H]⁺ | ¹H NMR (400 MHz, MeOD) δ 7.65 and 7.54 (2s, 1H, major and minor rotamer respectively), 7.39 (s, 1H), 5.72-5.62 (m, 1H), 5.28-5.18 (m, 1H), 4.76 and 4.75 (2dd, J = 13.4, 4.2 Hz, 1H, major and minor rotamer respectively), 4.68-4.57 (m, 3H), 4.43-4.32 (m, 1H), 4.25 (d, J = 14.6 Hz, 1H), 4.19 and 4.18 (2dd, J = 12.4, 4.2 Hz, 1H, major and minor rotamer respectively), 3.99 (ddd, J = 12.6, 5.8, 4.9 Hz, 1H), 3.90 (d, J = 14.8 Hz, 1H), 3.82 and 3.78 (2dd, J = 12.4, 9.9 Hz, 1H, major and minor rotamer respectively), 3.73-3.65 (m, 1H), 3.65-3.56 (m, 1H), 3.55-3.41 (m, 1.5H), 3.22-3.06 (m, 2.5H), 3.05 - 2.89 (m, 2H), 2.72 (d, J = 15.8 Hz, 1H), 2.41-2.28 (m, 1H), 2.27-1.91 (m, 7H), 1.86-1.63 (m, 5H), 0.99 and 0.98 (2d, J = 6.8 Hz, 3H, major and minor rotamer respectively). ¹⁹F NMR (376.5 MHz, MeOD) δ −145.5. |
| 54 (A) | 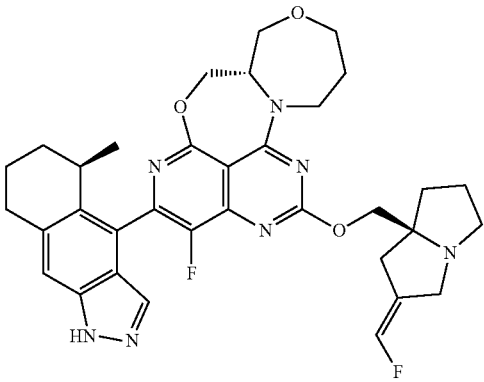 [SMILES: C[C@@H]1CCCc2cc3[nH]ncc3c(-c3nc4c5c(nc(OC[C@@]67CCCN6C/C(=C\F)C7)nc5c3F)N3CCCOC[C@H]3CO4)c21]<br>(8aS)-4-fluoro-2-{[(2Z,7aS)-2-(fluoromethylidene)tetrahydro-1H-pyrrolizin-7a(5H)-yl]methoxy}-5-[(5R)-5-methyl-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene | 630 [M + H]⁺ | ¹H NMR (400 MHz, MeOD) δ 7.64 and 7.54 (2s, 1H, major and minor rotamer respectively), 7.38 (s, 1H), 6.73 (d, J = 83.4 Hz, 1H), 5.28 - 5.19 (m, 1H), 4.75 and 4.74 (2dd, J = 13.2, 3.9 Hz, 1H, major and minor rotamer respectively), 4.62 and 4.60 (2d, J = 13.5 Hz, 1H, major and minor rotamer respectively), 4.50 - 4.41 (m, 2H), 4.39-4.29 (m, 1H), 4.21-4.14 (m, 1H), 4.13-4.03 (m, 1H), 3.99 (ddd, J = 10.4, 5.2, 4.6 Hz, 1H), 3.81 and 3.77 (2dd, J = 12.3, 10.0 Hz, 1H, major and minor rotamer respectively), 3.74-3.67 (m, 1H), 3.63-3.55 (m, 1H), 3.54-3.38 (m, 2H), 3.20-2.79 (m, 5H), 2.57 (d, J = 15.0 Hz, 1H), 2.27-2.15 (m, 2H), 2.11-1.90 (m, 6H), 1.84-1.69 (m, 2H), 0.99 and 0.97 (2d, J = 7.1 Hz, 3H, major and minor rotamer respectively). ¹⁹F NMR (376.5 MHz, MeOD) δ −145.22. |

| Example Num (Gen. Method) | Structure IUPAC name | Low Res Mass Spec | ¹H NMR (ppm); ¹⁹F NMR (ppm); optical rotation; |
|---|---|---|---|
| 55 (A) | (8aS)-4-fluoro-2-{[(2E,7aS)-2-(fluoromethylidene)tetrahydro-1H-pyrrolizin-7a(5H)-yl]methoxy}-5-[(5R)-5-methyl-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene | 630 [M + H]⁺ | ¹H NMR (400 MHz, MeOD) δ 7.65 and 7.55 (2s, 1H, major and minor rotamer respectively), 7.38 (s, 1H), 6.87 (d, J = 82.4 Hz, 1H), 5.32-5.17 (m, 1H), 4.76 and 4.75 (2dd, J = 13.3, 3.9 Hz, 1H, major and minor rotamer respectively), 4.66-4.50 (m, 3H), 4.42-4.31 (m, 1H), 4.22-4.16 (m, 1H), 4.15-4.07 (m, 1H), 3.99 (dt, J = 10.6, 5.0 Hz, 1H), 3.81 and 3.77 (2dd, J = 12.4, 9.9 Hz, 1H, major and minor rotamer respectively), 3.72-3.65 (m, 1H), 3.63-3.41 (m, 3.5H), 3.18-2.95 (m, 4.5H), 2.79 (d, J = 15.6 Hz, 1H), 2.34-1.91 (m, 8H), 1.84-1.67 (m, 2H), 0.99 and 0.98 (2d, J = 6.9 Hz, 3H, major and minor rotamer respectively). ¹⁹F NMR (376.5 MHz, MeOD) δ −145.36. |
| 56 (A+) | (8aS)-4-fluoro-5-[(5R*)-5-methoxy-5,6,7,8-tetrahydro-1H-benzo[f]indazol-4-yl]-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 628 [M + H]⁺ | ¹H NMR (400 MHz, MeOD) δ 7.78 and 7.68 (2s, 1H, minor and major rotamer respectively), 7.42 (s, 1H), 5.29-5.18 (m, 1H), 5.00 (s, 2H), 4.86-4.71 (m, 2H), 4.63 and 4.59 (2d, J = 13.1 Hz, 1H, minor and major rotamer respectively), 4.59 (d, J = 13.1 Hz, 1H), 4.40-4.29 (m, 3H), 4.18 (dd, J = 12.4, 4.0 Hz, 1H), 4.04-3.95 (m, 1H), 3.85-3.71 (m, 2H), 3.61-3.52 (m, 1H), 3.51-3.40 (m, 1H), 3.39-3.35 (m, 1H), 3.21 - 3.07 (m, 2H), 2.98-2.85 (m, 4H), 2.81 (d, J = 16.3 Hz, 1H), 2.77 - 2.70 (m, 1H), 2.50 (d, J = 15.8 Hz, 1H), 2.24-2.13 (m, 3H), 2.05-1.83 (m, 6H), 1.80-1.67 (m, 1H). |
| 57 (A+) | (8aS)-4-fluoro-5-[(5R*)-5-methoxy-5,6,7,8-tetrahydro-1H-benzo[f]indazol-4-yl]-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 628 [M + H]⁺ | ¹H NMR (400 MHz, MeOD) δ 7.72 (s, 1H), 7.43 and 7.42 (2s, 1H, minor and major rotamer respectively), 5.29-5.17 (m, 1H), 5.05-4.95 (m, 2H), 4.77-4.49 (m, 3H), 4.38-4.27 (m, 3H), 4.26-4.14 (m, 1H), 4.05-3.96 (m, 1H), 3.89 and 3.78 (2dd, J = 12.2, 10.0 Hz, 1H, minor and major rotamer respectively), 3.72 (d, J = 14.4 Hz, 1H), 3.64-3.51 (m, 1H), 3.49-3.38 (m, 1H), 3.36-3.32 (m, 1H), 3.19 - 3.06 (m, 2H), 2.98-2.85 (m, 4H), 2.79 (d, J = 15.4 Hz, 1H), 2.75-2.64 (m, 1H), 2.48 (d, J = 15.6 Hz, 1H), 2.24-2.10 (m, 3H), 2.03-1.80 (m, 6H), 1.79-1.69 (m, 1H). |

| Example Num (Gen. Method) | Structure IUPAC name | Low Res Mass Spec | $^1$H NMR (ppm); $^{19}$F NMR (ppm); optical rotation; |
|---|---|---|---|
| 58 (A+) | 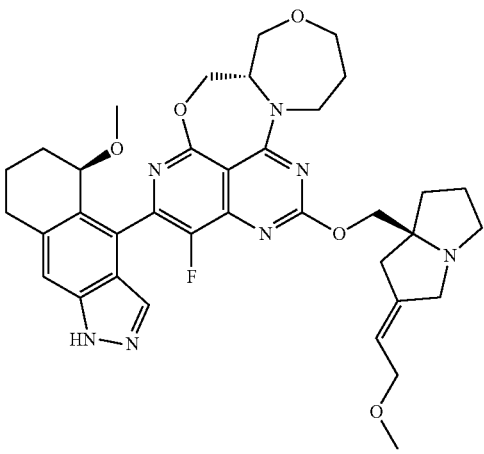 [SMILES: COC/C=C1\CN2CCC[C@@]2(COc2nc3c4c(nc(-c5c6c(cc7[nH]ncc57)CCC[C@H]6OC)c(F)c4n2)OC[C@@H]2COCCCN32)C1]<br>(8aS)-4-fluoro-2-{[(2Z,7aS)-2-(2-methoxyethylidene)tetrahydro-1H-pyrrolizin-7a(5H)-yl]methoxy}-5-[(5R*)-5-methoxy-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene | 672 [M + H]$^+$ | $^1$H NMR (400 MHz, MeOD) δ 7.78 and 7.68 (2s, 1H, minor and major isomer respectively), 7.42 (2s, 1H, minor and major isomer respectively), 5.55-5.48 (m, 1H), 5.28-5.17 (m, 1H), 4.79 (t, J = 3.7 Hz, 0.6H, major rotamer), 4.75 (dd, J = 13.5, 4.4 Hz, 1H), 4.62 and 4.59 (2d, J = 13.0 Hz, 1H, minor and major isomer respectively), 4.43-4.40 (m, 0.4H, minor rotamer), 4.38-4.26 (m, 3H), 4.18 (dd, J = 12.4, 4.0 Hz, 1H), 4.03-3.95 (m, 1H), 3.91 (d, J = 6.7 Hz, 2H), 3.85-3.70 (m, 2H), 3.57 and 3.54 (2ddd, J = 12.8, 8.6, 4.3 Hz, 1H, major and minor rotamer respectively), 3.49-3.35 (m, 2H), 3.31 (s, 3H), 3.20-3.07 (m, 2H), 2.98-2.85 (m, 4H), 2.82 (d, J = 15.9 Hz, 1H), 2.77-2.67 (m, 1H), 2.54 (d, J = 16.0 Hz, 1H), 2.25-2.10 (m, 3H), 2.06-1.81 (m, 6H), 1.80-1.67 (m, 1H). $^{19}$F NMR (376.5 MHz, MeOD) δ −145.28. |
| 59 (A+) | 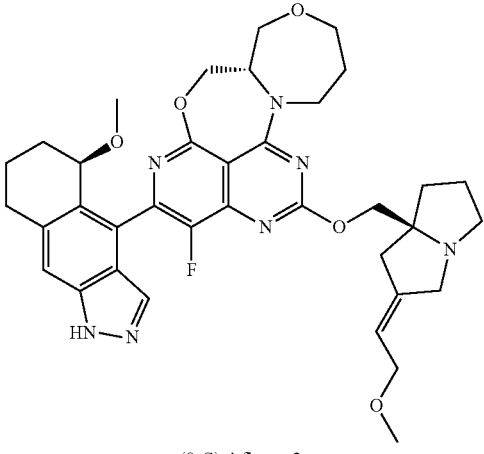<br>(8aS)-4-fluoro-2-{[(2Z,7aS)-2-(2-methoxyethylidene)tetrahydro-1H-pyrrolizin-7a(5H)-yl]methoxy}-5-[(5R*)-5-methoxy-5,6,7,8-tetrahydro-1H-benzo[f]indazol-4-yl]-8a,9,12,13-tetrahydro-8H,11H-7,10-dioxa-1,3,6,13a-tetraazanaphtho[1,8-ab]heptalene | 672 [M + H]$^+$ | $^1$H NMR (400 MHz, MeOD) δ 7.72 (s, 1H), 7.42 (s, 1H), 5.58-5.48 (m, 1H), 5.27-5.17 (m, 1H), 4.76-4.50 (m, 3H), 4.37-4.28 (m, 3H), 4.26-4.17 (m, 1H), 4.04-3.96 (m, 1H), 3.92 (d, J = 6.6 Hz, 2H), 3.90-3.73 (m, 2H), 3.64-3.50 (m, 1H), 3.49-3.39 (m, 2H), 3.31 (s, 3H), 3.23-3.16 (m, 1H), 3.14-3.07 (m, 1H), 2.97-2.80 (m, 5H), 2.79-2.71 (m, 1H), 2.56 (d, J = 16.0 Hz, 1H), 2.25-2.10 (m, 3H), 2.07-1.92 (m, 4H), 1.91-1.83 (m, 2H), 1.80-1.70 (m, 1H). $^{19}$F NMR (376.5 MHz, MeOD) δ −145.20. |

-continued

| Example Num (Gen. Method) | Structure IUPAC name | Low Res Mass Spec | ¹H NMR (ppm); ¹⁹F NMR (ppm); optical rotation; |
|---|---|---|---|
| 60 (A) | (1Z)-1-[(7aS)-7a-({[(8aS)-5-(6-chloro-5-cyclopropyl-1H-indazol-4-yl)-4-fluoro-8a,9,12,13-tetrahydro-8H,11H-7,10-dioxa-1,3,6,13a-tetraazanaphtho[1,8-ab]heptalen-2-yl]oxy}methyl)tetrahydro-1H-pyrrolizin-2(3H)-ylidene]propan-2-ol | 662 [M + H]⁺ | ¹H NMR (400 MHz, MeOD) δ 7.87 and 7.82 (2s, 1H, major and minor rotamer respectively), 7.75 (s, 1H), 5.43-5.35 (m, 1H), 5.28-5.19 (m, 1H), 4.79-4.72 (m, 1H), 4.63 and 4.59 (2d, J = 12.9 Hz, 1H, major and minor rotamer respectively), 4.45-4.17 (m, 5H), 4.06-3.95 (m, 1H), 3.92-3.70 (m, 2H), 3.65-3.56 (m, 1H), 3.52-3.34 (m, 2H), 3.20-3.09 (m, 1H), 2.85-2.62 (m, 2H), 2.56-2.44 (m, 1H), 2.27-2.08 (m, 2H), 2.08-1.80 (m, 5H), 1.24-1.15 (m, 3H), 0.95-0.85 (m, 1H), 0.70 (s, 1H), 0.31-0.09 (m, 2H). ¹⁹F NMR (376.5 MHz, MeOD) δ −143.90. |
| 61 (A) | (8aS)-5-(6-chloro-5-cyclopropyl-1H-indazol-4-yl)-4-fluoro-2-{[(1S,7aS*)-1-methoxy-6-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 648 [M + H]⁺ | ¹H NMR (400 MHz, MeOD) δ 7.87 and 7.82 (2s, 1H, major and minor rotamer respectively), 7.75 (s, 1H), 5.27-5.19 (m, 1H), 5.15 (s, 2H), 4.80-4.72 (m, 2H), 4.66-4.52 (m, 2H), 4.42-4.31 (m, 1H), 4.27-4.18 (m, 1H), 4.12 (d, J = 14.3 Hz, 1H), 4.05-3.96 (m, 2H), 3.88 and 3.80 (2dd, J = 12.4, 9.9 Hz, 1H, major and minor rotamer respectively), 3.69-3.43 (m, 4H), 3.38 (s, 3H), 3.06 (d, J = 16.3 Hz, 1H), 3.02 - 2.93 (m, 1H), 2.55 (d, J = 16.5 Hz, 1H), 2.29-1.94 (m, 5H), 0.99-0.83 (m, 1H), 0.75-0.63 (m, 1H), 0.34 - 0.10 (m, 2H). ¹⁹F NMR (376.5 MHz, MeOD) δ −144.1. |
| 62 (−)* *see experimental section for synthesis | (8aS)-5-[(5R)-3-chloro-5-methyl-5,6,7,8-tetrahydro-1H-benzo[f]indazol-4-yl]-4-fluoro-2-{[(7aS)-2-methylidenetetrahydro-1H-pyrrolizin-7a(5H)-yl]methoxy}-8a,9,12,13-tetrahydro-8H,11H-7,10-dioxa-1,3,6,13a-tetraazanaphtho[1,8-ab]heptalene | 646 [M + H]⁺ | ¹H NMR (600 MHz, DMSO 120° C.) δ ppm 8.51 (br s, 1H), 7.35 (s, 1H), 4.98-5.12 (m, 1H), 4.92 (d, J = 1.00 Hz, 2H), 4.63-4.71 (m, 1H), 4.50 - 4.63 (m, 1H), 4.25-4.38 (m, 1H), 4.09-4.24 (m, 3H), 3.89-3.99 (m, 1H), 3.68-3.78 (m, 1H), 3.52-3.65 (m, 2H), 3.41-3.52 (m, 1H), 3.26-3.36 (m, 1H), 3.22 (d, J = 1.00 Hz, 1 H), 3.04-3.12 (m, 2H), 2.89-3.02 (m, 2H), 2.56-2.73 (m, 2H), 2.36 - 2.45 (m, 1H), 1.94 (br dd, J = 5.18, 1.73 Hz, 4H), 1.66-1.86 (m, 5H), 1.06 (dd, J = 1.00 Hz, 3H). |

Binding Affinity and Kinetics Measurements by SPR

The binding affinity and kinetics were measured by Surface Plasmon Resonance (SPR) using BIACORE™ 8K or 8K+ (Cytiva, Marlborough, MA) instruments. Recombinant, C-terminal site-specific biotinylated, wild-type (WT) KRASGDP (aa1-185), G12DGDP KRAS (aa1-185), G12CGDP KRAS (aa2-184), G12VGDP KRAS (aa2-184), WT HRASGDP (aa2-184) and WT NRASGDP (aa2-185) proteins were purified in presence of 1 μM GDP.

The GDP-loaded KRAS proteins went through nucleotide exchange with GTPγS (a non-hydrolysable analog of GTP) in the presence of alkaline phosphatase beads to obtain WTGTPγS KRAS (aa1-185), G12DGTPγS KRAS (aa1-185), G12CGTPγS KRAS (aa2-184), G12VGTPγS KRAS (aa2-184), WT HRASGTPγS (aa2-184) and WT NRASGTPγS (aa2-185).

Binding measurements were performed in parallel sets of either WT/G12D/G12C/G12V KRAS or WT K/H/N RAS proteins in GDP and/or GTPγS-loaded forms.

BIACORE™ instrument was desorbed and docked with a Series S Sensor Chip SA. The proteins were diluted to 50 μg/mL with the assay buffer (50 mM HEPES, 150 mM NaCl, 10 μM GDP for GDP-loaded proteins or 10 μM GTPγS for GTPγS-loaded proteins, 5 mM MgCl2, 0.5 mM TCEP, 5% glycerol, 0.02% Tween-20, 2% DMSO, pH 7.2) and immobilized at a flow rate of 3 L/min at 10° C. with a contact time of 3-10 min. to capture ~3000-4000 RUs of proteins on the surface. The functionalized surface was then equilibrated with assay buffer for approximately 1 hour. Un-functionalized SA surfaces with no immobilized protein served as reference for binding kinetic analysis. Compound binding kinetics were measured in either multi-cycle or single-cycle kinetic format.

Multi-cycle kinetic analysis (MCK): A 2-fold, 10-point serial dilution of test compounds was set-up in a 96-well microplate (Greiner; Cat #650101) with a top concentration of either 10 μM or 100 μM. Binding kinetics was measured at 10° C. by injecting serial dilution of compounds onto both reference and RAS immobilized channels at a flow rate of 100 μL/min and association time of 90 seconds. Compound dissociation was monitored for at least 400 seconds during each cycle. No additional regeneration was used. DMSO calibration curve was obtained before and after compound analysis by injecting 0-4% of DMSO in assay buffer. A suitable compound with known affinity and kinetics was tested once in every experiment as a positive control to assess activity of the captured protein on the surface.

Single-cycle kinetic analysis (SCK): A 3-fold, 6-point serial dilution of compounds was set-up in a deep 96-well microplate (Greiner Bio; Cat #780201) with the highest concentration of 1 μM (concentration range: 0.004-1 μM). Binding kinetics was measured at 10° C. by injecting serial dilutions of compounds in increasing order onto reference as well as RAS immobilized channels at a flow rate of 100 μL/min and association time of 120 seconds. Compound dissociation was monitored for at least 3600 seconds. Two buffer blanks were also run in a single-cycle kinetics format before the compound run for double referencing. No additional regeneration was used. DMSO calibration curve was obtained before and after compound analysis by injecting 0-4% of DMSO in the assay buffer. A suitable compound with known affinity and kinetics was tested once in every experiment as a positive control to assess activity of the captured protein on the surface.

Both MCK and SCK data were processed and analyzed using BIACORE™ Insight evaluation software (Cytiva, Marlborough, MA)). The double-referenced and solvent-corrected data was fit to 1:1 Langmuir model to measure kinetic binding constant (KD), association rate (kon) and dissociation rate (koff). Dissociative half-life (t1/2) was calculated from the measured koff using standard equation (t1/2=0.693/koff). The adequateness of the fit was judged by c2 values and the randomness of residue distribution.

The KrasGDP SPR and KRasGTPgS SPR binding assay results for Examples are provided in Table 2 and Table 3 respectively. A geometric mean of binding constant $K_D$ was provided when an Example was tested more than once. A blank cell or 'nd' indicates no data was obtained for that Example in that specific assay at time of writing.

The binding constant $K_D$ shows that the exemplified compounds have potent binding capabilities to one or more of KRAS G12C, KRAS G12D, and KRAS G12V receptors, and may be selective (at least 10 times more potent) over HRAS and NRAS receptors.

TABLE 2

| | | | | | | |
|---|---|---|---|---|---|---|
| SPR binding assay results with GDP loaded proteins. Geomean KD values in nM. | | | | | | |
| Example No | KRAS Wild Type $K_D$ (nM) | KRAS G12D $K_D$ (nM) | KRAS G12C $K_D$ (nM) | KRAS G12V $K_D$ (nM) | HRAS Wild Type $K_D$ (nM) | NRAS Wild Type $K_D$ (nM) |
| 1 | 0.038 | 0.048 | 0.031 | 0.105 | nd | nd |
| 2 | 0.004 | 0.041 | 0.019 | 0.144 | nd | nd |
| 3 | >10,000 | >10,000 | >10,000 | >10,000 | nd | nd |
| 4 | 7.720 | 1.360 | 4.290 | 2.600 | nd | nd |
| 5 | 5.420 | 2.200 | 1.950 | 2.760 | nd | nd |
| 6 | 2.510 | 0.956 | 0.894 | 1.230 | nd | nd |
| 7 | nd | nd | nd | nd | nd | nd |
| 8 | nd | nd | nd | nd | nd | nd |
| 9 | nd | nd | nd | nd | nd | nd |
| 10 | 8.028 | 2.072 | 1.812 | 3.903 | nd | nd |
| 11 | 0.091 | 0.024 | 0.051 | 0.067 | nd | nd |
| 12 | 0.257 | 0.116 | 0.122 | 0.106 | nd | nd |
| 13 | <0.001 | 0.106 | 0.017 | 0.072 | nd | nd |

TABLE 3

SPR binding assay results with GTPγS loaded proteins. Geomean KD values in nM.

| Example No | KRAS Wild Type $K_D$ (nM) | KRAS G12D $K_D$ (nM) | KRAS G12C $K_D$ (nM) | KRAS G12V $K_D$ (nM) | HRAS Wild Type $K_D$ (nM) | NRAS Wild Type $K_D$ (nM) |
|---|---|---|---|---|---|---|
| 1 | 14 | 10 | 12 | 8 | >10,000 | >10,000 |
| 2 | 5 | 1 | 5 | 4 | >10,000 | >10,000 |
| 3 | >1000 | >1000 | >1000 | >1000 | nd | nd |
| 4 | 2290 | 2030 | 2270 | 1590 | nd | nd |
| 5 | 1450 | 1240 | 1557 | 1433 | nd | nd |
| 6 | 546 | 467 | 635 | 639 | nd | nd |
| 7 | 34 | 28 | 15 | 24 | nd | nd |
| 8 | 117 | 141 | 176 | 105 | nd | nd |
| 9 | 389 | 270 | 430 | 303 | nd | nd |
| 10 | 2880 | 2550 | 3230 | 2820 | nd | nd |
| 11 | 40 | 19 | 39 | 29 | nd | nd |
| 12 | 95 | 42 | 84 | 62 | nd | nd |
| 13 | 5 | 1 | 4 | 3 | nd | nd |
| 14 | 8 | 5 | 9 | 7 | nd | nd |
| 15 | 4 | 2 | 5 | 4 | nd | nd |
| 16 | 4 | 3 | 4 | 4 | >10,000 | >10,000 |
| 17 | 5 | 3 | 5 | 4 | nd | nd |
| 18 | 61 | 34 | 64 | 61 | nd | nd |
| 19 | 8 | 6 | 5 | 9 | >10,000 | >10,000 |
| 20 | 91 | 51 | 31 | 50 | >10,000 | >10,000 |
| 21 | 31 | 21 | 14 | 15 | >10,000 | >10,000 |
| 22 | nd | 250 | nd | nd | >10,000 | >10,000 |
| 23 | 3 | 3 | 3 | 2 | >10,000 | >10,000 |
| 24 | 7 | 5 | 4 | 5 | >10,000 | >10,000 |
| 25 | 4 | 3 | 2 | 2 | nd | nd |
| 26 | 2 | 1 | 1 | 1 | >10,000 | >10,000 |
| 27 | 9 | 4 | 3 | 6 | nd | nd |
| 28 | 3 | 1 | 2 | 2 | >10,000 | >10,000 |
| 29 | 1 | 1 | 1 | 2 | >10,000 | >10,000 |
| 30 | 4 | 2 | 3 | 4 | nd | nd |
| 31 | 10 | 6 | 7 | 5 | nd | nd |
| 32 | 46 | 19 | 39 | 36 | nd | nd |
| 33 | 8 | 6 | 6 | 6 | nd | nd |
| 34 | >10,000 | >10,000 | >10,000 | >10,000 | nd | nd |
| 35 | 11 | 8 | 12 | 12 | nd | nd |
| 36 | 7 | 3 | 5 | 9 | >10,000 | >10,000 |
| 37 | 3 | 2 | 3 | 4 | >10,000 | >10,000 |
| 38 | 4 | 2 | 3 | 4 | nd | nd |
| 39 | 2 | 1 | 2 | 2 | >10,000 | >10,000 |
| 40 | 6 | 4 | 7 | 6 | nd | nd |
| 41 | 5 | 2 | 4 | 4 | >10,000 | >10,000 |
| 42 | 68 | 24 | 33 | 32 | nd | nd |
| 43 | 742 | 493 | 539 | 677 | nd | nd |
| 44 | 3 | 2 | 3 | 3 | nd | nd |
| 45 | 3 | 1 | 3 | 2 | nd | nd |
| 46 | 4 | 3 | 3 | 4 | >10,000 | >10,000 |
| 47 | 3 | 2 | 4 | 4 | >10,000 | >10,000 |
| 48 | 65 | 35 | 72 | 41 | nd | nd |
| 49 | 63 | 41 | 73 | 58 | nd | nd |
| 50 | 53 | 31 | 47 | 42 | nd | nd |
| 51 | 12 | 6 | 8 | 7 | nd | nd |
| 52 | 28 | 17 | 19 | 17 | nd | nd |
| 53 | 1 | 1 | 1 | 2 | >10,000 | >10,000 |
| 54 | 1 | 1 | <1 | 1 | >10,000 | >10,000 |
| 55 | 3 | 2 | 1 | 2 | >10,000 | >10,000 |
| 56 | 23 | 34 | 10 | 23 | nd | nd |
| 57 | >1000 | >1000 | >1000 | >1000 | nd | nd |
| 58 | 61 | 74 | 42 | 81 | >10,000 | >10,000 |
| 59 | >1000 | >1000 | >1000 | >1000 | nd | nd |
| 60 | 25 | 11 | 26 | 18 | >10,000 | >10,000 |
| 61 | 5 | 3 | 4 | 5 | nd | nd |
| 62 | <1 | <1 | <1 | <1 | >10,000 | >10,000 |

KRAS Cell Titer Glo (CTG) Assay

The CellTiter-Glo® (CTG) Luminescent Cell Viability Assay is a homogeneous method of determining the number of viable cells in culture based on quantitation of the ATP present, an indicator of metabolically active cells. The CTG is designed for use with multi-well formats, making it ideal for automated high-throughput screening (HTS), cell proliferation and cytotoxicity assays. The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells per well in a 384-well format in 10 minutes after adding reagent and mixing.

Cells are grown in humidified 5% $CO_2$ incubator at 37° C. using the culture conditions outlined below. All cell culture media reagents were purchased from Gibco. Cell lines purchased from ATCC: H358 (non-small cell lung cancer cell line), SW620 (colorectal cancer cell line), PANC08.13 (RPMI1640+10% FBS+10 units/mL Insulin, pancreatic cancer cell line). Test and control compounds are dispensed as nanoliter drops according to desired final concentrations in 0.1% DMSO using Echo Acoustic Dispenser onto 384 assay plates (Corning, Cat #3764) prior to cell seeding. Cells were seeded in 40 μL volume per well at the following cell densities (cells per well): H358 (300), SW620 (750), PANC 08.13 (600). Cells are incubated in the presence of compound for 7-days. Viability is determined on Day 7 using CellTiter-Glo® (CTG) Luminescent Cell Viability Assay (Promega). CTG is added to a final volume of 20 μl per well and incubated at room temperature for 15 minutes before luminescence is captured using an EnVision Reader with LUM384 US protocol. Data is analyzed using Activity Base to determine compound response and will be represented either as a percent effect (PCTEFF) or percent control (PCTOCTL) as described: Zero percent effect control (ZPE) (Negative control)—100% DMSO. Hundred percent effect (HPE) (Positive control)—1 uM Trametinib (GSK1120212, MEK inhibitor) (4nl of 10 mM and 36nl of DMSO per well). The following equations/nomenclature are used (% Effect; PCTEFF) and (% of Control; PCTOCTL): PCTEFF: 100*(Raw_Data_Value −HPE/ZPE −HPE), PCTOCTL: 100*Raw_Data_Value/User_Defined_Array), where the User_Defined_Array is either summarized HPE or ZPE.

The CTG assay results for examples are provided in Table 4. A geometric mean of $IC_{50}$ (nM) was provided when an Example was tested more than once. Cells with "nd" indicate compound not tested in that particular assay at time of writing. It is to be understood that the geomean $IC_{50}$ data may change slightly over time with increasing repeat data (ie: increasing n #).

The CTG assay shows that selective exemplified compounds of the present invention have demonstrated anticancer activities for pancreatic cancer, non-small cell lung cancer, and colorectal cancer.

Examples provided show potent cellular activities very similar to phenol/naphthol analogs. This is not expected from literature disclosure. See Fell et al 2020 J. Med. Chem 63, 6679-6693.

TABLE 4

Cell proliferation assay results.
CTG geomean $IC_{50}$ data shown in nM.

| Example No. | Panc08.13 (7-day CTG) $IC_{50}$ (nM) | H358 (7-day CTG) $IC_{50}$ (nM) | SW620 (7-day CTG) $IC_{50}$ (nM) |
| --- | --- | --- | --- |
| 1 | 7 | 73 | 83 |
| 2 | <2 | 10 | 14 |
| 3 | >9990 | >9990 | >9990 |
| 4 | 299 | 534 | 3375 |
| 5 | 1043 | 2315 | 2681 |
| 6 | 404 | 847 | 1324 |
| 7 | 22 | 173 | 139 |
| 8 | 48 | 263 | 294 |
| 9 | 140 | 758 | 914 |
| 10 | 475 | 4539 | 9529 |
| 11 | 21 | 136 | 315 |
| 12 | 35 | 211 | 463 |
| 13 | 7 | 26 | 70 |
| 14 | 13 | 80 | 30 |
| 15 | 3 | 30 | 31 |
| 16 | 2 | 22 | 23 |
| 17 | 31 | 80 | 190 |
| 18 | 68 | 304 | 479 |
| 19 | 3 | 62 | 103 |
| 20 | 17 | 275 | 400 |
| 21 | 8 | 381 | 268 |
| 22 | 98 | 636 | 839 |
| 23 | 3 | 102 | 156 |
| 24 | 6 | 45 | 18 |
| 25 | 13 | 41 | 22 |
| 26 | 2 | 17 | 16 |
| 27 | 9 | 72 | 74 |
| 28 | 4 | 19 | 26 |
| 29 | <1 | 4 | 8 |
| 30 | 4 | 51 | 102 |
| 31 | 11 | 54 | 115 |
| 32 | 161 | 768 | 1419 |
| 33 | 18 | 58 | 103 |
| 34 | 9354 | >9990 | >9990 |
| 35 | 10 | 126 | 49 |
| 36 | 4 | 15 | 31 |
| 37 | 4 | 9 | 25 |
| 38 | 2 | 8 | 18 |
| 39 | <1 | 10 | 7 |
| 40 | 13 | 52 | 60 |
| 41 | 5 | 25 | 36 |
| 42 | 44 | 288 | 233 |
| 43 | 5511 | >9990 | >9990 |
| 44 | 125 | 43 | 94 |
| 45 | 20 | 19 | 32 |
| 46 | 5 | 15 | 45 |
| 47 | 10 | 14 | 11 |
| 48 | nd | nd | nd |
| 49 | nd | nd | nd |
| 50 | 105 | 206 | 75 |
| 51 | 10 | 27 | 40 |
| 52 | 20 | 27 | 50 |
| 53 | 5 | 8 | 4 |
| 54 | nd | nd | nd |
| 55 | 13 | 24 | 6 |
| 56 | 135 | 172 | 63 |
| 57 | nd | nd | nd |
| 58 | nd | nd | nd |
| 59 | nd | nd | nd |
| 60 | nd | nd | nd |
| 61 | 11 | 21 | 38 |
| 62 | nd | nd | nd |

It will be apparent to those skilled in the art that various modifications and variations may be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All references cited herein, including patents, patent applications, papers, textbooks, and the like, and the references cited therein, to the extent that they are not already, are hereby incorporated by reference in their entireties. In the event that one or more of the incorporated literature and similar materials differs from or contradicts this application, including but not limited to defined terms, term usage, described techniques, or the like, this application controls.

We claim:
1. A compound selected from the group consisting of:
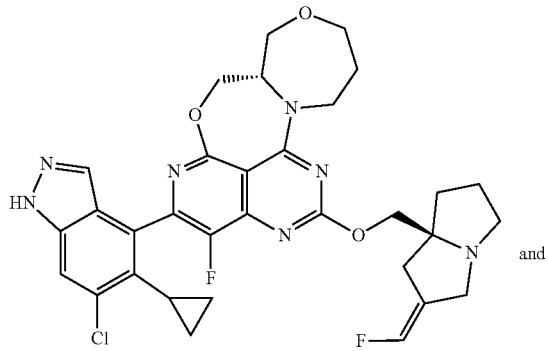
and
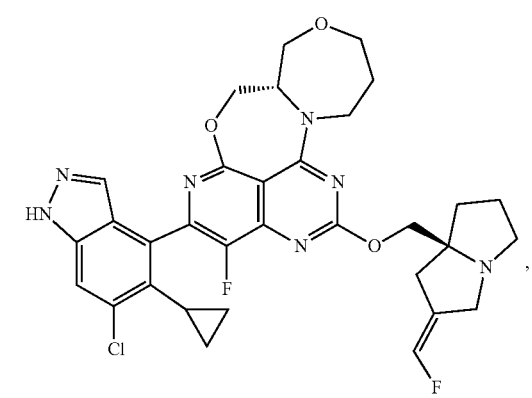
or a pharmaceutically acceptable salt thereof.
2. The compound of claim 1, that is:
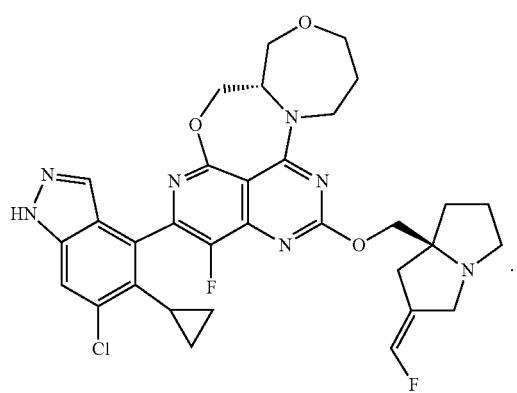 [SMILES: F/C=C1\CN2CCC[C@@]2(COc2nc3c4c(nc(-c5c(C6CC6)c(Cl)cc6[nH]ncc56)c(F)c4n2)OC[C@@H]2COCCCN32)C1 ; "."]
3. The compound of claim 1, that is:
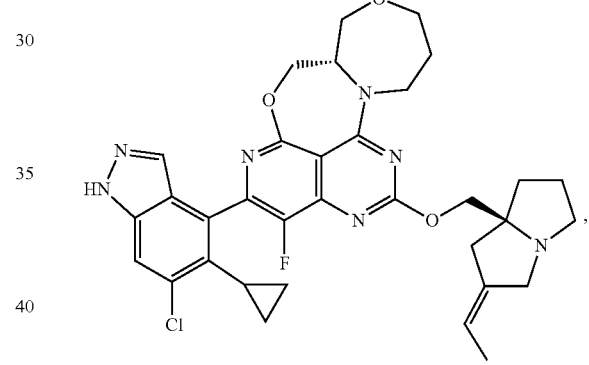
4. A compound,
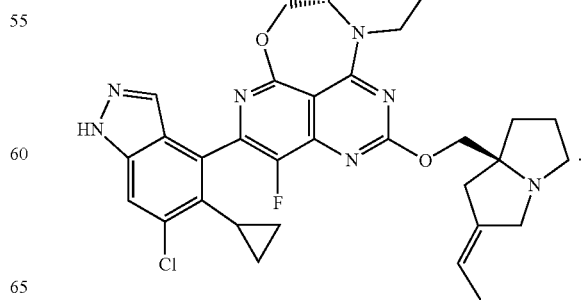
or a pharmaceutically acceptable salt thereof.
5. The compound of claim 4, that is:

6. A compound,
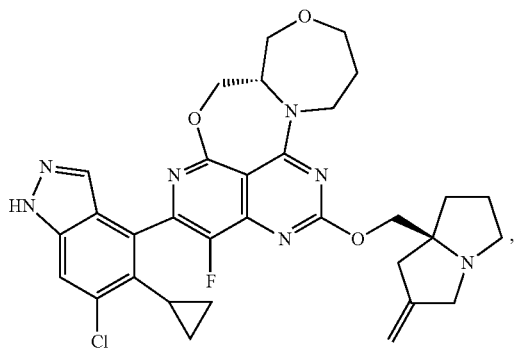 [SMILES: C=C1CN2CCC[C@@]2(COc2nc3c4c(nc(-c5c(C6CC6)c(Cl)cc6[nH]ncc56)c(F)c4n2)OC[C@@H]2COCCCN32)C1]
or a pharmaceutically acceptable salt thereof.
7. The compound of claim 6, that is:
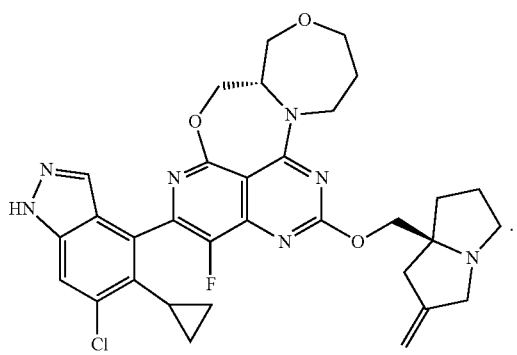 [SMILES: C=C1CN2CCC[C@@]2(COc2nc3c4c(nc(-c5c(C6CC6)c(Cl)cc6[nH]ncc56)c(F)c4n2)OC[C@@H]2COCCCN32)C1]
8. A compound,
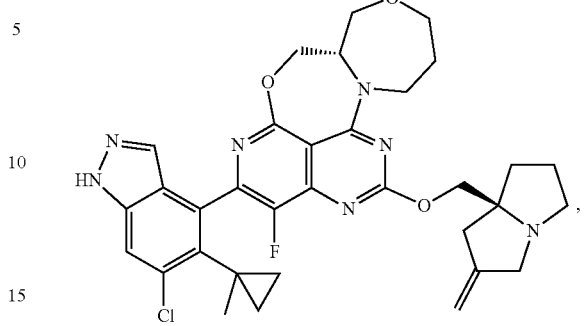
or a pharmaceutically acceptable salt thereof.
9. The compound of claim 8, that is:
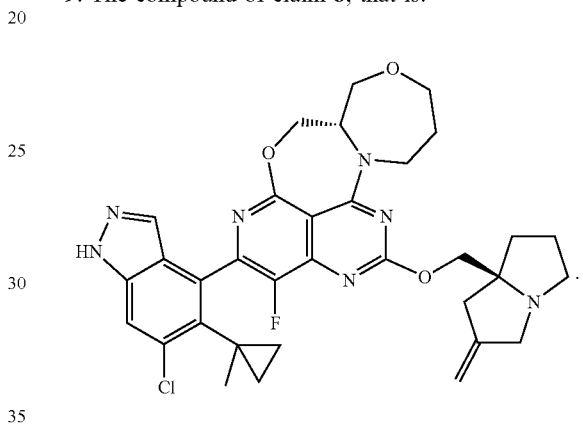
* * * * *